(12) United States Patent
Stafford et al.

(10) Patent No.: US 11,098,131 B2
(45) Date of Patent: Aug. 24, 2021

(54) ANTI-EPCAM ANTIBODIES, COMPOSITIONS COMPRISING ANTI-EPCAM ANTIBODIES AND METHODS OF MAKING AND USING ANTI-EPCAM ANTIBODIES

(71) Applicant: SUTRO BIOPHARMA, INC., South San Francisco, CA (US)

(72) Inventors: Ryan Stafford, Emeryville, CA (US); Alice Yam, Tiburon, CA (US); John Lee, San Francisco, CA (US); Stephanie Armstrong, South San Francisco, CA (US); Aaron Sato, Burlingame, CA (US)

(73) Assignee: SUTRO BIOPHARMA, INC., South San Francisco, CA (US)

( * ) Notice: Subject to any disclaimer, the term of this patent is extended or adjusted under 35 U.S.C. 154(b) by 160 days.

(21) Appl. No.: 15/748,634

(22) PCT Filed: Jul. 28, 2016

(86) PCT No.: PCT/US2016/044564
§ 371 (c)(1),
(2) Date: Jan. 29, 2018

(87) PCT Pub. No.: WO2017/023704
PCT Pub. Date: Feb. 9, 2017

(65) Prior Publication Data
US 2019/0002581 A1 Jan. 3, 2019

Related U.S. Application Data

(60) Provisional application No. 62/199,924, filed on Jul. 31, 2015.

(51) Int. Cl.
*C07K 16/30* (2006.01)
*A61P 35/00* (2006.01)
*C12N 15/62* (2006.01)
*C12N 15/85* (2006.01)

(52) U.S. Cl.
CPC .............. *C07K 16/30* (2013.01); *A61P 35/00* (2018.01); *C12N 15/62* (2013.01); *C12N 15/85* (2013.01); *C07K 2317/33* (2013.01); *C07K 2317/34* (2013.01); *C07K 2317/56* (2013.01); *C07K 2317/565* (2013.01); *C07K 2317/622* (2013.01); *C07K 2317/92* (2013.01)

(58) Field of Classification Search
CPC .......... C07K 16/30; A61P 35/00; C12N 15/62; C12N 15/85
See application file for complete search history.

(56) References Cited

U.S. PATENT DOCUMENTS

2007/0081993 A1* 4/2007 Kufer ................. C07K 16/2809
424/144.1

FOREIGN PATENT DOCUMENTS

| WO | WO 2004/106383 A1 | 12/2004 |
|---|---|---|
| WO | WO 2008/122551 A2 | 10/2008 |
| WO | WO 2010/115629 A2 | 10/2010 |
| WO | WO 2010/142990 A1 | 12/2010 |
| WO | WO 2013/131001 A1 | 9/2013 |
| WO | WO 2015/048901 A1 | 4/2015 |

OTHER PUBLICATIONS

Paul, Fundamental Immunology, 3rd Edition, 1993, pp. 292-295, under the heading "Fv Structure and Diversity in Three Dimensions". (Year: 1993).*
Rudikoff et al, Proc. Natl. Acad. Sci. USA 1982 vol. 79: p. 1979 (Year: 1982).*
Casset et al. BBRC 307: 198-205, 2003 (Year: 2003).*
Pascalis et al, The Journal of Immunology vol. 169: 3076-3084, 2002 (Year: 2002).*
International Search Report and Written Opinion of PCT/US2016/044564 dated Dec. 5, 2016; 27 pages.
Munz et al., "Side-by-side analysis of five clinically tested anti-EpCAM monoclonal antibodies", *Cancer Cell International, Biomed Central*, London, vol. 10, No. 1, Nov. 2, 2010, p. 44, XP021077267.
Ruf et al., "Characterisation of the new EpCAM-specific antibody H0-3: Implications for trifunctional antibody immunotherapy of cancer", *British Journal of Cancer*, vol. 97, No. 3, Jul. 31, 2007, pp. 315-321, XP055011283.
Schnell et al., "EpCAM: Structure and function in health and disease", *Biochimica et Biophysica Acta*, vol. 1828, No. 8, Aug. 2013, pp. 1989-2001, XP002762424.

* cited by examiner

*Primary Examiner* — Lei Yao
(74) *Attorney, Agent, or Firm* — Squire Patton Boggs (US) LLP

(57) ABSTRACT

Provided herein are antibodies that selectively bind to EpCAM and its isoforms and homologs, and compositions comprising the antibodies. Also provided are methods of using the antibodies, such as therapeutic and diagnostic methods.

29 Claims, 7 Drawing Sheets
Specification includes a Sequence Listing.

| SEQ_ID_NO:233 | 1464-A02 | EVQLLESGGGLVQPGGSLRLSCAASGFTFGVESMSWVRQAPGKGLEWVGAIDGGDGYTGY |
| --- | --- | --- |
| SEQ_ID_NO:234 | 1464-A08 | EVQLLESGGGLVQPGGSLRLSCAASGFTFSGSSMSWVRQAPGKGLEWVGAIAGGDGYTGY |
| SEQ_ID_NO:229 | 1304-G11 | EVQLLESGGGLVRPGGSLRLSCAASGFTFSGSSMSWVRQAPGKGLEWVGAIDGGDGYTNY |
| SEQ_ID_NO:238 | 1557-B03 | EVQLLESGGGLVQPGGSLRLSCAASGFTFRSSSMSWVRQAPGKGLEWVGAIGGHEGYTGY |
| SEQ_ID_NO:240 | 1557-C06 | EVQLLESGGGLVQPGGSLRLSCAASGFTFRGASMSWVRQAPGKGLEWVGAIDGSQGSTGY |
| SEQ_ID_NO:248 | 1557-G01 | EVQLLESGGGLVQPGGSLRLSCAASGFTFSVTSMSWMRQAPGKGLEWVGAIAGGESTGY |
| SEQ_ID_NO:252 | 1557-H04 | EVQLLESGGGLVQPGGSLRLSCAASGFTFSVTSMSWMRQAPGKGLEWVGAIAGGESTGY |
| SEQ_ID_NO:237 | 1557-A05 | EVQLLESGGGLVQPGGSLRLSCAASGFTFGGSSMSWVRQAPGKGLEWVGAIGGGESTGY |
| SEQ_ID_NO:245 | 1557-F02 | EVQLLESGGGLVQPGGSLRLSCAASGFTFRGSSMSWMRQAPGKGLEWVGAIDGGVSTGY |
| SEQ_ID_NO:242 | 1557-E08 | EVQLLESGGGLVQPGGSLRLSCAASGFTFRASSMSWVRQAPGKGLEWVGAIDGGESTGY |
| SEQ_ID_NO:243 | 1557-E11 | EVQLLESGGGLVQPGGSLRLSCAASGFTFRGSSMSWVRQAPGKGLEWVGAIDGGESTGY |
| SEQ_ID_NO:249 | 1557-G03 | EVQLLESGGGLVQPGGSLRLSCAASGFTFGGSSMSWVRQAPGKGLEWVGAIGGGEYTGY |
| SEQ_ID_NO:239 | 1557-B10 | EVQLLESGGGLVQPGGSLRLSCAASGFTFSFSGCSMSWVRQAPGKGLEWVGAIAGGENTGY |
| SEQ_ID_NO:235 | 1464-B04 | EVQLLESGGGLVQPGGSLRLSCAASGFTFSGSSMSWVRQAPGKGLEWVGAIDGGESTGY |
| SEQ_ID_NO:253 | 1557-H10 | EVQLLESGGGLVQPGGSLRLSCAASGFTFSGSSMSWVRQAPGKGLEWVGAIDGGESTGY |
| SEQ_ID_NO:236 | 1557-A04 | EVQLLESGGGLVQPGGSLRLSCAASGFTFSGSSMSWVRQAPGKGLEWVGAIDGGESTAY |
| SEQ_ID_NO:247 | 1557-F05 | EVQLLESGGGLVQPGGSLRLSCAASGFTFRGSSMSWVRQAPGKGLEWVGAIDGGESTGY |
| SEQ_ID_NO:250 | 1557-G04 | EVQLLESGGGLVQPGGSLRLSCAASGFTFCGSSMSWVRQAPGKGLEWVGAIDGGVSTGY |
| SEQ_ID_NO:246 | 1557-F03 | EVQLLESGGGLVQPGGSLRLSCAASGFTFSGFSMSWVRQAPGKGLEWVGAIAGGGSTGY |
| SEQ_ID_NO:251 | 1557-G06 | EVQLLESGGGLVQPGGSLRLSCAASGFTFSGSSMSWVRQAPGKGLEWVGAIDGGESTGY |
| SEQ_ID_NO:241 | 1557-E07 | EVQLLESGGGLVQPGGSLRLSCAASGFTFSGSSMSWVRQAPGKGLEWVGAIDGGESTGY |
| SEQ_ID_NO:244 | 1557-F01 | EVQLLESGGGLVQPGGSLRLSCAASGFTFSGSSMSWVRQAPGKGLEWVGAIDGGESTGY |
|  |  | ************.*:******** *******:******** * * |

FIG. 1A

| SEQ ID | Clone | Sequence |
|---|---|---|
| SEQ_ID_NO:233 | 1464-A02 | ADSVKDRFTISRDNSKNTLYLQMNSLRAEDTAVYYCAKAWHPQTYYGVDYWGQGTLVTVS |
| SEQ_ID_NO:234 | 1464-A08 | ADSVKGRFTISRDNSKNTLYLQMNSLRAEDTAVYYCAKGWHRQDYGQDYWGQGTLVTVS |
| SEQ_ID_NO:229 | 1304-G11 | ADSVRGRFTISRDNSKNTLYLQMNSLRAEDTAVYYCAKGWHPQTYYGLDYWGQGTLVTVS |
| SEQ_ID_NO:238 | 1557-B03 | ADSVKGRFTISRDNSKNTLYLQMNSLRAEDTAVYYCAKGWNPQTLYHLDYWGQGTLVTVS |
| SEQ_ID_NO:240 | 1557-C06 | ADSVKGRFTISRDNSKNTLYLQMNSLRAEDTAVYYCAKGWHPQTMYDLDYWGQGTLVTVS |
| SEQ_ID_NO:248 | 1557-G01 | ADSVKGRFTISRDNSKNTLYLQMNSLRAEDTAVYYCAKGWHPQTLYDLDYWGQGTLVTVS |
| SEQ_ID_NO:252 | 1557-H04 | ADSVKGRFTISRDNSKNTLYLQMNSLRAEDTAVYYCAKGWHPQTLYDLDYWGQGTLVTVS |
| SEQ_ID_NO:237 | 1557-A05 | ADSVKGRFTISRDNSKNTLYLQMNSLRAEDTAVYYCAKGWHDQSLYDRDYWGQGTLVTVS |
| SEQ_ID_NO:245 | 1557-F02 | ADSVKGRFTISRDNSKNTLYLQMNSLRAEDTAVYYCAKGWHPQTMYNLDYWGQGTLVTVS |
| SEQ_ID_NO:242 | 1557-E08 | ADSVKGRFTISRDNSKNTLYLQMNSLRAEDTAVYYCAKGWHPQTLYDLDYWGQGTLVTVS |
| SEQ_ID_NO:243 | 1557-E11 | ADSVKGRFTINRDNSKNTLYLQMNSLRAEDTAVYYCAKGWHPQSLYDLDYWGQGTLVTVS |
| SEQ_ID_NO:249 | 1557-G03 | ADSVKGRFTISRDNSKNTLYLQMNSLRAEDTAVYYCAKGWHPQTLYDLDYWGQGTLVTVS |
| SEQ_ID_NO:239 | 1557-B10 | ADSVKGRFTISRDNSKNTLYLQMNSLRAEDTAVYYCAKGWHPQTLYDLDYWGQGTLVTVS |
| SEQ_ID_NO:235 | 1464-B04 | ADSVKGRFTISRDNSKNTLYLQMNSLRAEDTAVYYCAKGWHPQSMYDLDYWGQGTLVTVS |
| SEQ_ID_NO:253 | 1557-H10 | ADSVKGRFTISRDNSKNTLYLQMNSLRAEDTAVYYCAKGWHPQTLYDLDYWGQGTLVTVS |
| SEQ_ID_NO:236 | 1557-A04 | ADSVKGRFTISRDNSKNTLYLQMNSLRAEDTAVYYCAKDWHPQTLYDLDYWGQGTLVTVS |
| SEQ_ID_NO:247 | 1557-F05 | ADSVKGRFTISRDNSKNTLYLQMNSLRAEDTAVYYCAKGWHPQTLYDLDYWGQGTLVTVS |
| SEQ_ID_NO:250 | 1557-G04 | ADSVKGRFTISRDNSKNTLYLQMNSLRAEDTAVYYCAKGWHPQTLYHLDYWGQGTLVTVS |
| SEQ_ID_NO:246 | 1557-F03 | ADSVKGRFTISRDNSKNTLYLQMNSLRAEDTAVYYCAKGWHPQTLYDLDYWGQGTLVTVS |
| SEQ_ID_NO:251 | 1557-G06 | ADSVKGRFTISRDNSKNTLYLQMNSLRAEDTAVYYCAKGWHPQTLYDLDYWGQGTLVTVS |
| SEQ_ID_NO:241 | 1557-E07 | ADSVKGRFTISRDNSKNTLYLQMNSLRAEDTAVYYCAKGWHPQTLYDLDYWGQGTLVTVS |
| SEQ_ID_NO:244 | 1557-F01 | ADSVKGRFTISRDNSKNTLYLQMNSLRAEDTAVYYCAKGWHPQTLYDLDYWGQGTLVTVS |
|  |  | **.:.:*.************************* * *.****** |

FIG. 1B

| | |
|---|---|
| SEQ_ID_NO:233_1464-A02 | S |
| SEQ_ID_NO:234_1464-A08 | S |
| SEQ_ID_NO:229_1304-G11 | S |
| SEQ_ID_NO:238_1557-B03 | S |
| SEQ_ID_NO:240_1557-C06 | S |
| SEQ_ID_NO:248_1557-G01 | S |
| SEQ_ID_NO:252_1557-H04 | S |
| SEQ_ID_NO:237_1557-A05 | S |
| SEQ_ID_NO:245_1557-F02 | S |
| SEQ_ID_NO:242_1557-E08 | S |
| SEQ_ID_NO:243_1557-E11 | S |
| SEQ_ID_NO:249_1557-G03 | S |
| SEQ_ID_NO:239_1557-B10 | S |
| SEQ_ID_NO:235_1464-B04 | S |
| SEQ_ID_NO:253_1557-H10 | S |
| SEQ_ID_NO:236_1557-A04 | S |
| SEQ_ID_NO:247_1557-F05 | S |
| SEQ_ID_NO:250_1557-G04 | S |
| SEQ_ID_NO:246_1557-F03 | S |
| SEQ_ID_NO:251_1557-G06 | S |
| SEQ_ID_NO:241_1557-E07 | S |
| SEQ_ID_NO:244_1557-F01 | * |

FIG. 1C

SEQ_ID_NO:231_1332-C01    EVQLLEQSGAELVRPGTSVKISCKASGYAFTNSWLGWVKQRPGHGLEWIGDIFPGSGNIH
SEQ_ID_NO:230_1332-A05    EVQLLEQSGAELVRPGTSVKISCKASDYAFANRWLGWVKQRPGHGLEWIGDIFPGSGNIH
SEQ_ID_NO:232_1332-F11    EVQLLEQSGAELVRPGTSVKISCKASGYAFANRWLGWVKQRPGHGLEWIGDIFPGSGNIH
                          ********************:  *.****:*  ***********************

FIG. 2A

SEQ_ID_NO:231_1332-C01    YNEKFKGKATLTADKSSSTAYMQLSSLTFEDSAVYFCARLRNWDMPMDYWGQGTTVTVSS
SEQ_ID_NO:230_1332-A05    YNEKFKGKATLTADKSSSTAYMQLSSLTFEDSAVYFCARLRNWEGPMDYWGQGTTVTVSS
SEQ_ID_NO:232_1332-F11    YNEKFKGKATLTADKSSSTAYMQLSSLTFEDSAVYFCARLRNWEGPMDYWGQGTTVTVSS
                          ****************************************:. *************

FIG. 2B

| SEQ_ID_NO:264_1557-B10 | EIVLTQSPGTLSLSPGERATLSCRASQGLASRYMAWYQQKPGQAPRLLIYGASSRATGIP |
| SEQ_ID_NO:268_1557-E11 | EIVLTQSPGTLSLSPGERATLSCRASQPVPNTTLAWYQQKPGQAPRLLIYGASSRATGIP |
| SEQ_ID_NO:262_1557-A05 | EIVLTQSPGTLSLSPGERATLSCSASQTVSSSYIAWYQQKPGQAPRLLIYGASSRATGIP |
| SEQ_ID_NO:277_1557-H04 | EIVLTQGPSTLSLSPGERATLSCRASQSVSTGYLAWYQQKPGQAPRLLIYGASSRATGIP |
| SEQ_ID_NO:259_1464-A08 | EIVLTQSPGTLSLSPGERATLGCRASQSVSSSYLAWYQQKPGQAPRLLIYGASSRATGIP |
| SEQ_ID_NO:254_1304-G11 | EIVLTQSPGTLSLSPGERATLSCRASQSVSSSYLAWYQQKPGQAPRLLIYGASSRATGIP |
| SEQ_ID_NO:271_1557-F03 | EIVLTQSPGTLSLSPGERATLSCRASQSVKTSDLAWYQQKPGQAPRLLIYGASSRATGIP |
| SEQ_ID_NO:266_1557-E07 | EIVLTQSPGTLSLSPGERATMSCRASQVLSSSSLAWYQQKPGQAPRLLIYGASSRATGIP |
| SEQ_ID_NO:263_1557-B03 | EIVLTQSPGTLSLSPGERATLSCRASQKCSSSSMAWYQQKPGQAPRLLIYGASSRATGIP |
| SEQ_ID_NO:272_1557-F05 | EIVLTQSPGTLSLSPGERATLSCRASQTVSPSVLAWYQQKPGQAPRLLIYGASSRATGIP |
| SEQ_ID_NO:273_1557-G01 | EIVLTQSPGTLSLSPGERATMSCRASQVLSSSSLAWYQQKPGQAPRLLIYGASSRATGIP |
| SEQ_ID_NO:278_1557-H10 | EIVLTQSPGTLSLSPGERATMSCRASQVLSSSSLAWYQQKPGQAPRLLIYGASSRATGIP |
| SEQ_ID_NO:267_1557-E08 | EIVLTQSPGTLSLSPGERATLSCRASQGDSSSVLAWYQEPGQAPRLLIYGASSRATGIP |
| SEQ_ID_NO:276_1557-G06 | EIVLTQSPGTLSLSPGERATLSCRASQSIPSSYLAWYQQKPGQAPRLLIYGASSRATGIP |
| SEQ_ID_NO:265_1557-C06 | EIVLTQSPGTLSLSPGERATLSCRASQRGTSSYLAWYQQKPGQAPRLLIYGASSRATGIP |
| SEQ_ID_NO:261_1557-A04 | EIVLTQSPGTLSLSPGERATLSCRASQNVSTNYLAWYQQKPGQAPRLLIYGASSRATGIP |
| SEQ_ID_NO:269_1557-F01 | EIVLTQSPGTLSLSPGERATLSCRASQSVSSSKLAWYQQKPGQAPRLLIYGASSRATGIP |
| SEQ_ID_NO:275_1557-G04 | EIVLTQSPGTLSLSPGERATLSCRASQSVSSSYLAWYQQKPGQAPRLLIYGASSRATGIP |
| SEQ_ID_NO:258_1464-A02 | EIVLTQSPGTLSLSPGERATLSCRASQSVSSSYLAWYQQKPGQAPRLLIYGASSRATGIP |
| SEQ_ID_NO:270_1557-F02 | EIVLTQSPGTLSLSPGERATLSCRASQSVSSSYLAWYQQKPGQAPRLLIYGASSRATGIP |
| SEQ_ID_NO:260_1464-B04 | EIVLTQSPGTLSLSPGERATLSCRASQSVSSSYLAWYQQKPGQAPRLLIYGASSRATGIP |
| SEQ_ID_NO:274_1557-G03 | EIVLTQSPGTLSLSPGERATLSCRASQSVHSSYLAWYQQKPGQAPRLLIYGASSRATGIP |
|  | ******.*.:********** *** .:******* : ****************** |

FIG. 3A

```
SEQ_ID_NO:264_1557-B10  DRFSGSGSGTDFTLTISRLEPEDFAVYYCQQVMTIPPTFGQGTKVEIK
SEQ_ID_NO:268_1557-E11  DRFSGSGSGTDFTLTISRLEPEDFAAYYCQQLVPSPPTFGQGTKVEIK
SEQ_ID_NO:262_1557-A05  DRFGGSGSGTDFTLTISRLEPEDFAVYYCQQLLTSPPTFGQGTKVEIK
SEQ_ID_NO:277_1557-H04  DRFSGSGSGTDFTLTISRLEPEDFAVYYCQQLVTRPPTFGQGTKVEIK
SEQ_ID_NO:259_1464-A08  DRFSGSGSGTDFTLTISRLEPEDFAVYYCQQNQAAPATFGQGTKVEIK
SEQ_ID_NO:254_1304-G11  DRFSGSSSGTDFTLTISRLEPEDFAVYYCQQYWYGPPTFGQGTKVEIK
SEQ_ID_NO:271_1557-F03  DRFSGSGSGTDFTLTISRLEPEDFAVYYCQQLVSKPPTFGQGTKVEIK
SEQ_ID_NO:266_1557-E07  DRFSGSGSGTDFTLTISRLEPEDFAVYYCQQRAAPPPTFGQGTKVEIK
SEQ_ID_NO:263_1557-B03  DRFSGSGSGTDFALTISRLEPEDFAVYYCQQLQTSPPTFGQGTKVEIK
SEQ_ID_NO:272_1557-F05  GRFSGSGSGTDFTLTISRLEPEDFAVYYCQQLVTNPPTFGQGTKVEIK
SEQ_ID_NO:273_1557-G01  DRFSGSGSGTDFTLTISRLEPEDFAVYYCQQLVTSPPTFGQGTKVEIK
SEQ_ID_NO:278_1557-H10  DRFSGSGSGTDFTLTISRLEPEDFAVYYCQQLVTAPPTFGQGTKVEIK
SEQ_ID_NO:267_1557-E08  DRFSGSGSGTDFTLTISRLEPEDFAVYYCQQLVPSPPTFGQGTKVEIK
SEQ_ID_NO:276_1557-G06  DRFSGSGSGTDFTLTISRLEPEDFAVYYCQQLATSPPTFGQGTKVEIK
SEQ_ID_NO:265_1557-C06  DRFSGSGSGTDFTLTISRLEPEDFAVYYCQQHVTSPPTFGQGTKVEIK
SEQ_ID_NO:261_1557-A04  DRFSGGSGSGTDFTLTISRLEPEDFAVYYCQQLVTNPPTFGQGTKVEIK
SEQ_ID_NO:269_1557-F01  DRFSGYGSGTDFTLTISRLEPEDFAVYYCQQLETIPPTFGQGTKVEIK
SEQ_ID_NO:275_1557-G04  DRFSGSGSGTDFTLTISRLEPEDFAVYYCQQDSFVPPTFGQGTKVEIK
SEQ_ID_NO:258_1464-A02  DRFSGSGSGTDFTLTISRLEPEDFAVYYCQQTSEAPPTFGQGTKVEIK
SEQ_ID_NO:270_1557-F02  DRFSGSGSGTDFTLTISRLEPEDFAVYYCQQLFNSPPTFGQGTKVEIK
SEQ_ID_NO:260_1464-B04  DRFSGSGSGTDFTLTISRLEPEDFAVYYCQQLVTSPPTFGQGTKVEIK
SEQ_ID_NO:274_1557-G03  DRFSGSGSGTDFTLTISRLEPEDFAVYYCQQLLSSPPTFGQGTKVEIK
                        :**.*  ******:********** ***:****** .  .*********
```

FIG. 3B

SEQ_ID_NO:256_1332-C01    ELVMTQSPSSLTVTAGEKVTMSCKSSQSLLNSGNQKNYLTWYQQKPGQPPKLLIYWASTR
SEQ_ID_NO:257_1332-F11    ELVMTQSPSSLTVTAGEKVTMSCKSSQSLLNSGNQKNYLTWYQQKPGQPPKLLIYRASTR
SEQ_ID_NO:255_1332-A05    ELVMTQSPSSLTVTAGEKVTMSCKSSQSLLNSGNQKNYLTWYQQKPGQPPKLLIYWASTR
                          ****************************************************.**

FIG. 4A

SEQ_ID_NO:256_1332-C01    ESGVPDRFTGSGSGTDFTLTISSVQAEDLAVYYCQNDYRYPLTFGAGTKLEIK
SEQ_ID_NO:257_1332-F11    ESGVPDRFTGSGSGTDFTLTISSVQAEDLAVYYCQNDSSYPLTFGAGTKLEIK
SEQ_ID_NO:255_1332-A05    ESGVPDRFTGSGSGTDFTLTISSVQAEDLAVYYCQNDLSYPLTFGAGTKLEIK
                          **********************************   **************

FIG. 4B

SEQUENCE LISTING

<160> NUMBER OF SEQ ID NOS: 362

<210> SEQ ID NO 1
<211> LENGTH: 314
<212> TYPE: PRT
<213> ORGANISM: Homo sapiens -continued

```
<220> FEATURE:
<221> NAME/KEY: misc_feature
<223> OTHER INFORMATION: hEpCAM

<400> SEQUENCE: 1

Met Ala Pro Pro Gln Val Leu Ala Phe Gly Leu Leu Leu Ala Ala Ala
1               5                   10                  15

Thr Ala Thr Phe Ala Ala Ala Gln Glu Glu Cys Val Cys Glu Asn Tyr
            20                  25                  30

Lys Leu Ala Val Asn Cys Phe Val Asn Asn Asn Arg Gln Cys Gln Cys
        35                  40                  45

Thr Ser Val Gly Ala Gln Asn Thr Val Ile Cys Ser Lys Leu Ala Ala
    50                  55                  60

Lys Cys Leu Val Met Lys Ala Glu Met Asn Gly Ser Lys Leu Gly Arg
65                  70                  75                  80

Arg Ala Lys Pro Glu Gly Ala Leu Gln Asn Asn Asp Gly Leu Tyr Asp
                85                  90                  95

Pro Asp Cys Asp Glu Ser Gly Leu Phe Lys Ala Lys Gln Cys Asn Gly
            100                 105                 110

Thr Ser Thr Cys Trp Cys Val Asn Thr Ala Gly Val Arg Arg Thr Asp
        115                 120                 125

Lys Asp Thr Glu Ile Thr Cys Ser Glu Arg Val Arg Thr Tyr Trp Ile
    130                 135                 140

Ile Ile Glu Leu Lys His Lys Ala Arg Glu Lys Pro Tyr Asp Ser Lys
145                 150                 155                 160

Ser Leu Arg Thr Ala Leu Gln Lys Glu Ile Thr Thr Arg Tyr Gln Leu
                165                 170                 175

Asp Pro Lys Phe Ile Thr Ser Ile Leu Tyr Glu Asn Asn Val Ile Thr
            180                 185                 190

Ile Asp Leu Val Gln Asn Ser Ser Gln Lys Thr Gln Asn Asp Val Asp
        195                 200                 205

Ile Ala Asp Val Ala Tyr Tyr Phe Glu Lys Asp Val Lys Gly Glu Ser
    210                 215                 220

Leu Phe His Ser Lys Lys Met Asp Leu Thr Val Asn Gly Glu Gln Leu
225                 230                 235                 240

Asp Leu Asp Pro Gly Gln Thr Leu Ile Tyr Tyr Val Asp Glu Lys Ala
                245                 250                 255

Pro Glu Phe Ser Met Gln Gly Leu Lys Ala Gly Val Ile Ala Val Ile
            260                 265                 270

Val Val Val Val Ile Ala Val Val Ala Gly Ile Val Val Leu Val Ile
        275                 280                 285

Ser Arg Lys Lys Arg Met Ala Lys Tyr Glu Lys Ala Glu Ile Lys Glu
    290                 295                 300

Met Gly Glu Met His Arg Glu Leu Asn Ala
305                 310

<210> SEQ ID NO 2
<211> LENGTH: 319
<212> TYPE: PRT
<213> ORGANISM: Macaca fascicularis
<220> FEATURE:
<221> NAME/KEY: misc_feature
<223> OTHER INFORMATION: cEpCAM

<400> SEQUENCE: 2

Met Ala Gln Ser Gly Gln Cys Leu Gln Glu Glu Gln Glu Thr Ser
1               5                   10                  15
```

```
Leu Gln Gln His Tyr Ser Phe Val Phe Leu Asn Phe Leu Glu Cys
             20                  25                  30

Val Cys Glu Asn Tyr Lys Leu Ala Val Asn Cys Phe Leu Asn Asp Asn
         35                  40                  45

Gly Gln Cys Gln Cys Thr Ser Ile Gly Ala Gln Asn Thr Val Leu Cys
 50                  55                  60

Ser Lys Leu Ala Ala Lys Cys Leu Val Met Lys Ala Glu Met Asn Gly
 65                  70                  75                  80

Ser Lys Leu Gly Arg Arg Ala Lys Pro Glu Gly Ala Leu Gln Asn Asn
                 85                  90                  95

Asp Gly Leu Tyr Asp Pro Asp Cys Asp Glu Ser Gly Leu Phe Lys Ala
            100                 105                 110

Lys Gln Cys Asn Gly Thr Ser Thr Cys Trp Cys Val Asn Thr Ala Gly
            115                 120                 125

Val Arg Arg Thr Asp Lys Asp Thr Glu Ile Thr Cys Ser Glu Arg Val
130                 135                 140

Arg Thr Tyr Trp Ile Ile Ile Glu Leu Lys His Lys Ala Arg Glu Lys
145                 150                 155                 160

Pro Tyr Asp Val Gln Ser Leu Arg Thr Ala Leu Glu Glu Ala Ile Lys
                165                 170                 175

Thr Arg Tyr Gln Leu Asp Pro Lys Phe Ile Thr Asn Ile Leu Tyr Glu
            180                 185                 190

Asp Asn Val Ile Thr Ile Asp Leu Val Gln Asn Ser Ser Gln Lys Thr
            195                 200                 205

Gln Asn Asp Val Asp Ile Ala Asp Val Ala Tyr Tyr Phe Glu Lys Asp
            210                 215                 220

Val Lys Gly Glu Ser Leu Phe His Ser Lys Lys Met Asp Leu Arg Val
225                 230                 235                 240

Asn Gly Glu Gln Leu Asp Leu Asp Pro Gly Gln Thr Leu Ile Tyr Tyr
                245                 250                 255

Val Asp Glu Lys Ala Pro Glu Phe Ser Met Gln Gly Leu Lys Ala Gly
            260                 265                 270

Val Ile Ala Val Ile Val Val Val Ile Ala Ile Val Ala Gly Ile
            275                 280                 285

Val Val Leu Val Ile Ser Arg Lys Lys Arg Met Ala Lys Tyr Glu Lys
            290                 295                 300

Ala Glu Ile Lys Glu Met Gly Glu Ile His Arg Glu Leu Asn Ala
305                 310                 315

<210> SEQ ID NO 3
<211> LENGTH: 315
<212> TYPE: PRT
<213> ORGANISM: Mus musculus
<220> FEATURE:
<221> NAME/KEY: misc_feature
<223> OTHER INFORMATION: mEpCAM

<400> SEQUENCE: 3

Met Ala Gly Pro Gln Ala Leu Ala Phe Gly Leu Leu Leu Ala Val Val
1               5                   10                  15

Thr Ala Thr Leu Ala Ala Ala Gln Arg Asp Cys Val Cys Asp Asn Tyr
             20                  25                  30

Lys Leu Ala Thr Ser Cys Ser Leu Asn Glu Tyr Gly Glu Cys Gln Cys
         35                  40                  45

Thr Ser Tyr Gly Thr Gln Asn Thr Val Ile Cys Ser Lys Leu Ala Ser
```

```
                50                  55                  60
Lys Cys Leu Ala Met Lys Ala Glu Met Thr His Ser Lys Ser Gly Arg
 65                  70                  75                  80

Arg Ile Lys Pro Glu Gly Ala Ile Gln Asn Asn Asp Gly Leu Tyr Asp
                 85                  90                  95

Pro Asp Cys Asp Glu Gln Gly Leu Phe Lys Ala Lys Gln Cys Asn Gly
                100                 105                 110

Thr Ala Thr Cys Trp Cys Val Asn Thr Ala Gly Val Arg Arg Thr Asp
                115                 120                 125

Lys Asp Thr Glu Ile Thr Cys Ser Glu Arg Val Arg Thr Tyr Trp Ile
                130                 135                 140

Ile Ile Glu Leu Lys His Lys Glu Arg Glu Ser Pro Tyr Asp His Gln
145                 150                 155                 160

Ser Leu Gln Thr Ala Leu Gln Glu Ala Phe Thr Ser Arg Tyr Lys Leu
                165                 170                 175

Asn Gln Lys Phe Ile Lys Asn Ile Met Tyr Glu Asn Asn Val Ile Thr
                180                 185                 190

Ile Asp Leu Met Gln Asn Ser Ser Gln Lys Thr Gln Asp Asp Val Asp
                195                 200                 205

Ile Ala Asp Val Ala Tyr Tyr Phe Glu Lys Asp Val Lys Gly Glu Ser
                210                 215                 220

Leu Phe His Ser Ser Lys Ser Met Asp Leu Arg Val Asn Gly Glu Pro
225                 230                 235                 240

Leu Asp Leu Asp Pro Gly Gln Thr Leu Ile Tyr Tyr Val Asp Glu Lys
                245                 250                 255

Ala Pro Glu Phe Ser Met Gln Gly Leu Thr Ala Gly Ile Ile Ala Val
                260                 265                 270

Ile Val Val Val Ser Leu Ala Val Ile Ala Gly Ile Val Val Leu Val
                275                 280                 285

Ile Ser Thr Arg Lys Lys Ser Ala Lys Tyr Glu Lys Ala Glu Ile Lys
                290                 295                 300

Glu Met Gly Glu Ile His Arg Glu Leu Asn Ala
305                 310                 315

<210> SEQ ID NO 4
<211> LENGTH: 7
<212> TYPE: PRT
<213> ORGANISM: Artificial Sequence
<220> FEATURE:
<223> OTHER INFORMATION: Synthetic: 1304-G11, CDR-H1

<400> SEQUENCE: 4

Gly Phe Thr Phe Ser Gly Ser
1               5

<210> SEQ ID NO 5
<211> LENGTH: 7
<212> TYPE: PRT
<213> ORGANISM: Artificial Sequence
<220> FEATURE:
<223> OTHER INFORMATION: Synthetic: 1332-A05, CDR-H1

<400> SEQUENCE: 5

Asp Tyr Ala Phe Ala Asn Arg
1               5

<210> SEQ ID NO 6
<211> LENGTH: 7
```

```
<212> TYPE: PRT
<213> ORGANISM: Artificial Sequence
<220> FEATURE:
<223> OTHER INFORMATION: Synthetic: 1332-C01, CDR-H1

<400> SEQUENCE: 6

Gly Tyr Ala Phe Thr Asn Ser
1               5

<210> SEQ ID NO 7
<211> LENGTH: 7
<212> TYPE: PRT
<213> ORGANISM: Artificial Sequence
<220> FEATURE:
<223> OTHER INFORMATION: Synthetic: 1332-F11, CDR-H1

<400> SEQUENCE: 7

Gly Tyr Ala Phe Ala Asn Arg
1               5

<210> SEQ ID NO 8
<211> LENGTH: 7
<212> TYPE: PRT
<213> ORGANISM: Artificial Sequence
<220> FEATURE:
<223> OTHER INFORMATION: Synthetic: 1464-A02, CDR-H1

<400> SEQUENCE: 8

Gly Phe Thr Phe Gly Val Glu
1               5

<210> SEQ ID NO 9
<211> LENGTH: 7
<212> TYPE: PRT
<213> ORGANISM: Artificial Sequence
<220> FEATURE:
<223> OTHER INFORMATION: Synthetic: 1464-A08, CDR-H1

<400> SEQUENCE: 9

Gly Phe Thr Phe Ser Gly Ser
1               5

<210> SEQ ID NO 10
<211> LENGTH: 7
<212> TYPE: PRT
<213> ORGANISM: Artificial Sequence
<220> FEATURE:
<223> OTHER INFORMATION: Synthetic: 1464-B04, CDR-H1

<400> SEQUENCE: 10

Gly Phe Thr Phe Ser Gly Ser
1               5

<210> SEQ ID NO 11
<211> LENGTH: 7
<212> TYPE: PRT
<213> ORGANISM: Artificial Sequence
<220> FEATURE:
<223> OTHER INFORMATION: Synthetic: 1557-A04, CDR-H1

<400> SEQUENCE: 11

Gly Phe Thr Phe Ser Gly Ser
1               5

<210> SEQ ID NO 12
<211> LENGTH: 7
<212> TYPE: PRT
```

<213> ORGANISM: Artificial Sequence
<220> FEATURE:
<223> OTHER INFORMATION: Synthetic: 1557-A05, CDR-H1

<400> SEQUENCE: 12

Gly Phe Thr Phe Gly Gly Ser
1               5

<210> SEQ ID NO 13
<211> LENGTH: 7
<212> TYPE: PRT
<213> ORGANISM: Artificial Sequence
<220> FEATURE:
<223> OTHER INFORMATION: Synthetic: 1557-B03, CDR-H1

<400> SEQUENCE: 13

Gly Phe Thr Phe Arg Ser Ser
1               5

<210> SEQ ID NO 14
<211> LENGTH: 7
<212> TYPE: PRT
<213> ORGANISM: Artificial Sequence
<220> FEATURE:
<223> OTHER INFORMATION: Synthetic: 1557-B10, CDR-H1

<400> SEQUENCE: 14

Gly Phe Thr Phe Ser Gly Cys
1               5

<210> SEQ ID NO 15
<211> LENGTH: 7
<212> TYPE: PRT
<213> ORGANISM: Artificial Sequence
<220> FEATURE:
<223> OTHER INFORMATION: Synthetic: 1557-C06, CDR-H1

<400> SEQUENCE: 15

Gly Phe Thr Phe Arg Gly Ala
1               5

<210> SEQ ID NO 16
<211> LENGTH: 7
<212> TYPE: PRT
<213> ORGANISM: Artificial Sequence
<220> FEATURE:
<223> OTHER INFORMATION: Synthetic: 1557-E07, CDR-H1

<400> SEQUENCE: 16

Gly Phe Thr Phe Ser Gly Ser
1               5

<210> SEQ ID NO 17
<211> LENGTH: 7
<212> TYPE: PRT
<213> ORGANISM: Artificial Sequence
<220> FEATURE:
<223> OTHER INFORMATION: Synthetic: 1557-E08, CDR-H1

<400> SEQUENCE: 17

Gly Phe Thr Phe Arg Ala Ser
1               5

<210> SEQ ID NO 18
<211> LENGTH: 7
<212> TYPE: PRT
<213> ORGANISM: Artificial Sequence

```
<220> FEATURE:
<223> OTHER INFORMATION: Synthetic: 1557-E11, CDR-H1

<400> SEQUENCE: 18

Gly Phe Thr Phe Arg Gly Ser
1               5

<210> SEQ ID NO 19
<211> LENGTH: 7
<212> TYPE: PRT
<213> ORGANISM: Artificial Sequence
<220> FEATURE:
<223> OTHER INFORMATION: Synthetic: 1557-F01, CDR-H1

<400> SEQUENCE: 19

Gly Phe Thr Phe Ser Gly Ser
1               5

<210> SEQ ID NO 20
<211> LENGTH: 7
<212> TYPE: PRT
<213> ORGANISM: Artificial Sequence
<220> FEATURE:
<223> OTHER INFORMATION: Synthetic: 1557-F02, CDR-H1

<400> SEQUENCE: 20

Gly Phe Thr Phe Arg Gly Ser
1               5

<210> SEQ ID NO 21
<211> LENGTH: 7
<212> TYPE: PRT
<213> ORGANISM: Artificial Sequence
<220> FEATURE:
<223> OTHER INFORMATION: Synthetic: 1557-F03, CDR-H1

<400> SEQUENCE: 21

Gly Phe Thr Phe Ser Gly Ser
1               5

<210> SEQ ID NO 22
<211> LENGTH: 7
<212> TYPE: PRT
<213> ORGANISM: Artificial Sequence
<220> FEATURE:
<223> OTHER INFORMATION: Synthetic: 1557-F05, CDR-H1

<400> SEQUENCE: 22

Gly Phe Thr Phe Arg Gly Ser
1               5

<210> SEQ ID NO 23
<211> LENGTH: 7
<212> TYPE: PRT
<213> ORGANISM: Artificial Sequence
<220> FEATURE:
<223> OTHER INFORMATION: Synthetic: 1557-G01, CDR-H1

<400> SEQUENCE: 23

Gly Phe Thr Phe Ser Val Thr
1               5

<210> SEQ ID NO 24
<211> LENGTH: 7
<212> TYPE: PRT
<213> ORGANISM: Artificial Sequence
<220> FEATURE:
```

<223> OTHER INFORMATION: Synthetic: 1557-G03, CDR-H1

<400> SEQUENCE: 24

Gly Phe Thr Phe Gly Gly Ser
1               5

<210> SEQ ID NO 25
<211> LENGTH: 7
<212> TYPE: PRT
<213> ORGANISM: Artificial Sequence
<220> FEATURE:
<223> OTHER INFORMATION: Synthetic: 1557-G04, CDR-H1

<400> SEQUENCE: 25

Gly Phe Thr Phe Cys Gly Ser
1               5

<210> SEQ ID NO 26
<211> LENGTH: 7
<212> TYPE: PRT
<213> ORGANISM: Artificial Sequence
<220> FEATURE:
<223> OTHER INFORMATION: Synthetic: 1557-G06, CDR-H1

<400> SEQUENCE: 26

Gly Phe Thr Phe Ser Gly Phe
1               5

<210> SEQ ID NO 27
<211> LENGTH: 7
<212> TYPE: PRT
<213> ORGANISM: Artificial Sequence
<220> FEATURE:
<223> OTHER INFORMATION: Synthetic: 1557-H04, CDR-H1

<400> SEQUENCE: 27

Gly Phe Thr Phe Ser Val Thr
1               5

<210> SEQ ID NO 28
<211> LENGTH: 7
<212> TYPE: PRT
<213> ORGANISM: Artificial Sequence
<220> FEATURE:
<223> OTHER INFORMATION: Synthetic: 1557-H10, CDR-H1

<400> SEQUENCE: 28

Gly Phe Thr Phe Ser Gly Ser
1               5

<210> SEQ ID NO 29
<211> LENGTH: 5
<212> TYPE: PRT
<213> ORGANISM: Artificial Sequence
<220> FEATURE:
<223> OTHER INFORMATION: Synthetic: 1304-G11, CDR-H1

<400> SEQUENCE: 29

Gly Ser Ser Met Ser
1               5

<210> SEQ ID NO 30
<211> LENGTH: 5
<212> TYPE: PRT
<213> ORGANISM: Artificial Sequence
<220> FEATURE:
<223> OTHER INFORMATION: Synthetic: 1332-A05, CDR-H1

<400> SEQUENCE: 30

Asn Arg Trp Leu Gly
1               5

<210> SEQ ID NO 31
<211> LENGTH: 5
<212> TYPE: PRT
<213> ORGANISM: Artificial Sequence
<220> FEATURE:
<223> OTHER INFORMATION: Synthetic: 1332-C01, CDR-H1

<400> SEQUENCE: 31

Asn Ser Trp Leu Gly
1               5

<210> SEQ ID NO 32
<211> LENGTH: 5
<212> TYPE: PRT
<213> ORGANISM: Artificial Sequence
<220> FEATURE:
<223> OTHER INFORMATION: Synthetic: 1332-F11, CDR-H1

<400> SEQUENCE: 32

Asn Arg Trp Leu Gly
1               5

<210> SEQ ID NO 33
<211> LENGTH: 5
<212> TYPE: PRT
<213> ORGANISM: Artificial Sequence
<220> FEATURE:
<223> OTHER INFORMATION: Synthetic: 1464-A02, CDR-H1

<400> SEQUENCE: 33

Val Glu Ser Met Ser
1               5

<210> SEQ ID NO 34
<211> LENGTH: 5
<212> TYPE: PRT
<213> ORGANISM: Artificial Sequence
<220> FEATURE:
<223> OTHER INFORMATION: Synthetic: 1464-A08, CDR-H1

<400> SEQUENCE: 34

Gly Ser Ser Met Ser
1               5

<210> SEQ ID NO 35
<211> LENGTH: 5
<212> TYPE: PRT
<213> ORGANISM: Artificial Sequence
<220> FEATURE:
<223> OTHER INFORMATION: Synthetic: 1464-B04, CDR-H1

<400> SEQUENCE: 35

Gly Ser Ser Met Ser
1               5

<210> SEQ ID NO 36
<211> LENGTH: 5
<212> TYPE: PRT
<213> ORGANISM: Artificial Sequence
<220> FEATURE:
<223> OTHER INFORMATION: Synthetic: 1557-A04, CDR-H1

```
<400> SEQUENCE: 36

Gly Ser Ser Met Ser
1               5

<210> SEQ ID NO 37
<211> LENGTH: 5
<212> TYPE: PRT
<213> ORGANISM: Artificial Sequence
<220> FEATURE:
<223> OTHER INFORMATION: Synthetic: 1557-A05, CDR-H1

<400> SEQUENCE: 37

Gly Ser Ser Met Ser
1               5

<210> SEQ ID NO 38
<211> LENGTH: 5
<212> TYPE: PRT
<213> ORGANISM: Artificial Sequence
<220> FEATURE:
<223> OTHER INFORMATION: Synthetic: 1557-B03, CDR-H1

<400> SEQUENCE: 38

Ser Ser Ser Met Ser
1               5

<210> SEQ ID NO 39
<211> LENGTH: 5
<212> TYPE: PRT
<213> ORGANISM: Artificial Sequence
<220> FEATURE:
<223> OTHER INFORMATION: Synthetic: 1557-B10, CDR-H1

<400> SEQUENCE: 39

Gly Cys Ser Met Ser
1               5

<210> SEQ ID NO 40
<211> LENGTH: 5
<212> TYPE: PRT
<213> ORGANISM: Artificial Sequence
<220> FEATURE:
<223> OTHER INFORMATION: Synthetic: 1557-C06, CDR-H1

<400> SEQUENCE: 40

Gly Ala Ser Met Ser
1               5

<210> SEQ ID NO 41
<211> LENGTH: 5
<212> TYPE: PRT
<213> ORGANISM: Artificial Sequence
<220> FEATURE:
<223> OTHER INFORMATION: Synthetic: 1557-E07, CDR-H1

<400> SEQUENCE: 41

Gly Ser Ser Met Ser
1               5

<210> SEQ ID NO 42
<211> LENGTH: 5
<212> TYPE: PRT
<213> ORGANISM: Artificial Sequence
<220> FEATURE:
<223> OTHER INFORMATION: Synthetic: 1557-E08, CDR-H1

<400> SEQUENCE: 42
```

Ala Ser Ser Met Ser
1               5

<210> SEQ ID NO 43
<211> LENGTH: 5
<212> TYPE: PRT
<213> ORGANISM: Artificial Sequence
<220> FEATURE:
<223> OTHER INFORMATION: Synthetic: 1557-E11, CDR-H1

<400> SEQUENCE: 43

Gly Ser Ser Met Ser
1               5

<210> SEQ ID NO 44
<211> LENGTH: 5
<212> TYPE: PRT
<213> ORGANISM: Artificial Sequence
<220> FEATURE:
<223> OTHER INFORMATION: Synthetic: 1557-F01, CDR-H1

<400> SEQUENCE: 44

Gly Ser Ser Met Ser
1               5

<210> SEQ ID NO 45
<211> LENGTH: 5
<212> TYPE: PRT
<213> ORGANISM: Artificial Sequence
<220> FEATURE:
<223> OTHER INFORMATION: Synthetic: 1557-F02, CDR-H1

<400> SEQUENCE: 45

Gly Ser Ser Met Ser
1               5

<210> SEQ ID NO 46
<211> LENGTH: 5
<212> TYPE: PRT
<213> ORGANISM: Artificial Sequence
<220> FEATURE:
<223> OTHER INFORMATION: Synthetic: 1557-F03, CDR-H1

<400> SEQUENCE: 46

Gly Ser Ser Met Ser
1               5

<210> SEQ ID NO 47
<211> LENGTH: 5
<212> TYPE: PRT
<213> ORGANISM: Artificial Sequence
<220> FEATURE:
<223> OTHER INFORMATION: Synthetic: 1557-F05, CDR-H1

<400> SEQUENCE: 47

Gly Ser Ser Met Ser
1               5

<210> SEQ ID NO 48
<211> LENGTH: 5
<212> TYPE: PRT
<213> ORGANISM: Artificial Sequence
<220> FEATURE:
<223> OTHER INFORMATION: Synthetic: 1557-G01, CDR-H1

<400> SEQUENCE: 48

Val Thr Ser Met Ser
1               5

<210> SEQ ID NO 49
<211> LENGTH: 5
<212> TYPE: PRT
<213> ORGANISM: Artificial Sequence
<220> FEATURE:
<223> OTHER INFORMATION: Synthetic: 1557-G03, CDR-H1

<400> SEQUENCE: 49

Gly Ser Ser Met Ser
1               5

<210> SEQ ID NO 50
<211> LENGTH: 5
<212> TYPE: PRT
<213> ORGANISM: Artificial Sequence
<220> FEATURE:
<223> OTHER INFORMATION: Synthetic: 1557-G04, CDR-H1

<400> SEQUENCE: 50

Gly Ser Ser Met Ser
1               5

<210> SEQ ID NO 51
<211> LENGTH: 5
<212> TYPE: PRT
<213> ORGANISM: Artificial Sequence
<220> FEATURE:
<223> OTHER INFORMATION: Synthetic: 1557-G06, CDR-H1

<400> SEQUENCE: 51

Gly Phe Ser Met Ser
1               5

<210> SEQ ID NO 52
<211> LENGTH: 5
<212> TYPE: PRT
<213> ORGANISM: Artificial Sequence
<220> FEATURE:
<223> OTHER INFORMATION: Synthetic: 1557-H04, CDR-H1

<400> SEQUENCE: 52

Val Thr Ser Met Ser
1               5

<210> SEQ ID NO 53
<211> LENGTH: 5
<212> TYPE: PRT
<213> ORGANISM: Artificial Sequence
<220> FEATURE:
<223> OTHER INFORMATION: Synthetic: 1557-H10, CDR-H1

<400> SEQUENCE: 53

Gly Ser Ser Met Ser
1               5

<210> SEQ ID NO 54
<211> LENGTH: 6
<212> TYPE: PRT
<213> ORGANISM: Artificial Sequence
<220> FEATURE:
<223> OTHER INFORMATION: Synthetic: 1304-G11, CDR-H2

<400> SEQUENCE: 54

Asp Gly Gly Asp Gly Tyr

<210> SEQ ID NO 55
<211> LENGTH: 6
<212> TYPE: PRT
<213> ORGANISM: Artificial Sequence
<220> FEATURE:
<223> OTHER INFORMATION: Synthetic: 1332-A05, CDR-H2

<400> SEQUENCE: 55

Phe Pro Gly Ser Gly Asn
1               5

<210> SEQ ID NO 56
<211> LENGTH: 6
<212> TYPE: PRT
<213> ORGANISM: Artificial Sequence
<220> FEATURE:
<223> OTHER INFORMATION: Synthetic: 1332-C01, CDR-H2

<400> SEQUENCE: 56

Phe Pro Gly Ser Gly Asn
1               5

<210> SEQ ID NO 57
<211> LENGTH: 6
<212> TYPE: PRT
<213> ORGANISM: Artificial Sequence
<220> FEATURE:
<223> OTHER INFORMATION: Synthetic: 1332-F11, CDR-H2

<400> SEQUENCE: 57

Phe Pro Gly Ser Gly Asn
1               5

<210> SEQ ID NO 58
<211> LENGTH: 6
<212> TYPE: PRT
<213> ORGANISM: Artificial Sequence
<220> FEATURE:
<223> OTHER INFORMATION: Synthetic: 1464-A02, CDR-H2

<400> SEQUENCE: 58

Asp Gly Gly Asp Gly Tyr
1               5

<210> SEQ ID NO 59
<211> LENGTH: 6
<212> TYPE: PRT
<213> ORGANISM: Artificial Sequence
<220> FEATURE:
<223> OTHER INFORMATION: Synthetic: 1464-A08, CDR-H2

<400> SEQUENCE: 59

Ala Gly Gly Asp Gly Tyr
1               5

<210> SEQ ID NO 60
<211> LENGTH: 6
<212> TYPE: PRT
<213> ORGANISM: Artificial Sequence
<220> FEATURE:
<223> OTHER INFORMATION: Synthetic: 1464-B04, CDR-H2

<400> SEQUENCE: 60

Asp Gly Gly Glu Gly Tyr
1               5

```
<210> SEQ ID NO 61
<211> LENGTH: 6
<212> TYPE: PRT
<213> ORGANISM: Artificial Sequence
<220> FEATURE:
<223> OTHER INFORMATION: Synthetic: 1557-A04, CDR-H2

<400> SEQUENCE: 61

Asp Gly Gly Glu Gly Ser
1               5

<210> SEQ ID NO 62
<211> LENGTH: 6
<212> TYPE: PRT
<213> ORGANISM: Artificial Sequence
<220> FEATURE:
<223> OTHER INFORMATION: Synthetic: 1557-A05, CDR-H2

<400> SEQUENCE: 62

Gly Gly Gly Glu Gly Ser
1               5

<210> SEQ ID NO 63
<211> LENGTH: 6
<212> TYPE: PRT
<213> ORGANISM: Artificial Sequence
<220> FEATURE:
<223> OTHER INFORMATION: Synthetic: 1557-B03, CDR-H2

<400> SEQUENCE: 63

Gly Gly His Glu Gly Tyr
1               5

<210> SEQ ID NO 64
<211> LENGTH: 6
<212> TYPE: PRT
<213> ORGANISM: Artificial Sequence
<220> FEATURE:
<223> OTHER INFORMATION: Synthetic: 1557-B10, CDR-H2

<400> SEQUENCE: 64

Ala Gly Gly Glu Gly Asn
1               5

<210> SEQ ID NO 65
<211> LENGTH: 6
<212> TYPE: PRT
<213> ORGANISM: Artificial Sequence
<220> FEATURE:
<223> OTHER INFORMATION: Synthetic: 1557-C06, CDR-H2

<400> SEQUENCE: 65

Asp Gly Ser Gln Gly Ser
1               5

<210> SEQ ID NO 66
<211> LENGTH: 6
<212> TYPE: PRT
<213> ORGANISM: Artificial Sequence
<220> FEATURE:
<223> OTHER INFORMATION: Synthetic: 1557-E07, CDR-H2

<400> SEQUENCE: 66

Asp Gly Gly Glu Gly Ser
1               5
```

<210> SEQ ID NO 67
<211> LENGTH: 6
<212> TYPE: PRT
<213> ORGANISM: Artificial Sequence
<220> FEATURE:
<223> OTHER INFORMATION: Synthetic: 1557-E08, CDR-H2

<400> SEQUENCE: 67

Asp Gly Gly Val Gly Ser
1               5

<210> SEQ ID NO 68
<211> LENGTH: 6
<212> TYPE: PRT
<213> ORGANISM: Artificial Sequence
<220> FEATURE:
<223> OTHER INFORMATION: Synthetic: 1557-E11, CDR-H2

<400> SEQUENCE: 68

Asp Gly Gly Glu Gly Ser
1               5

<210> SEQ ID NO 69
<211> LENGTH: 6
<212> TYPE: PRT
<213> ORGANISM: Artificial Sequence
<220> FEATURE:
<223> OTHER INFORMATION: Synthetic: 1557-F01, CDR-H2

<400> SEQUENCE: 69

Asp Gly Gly Glu Gly Ser
1               5

<210> SEQ ID NO 70
<211> LENGTH: 6
<212> TYPE: PRT
<213> ORGANISM: Artificial Sequence
<220> FEATURE:
<223> OTHER INFORMATION: Synthetic: 1557-F02, CDR-H2

<400> SEQUENCE: 70

Asp Gly Gly Glu Gly Ser
1               5

<210> SEQ ID NO 71
<211> LENGTH: 6
<212> TYPE: PRT
<213> ORGANISM: Artificial Sequence
<220> FEATURE:
<223> OTHER INFORMATION: Synthetic: 1557-F03, CDR-H2

<400> SEQUENCE: 71

Ala Gly Gly Gly Gly Ser
1               5

<210> SEQ ID NO 72
<211> LENGTH: 6
<212> TYPE: PRT
<213> ORGANISM: Artificial Sequence
<220> FEATURE:
<223> OTHER INFORMATION: Synthetic: 1557-F05, CDR-H2

<400> SEQUENCE: 72

Asp Gly Gly Glu Gly Ser
1               5

```
<210> SEQ ID NO 73
<211> LENGTH: 6
<212> TYPE: PRT
<213> ORGANISM: Artificial Sequence
<220> FEATURE:
<223> OTHER INFORMATION: Synthetic: 1557-G01, CDR-H2

<400> SEQUENCE: 73

Ala Gly Gly Glu Gly Ser
1               5

<210> SEQ ID NO 74
<211> LENGTH: 6
<212> TYPE: PRT
<213> ORGANISM: Artificial Sequence
<220> FEATURE:
<223> OTHER INFORMATION: Synthetic: 1557-G03, CDR-H2

<400> SEQUENCE: 74

Gly Gly Gly Glu Gly Tyr
1               5

<210> SEQ ID NO 75
<211> LENGTH: 6
<212> TYPE: PRT
<213> ORGANISM: Artificial Sequence
<220> FEATURE:
<223> OTHER INFORMATION: Synthetic: 1557-G04, CDR-H2

<400> SEQUENCE: 75

Asp Gly Gly Val Gly Ser
1               5

<210> SEQ ID NO 76
<211> LENGTH: 6
<212> TYPE: PRT
<213> ORGANISM: Artificial Sequence
<220> FEATURE:
<223> OTHER INFORMATION: Synthetic: 1557-G06, CDR-H2

<400> SEQUENCE: 76

Asp Gly Gly Glu Gly Ser
1               5

<210> SEQ ID NO 77
<211> LENGTH: 6
<212> TYPE: PRT
<213> ORGANISM: Artificial Sequence
<220> FEATURE:
<223> OTHER INFORMATION: Synthetic: 1557-H04, CDR-H2

<400> SEQUENCE: 77

Ala Gly Gly Glu Gly Ser
1               5

<210> SEQ ID NO 78
<211> LENGTH: 6
<212> TYPE: PRT
<213> ORGANISM: Artificial Sequence
<220> FEATURE:
<223> OTHER INFORMATION: Synthetic: 1557-H10, CDR-H2

<400> SEQUENCE: 78

Asp Gly Gly Glu Gly Ser
1               5

<210> SEQ ID NO 79
```

```
<211> LENGTH: 17
<212> TYPE: PRT
<213> ORGANISM: Artificial Sequence
<220> FEATURE:
<223> OTHER INFORMATION: Synthetic: 1304-G11, CDR-H2

<400> SEQUENCE: 79

Ala Ile Asp Gly Gly Asp Gly Tyr Thr Asn Tyr Ala Asp Ser Val Arg
1               5                   10                  15

Gly

<210> SEQ ID NO 80
<211> LENGTH: 17
<212> TYPE: PRT
<213> ORGANISM: Artificial Sequence
<220> FEATURE:
<223> OTHER INFORMATION: Synthetic: 1332-A05, CDR-H2

<400> SEQUENCE: 80

Asp Ile Phe Pro Gly Ser Gly Asn Ile His Tyr Asn Glu Lys Phe Lys
1               5                   10                  15

Gly

<210> SEQ ID NO 81
<211> LENGTH: 17
<212> TYPE: PRT
<213> ORGANISM: Artificial Sequence
<220> FEATURE:
<223> OTHER INFORMATION: Synthetic: 1332-C01, CDR-H2

<400> SEQUENCE: 81

Asp Ile Phe Pro Gly Ser Gly Asn Ile His Tyr Asn Glu Lys Phe Lys
1               5                   10                  15

Gly

<210> SEQ ID NO 82
<211> LENGTH: 17
<212> TYPE: PRT
<213> ORGANISM: Artificial Sequence
<220> FEATURE:
<223> OTHER INFORMATION: Synthetic: 1332-F11, CDR-H2

<400> SEQUENCE: 82

Asp Ile Phe Pro Gly Ser Gly Asn Ile His Tyr Asn Glu Lys Phe Lys
1               5                   10                  15

Gly

<210> SEQ ID NO 83
<211> LENGTH: 17
<212> TYPE: PRT
<213> ORGANISM: Artificial Sequence
<220> FEATURE:
<223> OTHER INFORMATION: Synthetic: 1464-A02, CDR-H2

<400> SEQUENCE: 83

Ala Ile Asp Gly Gly Asp Gly Tyr Thr Gly Tyr Ala Asp Ser Val Lys
1               5                   10                  15

Asp

<210> SEQ ID NO 84
<211> LENGTH: 17
<212> TYPE: PRT
<213> ORGANISM: Artificial Sequence
<220> FEATURE:
```

```
<223> OTHER INFORMATION: Synthetic: 1464-A08, CDR-H2

<400> SEQUENCE: 84

Ala Ile Ala Gly Gly Asp Gly Tyr Thr Gly Tyr Ala Asp Ser Val Lys
1               5                   10                  15

Gly

<210> SEQ ID NO 85
<211> LENGTH: 17
<212> TYPE: PRT
<213> ORGANISM: Artificial Sequence
<220> FEATURE:
<223> OTHER INFORMATION: Synthetic: 1464-B04, CDR-H2

<400> SEQUENCE: 85

Ala Ile Asp Gly Gly Glu Gly Tyr Thr Ser Tyr Ala Asp Ser Val Lys
1               5                   10                  15

Gly

<210> SEQ ID NO 86
<211> LENGTH: 17
<212> TYPE: PRT
<213> ORGANISM: Artificial Sequence
<220> FEATURE:
<223> OTHER INFORMATION: Synthetic: 1557-A04, CDR-H2

<400> SEQUENCE: 86

Ala Ile Asp Gly Gly Glu Gly Ser Thr Ala Tyr Ala Asp Ser Val Lys
1               5                   10                  15

Gly

<210> SEQ ID NO 87
<211> LENGTH: 17
<212> TYPE: PRT
<213> ORGANISM: Artificial Sequence
<220> FEATURE:
<223> OTHER INFORMATION: Synthetic: 1557-A05, CDR-H2

<400> SEQUENCE: 87

Ala Ile Gly Gly Gly Glu Gly Ser Thr Gly Tyr Ala Asp Ser Val Lys
1               5                   10                  15

Gly

<210> SEQ ID NO 88
<211> LENGTH: 17
<212> TYPE: PRT
<213> ORGANISM: Artificial Sequence
<220> FEATURE:
<223> OTHER INFORMATION: Synthetic: 1557-B03, CDR-H2

<400> SEQUENCE: 88

Ala Ile Gly Gly His Glu Gly Tyr Thr Gly Tyr Ala Asp Ser Val Lys
1               5                   10                  15

Gly

<210> SEQ ID NO 89
<211> LENGTH: 17
<212> TYPE: PRT
<213> ORGANISM: Artificial Sequence
<220> FEATURE:
<223> OTHER INFORMATION: Synthetic: 1557-B10, CDR-H2

<400> SEQUENCE: 89
```

-continued

Ala Ile Ala Gly Gly Glu Gly Asn Thr Gly Tyr Ala Asp Ser Val Lys
1               5                   10                  15

Gly

<210> SEQ ID NO 90
<211> LENGTH: 17
<212> TYPE: PRT
<213> ORGANISM: Artificial Sequence
<220> FEATURE:
<223> OTHER INFORMATION: Synthetic: 1557-C06, CDR-H2

<400> SEQUENCE: 90

Ala Ile Asp Gly Ser Gln Gly Ser Thr Gly Tyr Ala Asp Ser Val Lys
1               5                   10                  15

Gly

<210> SEQ ID NO 91
<211> LENGTH: 17
<212> TYPE: PRT
<213> ORGANISM: Artificial Sequence
<220> FEATURE:
<223> OTHER INFORMATION: Synthetic: 1557-E07, CDR-H2

<400> SEQUENCE: 91

Ala Ile Asp Gly Gly Glu Gly Ser Thr Gly Tyr Ala Asp Ser Val Lys
1               5                   10                  15

Gly

<210> SEQ ID NO 92
<211> LENGTH: 17
<212> TYPE: PRT
<213> ORGANISM: Artificial Sequence
<220> FEATURE:
<223> OTHER INFORMATION: Synthetic: 1557-E08, CDR-H2

<400> SEQUENCE: 92

Ala Ile Asp Gly Gly Val Gly Ser Thr Gly Tyr Ala Asp Ser Val Lys
1               5                   10                  15

Gly

<210> SEQ ID NO 93
<211> LENGTH: 17
<212> TYPE: PRT
<213> ORGANISM: Artificial Sequence
<220> FEATURE:
<223> OTHER INFORMATION: Synthetic: 1557-E11, CDR-H2

<400> SEQUENCE: 93

Ala Ile Asp Gly Gly Glu Gly Ser Thr Gly Tyr Ala Asp Ser Val Lys
1               5                   10                  15

Gly

<210> SEQ ID NO 94
<211> LENGTH: 17
<212> TYPE: PRT
<213> ORGANISM: Artificial Sequence
<220> FEATURE:
<223> OTHER INFORMATION: Synthetic: 1557-F01, CDR-H2

<400> SEQUENCE: 94

Ala Ile Asp Gly Gly Glu Gly Ser Thr Gly Tyr Ala Asp Ser Val Lys
1               5                   10                  15

Gly

<210> SEQ ID NO 95
<211> LENGTH: 17
<212> TYPE: PRT
<213> ORGANISM: Artificial Sequence
<220> FEATURE:
<223> OTHER INFORMATION: Synthetic: 1557-F02, CDR-H2

<400> SEQUENCE: 95

Ala Ile Asp Gly Gly Glu Gly Ser Thr Gly Tyr Ala Asp Ser Val Lys
1               5                   10                  15

Gly

<210> SEQ ID NO 96
<211> LENGTH: 17
<212> TYPE: PRT
<213> ORGANISM: Artificial Sequence
<220> FEATURE:
<223> OTHER INFORMATION: Synthetic: 1557-F03, CDR-H2

<400> SEQUENCE: 96

Ala Ile Ala Gly Gly Gly Gly Ser Thr Gly Tyr Ala Asp Ser Val Lys
1               5                   10                  15

Gly

<210> SEQ ID NO 97
<211> LENGTH: 17
<212> TYPE: PRT
<213> ORGANISM: Artificial Sequence
<220> FEATURE:
<223> OTHER INFORMATION: Synthetic: 1557-F05, CDR-H2

<400> SEQUENCE: 97

Ala Ile Asp Gly Gly Glu Gly Ser Thr Gly Tyr Ala Asp Ser Val Lys
1               5                   10                  15

Gly

<210> SEQ ID NO 98
<211> LENGTH: 17
<212> TYPE: PRT
<213> ORGANISM: Artificial Sequence
<220> FEATURE:
<223> OTHER INFORMATION: Synthetic: 1557-G01, CDR-H2

<400> SEQUENCE: 98

Ala Ile Ala Gly Gly Glu Gly Ser Thr Gly Tyr Ala Asp Ser Val Lys
1               5                   10                  15

Gly

<210> SEQ ID NO 99
<211> LENGTH: 17
<212> TYPE: PRT
<213> ORGANISM: Artificial Sequence
<220> FEATURE:
<223> OTHER INFORMATION: Synthetic: 1557-G03, CDR-H2

<400> SEQUENCE: 99

Ala Ile Gly Gly Gly Glu Gly Tyr Thr Gly Tyr Ala Asp Ser Val Lys
1               5                   10                  15

Gly

<210> SEQ ID NO 100
<211> LENGTH: 17

```
<212> TYPE: PRT
<213> ORGANISM: Artificial Sequence
<220> FEATURE:
<223> OTHER INFORMATION: Synthetic: 1557-G04, CDR-H2

<400> SEQUENCE: 100

Ala Ile Asp Gly Gly Val Gly Ser Thr Gly Tyr Ala Asp Ser Val Lys
1               5                   10                  15

Gly

<210> SEQ ID NO 101
<211> LENGTH: 17
<212> TYPE: PRT
<213> ORGANISM: Artificial Sequence
<220> FEATURE:
<223> OTHER INFORMATION: Synthetic: 1557-G06, CDR-H2

<400> SEQUENCE: 101

Ala Ile Asp Gly Gly Glu Gly Ser Thr Gly Tyr Ala Asp Ser Val Lys
1               5                   10                  15

Gly

<210> SEQ ID NO 102
<211> LENGTH: 17
<212> TYPE: PRT
<213> ORGANISM: Artificial Sequence
<220> FEATURE:
<223> OTHER INFORMATION: Synthetic: 1557-H04, CDR-H2

<400> SEQUENCE: 102

Ala Ile Ala Gly Gly Glu Gly Ser Thr Gly Tyr Ala Asp Ser Val Lys
1               5                   10                  15

Gly

<210> SEQ ID NO 103
<211> LENGTH: 17
<212> TYPE: PRT
<213> ORGANISM: Artificial Sequence
<220> FEATURE:
<223> OTHER INFORMATION: Synthetic: 1557-H10, CDR-H2

<400> SEQUENCE: 103

Ala Ile Asp Gly Gly Glu Gly Ser Thr Gly Tyr Ala Asp Ser Val Lys
1               5                   10                  15

Gly

<210> SEQ ID NO 104
<211> LENGTH: 12
<212> TYPE: PRT
<213> ORGANISM: Artificial Sequence
<220> FEATURE:
<223> OTHER INFORMATION: Synthetic: 1304-G11, CDR-H3

<400> SEQUENCE: 104

Gly Trp His Pro Gln Thr Tyr Tyr Gly Leu Asp Tyr
1               5                   10

<210> SEQ ID NO 105
<211> LENGTH: 10
<212> TYPE: PRT
<213> ORGANISM: Artificial Sequence
<220> FEATURE:
<223> OTHER INFORMATION: Synthetic: 1332-A05, CDR-H3

<400> SEQUENCE: 105
```

```
Leu Arg Asn Trp Glu Gly Pro Met Asp Tyr
1               5                   10

<210> SEQ ID NO 106
<211> LENGTH: 10
<212> TYPE: PRT
<213> ORGANISM: Artificial Sequence
<220> FEATURE:
<223> OTHER INFORMATION: Synthetic: 1332-C01, CDR-H3

<400> SEQUENCE: 106

Leu Arg Asn Trp Asp Met Pro Met Asp Tyr
1               5                   10

<210> SEQ ID NO 107
<211> LENGTH: 10
<212> TYPE: PRT
<213> ORGANISM: Artificial Sequence
<220> FEATURE:
<223> OTHER INFORMATION: Synthetic: 1332-F11, CDR-H3

<400> SEQUENCE: 107

Leu Arg Asn Trp Glu Gly Pro Met Asp Tyr
1               5                   10

<210> SEQ ID NO 108
<211> LENGTH: 12
<212> TYPE: PRT
<213> ORGANISM: Artificial Sequence
<220> FEATURE:
<223> OTHER INFORMATION: Synthetic: 1464-A02, CDR-H3

<400> SEQUENCE: 108

Ala Trp His Pro Gln Thr Tyr Tyr Gly Val Asp Tyr
1               5                   10

<210> SEQ ID NO 109
<211> LENGTH: 12
<212> TYPE: PRT
<213> ORGANISM: Artificial Sequence
<220> FEATURE:
<223> OTHER INFORMATION: Synthetic: 1464-A08, CDR-H3

<400> SEQUENCE: 109

Gly Trp His Arg Gln Asp Tyr Tyr Gly Gln Asp Tyr
1               5                   10

<210> SEQ ID NO 110
<211> LENGTH: 12
<212> TYPE: PRT
<213> ORGANISM: Artificial Sequence
<220> FEATURE:
<223> OTHER INFORMATION: Synthetic: 1464-B04, CDR-H3

<400> SEQUENCE: 110

Gly Trp His Pro Gln Thr Leu Tyr Asp Leu Asp Tyr
1               5                   10

<210> SEQ ID NO 111
<211> LENGTH: 12
<212> TYPE: PRT
<213> ORGANISM: Artificial Sequence
<220> FEATURE:
<223> OTHER INFORMATION: Synthetic: 1557-A04, CDR-H3

<400> SEQUENCE: 111
```

Gly Trp His Pro Gln Thr Met Tyr Asp Leu Asp Tyr
1               5                   10

<210> SEQ ID NO 112
<211> LENGTH: 12
<212> TYPE: PRT
<213> ORGANISM: Artificial Sequence
<220> FEATURE:
<223> OTHER INFORMATION: Synthetic: 1557-A05, CDR-H3

<400> SEQUENCE: 112

Gly Trp His Asp Gln Ser Leu Tyr Asp Arg Asp Tyr
1               5                   10

<210> SEQ ID NO 113
<211> LENGTH: 12
<212> TYPE: PRT
<213> ORGANISM: Artificial Sequence
<220> FEATURE:
<223> OTHER INFORMATION: Synthetic: 1557-B03, CDR-H3

<400> SEQUENCE: 113

Gly Trp Asn Pro Gln Thr Leu Tyr His Leu Asp Tyr
1               5                   10

<210> SEQ ID NO 114
<211> LENGTH: 12
<212> TYPE: PRT
<213> ORGANISM: Artificial Sequence
<220> FEATURE:
<223> OTHER INFORMATION: Synthetic: 1557-B10, CDR-H3

<400> SEQUENCE: 114

Gly Trp His Pro Gln Thr Leu Tyr Asp Leu Asp Tyr
1               5                   10

<210> SEQ ID NO 115
<211> LENGTH: 12
<212> TYPE: PRT
<213> ORGANISM: Artificial Sequence
<220> FEATURE:
<223> OTHER INFORMATION: Synthetic: 1557-C06, CDR-H3

<400> SEQUENCE: 115

Gly Trp His Pro Gln Thr Met Tyr Asp Leu Asp Tyr
1               5                   10

<210> SEQ ID NO 116
<211> LENGTH: 12
<212> TYPE: PRT
<213> ORGANISM: Artificial Sequence
<220> FEATURE:
<223> OTHER INFORMATION: Synthetic: 1557-E07, CDR-H3

<400> SEQUENCE: 116

Gly Trp His Pro Gln Thr Leu Tyr Asp Leu Asp Tyr
1               5                   10

<210> SEQ ID NO 117
<211> LENGTH: 12
<212> TYPE: PRT
<213> ORGANISM: Artificial Sequence
<220> FEATURE:
<223> OTHER INFORMATION: Synthetic: 1557-E08, CDR-H3

<400> SEQUENCE: 117

Gly Trp His Pro Gln Thr Leu Tyr Asp Leu Asp Tyr

```
1               5                  10

<210> SEQ ID NO 118
<211> LENGTH: 12
<212> TYPE: PRT
<213> ORGANISM: Artificial Sequence
<220> FEATURE:
<223> OTHER INFORMATION: Synthetic: 1557-E11, CDR-H3

<400> SEQUENCE: 118

Gly Trp His Pro Gln Ser Leu Tyr Asp Leu Asp Tyr
1               5                  10

<210> SEQ ID NO 119
<211> LENGTH: 12
<212> TYPE: PRT
<213> ORGANISM: Artificial Sequence
<220> FEATURE:
<223> OTHER INFORMATION: Synthetic: 1557-F01, CDR-H3

<400> SEQUENCE: 119

Gly Trp His Pro Gln Thr Leu Tyr Asp Leu Asp Tyr
1               5                  10

<210> SEQ ID NO 120
<211> LENGTH: 12
<212> TYPE: PRT
<213> ORGANISM: Artificial Sequence
<220> FEATURE:
<223> OTHER INFORMATION: Synthetic: 1557-F02, CDR-H3

<400> SEQUENCE: 120

Gly Trp His Pro Gln Thr Met Tyr Asn Leu Asp Tyr
1               5                  10

<210> SEQ ID NO 121
<211> LENGTH: 12
<212> TYPE: PRT
<213> ORGANISM: Artificial Sequence
<220> FEATURE:
<223> OTHER INFORMATION: Synthetic: 1557-F03, CDR-H3

<400> SEQUENCE: 121

Gly Trp His Pro Gln Thr Leu Tyr Asp Leu Asp Tyr
1               5                  10

<210> SEQ ID NO 122
<211> LENGTH: 12
<212> TYPE: PRT
<213> ORGANISM: Artificial Sequence
<220> FEATURE:
<223> OTHER INFORMATION: Synthetic: 1557-F05, CDR-H3

<400> SEQUENCE: 122

Asp Trp His Pro Gln Thr Leu Tyr Asp Leu Asp Tyr
1               5                  10

<210> SEQ ID NO 123
<211> LENGTH: 12
<212> TYPE: PRT
<213> ORGANISM: Artificial Sequence
<220> FEATURE:
<223> OTHER INFORMATION: Synthetic: 1557-G01, CDR-H3

<400> SEQUENCE: 123

Gly Trp His Pro Gln Thr Leu Tyr Asp Leu Asp Tyr
1               5                  10
```

<210> SEQ ID NO 124
<211> LENGTH: 12
<212> TYPE: PRT
<213> ORGANISM: Artificial Sequence
<220> FEATURE:
<223> OTHER INFORMATION: Synthetic: 1557-G03, CDR-H3

<400> SEQUENCE: 124

Gly Trp His Pro Gln Thr Leu Tyr Asp Leu Asp Tyr
1               5                   10

<210> SEQ ID NO 125
<211> LENGTH: 12
<212> TYPE: PRT
<213> ORGANISM: Artificial Sequence
<220> FEATURE:
<223> OTHER INFORMATION: Synthetic: 1557-G04, CDR-H3

<400> SEQUENCE: 125

Gly Trp His Pro Gln Thr Leu Tyr Asp Leu Asp Tyr
1               5                   10

<210> SEQ ID NO 126
<211> LENGTH: 12
<212> TYPE: PRT
<213> ORGANISM: Artificial Sequence
<220> FEATURE:
<223> OTHER INFORMATION: Synthetic: 1557-G06, CDR-H3

<400> SEQUENCE: 126

Gly Trp His Pro Gln Thr Leu Tyr His Leu Asp Tyr
1               5                   10

<210> SEQ ID NO 127
<211> LENGTH: 12
<212> TYPE: PRT
<213> ORGANISM: Artificial Sequence
<220> FEATURE:
<223> OTHER INFORMATION: Synthetic: 1557-H04, CDR-H3

<400> SEQUENCE: 127

Gly Trp His Pro Gln Thr Leu Tyr Asp Leu Asp Tyr
1               5                   10

<210> SEQ ID NO 128
<211> LENGTH: 12
<212> TYPE: PRT
<213> ORGANISM: Artificial Sequence
<220> FEATURE:
<223> OTHER INFORMATION: Synthetic: 1557-H10, CDR-H3

<400> SEQUENCE: 128

Gly Trp His Pro Gln Ser Met Tyr Asp Leu Asp Tyr
1               5                   10

<210> SEQ ID NO 129
<211> LENGTH: 12
<212> TYPE: PRT
<213> ORGANISM: Artificial Sequence
<220> FEATURE:
<223> OTHER INFORMATION: Synthetic: 1304-G11, CDR-L1

<400> SEQUENCE: 129

Arg Ala Ser Gln Ser Val Ser Ser Tyr Leu Ala
1               5                   10

<210> SEQ ID NO 130
<211> LENGTH: 17
<212> TYPE: PRT
<213> ORGANISM: Artificial Sequence
<220> FEATURE:
<223> OTHER INFORMATION: Synthetic: 1332-A05, CDR-L1

<400> SEQUENCE: 130

Lys Ser Ser Gln Ser Leu Leu Asn Ser Gly Asn Gln Lys Asn Tyr Leu
1               5                   10                  15

Thr

<210> SEQ ID NO 131
<211> LENGTH: 17
<212> TYPE: PRT
<213> ORGANISM: Artificial Sequence
<220> FEATURE:
<223> OTHER INFORMATION: Synthetic: 1332-C01, CDR-L1

<400> SEQUENCE: 131

Lys Ser Ser Gln Ser Leu Leu Asn Ser Gly Asn Gln Lys Asn Tyr Leu
1               5                   10                  15

Thr

<210> SEQ ID NO 132
<211> LENGTH: 17
<212> TYPE: PRT
<213> ORGANISM: Artificial Sequence
<220> FEATURE:
<223> OTHER INFORMATION: Synthetic: 1332-F11, CDR-L1

<400> SEQUENCE: 132

Lys Ser Ser Gln Ser Leu Leu Asn Ser Gly Asn Gln Lys Asn Tyr Leu
1               5                   10                  15

Thr

<210> SEQ ID NO 133
<211> LENGTH: 12
<212> TYPE: PRT
<213> ORGANISM: Artificial Sequence
<220> FEATURE:
<223> OTHER INFORMATION: Synthetic: 1464-A02, CDR-L1

<400> SEQUENCE: 133

Arg Ala Ser Gln Ser Val Ser Ser Ser Tyr Leu Ala
1               5                   10

<210> SEQ ID NO 134
<211> LENGTH: 12
<212> TYPE: PRT
<213> ORGANISM: Artificial Sequence
<220> FEATURE:
<223> OTHER INFORMATION: Synthetic: 1464-A08, CDR-L1

<400> SEQUENCE: 134

Arg Ala Ser Gln Ser Val Ser Ser Ser Tyr Leu Ala
1               5                   10

<210> SEQ ID NO 135
<211> LENGTH: 12
<212> TYPE: PRT
<213> ORGANISM: Artificial Sequence
<220> FEATURE:
<223> OTHER INFORMATION: Synthetic: 1464-B04, CDR-L1

<400> SEQUENCE: 135

Arg Ala Ser Gln Ser Val Ser Ser Ser Tyr Leu Ala
1               5                   10

<210> SEQ ID NO 136
<211> LENGTH: 12
<212> TYPE: PRT
<213> ORGANISM: Artificial Sequence
<220> FEATURE:
<223> OTHER INFORMATION: Synthetic: 1557-A04, CDR-L1

<400> SEQUENCE: 136

Arg Ala Ser Gln Asn Val Ser Thr Asn Tyr Leu Ala
1               5                   10

<210> SEQ ID NO 137
<211> LENGTH: 12
<212> TYPE: PRT
<213> ORGANISM: Artificial Sequence
<220> FEATURE:
<223> OTHER INFORMATION: Synthetic: 1557-A05, CDR-L1

<400> SEQUENCE: 137

Ser Ala Ser Gln Thr Val Ser Ser Ser Tyr Ile Ala
1               5                   10

<210> SEQ ID NO 138
<211> LENGTH: 12
<212> TYPE: PRT
<213> ORGANISM: Artificial Sequence
<220> FEATURE:
<223> OTHER INFORMATION: Synthetic: 1557-B03, CDR-L1

<400> SEQUENCE: 138

Arg Ala Ser Gln Lys Cys Ser Ser Ser Met Ala
1               5                   10

<210> SEQ ID NO 139
<211> LENGTH: 12
<212> TYPE: PRT
<213> ORGANISM: Artificial Sequence
<220> FEATURE:
<223> OTHER INFORMATION: Synthetic: 1557-B10, CDR-L1

<400> SEQUENCE: 139

Arg Ala Ser Gln Gly Leu Ala Ser Arg Tyr Met Ala
1               5                   10

<210> SEQ ID NO 140
<211> LENGTH: 12
<212> TYPE: PRT
<213> ORGANISM: Artificial Sequence
<220> FEATURE:
<223> OTHER INFORMATION: Synthetic: 1557-C06, CDR-L1

<400> SEQUENCE: 140

Arg Ala Ser Gln Arg Gly Thr Ser Ser Tyr Leu Ala
1               5                   10

<210> SEQ ID NO 141
<211> LENGTH: 12
<212> TYPE: PRT
<213> ORGANISM: Artificial Sequence
<220> FEATURE:
<223> OTHER INFORMATION: Synthetic: 1557-E07, CDR-L1

<400> SEQUENCE: 141

```
Arg Ala Ser Gln Val Leu Ser Ser Ser Leu Ala
1               5                   10

<210> SEQ ID NO 142
<211> LENGTH: 12
<212> TYPE: PRT
<213> ORGANISM: Artificial Sequence
<220> FEATURE:
<223> OTHER INFORMATION: Synthetic: 1557-E08, CDR-L1

<400> SEQUENCE: 142

Arg Ala Ser Gln Gly Asp Ser Ser Ser Val Leu Ala
1               5                   10

<210> SEQ ID NO 143
<211> LENGTH: 12
<212> TYPE: PRT
<213> ORGANISM: Artificial Sequence
<220> FEATURE:
<223> OTHER INFORMATION: Synthetic: 1557-E11, CDR-L1

<400> SEQUENCE: 143

Arg Ala Ser Gln Pro Val Pro Asn Thr Thr Leu Ala
1               5                   10

<210> SEQ ID NO 144
<211> LENGTH: 12
<212> TYPE: PRT
<213> ORGANISM: Artificial Sequence
<220> FEATURE:
<223> OTHER INFORMATION: Synthetic: 1557-F01, CDR-L1

<400> SEQUENCE: 144

Arg Ala Ser Gln Ser Val Ser Ser Ser Lys Leu Ala
1               5                   10

<210> SEQ ID NO 145
<211> LENGTH: 12
<212> TYPE: PRT
<213> ORGANISM: Artificial Sequence
<220> FEATURE:
<223> OTHER INFORMATION: Synthetic: 1557-F02, CDR-L1

<400> SEQUENCE: 145

Arg Ala Ser Gln Ser Val Ser Ser Ser Tyr Leu Ala
1               5                   10

<210> SEQ ID NO 146
<211> LENGTH: 12
<212> TYPE: PRT
<213> ORGANISM: Artificial Sequence
<220> FEATURE:
<223> OTHER INFORMATION: Synthetic: 1557-F03, CDR-L1

<400> SEQUENCE: 146

Arg Ala Ser Gln Ser Val Lys Thr Ser Asp Leu Ala
1               5                   10

<210> SEQ ID NO 147
<211> LENGTH: 12
<212> TYPE: PRT
<213> ORGANISM: Artificial Sequence
<220> FEATURE:
<223> OTHER INFORMATION: Synthetic: 1557-F05, CDR-L1

<400> SEQUENCE: 147
```

Arg Ala Ser Gln Thr Val Ser Pro Ser Val Leu Ala
1               5                   10

<210> SEQ ID NO 148
<211> LENGTH: 12
<212> TYPE: PRT
<213> ORGANISM: Artificial Sequence
<220> FEATURE:
<223> OTHER INFORMATION: Synthetic: 1557-G01, CDR-L1

<400> SEQUENCE: 148

Arg Ala Ser Gln Val Leu Ser Ser Ser Ser Leu Ala
1               5                   10

<210> SEQ ID NO 149
<211> LENGTH: 12
<212> TYPE: PRT
<213> ORGANISM: Artificial Sequence
<220> FEATURE:
<223> OTHER INFORMATION: Synthetic: 1557-G03, CDR-L1

<400> SEQUENCE: 149

Arg Ala Ser Gln Ser Val His Ser Ser Tyr Leu Ala
1               5                   10

<210> SEQ ID NO 150
<211> LENGTH: 12
<212> TYPE: PRT
<213> ORGANISM: Artificial Sequence
<220> FEATURE:
<223> OTHER INFORMATION: Synthetic: 1557-G04, CDR-L1

<400> SEQUENCE: 150

Arg Ala Ser Gln Ser Val Ser Ser Ser Tyr Leu Ala
1               5                   10

<210> SEQ ID NO 151
<211> LENGTH: 12
<212> TYPE: PRT
<213> ORGANISM: Artificial Sequence
<220> FEATURE:
<223> OTHER INFORMATION: Synthetic: 1557-G06, CDR-L1

<400> SEQUENCE: 151

Arg Ala Ser Gln Ser Ile Pro Ser Ser Tyr Leu Ala
1               5                   10

<210> SEQ ID NO 152
<211> LENGTH: 12
<212> TYPE: PRT
<213> ORGANISM: Artificial Sequence
<220> FEATURE:
<223> OTHER INFORMATION: Synthetic: 1557-H04, CDR-L1

<400> SEQUENCE: 152

Arg Ala Ser Gln Ser Val Ser Thr Gly Tyr Leu Ala
1               5                   10

<210> SEQ ID NO 153
<211> LENGTH: 12
<212> TYPE: PRT
<213> ORGANISM: Artificial Sequence
<220> FEATURE:
<223> OTHER INFORMATION: Synthetic: 1557-H10, CDR-L1

<400> SEQUENCE: 153

Arg Ala Ser Gln Val Leu Ser Ser Ser Ser Leu Ala

<210> SEQ ID NO 154
<211> LENGTH: 7
<212> TYPE: PRT
<213> ORGANISM: Artificial Sequence
<220> FEATURE:
<223> OTHER INFORMATION: Synthetic: 1304-G11, CDR-L2

<400> SEQUENCE: 154

Gly Ala Ser Ser Arg Ala Thr
1               5

<210> SEQ ID NO 155
<211> LENGTH: 7
<212> TYPE: PRT
<213> ORGANISM: Artificial Sequence
<220> FEATURE:
<223> OTHER INFORMATION: Synthetic: 1332-A05, CDR-L2

<400> SEQUENCE: 155

Trp Ala Ser Thr Arg Glu Ser
1               5

<210> SEQ ID NO 156
<211> LENGTH: 7
<212> TYPE: PRT
<213> ORGANISM: Artificial Sequence
<220> FEATURE:
<223> OTHER INFORMATION: Synthetic: 1332-C01, CDR-L2

<400> SEQUENCE: 156

Trp Ala Ser Thr Arg Glu Ser
1               5

<210> SEQ ID NO 157
<211> LENGTH: 7
<212> TYPE: PRT
<213> ORGANISM: Artificial Sequence
<220> FEATURE:
<223> OTHER INFORMATION: Synthetic: 1332-F11, CDR-L2

<400> SEQUENCE: 157

Arg Ala Ser Thr Arg Glu Ser
1               5

<210> SEQ ID NO 158
<211> LENGTH: 7
<212> TYPE: PRT
<213> ORGANISM: Artificial Sequence
<220> FEATURE:
<223> OTHER INFORMATION: Synthetic: 1464-A02, CDR-L2

<400> SEQUENCE: 158

Gly Ala Ser Ser Arg Ala Thr
1               5

<210> SEQ ID NO 159
<211> LENGTH: 7
<212> TYPE: PRT
<213> ORGANISM: Artificial Sequence
<220> FEATURE:
<223> OTHER INFORMATION: Synthetic: 1464-A08, CDR-L2

<400> SEQUENCE: 159

Gly Ala Ser Ser Arg Ala Thr
1               5

```
<210> SEQ ID NO 160
<211> LENGTH: 7
<212> TYPE: PRT
<213> ORGANISM: Artificial Sequence
<220> FEATURE:
<223> OTHER INFORMATION: Synthetic: 1464-B04, CDR-L2

<400> SEQUENCE: 160

Gly Ala Ser Ser Arg Ala Thr
1               5

<210> SEQ ID NO 161
<211> LENGTH: 7
<212> TYPE: PRT
<213> ORGANISM: Artificial Sequence
<220> FEATURE:
<223> OTHER INFORMATION: Synthetic: 1557-A04, CDR-L2

<400> SEQUENCE: 161

Gly Ala Ser Ser Arg Ala Thr
1               5

<210> SEQ ID NO 162
<211> LENGTH: 7
<212> TYPE: PRT
<213> ORGANISM: Artificial Sequence
<220> FEATURE:
<223> OTHER INFORMATION: Synthetic: 1557-A05, CDR-L2

<400> SEQUENCE: 162

Gly Ala Ser Ser Arg Ala Thr
1               5

<210> SEQ ID NO 163
<211> LENGTH: 7
<212> TYPE: PRT
<213> ORGANISM: Artificial Sequence
<220> FEATURE:
<223> OTHER INFORMATION: Synthetic: 1557-B03, CDR-L2

<400> SEQUENCE: 163

Gly Ala Ser Ser Arg Ala Thr
1               5

<210> SEQ ID NO 164
<211> LENGTH: 7
<212> TYPE: PRT
<213> ORGANISM: Artificial Sequence
<220> FEATURE:
<223> OTHER INFORMATION: Synthetic: 1557-B10, CDR-L2

<400> SEQUENCE: 164

Gly Ala Ser Ser Arg Ala Thr
1               5

<210> SEQ ID NO 165
<211> LENGTH: 7
<212> TYPE: PRT
<213> ORGANISM: Artificial Sequence
<220> FEATURE:
<223> OTHER INFORMATION: Synthetic: 1557-C06, CDR-L2

<400> SEQUENCE: 165

Gly Ala Ser Ser Arg Ala Thr
1               5
```

<210> SEQ ID NO 166
<211> LENGTH: 7
<212> TYPE: PRT
<213> ORGANISM: Artificial Sequence
<220> FEATURE:
<223> OTHER INFORMATION: Synthetic: 1557-E07, CDR-L2

<400> SEQUENCE: 166

Gly Ala Ser Ser Arg Ala Thr
1               5

<210> SEQ ID NO 167
<211> LENGTH: 7
<212> TYPE: PRT
<213> ORGANISM: Artificial Sequence
<220> FEATURE:
<223> OTHER INFORMATION: Synthetic: 1557-E08, CDR-L2

<400> SEQUENCE: 167

Gly Ala Ser Ser Arg Ala Thr
1               5

<210> SEQ ID NO 168
<211> LENGTH: 7
<212> TYPE: PRT
<213> ORGANISM: Artificial Sequence
<220> FEATURE:
<223> OTHER INFORMATION: Synthetic: 1557-E11, CDR-L2

<400> SEQUENCE: 168

Gly Ala Ser Ser Arg Ala Thr
1               5

<210> SEQ ID NO 169
<211> LENGTH: 7
<212> TYPE: PRT
<213> ORGANISM: Artificial Sequence
<220> FEATURE:
<223> OTHER INFORMATION: Synthetic: 1557-F01, CDR-L2

<400> SEQUENCE: 169

Gly Ala Ser Ser Arg Ala Thr
1               5

<210> SEQ ID NO 170
<211> LENGTH: 7
<212> TYPE: PRT
<213> ORGANISM: Artificial Sequence
<220> FEATURE:
<223> OTHER INFORMATION: Synthetic: 1557-F02, CDR-L2

<400> SEQUENCE: 170

Gly Ala Ser Ser Arg Ala Thr
1               5

<210> SEQ ID NO 171
<211> LENGTH: 7
<212> TYPE: PRT
<213> ORGANISM: Artificial Sequence
<220> FEATURE:
<223> OTHER INFORMATION: Synthetic: 1557-F03, CDR-L2

<400> SEQUENCE: 171

Gly Ala Ser Ser Arg Ala Thr
1               5

<210> SEQ ID NO 172
<211> LENGTH: 7
<212> TYPE: PRT
<213> ORGANISM: Artificial Sequence
<220> FEATURE:
<223> OTHER INFORMATION: Synthetic: 1557-F05, CDR-L2

<400> SEQUENCE: 172

Gly Ala Ser Ser Arg Ala Thr
1               5

<210> SEQ ID NO 173
<211> LENGTH: 7
<212> TYPE: PRT
<213> ORGANISM: Artificial Sequence
<220> FEATURE:
<223> OTHER INFORMATION: Synthetic: 1557-G01, CDR-L2

<400> SEQUENCE: 173

Gly Ala Ser Ser Arg Ala Thr
1               5

<210> SEQ ID NO 174
<211> LENGTH: 7
<212> TYPE: PRT
<213> ORGANISM: Artificial Sequence
<220> FEATURE:
<223> OTHER INFORMATION: Synthetic: 1557-G03, CDR-L2

<400> SEQUENCE: 174

Gly Ala Ser Ser Arg Ala Thr
1               5

<210> SEQ ID NO 175
<211> LENGTH: 7
<212> TYPE: PRT
<213> ORGANISM: Artificial Sequence
<220> FEATURE:
<223> OTHER INFORMATION: Synthetic: 1557-G04, CDR-L2

<400> SEQUENCE: 175

Gly Ala Ser Ser Arg Ala Thr
1               5

<210> SEQ ID NO 176
<211> LENGTH: 7
<212> TYPE: PRT
<213> ORGANISM: Artificial Sequence
<220> FEATURE:
<223> OTHER INFORMATION: Synthetic: 1557-G06, CDR-L2

<400> SEQUENCE: 176

Gly Ala Ser Ser Arg Ala Thr
1               5

<210> SEQ ID NO 177
<211> LENGTH: 7
<212> TYPE: PRT
<213> ORGANISM: Artificial Sequence
<220> FEATURE:
<223> OTHER INFORMATION: Synthetic: 1557-H04, CDR-L2

<400> SEQUENCE: 177

Gly Ala Ser Ser Arg Ala Thr
1               5

<210> SEQ ID NO 178

```
<211> LENGTH: 7
<212> TYPE: PRT
<213> ORGANISM: Artificial Sequence
<220> FEATURE:
<223> OTHER INFORMATION: Synthetic: 1557-H10, CDR-L2

<400> SEQUENCE: 178

Gly Ala Ser Ser Arg Ala Thr
1               5

<210> SEQ ID NO 179
<211> LENGTH: 9
<212> TYPE: PRT
<213> ORGANISM: Artificial Sequence
<220> FEATURE:
<223> OTHER INFORMATION: Synthetic: 1304-G11, CDR-L3

<400> SEQUENCE: 179

Gln Gln Tyr Trp Tyr Gly Pro Pro Thr
1               5

<210> SEQ ID NO 180
<211> LENGTH: 9
<212> TYPE: PRT
<213> ORGANISM: Artificial Sequence
<220> FEATURE:
<223> OTHER INFORMATION: Synthetic: 1332-A05, CDR-L3

<400> SEQUENCE: 180

Gln Asn Asp Leu Ser Tyr Pro Leu Thr
1               5

<210> SEQ ID NO 181
<211> LENGTH: 9
<212> TYPE: PRT
<213> ORGANISM: Artificial Sequence
<220> FEATURE:
<223> OTHER INFORMATION: Synthetic: 1332-C01, CDR-L3

<400> SEQUENCE: 181

Gln Asn Asp Tyr Arg Tyr Pro Leu Thr
1               5

<210> SEQ ID NO 182
<211> LENGTH: 9
<212> TYPE: PRT
<213> ORGANISM: Artificial Sequence
<220> FEATURE:
<223> OTHER INFORMATION: Synthetic: 1332-F11, CDR-L3

<400> SEQUENCE: 182

Gln Asn Asp Ser Ser Tyr Pro Leu Thr
1               5

<210> SEQ ID NO 183
<211> LENGTH: 9
<212> TYPE: PRT
<213> ORGANISM: Artificial Sequence
<220> FEATURE:
<223> OTHER INFORMATION: Synthetic: 1464-A02, CDR-L3

<400> SEQUENCE: 183

Gln Gln Thr Ser Glu Ala Pro Pro Thr
1               5

<210> SEQ ID NO 184
<211> LENGTH: 9
```

```
<212> TYPE: PRT
<213> ORGANISM: Artificial Sequence
<220> FEATURE:
<223> OTHER INFORMATION: Synthetic: 1464-A08, CDR-L3

<400> SEQUENCE: 184

Gln Gln Asn Gln Ala Ala Pro Ala Thr
1               5

<210> SEQ ID NO 185
<211> LENGTH: 9
<212> TYPE: PRT
<213> ORGANISM: Artificial Sequence
<220> FEATURE:
<223> OTHER INFORMATION: Synthetic: 1464-B04, CDR-L3

<400> SEQUENCE: 185

Gln Gln Leu Val Thr Ser Pro Pro Thr
1               5

<210> SEQ ID NO 186
<211> LENGTH: 9
<212> TYPE: PRT
<213> ORGANISM: Artificial Sequence
<220> FEATURE:
<223> OTHER INFORMATION: Synthetic: 1557-A04, CDR-L3

<400> SEQUENCE: 186

Gln Gln Leu Val Thr Asn Pro Pro Thr
1               5

<210> SEQ ID NO 187
<211> LENGTH: 9
<212> TYPE: PRT
<213> ORGANISM: Artificial Sequence
<220> FEATURE:
<223> OTHER INFORMATION: Synthetic: 1557-A05, CDR-L3

<400> SEQUENCE: 187

Gln Gln Leu Leu Thr Ser Pro Pro Thr
1               5

<210> SEQ ID NO 188
<211> LENGTH: 9
<212> TYPE: PRT
<213> ORGANISM: Artificial Sequence
<220> FEATURE:
<223> OTHER INFORMATION: Synthetic: 1557-B03, CDR-L3

<400> SEQUENCE: 188

Gln Gln Leu Gln Thr Ser Pro Pro Thr
1               5

<210> SEQ ID NO 189
<211> LENGTH: 9
<212> TYPE: PRT
<213> ORGANISM: Artificial Sequence
<220> FEATURE:
<223> OTHER INFORMATION: Synthetic: 1557-B10, CDR-L3

<400> SEQUENCE: 189

Gln Gln Val Met Thr Ile Pro Pro Thr
1               5

<210> SEQ ID NO 190
<211> LENGTH: 9
<212> TYPE: PRT
```

```
<213> ORGANISM: Artificial Sequence
<220> FEATURE:
<223> OTHER INFORMATION: Synthetic: 1557-C06, CDR-L3

<400> SEQUENCE: 190

Gln Gln His Val Thr Ser Pro Pro Thr
1               5

<210> SEQ ID NO 191
<211> LENGTH: 9
<212> TYPE: PRT
<213> ORGANISM: Artificial Sequence
<220> FEATURE:
<223> OTHER INFORMATION: Synthetic: 1557-E07, CDR-L3

<400> SEQUENCE: 191

Gln Gln Arg Ala Ala Pro Pro Pro Thr
1               5

<210> SEQ ID NO 192
<211> LENGTH: 9
<212> TYPE: PRT
<213> ORGANISM: Artificial Sequence
<220> FEATURE:
<223> OTHER INFORMATION: Synthetic: 1557-E08, CDR-L3

<400> SEQUENCE: 192

Gln Gln Leu Val Pro Ser Pro Pro Thr
1               5

<210> SEQ ID NO 193
<211> LENGTH: 9
<212> TYPE: PRT
<213> ORGANISM: Artificial Sequence
<220> FEATURE:
<223> OTHER INFORMATION: Synthetic: 1557-E11, CDR-L3

<400> SEQUENCE: 193

Gln Gln Leu Val Pro Ser Pro Pro Thr
1               5

<210> SEQ ID NO 194
<211> LENGTH: 9
<212> TYPE: PRT
<213> ORGANISM: Artificial Sequence
<220> FEATURE:
<223> OTHER INFORMATION: Synthetic: 1557-F01, CDR-L3

<400> SEQUENCE: 194

Gln Gln Leu Glu Thr Ile Pro Pro Thr
1               5

<210> SEQ ID NO 195
<211> LENGTH: 9
<212> TYPE: PRT
<213> ORGANISM: Artificial Sequence
<220> FEATURE:
<223> OTHER INFORMATION: Synthetic: 1557-F02, CDR-L3

<400> SEQUENCE: 195

Gln Gln Leu Phe Asn Ser Pro Pro Thr
1               5

<210> SEQ ID NO 196
<211> LENGTH: 9
<212> TYPE: PRT
<213> ORGANISM: Artificial Sequence
```

```
<220> FEATURE:
<223> OTHER INFORMATION: Synthetic: 1557-F03, CDR-L3

<400> SEQUENCE: 196

Gln Gln Leu Val Ser Lys Pro Pro Thr
1               5

<210> SEQ ID NO 197
<211> LENGTH: 9
<212> TYPE: PRT
<213> ORGANISM: Artificial Sequence
<220> FEATURE:
<223> OTHER INFORMATION: Synthetic: 1557-F05, CDR-L3

<400> SEQUENCE: 197

Gln Gln Leu Val Thr Asn Pro Pro Thr
1               5

<210> SEQ ID NO 198
<211> LENGTH: 9
<212> TYPE: PRT
<213> ORGANISM: Artificial Sequence
<220> FEATURE:
<223> OTHER INFORMATION: Synthetic: 1557-G01, CDR-L3

<400> SEQUENCE: 198

Gln Gln Leu Val Thr Ser Pro Pro Thr
1               5

<210> SEQ ID NO 199
<211> LENGTH: 9
<212> TYPE: PRT
<213> ORGANISM: Artificial Sequence
<220> FEATURE:
<223> OTHER INFORMATION: Synthetic: 1557-G03, CDR-L3

<400> SEQUENCE: 199

Gln Gln Leu Leu Ser Ser Pro Pro Thr
1               5

<210> SEQ ID NO 200
<211> LENGTH: 9
<212> TYPE: PRT
<213> ORGANISM: Artificial Sequence
<220> FEATURE:
<223> OTHER INFORMATION: Synthetic: 1557-G04, CDR-L3

<400> SEQUENCE: 200

Gln Gln Asp Ser Phe Val Pro Pro Thr
1               5

<210> SEQ ID NO 201
<211> LENGTH: 9
<212> TYPE: PRT
<213> ORGANISM: Artificial Sequence
<220> FEATURE:
<223> OTHER INFORMATION: Synthetic: 1557-G06, CDR-L3

<400> SEQUENCE: 201

Gln Gln Leu Ala Thr Ser Pro Pro Thr
1               5

<210> SEQ ID NO 202
<211> LENGTH: 9
<212> TYPE: PRT
<213> ORGANISM: Artificial Sequence
<220> FEATURE:
```

<223> OTHER INFORMATION: Synthetic: 1557-H04, CDR-L3

<400> SEQUENCE: 202

Gln Gln Leu Val Thr Arg Pro Pro Thr
1               5

<210> SEQ ID NO 203
<211> LENGTH: 9
<212> TYPE: PRT
<213> ORGANISM: Artificial Sequence
<220> FEATURE:
<223> OTHER INFORMATION: Synthetic: 1557-H10, CDR-L3

<400> SEQUENCE: 203

Gln Gln Leu Val Thr Ala Pro Pro Thr
1               5

<210> SEQ ID NO 204
<211> LENGTH: 492
<212> TYPE: PRT
<213> ORGANISM: Artificial Sequence
<220> FEATURE:
<223> OTHER INFORMATION: Synthetic: 1304-G11, scFv-Fc

<400> SEQUENCE: 204

Met Glu Val Gln Leu Leu Glu Ser Gly Gly Gly Leu Val Arg Pro Gly
1               5                   10                  15

Gly Ser Leu Arg Leu Ser Cys Ala Ala Ser Gly Phe Thr Phe Ser Gly
            20                  25                  30

Ser Ser Met Ser Trp Val Arg Gln Ala Pro Gly Lys Gly Leu Glu Trp
        35                  40                  45

Val Gly Ala Ile Asp Gly Gly Asp Gly Tyr Thr Asn Tyr Ala Asp Ser
    50                  55                  60

Val Arg Gly Arg Phe Thr Ile Ser Arg Asp Asn Ser Lys Asn Thr Leu
65                  70                  75                  80

Tyr Leu Gln Met Asn Ser Leu Arg Ala Glu Asp Thr Ala Val Tyr Tyr
                85                  90                  95

Cys Ala Lys Gly Trp His Pro Gln Thr Tyr Tyr Gly Leu Asp Tyr Trp
            100                 105                 110

Gly Gln Gly Thr Leu Val Thr Val Ser Ser Gly Gly Gly Gly Ser Gly
        115                 120                 125

Gly Gly Gly Ser Gly Gly Gly Gly Ser Glu Ile Val Leu Thr Gln Ser
    130                 135                 140

Pro Gly Thr Leu Ser Leu Ser Pro Gly Glu Arg Ala Thr Leu Ser Cys
145                 150                 155                 160

Arg Ala Ser Gln Ser Val Ser Ser Ser Tyr Leu Ala Trp Tyr Gln Gln
                165                 170                 175

Lys Pro Gly Gln Ala Pro Arg Leu Leu Ile Tyr Gly Ala Ser Ser Arg
            180                 185                 190

Ala Thr Gly Ile Pro Asp Arg Phe Ser Gly Ser Ser Gly Thr Asp
        195                 200                 205

Phe Thr Leu Thr Ile Ser Arg Leu Glu Pro Glu Asp Phe Ala Val Tyr
    210                 215                 220

Tyr Cys Gln Gln Tyr Trp Tyr Gly Pro Pro Thr Phe Gly Gln Gly Thr
225                 230                 235                 240

Lys Val Glu Ile Lys Ala Ala Gly Ser Asp Gln Glu Pro Lys Ser Ser
                245                 250                 255

Asp Lys Thr His Thr Cys Pro Pro Cys Ser Ala Pro Glu Leu Leu Gly

```
            260                 265                 270
Gly Ser Ser Val Phe Leu Phe Pro Pro Lys Pro Lys Asp Thr Leu Met
            275                 280                 285

Ile Ser Arg Thr Pro Glu Val Thr Cys Val Val Val Asp Val Ser His
        290                 295                 300

Glu Asp Pro Glu Val Lys Phe Asn Trp Tyr Val Asp Gly Val Glu Val
305                 310                 315                 320

His Asn Ala Lys Thr Lys Pro Arg Glu Glu Gln Tyr Asn Ser Thr Tyr
                325                 330                 335

Arg Val Val Ser Val Leu Thr Val Leu His Gln Asp Trp Leu Asn Gly
            340                 345                 350

Lys Glu Tyr Lys Cys Lys Val Ser Asn Lys Ala Leu Pro Ala Pro Ile
        355                 360                 365

Glu Lys Thr Ile Ser Lys Ala Lys Gly Gln Pro Arg Glu Pro Gln Val
    370                 375                 380

Tyr Thr Leu Pro Pro Ser Arg Asp Glu Leu Thr Lys Asn Gln Val Ser
385                 390                 395                 400

Leu Thr Cys Leu Val Lys Gly Phe Tyr Pro Ser Asp Ile Ala Val Glu
                405                 410                 415

Trp Glu Ser Asn Gly Gln Pro Glu Asn Asn Tyr Lys Thr Thr Pro Pro
            420                 425                 430

Val Leu Asp Ser Asp Gly Ser Phe Phe Leu Tyr Ser Lys Leu Thr Val
        435                 440                 445

Asp Lys Ser Arg Trp Gln Gln Gly Asn Val Phe Ser Cys Ser Val Met
    450                 455                 460

His Glu Ala Leu His Asn His Tyr Thr Gln Lys Ser Leu Ser Leu Ser
465                 470                 475                 480

Pro Gly Lys Gly Gly Ser His His His His His His
                485                 490

<210> SEQ ID NO 205
<211> LENGTH: 507
<212> TYPE: PRT
<213> ORGANISM: Artificial Sequence
<220> FEATURE:
<223> OTHER INFORMATION: Synthetic: 1332-A05, scFv-Fc

<400> SEQUENCE: 205

Met Glu Leu Val Met Thr Gln Ser Pro Ser Ser Leu Thr Val Thr Ala
1               5                   10                  15

Gly Glu Lys Val Thr Met Ser Cys Lys Ser Ser Gln Ser Leu Leu Asn
            20                  25                  30

Ser Gly Asn Gln Lys Asn Tyr Leu Thr Trp Tyr Gln Gln Lys Pro Gly
        35                  40                  45

Gln Pro Pro Lys Leu Leu Ile Tyr Trp Ala Ser Thr Arg Glu Ser Gly
    50                  55                  60

Val Pro Asp Arg Phe Thr Gly Ser Gly Ser Gly Thr Asp Phe Thr Leu
65                  70                  75                  80

Thr Ile Ser Ser Val Gln Ala Glu Asp Leu Ala Val Tyr Tyr Cys Gln
                85                  90                  95

Asn Asp Leu Ser Tyr Pro Leu Thr Phe Gly Ala Gly Thr Lys Leu Glu
            100                 105                 110

Ile Lys Gly Gly Gly Gly Ser Gly Gly Gly Ser Gly Gly Gly Gly
        115                 120                 125

Ser Glu Val Gln Leu Leu Glu Gln Ser Gly Ala Glu Leu Val Arg Pro
```

```
            130                 135                 140
Gly Thr Ser Val Lys Ile Ser Cys Lys Ala Ser Asp Tyr Ala Phe Ala
145                 150                 155                 160

Asn Arg Trp Leu Gly Trp Val Lys Gln Arg Pro Gly His Gly Leu Glu
                165                 170                 175

Trp Ile Gly Asp Ile Phe Pro Gly Ser Gly Asn Ile His Tyr Asn Glu
            180                 185                 190

Lys Phe Lys Gly Lys Ala Thr Leu Thr Ala Asp Lys Ser Ser Ser Thr
        195                 200                 205

Ala Tyr Met Gln Leu Ser Ser Leu Thr Phe Glu Asp Ser Ala Val Tyr
    210                 215                 220

Phe Cys Ala Arg Leu Arg Asn Trp Glu Gly Pro Met Asp Tyr Trp Gly
225                 230                 235                 240

Gln Gly Thr Thr Val Thr Val Ser Ser Ala Ala Gly Ser Asp Gln Glu
                245                 250                 255

Pro Lys Ser Ser Asp Lys Thr His Thr Cys Pro Pro Cys Ser Ala Pro
            260                 265                 270

Glu Leu Leu Gly Gly Ser Ser Val Phe Leu Phe Pro Pro Lys Pro Lys
        275                 280                 285

Asp Thr Leu Met Ile Ser Arg Thr Pro Glu Val Thr Cys Val Val Val
    290                 295                 300

Asp Val Ser His Glu Asp Pro Glu Val Lys Phe Asn Trp Tyr Val Asp
305                 310                 315                 320

Gly Val Glu Val His Asn Ala Lys Thr Lys Pro Arg Glu Glu Gln Tyr
                325                 330                 335

Asn Ser Thr Tyr Arg Val Val Ser Val Leu Thr Val Leu His Gln Asp
            340                 345                 350

Trp Leu Asn Gly Lys Glu Tyr Lys Cys Lys Val Ser Asn Lys Ala Leu
        355                 360                 365

Pro Ala Pro Ile Glu Lys Thr Ile Ser Lys Ala Lys Gly Gln Pro Arg
    370                 375                 380

Glu Pro Gln Val Tyr Thr Leu Pro Pro Ser Arg Asp Glu Leu Thr Lys
385                 390                 395                 400

Asn Gln Val Ser Leu Thr Cys Leu Val Lys Gly Phe Tyr Pro Ser Asp
                405                 410                 415

Ile Ala Val Glu Trp Glu Ser Asn Gly Gln Pro Glu Asn Asn Tyr Lys
            420                 425                 430

Thr Thr Pro Pro Val Leu Asp Ser Asp Gly Ser Phe Phe Leu Tyr Ser
        435                 440                 445

Lys Leu Thr Val Asp Lys Ser Arg Trp Gln Gln Gly Asn Val Phe Ser
    450                 455                 460

Cys Ser Val Met His Glu Ala Leu His Asn His Tyr Thr Gln Lys Ser
465                 470                 475                 480

Leu Ser Leu Ser Pro Gly Lys Gly Ser Gly Asp Tyr Lys Asp Asp Asp
                485                 490                 495

Asp Lys Gly Ser Gly His His His His His His
            500                 505

<210> SEQ ID NO 206
<211> LENGTH: 507
<212> TYPE: PRT
<213> ORGANISM: Artificial Sequence
<220> FEATURE:
<223> OTHER INFORMATION: Synthetic: 1332-C01, scFv-Fc
```

```
<400> SEQUENCE: 206

Met Glu Leu Val Met Thr Gln Ser Pro Ser Leu Thr Val Thr Ala
1               5                   10                  15

Gly Glu Lys Val Thr Met Ser Cys Lys Ser Ser Gln Ser Leu Leu Asn
            20                  25                  30

Ser Gly Asn Gln Lys Asn Tyr Leu Thr Trp Tyr Gln Lys Pro Gly
        35                  40                  45

Gln Pro Pro Lys Leu Leu Ile Tyr Trp Ala Ser Thr Arg Glu Ser Gly
    50                  55                  60

Val Pro Asp Arg Phe Thr Gly Ser Gly Ser Gly Thr Asp Phe Thr Leu
65                  70                  75                  80

Thr Ile Ser Ser Val Gln Ala Glu Asp Leu Ala Val Tyr Tyr Cys Gln
                85                  90                  95

Asn Asp Tyr Arg Tyr Pro Leu Thr Phe Gly Ala Gly Thr Lys Leu Glu
            100                 105                 110

Ile Lys Gly Gly Gly Gly Ser Gly Gly Gly Gly Ser Gly Gly Gly Gly
        115                 120                 125

Ser Glu Val Gln Leu Leu Glu Gln Ser Gly Ala Glu Leu Val Arg Pro
130                 135                 140

Gly Thr Ser Val Lys Ile Ser Cys Lys Ala Ser Gly Tyr Ala Phe Thr
145                 150                 155                 160

Asn Ser Trp Leu Gly Trp Val Lys Gln Arg Pro Gly His Gly Leu Glu
                165                 170                 175

Trp Ile Gly Asp Ile Phe Pro Gly Ser Gly Asn Ile His Tyr Asn Glu
            180                 185                 190

Lys Phe Lys Gly Lys Ala Thr Leu Thr Ala Asp Lys Ser Ser Ser Thr
        195                 200                 205

Ala Tyr Met Gln Leu Ser Ser Leu Thr Phe Glu Asp Ser Ala Val Tyr
    210                 215                 220

Phe Cys Ala Arg Leu Arg Asn Trp Asp Met Pro Met Asp Tyr Trp Gly
225                 230                 235                 240

Gln Gly Thr Thr Val Thr Val Ser Ser Ala Ala Gly Ser Asp Gln Glu
                245                 250                 255

Pro Lys Ser Ser Asp Lys Thr His Thr Cys Pro Pro Cys Ser Ala Pro
            260                 265                 270

Glu Leu Leu Gly Gly Ser Ser Val Phe Leu Phe Pro Pro Lys Pro Lys
        275                 280                 285

Asp Thr Leu Met Ile Ser Arg Thr Pro Glu Val Thr Cys Val Val Val
    290                 295                 300

Asp Val Ser His Glu Asp Pro Glu Val Lys Phe Asn Trp Tyr Val Asp
305                 310                 315                 320

Gly Val Glu Val His Asn Ala Lys Thr Lys Pro Arg Glu Glu Gln Tyr
                325                 330                 335

Asn Ser Thr Tyr Arg Val Val Ser Val Leu Thr Val Leu His Gln Asp
            340                 345                 350

Trp Leu Asn Gly Lys Glu Tyr Lys Cys Lys Val Ser Asn Lys Ala Leu
        355                 360                 365

Pro Ala Pro Ile Glu Lys Thr Ile Ser Lys Ala Lys Gly Gln Pro Arg
    370                 375                 380

Glu Pro Gln Val Tyr Thr Leu Pro Pro Ser Arg Asp Glu Leu Thr Lys
385                 390                 395                 400

Asn Gln Val Ser Leu Thr Cys Leu Val Lys Gly Phe Tyr Pro Ser Asp
                405                 410                 415
```

```
Ile Ala Val Glu Trp Glu Ser Asn Gly Gln Pro Glu Asn Asn Tyr Lys
            420                 425                 430

Thr Thr Pro Pro Val Leu Asp Ser Asp Gly Ser Phe Phe Leu Tyr Ser
            435                 440                 445

Lys Leu Thr Val Asp Lys Ser Arg Trp Gln Gln Gly Asn Val Phe Ser
            450                 455                 460

Cys Ser Val Met His Glu Ala Leu His Asn His Tyr Thr Gln Lys Ser
465                 470                 475                 480

Leu Ser Leu Ser Pro Gly Lys Gly Ser Gly Asp Tyr Lys Asp Asp Asp
                485                 490                 495

Asp Lys Gly Ser Gly His His His His His
            500                 505

<210> SEQ ID NO 207
<211> LENGTH: 507
<212> TYPE: PRT
<213> ORGANISM: Artificial Sequence
<220> FEATURE:
<223> OTHER INFORMATION: Synthetic: 1332-F11, scFv-Fc

<400> SEQUENCE: 207

Met Glu Leu Val Met Thr Gln Ser Pro Ser Ser Leu Thr Val Thr Ala
1               5                   10                  15

Gly Glu Lys Val Thr Met Ser Cys Lys Ser Ser Gln Ser Leu Leu Asn
            20                  25                  30

Ser Gly Asn Gln Lys Asn Tyr Leu Thr Trp Tyr Gln Gln Lys Pro Gly
        35                  40                  45

Gln Pro Pro Lys Leu Leu Ile Tyr Arg Ala Ser Thr Arg Glu Ser Gly
    50                  55                  60

Val Pro Asp Arg Phe Thr Gly Ser Gly Ser Gly Thr Asp Phe Thr Leu
65                  70                  75                  80

Thr Ile Ser Ser Val Gln Ala Glu Asp Leu Ala Val Tyr Tyr Cys Gln
                85                  90                  95

Asn Asp Ser Ser Tyr Pro Leu Thr Phe Gly Ala Gly Thr Lys Leu Glu
            100                 105                 110

Ile Lys Gly Gly Gly Gly Ser Gly Gly Gly Ser Gly Gly Gly Gly
        115                 120                 125

Ser Glu Val Gln Leu Leu Glu Gln Ser Gly Ala Glu Leu Val Arg Pro
    130                 135                 140

Gly Thr Ser Val Lys Ile Ser Cys Lys Ala Ser Gly Tyr Ala Phe Ala
145                 150                 155                 160

Asn Arg Trp Leu Gly Trp Val Lys Gln Arg Pro Gly His Gly Leu Glu
                165                 170                 175

Trp Ile Gly Asp Ile Phe Pro Gly Ser Gly Asn Ile His Tyr Asn Glu
            180                 185                 190

Lys Phe Lys Gly Lys Ala Thr Leu Thr Ala Asp Lys Ser Ser Ser Thr
        195                 200                 205

Ala Tyr Met Gln Leu Ser Ser Leu Thr Phe Glu Asp Ser Ala Val Tyr
    210                 215                 220

Phe Cys Ala Arg Leu Arg Asn Trp Glu Gly Pro Met Asp Tyr Trp Gly
225                 230                 235                 240

Gln Gly Thr Thr Val Thr Val Ser Ser Ala Ala Gly Ser Asp Gln Glu
                245                 250                 255

Pro Lys Ser Ser Asp Lys Thr His Thr Cys Pro Pro Cys Ser Ala Pro
            260                 265                 270
```

-continued

Glu Leu Leu Gly Gly Ser Ser Val Phe Leu Phe Pro Pro Lys Pro Lys
            275                 280                 285

Asp Thr Leu Met Ile Ser Arg Thr Pro Glu Val Thr Cys Val Val Val
    290                 295                 300

Asp Val Ser His Glu Asp Pro Glu Val Lys Phe Asn Trp Tyr Val Asp
305                 310                 315                 320

Gly Val Glu Val His Asn Ala Lys Thr Lys Pro Arg Glu Glu Gln Tyr
                325                 330                 335

Asn Ser Thr Tyr Arg Val Val Ser Val Leu Thr Val Leu His Gln Asp
                340                 345                 350

Trp Leu Asn Gly Lys Glu Tyr Lys Cys Lys Val Ser Asn Lys Ala Leu
            355                 360                 365

Pro Ala Pro Ile Glu Lys Thr Ile Ser Lys Ala Lys Gly Gln Pro Arg
        370                 375                 380

Glu Pro Gln Val Tyr Thr Leu Pro Pro Ser Arg Asp Glu Leu Thr Lys
385                 390                 395                 400

Asn Gln Val Ser Leu Thr Cys Leu Val Lys Gly Phe Tyr Pro Ser Asp
                405                 410                 415

Ile Ala Val Glu Trp Glu Ser Asn Gly Gln Pro Glu Asn Asn Tyr Lys
            420                 425                 430

Thr Thr Pro Pro Val Leu Asp Ser Asp Gly Ser Phe Phe Leu Tyr Ser
        435                 440                 445

Lys Leu Thr Val Asp Lys Ser Arg Trp Gln Gln Gly Asn Val Phe Ser
    450                 455                 460

Cys Ser Val Met His Glu Ala Leu His Asn His Tyr Thr Gln Lys Ser
465                 470                 475                 480

Leu Ser Leu Ser Pro Gly Lys Gly Ser Gly Asp Tyr Lys Asp Asp Asp
                485                 490                 495

Asp Lys Gly Ser Gly His His His His His His
            500                 505

<210> SEQ ID NO 208
<211> LENGTH: 503
<212> TYPE: PRT
<213> ORGANISM: Artificial Sequence
<220> FEATURE:
<223> OTHER INFORMATION: Synthetic: 1464-A02, scFv-Fc

<400> SEQUENCE: 208

Met Glu Val Gln Leu Leu Glu Ser Gly Gly Gly Leu Val Gln Pro Gly
1               5                   10                  15

Gly Ser Leu Arg Leu Ser Cys Ala Ala Ser Gly Phe Thr Phe Gly Val
            20                  25                  30

Glu Ser Met Ser Trp Val Arg Gln Ala Pro Gly Lys Gly Leu Glu Trp
        35                  40                  45

Val Gly Ala Ile Asp Gly Asp Gly Tyr Thr Gly Tyr Ala Asp Ser
    50                  55                  60

Val Lys Asp Arg Phe Thr Ile Ser Arg Asp Asn Ser Lys Asn Thr Leu
65                  70                  75                  80

Tyr Leu Gln Met Asn Ser Leu Arg Ala Glu Asp Thr Ala Val Tyr Tyr
                85                  90                  95

Cys Ala Lys Ala Trp His Pro Gln Thr Tyr Tyr Gly Val Asp Tyr Trp
            100                 105                 110

Gly Gln Gly Thr Leu Val Thr Val Ser Ser Gly Gly Gly Gly Ser Gly
        115                 120                 125

Gly Gly Gly Ser Gly Gly Gly Ser Glu Ile Val Leu Thr Gln Ser
            130                 135                 140

Pro Gly Thr Leu Ser Leu Ser Pro Gly Glu Arg Ala Thr Leu Ser Cys
145                 150                 155                 160

Arg Ala Ser Gln Ser Val Ser Ser Tyr Leu Ala Trp Tyr Gln Gln
                165                 170                 175

Lys Pro Gly Gln Ala Pro Arg Leu Leu Ile Tyr Gly Ala Ser Ser Arg
            180                 185                 190

Ala Thr Gly Ile Pro Asp Arg Phe Ser Gly Ser Gly Ser Gly Thr Asp
            195                 200                 205

Phe Thr Leu Thr Ile Ser Arg Leu Glu Pro Glu Asp Phe Ala Val Tyr
210                 215                 220

Tyr Cys Gln Gln Thr Ser Glu Ala Pro Pro Thr Phe Gly Gln Gly Thr
225                 230                 235                 240

Lys Val Glu Ile Lys Ala Ala Gly Ser Asp Gln Glu Pro Lys Ser Ser
                245                 250                 255

Asp Lys Thr His Thr Cys Pro Pro Cys Ser Ala Pro Glu Leu Leu Gly
            260                 265                 270

Gly Ser Ser Val Phe Leu Phe Pro Pro Lys Pro Lys Asp Thr Leu Met
            275                 280                 285

Ile Ser Arg Thr Pro Glu Val Thr Cys Val Val Val Asp Val Ser His
290                 295                 300

Glu Asp Pro Glu Val Lys Phe Asn Trp Tyr Val Asp Gly Val Glu Val
305                 310                 315                 320

His Asn Ala Lys Thr Lys Pro Arg Glu Glu Gln Tyr Asn Ser Thr Tyr
                325                 330                 335

Arg Val Val Ser Val Leu Thr Val Leu His Gln Asp Trp Leu Asn Gly
            340                 345                 350

Lys Glu Tyr Lys Cys Lys Val Ser Asn Lys Ala Leu Pro Ala Pro Ile
            355                 360                 365

Glu Lys Thr Ile Ser Lys Ala Lys Gly Gln Pro Arg Glu Pro Gln Val
370                 375                 380

Tyr Thr Leu Pro Pro Ser Arg Asp Glu Leu Thr Lys Asn Gln Val Ser
385                 390                 395                 400

Leu Thr Cys Leu Val Lys Gly Phe Tyr Pro Ser Asp Ile Ala Val Glu
                405                 410                 415

Trp Glu Ser Asn Gly Gln Pro Glu Asn Asn Tyr Lys Thr Thr Pro Pro
            420                 425                 430

Val Leu Asp Ser Asp Gly Ser Phe Phe Leu Tyr Ser Lys Leu Thr Val
            435                 440                 445

Asp Lys Ser Arg Trp Gln Gln Gly Asn Val Phe Ser Cys Ser Val Met
450                 455                 460

His Glu Ala Leu His Asn His Tyr Thr Gln Lys Ser Leu Ser Leu Ser
465                 470                 475                 480

Pro Gly Lys Gly Ser Gly Asp Tyr Lys Asp Asp Asp Lys Gly Ser
                485                 490                 495

Gly His His His His His His
            500

<210> SEQ ID NO 209
<211> LENGTH: 503
<212> TYPE: PRT
<213> ORGANISM: Artificial Sequence
<220> FEATURE:

<223> OTHER INFORMATION: Synthetic: 1464-A08, scFv-Fc

<400> SEQUENCE: 209

```
Met Glu Val Gln Leu Leu Glu Ser Gly Gly Gly Leu Val Gln Pro Gly
1               5                   10                  15

Gly Ser Leu Arg Leu Ser Cys Ala Ala Ser Gly Phe Thr Phe Ser Gly
            20                  25                  30

Ser Ser Met Ser Trp Val Arg Gln Ala Pro Gly Lys Gly Leu Glu Trp
        35                  40                  45

Val Gly Ala Ile Ala Gly Gly Asp Gly Tyr Thr Gly Tyr Ala Asp Ser
    50                  55                  60

Val Lys Gly Arg Phe Thr Ile Ser Arg Asp Asn Ser Lys Asn Thr Leu
65                  70                  75                  80

Tyr Leu Gln Met Asn Ser Leu Arg Ala Glu Asp Thr Ala Val Tyr Tyr
                85                  90                  95

Cys Ala Lys Gly Trp His Arg Gln Asp Tyr Tyr Gly Gln Asp Tyr Trp
            100                 105                 110

Gly Gln Gly Thr Leu Val Thr Val Ser Ser Gly Gly Gly Ser Gly
        115                 120                 125

Gly Gly Gly Ser Gly Gly Gly Ser Glu Ile Val Leu Thr Gln Ser
    130                 135                 140

Pro Gly Thr Leu Ser Leu Ser Pro Gly Glu Arg Ala Thr Leu Gly Cys
145                 150                 155                 160

Arg Ala Ser Gln Ser Val Ser Ser Ser Tyr Leu Ala Trp Tyr Gln Gln
                165                 170                 175

Lys Pro Gly Gln Ala Pro Arg Leu Leu Ile Tyr Gly Ala Ser Ser Arg
            180                 185                 190

Ala Thr Gly Ile Pro Asp Arg Phe Ser Gly Ser Gly Ser Gly Thr Asp
        195                 200                 205

Phe Thr Leu Thr Ile Ser Arg Leu Glu Pro Glu Asp Phe Ala Val Tyr
    210                 215                 220

Tyr Cys Gln Gln Asn Gln Ala Ala Pro Ala Thr Phe Gly Gln Gly Thr
225                 230                 235                 240

Lys Val Glu Ile Lys Ala Ala Gly Ser Asp Gln Glu Pro Lys Ser Ser
                245                 250                 255

Asp Lys Thr His Thr Cys Pro Pro Cys Ser Ala Pro Glu Leu Leu Gly
            260                 265                 270

Gly Ser Ser Val Phe Leu Phe Pro Pro Lys Pro Lys Asp Thr Leu Met
        275                 280                 285

Ile Ser Arg Thr Pro Glu Val Thr Cys Val Val Val Asp Val Ser His
    290                 295                 300

Glu Asp Pro Glu Val Lys Phe Asn Trp Tyr Val Asp Gly Val Glu Val
305                 310                 315                 320

His Asn Ala Lys Thr Lys Pro Arg Glu Glu Gln Tyr Asn Ser Thr Tyr
                325                 330                 335

Arg Val Val Ser Val Leu Thr Val Leu His Gln Asp Trp Leu Asn Gly
            340                 345                 350

Lys Glu Tyr Lys Cys Lys Val Ser Asn Lys Ala Leu Pro Ala Pro Ile
        355                 360                 365

Glu Lys Thr Ile Ser Lys Ala Lys Gly Gln Pro Arg Glu Pro Gln Val
    370                 375                 380

Tyr Thr Leu Pro Pro Ser Arg Asp Glu Leu Thr Lys Asn Gln Val Ser
385                 390                 395                 400
```

```
Leu Thr Cys Leu Val Lys Gly Phe Tyr Pro Ser Asp Ile Ala Val Glu
                405                 410                 415

Trp Glu Ser Asn Gly Gln Pro Glu Asn Asn Tyr Lys Thr Thr Pro Pro
            420                 425                 430

Val Leu Asp Ser Asp Gly Ser Phe Phe Leu Tyr Ser Lys Leu Thr Val
            435                 440                 445

Asp Lys Ser Arg Trp Gln Gln Gly Asn Val Phe Ser Cys Ser Val Met
        450                 455                 460

His Glu Ala Leu His Asn His Tyr Thr Gln Lys Ser Leu Ser Leu Ser
465                 470                 475                 480

Pro Gly Lys Gly Ser Gly Asp Tyr Lys Asp Asp Asp Asp Lys Gly Ser
            485                 490                 495

Gly His His His His His His
            500

<210> SEQ ID NO 210
<211> LENGTH: 503
<212> TYPE: PRT
<213> ORGANISM: Artificial Sequence
<220> FEATURE:
<223> OTHER INFORMATION: Synthetic: 1464-B04, scFv-Fc

<400> SEQUENCE: 210

Met Glu Val Gln Leu Leu Glu Ser Gly Gly Gly Leu Val Gln Pro Gly
1               5                   10                  15

Gly Ser Leu Arg Leu Ser Cys Ala Ala Ser Gly Phe Thr Phe Ser Gly
            20                  25                  30

Ser Ser Met Ser Trp Val Arg Gln Ala Pro Gly Lys Gly Leu Glu Trp
        35                  40                  45

Val Gly Ala Ile Asp Gly Gly Glu Gly Tyr Thr Ser Tyr Ala Asp Ser
    50                  55                  60

Val Lys Gly Arg Phe Thr Ile Ser Arg Asp Asn Ser Lys Asn Thr Leu
65                  70                  75                  80

Tyr Leu Gln Met Asn Ser Leu Arg Ala Glu Asp Thr Ala Val Tyr Tyr
                85                  90                  95

Cys Ala Lys Gly Trp His Pro Gln Thr Leu Tyr Asp Leu Asp Tyr Trp
            100                 105                 110

Gly Gln Gly Thr Leu Val Thr Val Ser Ser Gly Gly Gly Gly Ser Gly
        115                 120                 125

Gly Gly Gly Ser Gly Gly Gly Ser Glu Ile Val Leu Thr Gln Ser
    130                 135                 140

Pro Gly Thr Leu Ser Leu Ser Pro Gly Glu Arg Ala Thr Leu Ser Cys
145                 150                 155                 160

Arg Ala Ser Gln Ser Val Ser Ser Ser Tyr Leu Ala Trp Tyr Gln Gln
                165                 170                 175

Lys Pro Gly Gln Ala Pro Arg Leu Leu Ile Tyr Gly Ala Ser Ser Arg
            180                 185                 190

Ala Thr Gly Ile Pro Asp Arg Phe Ser Gly Ser Gly Ser Gly Thr Asp
        195                 200                 205

Phe Thr Leu Thr Ile Ser Arg Leu Glu Pro Glu Asp Phe Ala Val Tyr
    210                 215                 220

Tyr Cys Gln Gln Leu Val Thr Ser Pro Pro Thr Phe Gly Gln Gly Thr
225                 230                 235                 240

Lys Val Glu Ile Lys Ala Ala Gly Ser Asp Gln Glu Pro Lys Ser Ser
                245                 250                 255
```

```
Asp Lys Thr His Thr Cys Pro Pro Cys Ser Ala Pro Glu Leu Leu Gly
            260                 265                 270

Gly Ser Ser Val Phe Leu Phe Pro Pro Lys Pro Lys Asp Thr Leu Met
        275                 280                 285

Ile Ser Arg Thr Pro Glu Val Thr Cys Val Val Val Asp Val Ser His
    290                 295                 300

Glu Asp Pro Glu Val Lys Phe Asn Trp Tyr Val Asp Gly Val Glu Val
305                 310                 315                 320

His Asn Ala Lys Thr Lys Pro Arg Glu Glu Gln Tyr Asn Ser Thr Tyr
                325                 330                 335

Arg Val Val Ser Val Leu Thr Val Leu His Gln Asp Trp Leu Asn Gly
            340                 345                 350

Lys Glu Tyr Lys Cys Lys Val Ser Asn Lys Ala Leu Pro Ala Pro Ile
        355                 360                 365

Glu Lys Thr Ile Ser Lys Ala Lys Gly Gln Pro Arg Glu Pro Gln Val
    370                 375                 380

Tyr Thr Leu Pro Pro Ser Arg Asp Glu Leu Thr Lys Asn Gln Val Ser
385                 390                 395                 400

Leu Thr Cys Leu Val Lys Gly Phe Tyr Pro Ser Asp Ile Ala Val Glu
                405                 410                 415

Trp Glu Ser Asn Gly Gln Pro Glu Asn Asn Tyr Lys Thr Thr Pro Pro
            420                 425                 430

Val Leu Asp Ser Asp Gly Ser Phe Phe Leu Tyr Ser Lys Leu Thr Val
        435                 440                 445

Asp Lys Ser Arg Trp Gln Gln Gly Asn Val Phe Ser Cys Ser Val Met
    450                 455                 460

His Glu Ala Leu His Asn His Tyr Thr Gln Lys Ser Leu Ser Leu Ser
465                 470                 475                 480

Pro Gly Lys Gly Ser Gly Asp Tyr Lys Asp Asp Asp Asp Lys Gly Ser
                485                 490                 495

Gly His His His His His His
            500

<210> SEQ ID NO 211
<211> LENGTH: 503
<212> TYPE: PRT
<213> ORGANISM: Artificial Sequence
<220> FEATURE:
<223> OTHER INFORMATION: Synthetic: 1557-A04, scFv-Fc

<400> SEQUENCE: 211

Met Glu Val Gln Leu Leu Glu Ser Gly Gly Gly Leu Val Gln Pro Gly
1               5                   10                  15

Gly Ser Leu Arg Leu Ser Cys Ala Ala Ser Gly Phe Thr Phe Ser Gly
            20                  25                  30

Ser Ser Met Ser Trp Val Arg Gln Ala Pro Gly Lys Gly Leu Glu Trp
        35                  40                  45

Val Gly Ala Ile Asp Gly Glu Gly Ser Thr Ala Tyr Ala Asp Ser
    50                  55                  60

Val Lys Gly Arg Phe Thr Ile Ser Arg Asp Asn Ser Lys Asn Thr Leu
65                  70                  75                  80

Tyr Leu Gln Met Asn Ser Leu Arg Ala Glu Asp Thr Ala Val Tyr Tyr
                85                  90                  95

Cys Ala Lys Gly Trp His Pro Gln Thr Met Tyr Asp Leu Asp Tyr Trp
            100                 105                 110
```

Gly Gln Gly Thr Leu Val Thr Val Ser Ser Gly Gly Gly Ser Gly
            115                 120                 125

Gly Gly Gly Ser Gly Gly Gly Asn Glu Ile Val Leu Thr Gln Ser
130                 135                 140

Pro Gly Thr Leu Ser Leu Ser Pro Gly Glu Arg Ala Thr Leu Ser Cys
145                 150                 155                 160

Arg Ala Ser Gln Asn Val Ser Thr Asn Tyr Leu Ala Trp Tyr Gln Gln
                165                 170                 175

Lys Pro Gly Gln Ala Pro Arg Leu Leu Ile Tyr Gly Ala Ser Ser Arg
            180                 185                 190

Ala Thr Gly Ile Pro Asp Arg Phe Ser Gly Ser Gly Ser Gly Thr Asp
        195                 200                 205

Phe Thr Leu Thr Ile Ser Arg Leu Glu Pro Glu Asp Phe Ala Val Tyr
210                 215                 220

Tyr Cys Gln Gln Leu Val Thr Asn Pro Pro Thr Phe Gly Gln Gly Thr
225                 230                 235                 240

Lys Val Glu Ile Lys Ala Ala Gly Ser Asp Gln Glu Pro Lys Ser Ser
                245                 250                 255

Asp Lys Thr His Thr Cys Pro Pro Cys Ser Ala Pro Glu Leu Leu Gly
            260                 265                 270

Gly Ser Ser Val Phe Leu Phe Pro Pro Lys Pro Lys Asp Thr Leu Met
        275                 280                 285

Ile Ser Arg Thr Pro Glu Val Thr Cys Val Val Val Asp Val Ser His
290                 295                 300

Glu Asp Pro Glu Val Lys Phe Asn Trp Tyr Val Asp Gly Val Glu Val
305                 310                 315                 320

His Asn Ala Lys Thr Lys Pro Arg Glu Glu Gln Tyr Asn Ser Thr Tyr
                325                 330                 335

Arg Val Val Ser Val Leu Thr Val Leu His Gln Asp Trp Leu Asn Gly
            340                 345                 350

Lys Glu Tyr Lys Cys Lys Val Ser Asn Lys Ala Leu Pro Ala Pro Ile
        355                 360                 365

Glu Lys Thr Ile Ser Lys Ala Lys Gly Gln Pro Arg Glu Pro Gln Val
370                 375                 380

Tyr Thr Leu Pro Pro Ser Arg Asp Glu Leu Thr Lys Asn Gln Val Ser
385                 390                 395                 400

Leu Thr Cys Leu Val Lys Gly Phe Tyr Pro Ser Asp Ile Ala Val Glu
                405                 410                 415

Trp Glu Ser Asn Gly Gln Pro Glu Asn Asn Tyr Lys Thr Thr Pro Pro
            420                 425                 430

Val Leu Asp Ser Asp Gly Ser Phe Phe Leu Tyr Ser Lys Leu Thr Val
        435                 440                 445

Asp Lys Ser Arg Trp Gln Gln Gly Asn Val Phe Ser Cys Ser Val Met
450                 455                 460

His Glu Ala Leu His Asn His Tyr Thr Gln Lys Ser Leu Ser Leu Ser
465                 470                 475                 480

Pro Gly Lys Gly Ser Gly Asp Tyr Lys Asp Asp Asp Asp Lys Gly Ser
                485                 490                 495

Gly His His His His His His
            500

<210> SEQ ID NO 212
<211> LENGTH: 503
<212> TYPE: PRT

-continued

<213> ORGANISM: Artificial Sequence
<220> FEATURE:
<223> OTHER INFORMATION: Synthetic: 1557-A05, scFv-Fc

<400> SEQUENCE: 212

Met Glu Val Gln Leu Leu Glu Ser Gly Gly Gly Leu Val Gln Pro Gly
1               5                   10                  15

Gly Ser Leu Arg Leu Ser Cys Ala Ala Ser Gly Phe Thr Phe Gly Gly
            20                  25                  30

Ser Ser Met Ser Trp Val Arg Gln Ala Pro Gly Lys Gly Leu Glu Trp
        35                  40                  45

Val Gly Ala Ile Gly Gly Glu Gly Ser Thr Gly Tyr Ala Asp Ser
    50                  55                  60

Val Lys Gly Arg Phe Thr Ile Ser Arg Asp Asn Ser Lys Asn Thr Leu
65                  70                  75                  80

Tyr Leu Gln Met Asn Ser Leu Arg Ala Glu Asp Thr Ala Val Tyr Tyr
                85                  90                  95

Cys Ala Lys Gly Trp His Asp Gln Ser Leu Tyr Asp Arg Asp Tyr Trp
            100                 105                 110

Gly Gln Gly Thr Leu Val Thr Val Ser Ser Gly Gly Gly Gly Ser Gly
        115                 120                 125

Gly Gly Gly Ser Gly Gly Gly Ser Glu Ile Val Leu Thr Gln Ser
    130                 135                 140

Pro Gly Thr Leu Ser Leu Ser Pro Gly Glu Arg Ala Thr Leu Ser Cys
145                 150                 155                 160

Ser Ala Ser Gln Thr Val Ser Ser Ser Tyr Ile Ala Trp Tyr Gln Gln
                165                 170                 175

Lys Pro Gly Gln Ala Pro Arg Leu Leu Ile Tyr Gly Ala Ser Ser Arg
            180                 185                 190

Ala Thr Gly Ile Pro Asp Arg Phe Gly Gly Ser Gly Ser Gly Thr Asp
        195                 200                 205

Phe Thr Leu Thr Ile Ser Arg Leu Glu Pro Glu Asp Phe Ala Val Tyr
    210                 215                 220

Tyr Cys Gln Gln Leu Leu Thr Ser Pro Pro Thr Phe Gly Gln Gly Thr
225                 230                 235                 240

Lys Val Glu Ile Lys Ala Ala Gly Ser Asp Gln Glu Pro Lys Ser Ser
                245                 250                 255

Asp Lys Thr His Thr Cys Pro Pro Cys Ser Ala Pro Glu Leu Leu Gly
            260                 265                 270

Gly Ser Ser Val Phe Leu Phe Pro Pro Lys Pro Lys Asp Thr Leu Met
        275                 280                 285

Ile Ser Arg Thr Pro Glu Val Thr Cys Val Val Val Asp Val Ser His
    290                 295                 300

Glu Asp Pro Glu Val Lys Phe Asn Trp Tyr Val Asp Gly Val Glu Val
305                 310                 315                 320

His Asn Ala Lys Thr Lys Pro Arg Glu Glu Gln Tyr Asn Ser Thr Tyr
                325                 330                 335

Arg Val Val Ser Val Leu Thr Val Leu His Gln Asp Trp Leu Asn Gly
            340                 345                 350

Lys Glu Tyr Lys Cys Lys Val Ser Asn Lys Ala Leu Pro Ala Pro Ile
        355                 360                 365

Glu Lys Thr Ile Ser Lys Ala Lys Gly Gln Pro Arg Glu Pro Gln Val
    370                 375                 380

Tyr Thr Leu Pro Pro Ser Arg Asp Glu Leu Thr Lys Asn Gln Val Ser

```
385                 390                 395                 400

Leu Thr Cys Leu Val Lys Gly Phe Tyr Pro Ser Asp Ile Ala Val Glu
                405                 410                 415

Trp Glu Ser Asn Gly Gln Pro Glu Asn Asn Tyr Lys Thr Thr Pro Pro
                420                 425                 430

Val Leu Asp Ser Asp Gly Ser Phe Phe Leu Tyr Ser Lys Leu Thr Val
                435                 440                 445

Asp Lys Ser Arg Trp Gln Gln Gly Asn Val Phe Ser Cys Ser Val Met
    450                 455                 460

His Glu Ala Leu His Asn His Tyr Thr Gln Lys Ser Leu Ser Leu Ser
465                 470                 475                 480

Pro Gly Lys Gly Ser Gly Asp Tyr Lys Asp Asp Asp Asp Lys Gly Ser
                485                 490                 495

Gly His His His His His His
                500

<210> SEQ ID NO 213
<211> LENGTH: 503
<212> TYPE: PRT
<213> ORGANISM: Artificial Sequence
<220> FEATURE:
<223> OTHER INFORMATION: Synthetic: 1557-B03, scFv-Fc

<400> SEQUENCE: 213

Met Glu Val Gln Leu Leu Glu Ser Gly Gly Gly Leu Val Gln Pro Gly
1               5                   10                  15

Gly Ser Leu Arg Leu Ser Cys Ala Ala Ser Gly Phe Thr Phe Arg Ser
                20                  25                  30

Ser Ser Met Ser Trp Val Arg Gln Ala Pro Gly Lys Gly Leu Glu Trp
            35                  40                  45

Val Gly Ala Ile Gly Gly His Glu Gly Tyr Thr Gly Tyr Ala Asp Ser
    50                  55                  60

Val Lys Gly Arg Phe Thr Ile Ser Arg Asp Asn Ser Lys Asn Thr Leu
65                  70                  75                  80

Tyr Leu Gln Met Asn Ser Leu Arg Ala Glu Asp Thr Ala Val Tyr Tyr
                85                  90                  95

Cys Ala Lys Gly Trp Asn Pro Gln Thr Leu Tyr His Leu Asp Tyr Trp
                100                 105                 110

Gly Gln Gly Thr Leu Val Thr Val Ser Ser Gly Gly Gly Gly Ser Gly
            115                 120                 125

Gly Gly Gly Ser Gly Gly Gly Ser Glu Ile Val Leu Thr Gln Ser
    130                 135                 140

Pro Gly Thr Leu Ser Leu Ser Pro Gly Glu Arg Ala Thr Leu Ser Cys
145                 150                 155                 160

Arg Ala Ser Gln Lys Cys Ser Ser Ser Met Ala Trp Tyr Gln Gln
                165                 170                 175

Lys Pro Gly Gln Ala Pro Arg Leu Leu Ile Tyr Gly Ala Ser Ser Arg
            180                 185                 190

Ala Thr Gly Ile Pro Asp Arg Phe Ser Gly Ser Gly Ser Gly Thr Asp
                195                 200                 205

Phe Thr Leu Thr Ile Ser Arg Leu Glu Pro Glu Asp Phe Ala Val Tyr
            210                 215                 220

Tyr Cys Gln Gln Leu Gln Thr Ser Pro Pro Thr Phe Gly Gln Gly Thr
225                 230                 235                 240

Lys Val Glu Ile Lys Ala Ala Gly Ser Asp Gln Glu Pro Lys Ser Ser
```

```
            245                 250                 255
Asp Lys Thr His Thr Cys Pro Cys Ser Ala Pro Glu Leu Leu Gly
            260                 265                 270

Gly Ser Ser Val Phe Leu Phe Pro Pro Lys Pro Lys Asp Thr Leu Met
                275                 280                 285

Ile Ser Arg Thr Pro Glu Val Thr Cys Val Val Val Asp Val Ser His
        290                 295                 300

Glu Asp Pro Glu Val Lys Phe Asn Trp Tyr Val Asp Gly Val Glu Val
305                 310                 315                 320

His Asn Ala Lys Thr Lys Pro Arg Glu Glu Gln Tyr Asn Ser Thr Tyr
                325                 330                 335

Arg Val Val Ser Val Leu Thr Val Leu His Gln Asp Trp Leu Asn Gly
            340                 345                 350

Lys Glu Tyr Lys Cys Lys Val Ser Asn Lys Ala Leu Pro Ala Pro Ile
                355                 360                 365

Glu Lys Thr Ile Ser Lys Ala Lys Gly Gln Pro Arg Glu Pro Gln Val
            370                 375                 380

Tyr Thr Leu Pro Pro Ser Arg Asp Glu Leu Thr Lys Asn Gln Val Ser
385                 390                 395                 400

Leu Thr Cys Leu Val Lys Gly Phe Tyr Pro Ser Asp Ile Ala Val Glu
                405                 410                 415

Trp Glu Ser Asn Gly Gln Pro Glu Asn Asn Tyr Lys Thr Thr Pro Pro
            420                 425                 430

Val Leu Asp Ser Asp Gly Ser Phe Phe Leu Tyr Ser Lys Leu Thr Val
                435                 440                 445

Asp Lys Ser Arg Trp Gln Gln Gly Asn Val Phe Ser Cys Ser Val Met
            450                 455                 460

His Glu Ala Leu His Asn His Tyr Thr Gln Lys Ser Leu Ser Leu Ser
465                 470                 475                 480

Pro Gly Lys Gly Ser Gly Asp Tyr Lys Asp Asp Asp Asp Lys Gly Ser
                485                 490                 495

Gly His His His His His His
            500

<210> SEQ ID NO 214
<211> LENGTH: 503
<212> TYPE: PRT
<213> ORGANISM: Artificial Sequence
<220> FEATURE:
<223> OTHER INFORMATION: Synthetic: 1557-B10, scFv-Fc

<400> SEQUENCE: 214

Met Glu Val Gln Leu Leu Glu Ser Gly Gly Gly Leu Val Gln Pro Gly
1               5                   10                  15

Gly Ser Leu Arg Leu Ser Cys Ala Ala Ser Gly Phe Thr Phe Ser Gly
                20                  25                  30

Cys Ser Met Ser Trp Val Arg Gln Ala Pro Gly Lys Gly Leu Glu Trp
            35                  40                  45

Val Gly Ala Ile Ala Gly Gly Glu Gly Asn Thr Gly Tyr Ala Asp Ser
        50                  55                  60

Val Lys Gly Arg Phe Thr Ile Ser Arg Asp Asn Ser Lys Asn Thr Leu
65                  70                  75                  80

Tyr Leu Gln Met Asn Ser Leu Arg Ala Glu Asp Thr Ala Val Tyr Tyr
                85                  90                  95

Cys Ala Lys Gly Trp His Pro Gln Thr Leu Tyr Asp Leu Asp Tyr Trp
```

```
            100                 105                 110
Gly Gln Gly Thr Leu Val Thr Val Ser Ser Gly Gly Gly Ser Gly
            115                 120                 125
Gly Gly Gly Ser Gly Gly Gly Ser Glu Ile Val Leu Thr Gln Ser
            130                 135                 140
Pro Gly Thr Leu Ser Leu Ser Pro Gly Glu Arg Ala Thr Leu Ser Cys
145                 150                 155                 160
Arg Ala Ser Gln Gly Leu Ala Ser Arg Tyr Met Ala Trp Tyr Gln Gln
                    165                 170                 175
Lys Pro Gly Gln Ala Pro Arg Leu Leu Ile Tyr Gly Ala Ser Ser Arg
                    180                 185                 190
Ala Thr Gly Ile Pro Asp Arg Phe Ser Gly Ser Gly Ser Gly Thr Asp
                    195                 200                 205
Phe Thr Leu Thr Ile Ser Arg Leu Glu Pro Glu Asp Phe Ala Val Tyr
                    210                 215                 220
Tyr Cys Gln Gln Val Met Thr Ile Pro Pro Thr Phe Gly Gln Gly Thr
225                 230                 235                 240
Lys Val Glu Ile Lys Ala Ala Gly Ser Asp Gln Glu Pro Lys Ser Ser
                    245                 250                 255
Asp Lys Thr His Thr Cys Pro Pro Cys Ser Ala Pro Glu Leu Leu Gly
                    260                 265                 270
Gly Ser Ser Val Phe Leu Phe Pro Pro Lys Pro Lys Asp Thr Leu Met
                    275                 280                 285
Ile Ser Arg Thr Pro Glu Val Thr Cys Val Val Val Asp Val Ser His
                    290                 295                 300
Glu Asp Pro Glu Val Lys Phe Asn Trp Tyr Val Asp Gly Val Glu Val
305                 310                 315                 320
His Asn Ala Lys Thr Lys Pro Arg Glu Glu Gln Tyr Asn Ser Thr Tyr
                    325                 330                 335
Arg Val Val Ser Val Leu Thr Val Leu His Gln Asp Trp Leu Asn Gly
                    340                 345                 350
Lys Glu Tyr Lys Cys Lys Val Ser Asn Lys Ala Leu Pro Ala Pro Ile
                    355                 360                 365
Glu Lys Thr Ile Ser Lys Ala Lys Gly Gln Pro Arg Glu Pro Gln Val
                    370                 375                 380
Tyr Thr Leu Pro Pro Ser Arg Asp Glu Leu Thr Lys Asn Gln Val Ser
385                 390                 395                 400
Leu Thr Cys Leu Val Lys Gly Phe Tyr Pro Ser Asp Ile Ala Val Glu
                    405                 410                 415
Trp Glu Ser Asn Gly Gln Pro Glu Asn Asn Tyr Lys Thr Thr Pro Pro
                    420                 425                 430
Val Leu Asp Ser Asp Gly Ser Phe Phe Leu Tyr Ser Lys Leu Thr Val
                    435                 440                 445
Asp Lys Ser Arg Trp Gln Gln Gly Asn Val Phe Ser Cys Ser Val Met
                    450                 455                 460
His Glu Ala Leu His Asn His Tyr Thr Gln Lys Ser Leu Ser Leu Ser
465                 470                 475                 480
Pro Gly Lys Gly Ser Gly Asp Tyr Lys Asp Asp Asp Asp Lys Gly Ser
                    485                 490                 495
Gly His His His His His His
            500

<210> SEQ ID NO 215
```

<211> LENGTH: 503
<212> TYPE: PRT
<213> ORGANISM: Artificial Sequence
<220> FEATURE:
<223> OTHER INFORMATION: Synthetic: 1557-C06, scFv-Fc

<400> SEQUENCE: 215

```
Met Glu Val Gln Leu Leu Glu Ser Gly Gly Gly Leu Val Gln Pro Gly
1               5                   10                  15

Gly Ser Leu Arg Leu Ser Cys Ala Ala Ser Gly Phe Thr Phe Arg Gly
            20                  25                  30

Ala Ser Met Ser Trp Val Arg Gln Ala Pro Gly Lys Gly Leu Glu Trp
        35                  40                  45

Val Gly Ala Ile Asp Gly Ser Gln Gly Ser Thr Gly Tyr Ala Asp Ser
    50                  55                  60

Val Lys Gly Arg Phe Thr Ile Ser Arg Asp Asn Ser Lys Asn Thr Leu
65                  70                  75                  80

Tyr Leu Gln Met Asn Ser Leu Arg Ala Glu Asp Thr Ala Val Tyr Tyr
                85                  90                  95

Cys Ala Lys Gly Trp His Pro Gln Thr Met Tyr Asp Leu Asp Tyr Trp
            100                 105                 110

Gly Gln Gly Thr Leu Val Thr Val Ser Ser Gly Gly Cys Gly Ser Gly
        115                 120                 125

Gly Gly Gly Ser Gly Gly Gly Ser Glu Ile Val Leu Thr Gln Ser
    130                 135                 140

Pro Gly Thr Leu Ser Leu Ser Pro Gly Glu Arg Ala Thr Leu Ser Cys
145                 150                 155                 160

Arg Ala Ser Gln Arg Gly Thr Ser Ser Tyr Leu Ala Trp Tyr Gln Gln
                165                 170                 175

Lys Pro Gly Gln Ala Pro Arg Leu Leu Ile Tyr Gly Ala Ser Ser Arg
            180                 185                 190

Ala Thr Gly Ile Pro Asp Arg Phe Ser Gly Ser Gly Ser Gly Thr Asp
        195                 200                 205

Phe Thr Leu Thr Ile Ser Arg Leu Glu Pro Glu Asp Phe Ala Val Tyr
    210                 215                 220

Tyr Cys Gln Gln His Val Thr Ser Pro Pro Thr Phe Gly Gln Gly Thr
225                 230                 235                 240

Lys Val Glu Ile Lys Ala Ala Gly Ser Asp Gln Glu Pro Lys Ser Ser
                245                 250                 255

Asp Lys Thr His Thr Cys Pro Pro Cys Ser Ala Pro Glu Leu Leu Gly
            260                 265                 270

Gly Ser Ser Val Phe Leu Phe Pro Pro Lys Pro Lys Asp Thr Leu Met
        275                 280                 285

Ile Ser Arg Thr Pro Glu Val Thr Cys Val Val Val Asp Val Ser His
    290                 295                 300

Glu Asp Pro Glu Val Lys Phe Asn Trp Tyr Val Asp Gly Val Glu Val
305                 310                 315                 320

His Asn Ala Lys Thr Lys Pro Arg Glu Glu Gln Tyr Asn Ser Thr Tyr
                325                 330                 335

Arg Val Val Ser Val Leu Thr Val Leu His Gln Asp Trp Leu Asn Gly
            340                 345                 350

Lys Glu Tyr Lys Cys Lys Val Ser Asn Lys Ala Leu Pro Ala Pro Ile
        355                 360                 365

Glu Lys Thr Ile Ser Lys Ala Lys Gly Gln Pro Arg Glu Pro Gln Val
    370                 375                 380
```

Tyr Thr Leu Pro Pro Ser Arg Asp Glu Leu Thr Lys Asn Gln Val Ser
385                 390                 395                 400

Leu Thr Cys Leu Val Lys Gly Phe Tyr Pro Ser Asp Ile Ala Val Glu
            405                 410                 415

Trp Glu Ser Asn Gly Gln Pro Glu Asn Asn Tyr Lys Thr Thr Pro Pro
        420                 425                 430

Val Leu Asp Ser Asp Gly Ser Phe Phe Leu Tyr Ser Lys Leu Thr Val
            435                 440                 445

Asp Lys Ser Arg Trp Gln Gln Gly Asn Val Phe Ser Cys Ser Val Met
        450                 455                 460

His Glu Ala Leu His Asn His Tyr Thr Gln Lys Ser Leu Ser Leu Ser
465                 470                 475                 480

Pro Gly Lys Gly Ser Gly Asp Tyr Lys Asp Asp Asp Asp Lys Gly Ser
                485                 490                 495

Gly His His His His His His
            500

<210> SEQ ID NO 216
<211> LENGTH: 503
<212> TYPE: PRT
<213> ORGANISM: Artificial Sequence
<220> FEATURE:
<223> OTHER INFORMATION: Synthetic: 1557-E07, scFv-Fc

<400> SEQUENCE: 216

Met Glu Val Gln Leu Leu Glu Ser Gly Gly Gly Leu Val Gln Pro Gly
1               5                   10                  15

Gly Ser Leu Arg Leu Ser Cys Ala Ala Ser Gly Phe Thr Phe Ser Gly
            20                  25                  30

Ser Ser Met Ser Trp Val Arg Gln Ala Pro Gly Lys Gly Leu Glu Trp
        35                  40                  45

Val Gly Ala Ile Asp Gly Gly Glu Gly Ser Thr Gly Tyr Ala Asp Ser
    50                  55                  60

Val Lys Gly Arg Phe Thr Ile Ser Arg Asp Asn Ser Lys Asn Thr Leu
65                  70                  75                  80

Tyr Leu Gln Met Asn Ser Leu Arg Ala Glu Asp Thr Ala Val Tyr Tyr
                85                  90                  95

Cys Ala Lys Gly Trp His Pro Gln Thr Leu Tyr Asp Leu Asp Tyr Trp
            100                 105                 110

Gly Gln Gly Thr Leu Val Thr Val Ser Ser Gly Gly Gly Gly Ser Gly
        115                 120                 125

Gly Gly Gly Ser Gly Gly Gly Ser Glu Ile Val Leu Thr Gln Ser
    130                 135                 140

Pro Gly Thr Leu Ser Leu Ser Pro Gly Glu Arg Ala Thr Met Ser Cys
145                 150                 155                 160

Arg Ala Ser Gln Val Leu Ser Ser Ser Leu Ala Trp Tyr Gln Gln
                165                 170                 175

Lys Pro Gly Gln Ala Pro Arg Leu Leu Ile Tyr Gly Ala Ser Ser Arg
            180                 185                 190

Ala Thr Gly Ile Pro Asp Arg Phe Ser Gly Ser Gly Ser Gly Thr Asp
        195                 200                 205

Phe Ala Leu Thr Ile Ser Arg Leu Glu Pro Glu Asp Phe Ala Val Tyr
    210                 215                 220

Tyr Cys Gln Gln Arg Ala Ala Pro Pro Thr Phe Gly Gln Gly Thr
225                 230                 235                 240

```
Lys Val Glu Ile Lys Ala Ala Gly Ser Asp Gln Pro Lys Ser Ser
                245                 250                 255

Asp Lys Thr His Thr Cys Pro Pro Cys Ser Ala Pro Glu Leu Leu Gly
                260                 265                 270

Gly Ser Ser Val Phe Leu Phe Pro Pro Lys Pro Lys Asp Thr Leu Met
                275                 280                 285

Ile Ser Arg Thr Pro Glu Val Thr Cys Val Val Val Asp Val Ser His
                290                 295                 300

Glu Asp Pro Glu Val Lys Phe Asn Trp Tyr Val Asp Gly Val Glu Val
305                 310                 315                 320

His Asn Ala Lys Thr Lys Pro Arg Glu Glu Gln Tyr Asn Ser Thr Tyr
                325                 330                 335

Arg Val Val Ser Val Leu Thr Val Leu His Gln Asp Trp Leu Asn Gly
                340                 345                 350

Lys Glu Tyr Lys Cys Lys Val Ser Asn Lys Ala Leu Pro Ala Pro Ile
                355                 360                 365

Glu Lys Thr Ile Ser Lys Ala Lys Gly Gln Pro Arg Glu Pro Gln Val
                370                 375                 380

Tyr Thr Leu Pro Pro Ser Arg Asp Glu Leu Thr Lys Asn Gln Val Ser
385                 390                 395                 400

Leu Thr Cys Leu Val Lys Gly Phe Tyr Pro Ser Asp Ile Ala Val Glu
                405                 410                 415

Trp Glu Ser Asn Gly Gln Pro Glu Asn Asn Tyr Lys Thr Thr Pro Pro
                420                 425                 430

Val Leu Asp Ser Asp Gly Ser Phe Phe Leu Tyr Ser Lys Leu Thr Val
                435                 440                 445

Asp Lys Ser Arg Trp Gln Gln Gly Asn Val Phe Ser Cys Ser Val Met
                450                 455                 460

His Glu Ala Leu His Asn His Tyr Thr Gln Lys Ser Leu Ser Leu Ser
465                 470                 475                 480

Pro Gly Lys Gly Ser Gly Asp Tyr Lys Asp Asp Asp Asp Lys Gly Ser
                485                 490                 495

Gly His His His His His His
                500

<210> SEQ ID NO 217
<211> LENGTH: 503
<212> TYPE: PRT
<213> ORGANISM: Artificial Sequence
<220> FEATURE:
<223> OTHER INFORMATION: Synthetic: 1557-E08, scFv-Fc

<400> SEQUENCE: 217

Met Glu Val Gln Leu Leu Glu Ser Gly Gly Gly Leu Val Gln Pro Gly
1               5                   10                  15

Gly Ser Leu Arg Leu Ser Cys Ala Ala Ser Gly Phe Thr Phe Arg Ala
                20                  25                  30

Ser Ser Met Ser Trp Met Arg Gln Ala Pro Gly Lys Gly Leu Glu Trp
                35                  40                  45

Val Gly Ala Ile Asp Gly Gly Val Gly Ser Thr Gly Tyr Ala Asp Ser
                50                  55                  60

Val Lys Gly Arg Phe Thr Ile Ser Arg Asp Asn Ser Lys Asn Thr Leu
65                  70                  75                  80

Tyr Leu Gln Met Asn Ser Leu Arg Ala Glu Asp Thr Ala Val Tyr Tyr
                85                  90                  95
```

```
Cys Ala Lys Gly Trp His Pro Gln Thr Leu Tyr Asp Leu Asp Tyr Trp
            100                 105                 110

Gly Gln Gly Thr Leu Val Thr Val Ser Ser Gly Gly Gly Gly Ser Gly
            115                 120                 125

Gly Gly Gly Ser Gly Gly Gly Ser Glu Ile Val Leu Thr Gln Ser
            130                 135                 140

Pro Gly Thr Leu Ser Leu Ser Pro Gly Glu Arg Ala Thr Leu Ser Cys
145                 150                 155                 160

Arg Ala Ser Gln Gly Asp Ser Ser Val Leu Ala Trp Tyr Gln Gln
                165                 170                 175

Lys Pro Gly Gln Ala Pro Arg Leu Leu Ile Tyr Gly Ala Ser Ser Arg
            180                 185                 190

Ala Thr Gly Ile Pro Asp Arg Phe Ser Gly Ser Gly Ser Gly Thr Asp
            195                 200                 205

Phe Thr Leu Thr Ile Ser Arg Leu Glu Pro Glu Asp Phe Ala Val Tyr
            210                 215                 220

Tyr Cys Gln Gln Leu Val Pro Ser Pro Pro Thr Phe Gly Gln Gly Thr
225                 230                 235                 240

Lys Val Glu Ile Lys Ala Ala Gly Ser Asp Gln Glu Pro Lys Ser Ser
            245                 250                 255

Asp Lys Thr His Thr Cys Pro Pro Cys Ser Ala Pro Glu Leu Leu Gly
            260                 265                 270

Gly Ser Ser Val Phe Leu Phe Pro Pro Lys Pro Lys Asp Thr Leu Met
            275                 280                 285

Ile Ser Arg Thr Pro Glu Val Thr Cys Val Val Val Asp Val Ser His
            290                 295                 300

Glu Asp Pro Glu Val Lys Phe Asn Trp Tyr Val Asp Gly Val Glu Val
305                 310                 315                 320

His Asn Ala Lys Thr Lys Pro Arg Glu Glu Gln Tyr Asn Ser Thr Tyr
            325                 330                 335

Arg Val Val Ser Val Leu Thr Val Leu His Gln Asp Trp Leu Asn Gly
            340                 345                 350

Lys Glu Tyr Lys Cys Lys Val Ser Asn Lys Ala Leu Pro Ala Pro Ile
            355                 360                 365

Glu Lys Thr Ile Ser Lys Ala Lys Gly Gln Pro Arg Glu Pro Gln Val
            370                 375                 380

Tyr Thr Leu Pro Pro Ser Arg Asp Glu Leu Thr Lys Asn Gln Val Ser
385                 390                 395                 400

Leu Thr Cys Leu Val Lys Gly Phe Tyr Pro Ser Asp Ile Ala Val Glu
                405                 410                 415

Trp Glu Ser Asn Gly Gln Pro Glu Asn Asn Tyr Lys Thr Thr Pro Pro
            420                 425                 430

Val Leu Asp Ser Asp Gly Ser Phe Phe Leu Tyr Ser Lys Leu Thr Val
            435                 440                 445

Asp Lys Ser Arg Trp Gln Gln Gly Asn Val Phe Ser Cys Ser Val Met
            450                 455                 460

His Glu Ala Leu His Asn His Tyr Thr Gln Lys Ser Leu Ser Leu Ser
465                 470                 475                 480

Pro Gly Lys Gly Ser Gly Asp Tyr Lys Asp Asp Asp Lys Gly Ser
                485                 490                 495

Gly His His His His His
            500
```

<210> SEQ ID NO 218
<211> LENGTH: 503
<212> TYPE: PRT
<213> ORGANISM: Artificial Sequence
<220> FEATURE:
<223> OTHER INFORMATION: Synthetic: 1557-E11, scFv-Fc

<400> SEQUENCE: 218

```
Met Glu Val Gln Leu Leu Glu Ser Gly Gly Gly Leu Val Gln Pro Gly
1               5                   10                  15

Gly Ser Leu Arg Leu Ser Cys Ala Ala Ser Gly Phe Thr Phe Arg Gly
            20                  25                  30

Ser Ser Met Ser Trp Val Arg Gln Ala Pro Gly Lys Gly Leu Glu Trp
        35                  40                  45

Val Gly Ala Ile Asp Gly Glu Gly Ser Thr Gly Tyr Ala Asp Ser
    50                  55                  60

Val Lys Gly Arg Phe Thr Ile Asn Arg Asp Asn Ser Lys Asn Thr Leu
65                  70                  75                  80

Tyr Leu Gln Met Asn Ser Leu Arg Ala Glu Asp Thr Ala Val Tyr Tyr
                85                  90                  95

Cys Ala Lys Gly Trp His Pro Gln Ser Leu Tyr Asp Leu Asp Tyr Trp
            100                 105                 110

Gly Gln Gly Thr Leu Val Thr Val Ser Ser Gly Gly Gly Gly Ser Gly
        115                 120                 125

Gly Gly Asp Ser Gly Gly Gly Ser Glu Ile Val Leu Thr Gln Ser
    130                 135                 140

Pro Gly Thr Leu Ser Leu Ser Pro Gly Glu Arg Ala Thr Leu Ser Cys
145                 150                 155                 160

Arg Ala Ser Gln Pro Val Pro Asn Thr Thr Leu Ala Trp Tyr Gln Gln
                165                 170                 175

Lys Pro Gly Gln Ala Pro Arg Leu Leu Ile Tyr Gly Ala Ser Ser Arg
            180                 185                 190

Ala Thr Gly Ile Pro Asp Arg Phe Ser Gly Ser Gly Ser Gly Thr Asp
        195                 200                 205

Phe Thr Leu Thr Ile Ser Arg Leu Glu Pro Glu Asp Phe Ala Ala Tyr
    210                 215                 220

Tyr Cys Gln Gln Leu Val Pro Ser Pro Pro Thr Phe Gly Gln Gly Thr
225                 230                 235                 240

Lys Val Glu Ile Lys Ala Ala Gly Ser Asp Gln Glu Pro Lys Ser Ser
                245                 250                 255

Asp Lys Thr His Thr Cys Pro Pro Cys Ser Ala Pro Glu Leu Leu Gly
            260                 265                 270

Gly Ser Ser Val Phe Leu Phe Pro Pro Lys Pro Lys Asp Thr Leu Met
        275                 280                 285

Ile Ser Arg Thr Pro Glu Val Thr Cys Val Val Val Asp Val Ser His
    290                 295                 300

Glu Asp Pro Glu Val Lys Phe Asn Trp Tyr Val Asp Gly Val Glu Val
305                 310                 315                 320

His Asn Ala Lys Thr Lys Pro Arg Glu Glu Gln Tyr Asn Ser Thr Tyr
                325                 330                 335

Arg Val Val Ser Val Leu Thr Val Leu His Gln Asp Trp Leu Asn Gly
            340                 345                 350

Lys Glu Tyr Lys Cys Lys Val Ser Asn Lys Ala Leu Pro Ala Pro Ile
        355                 360                 365
```

```
Glu Lys Thr Ile Ser Lys Ala Lys Gly Gln Pro Arg Glu Pro Gln Val
    370                 375                 380

Tyr Thr Leu Pro Pro Ser Arg Asp Glu Leu Thr Lys Asn Gln Val Ser
385                 390                 395                 400

Leu Thr Cys Leu Val Lys Gly Phe Tyr Pro Ser Asp Ile Ala Val Glu
            405                 410                 415

Trp Glu Ser Asn Gly Gln Pro Glu Asn Asn Tyr Lys Thr Thr Pro Pro
        420                 425                 430

Val Leu Asp Ser Asp Gly Ser Phe Phe Leu Tyr Ser Lys Leu Thr Val
            435                 440                 445

Asp Lys Ser Arg Trp Gln Gln Gly Asn Val Phe Ser Cys Ser Val Met
450                 455                 460

His Glu Ala Leu His Asn His Tyr Thr Gln Lys Ser Leu Ser Leu Ser
465                 470                 475                 480

Pro Gly Lys Gly Ser Gly Asp Tyr Lys Asp Asp Asp Asp Lys Gly Ser
                485                 490                 495

Gly His His His His His His
            500
```

<210> SEQ ID NO 219
<211> LENGTH: 503
<212> TYPE: PRT
<213> ORGANISM: Artificial Sequence
<220> FEATURE:
<223> OTHER INFORMATION: Synthetic: 1557-F01, scFv-Fc

<400> SEQUENCE: 219

```
Met Glu Val Gln Leu Leu Glu Ser Gly Gly Gly Leu Val Gln Pro Gly
1               5                   10                  15

Gly Ser Leu Arg Leu Ser Cys Ala Ala Ser Gly Phe Thr Phe Ser Gly
            20                  25                  30

Ser Ser Met Ser Trp Val Arg Gln Ala Pro Gly Lys Gly Leu Glu Trp
        35                  40                  45

Val Gly Ala Ile Asp Gly Gly Glu Gly Ser Thr Gly Tyr Ala Asp Ser
    50                  55                  60

Val Lys Gly Arg Phe Thr Ile Ser Arg Asp Asn Ser Lys Asn Thr Leu
65                  70                  75                  80

Tyr Leu Gln Met Asn Ser Leu Arg Ala Glu Asp Thr Ala Val Tyr Tyr
                85                  90                  95

Cys Ala Lys Gly Trp His Pro Gln Thr Leu Tyr Asp Leu Asp Tyr Trp
            100                 105                 110

Gly Gln Gly Thr Leu Val Thr Val Ser Ser Gly Gly Gly Gly Ser Gly
        115                 120                 125

Gly Gly Gly Ser Gly Gly Gly Gly Ser Glu Ile Val Leu Thr Gln Ser
    130                 135                 140

Pro Gly Thr Leu Ser Leu Ser Pro Gly Glu Arg Ala Thr Leu Ser Cys
145                 150                 155                 160

Arg Ala Ser Gln Ser Val Ser Ser Lys Leu Ala Trp Tyr Gln Gln
                165                 170                 175

Lys Pro Gly Gln Ala Pro Arg Leu Leu Ile Tyr Gly Ala Ser Ser Arg
            180                 185                 190

Ala Thr Gly Ile Pro Asp Arg Phe Ser Gly Tyr Gly Ser Gly Thr Asp
        195                 200                 205

Phe Thr Leu Thr Ile Ser Arg Leu Glu Pro Glu Asp Phe Ala Val Tyr
    210                 215                 220
```

```
Tyr Cys Gln Gln Leu Glu Thr Ile Pro Pro Thr Phe Gly Gln Gly Thr
225                 230                 235                 240

Lys Val Glu Ile Lys Ala Ala Gly Ser Asp Gln Glu Pro Lys Ser Ser
            245                 250                 255

Asp Lys Thr His Thr Cys Pro Pro Cys Ser Ala Pro Glu Leu Leu Gly
            260                 265                 270

Gly Ser Ser Val Phe Leu Phe Pro Pro Lys Pro Lys Asp Thr Leu Met
            275                 280                 285

Ile Ser Arg Thr Pro Glu Val Thr Cys Val Val Val Asp Val Ser His
            290                 295                 300

Glu Asp Pro Glu Val Lys Phe Asn Trp Tyr Val Asp Gly Val Glu Val
305                 310                 315                 320

His Asn Ala Lys Thr Lys Pro Arg Glu Glu Gln Tyr Asn Ser Thr Tyr
            325                 330                 335

Arg Val Val Ser Val Leu Thr Val Leu His Gln Asp Trp Leu Asn Gly
            340                 345                 350

Lys Glu Tyr Lys Cys Lys Val Ser Asn Lys Ala Leu Pro Ala Pro Ile
            355                 360                 365

Glu Lys Thr Ile Ser Lys Ala Lys Gly Gln Pro Arg Glu Pro Gln Val
370                 375                 380

Tyr Thr Leu Pro Pro Ser Arg Asp Glu Leu Thr Lys Asn Gln Val Ser
385                 390                 395                 400

Leu Thr Cys Leu Val Lys Gly Phe Tyr Pro Ser Asp Ile Ala Val Glu
            405                 410                 415

Trp Glu Ser Asn Gly Gln Pro Glu Asn Asn Tyr Lys Thr Thr Pro Pro
            420                 425                 430

Val Leu Asp Ser Asp Gly Ser Phe Phe Leu Tyr Ser Lys Leu Thr Val
            435                 440                 445

Asp Lys Ser Arg Trp Gln Gln Gly Asn Val Phe Ser Cys Ser Val Met
            450                 455                 460

His Glu Ala Leu His Asn His Tyr Thr Gln Lys Ser Leu Ser Leu Ser
465                 470                 475                 480

Pro Gly Lys Gly Ser Gly Asp Tyr Lys Asp Asp Asp Asp Lys Gly Ser
            485                 490                 495

Gly His His His His His His
            500

<210> SEQ ID NO 220
<211> LENGTH: 503
<212> TYPE: PRT
<213> ORGANISM: Artificial Sequence
<220> FEATURE:
<223> OTHER INFORMATION: Synthetic: 1557-F02, scFv-Fc

<400> SEQUENCE: 220

Met Glu Val Gln Leu Leu Glu Ser Gly Gly Gly Leu Val Gln Pro Gly
1               5                   10                  15

Gly Ser Leu Arg Leu Ser Cys Ala Ala Ser Gly Phe Thr Phe Arg Gly
            20                  25                  30

Ser Ser Met Ser Trp Val Arg Gln Ala Pro Gly Lys Gly Leu Glu Trp
        35                  40                  45

Val Gly Ala Ile Asp Gly Gly Glu Ser Thr Gly Tyr Ala Asp Ser
    50                  55                  60

Val Lys Gly Arg Phe Thr Ile Ser Arg Asp Asn Ser Lys Asn Thr Leu
65                  70                  75                  80
```

```
Tyr Leu Gln Met Asn Ser Leu Arg Ala Glu Asp Thr Ala Val Tyr Tyr
                 85                  90                  95

Cys Ala Lys Gly Trp His Pro Gln Thr Met Tyr Asn Leu Asp Tyr Trp
            100                 105                 110

Gly Gln Gly Thr Leu Val Thr Val Ser Ser Gly Gly Gly Gly Ser Gly
            115                 120                 125

Gly Gly Gly Ser Gly Gly Gly Ser Glu Ile Val Leu Thr Gln Ser
        130                 135                 140

Pro Gly Thr Leu Ser Leu Ser Pro Gly Glu Arg Ala Thr Leu Ser Cys
145                 150                 155                 160

Arg Ala Ser Gln Ser Val Ser Ser Ser Tyr Leu Ala Trp Tyr Gln Gln
                165                 170                 175

Lys Pro Gly Gln Ala Pro Arg Leu Leu Ile Tyr Gly Ala Ser Ser Arg
            180                 185                 190

Ala Thr Gly Ile Pro Asp Arg Phe Ser Gly Ser Gly Ser Gly Thr Asp
            195                 200                 205

Phe Thr Leu Thr Ile Ser Arg Leu Glu Pro Glu Asp Phe Ala Val Tyr
            210                 215                 220

Tyr Cys Gln Gln Leu Phe Asn Ser Pro Pro Thr Phe Gly Gln Gly Thr
225                 230                 235                 240

Lys Val Glu Ile Lys Ala Ala Gly Ser Asp Gln Glu Pro Lys Ser Ser
                245                 250                 255

Asp Lys Thr His Thr Cys Pro Pro Cys Ser Ala Pro Glu Leu Leu Gly
            260                 265                 270

Gly Ser Ser Val Phe Leu Phe Pro Pro Lys Pro Lys Asp Thr Leu Met
            275                 280                 285

Ile Ser Arg Thr Pro Glu Val Thr Cys Val Val Val Asp Val Ser His
            290                 295                 300

Glu Asp Pro Glu Val Lys Phe Asn Trp Tyr Val Asp Gly Val Glu Val
305                 310                 315                 320

His Asn Ala Lys Thr Lys Pro Arg Glu Glu Gln Tyr Asn Ser Thr Tyr
                325                 330                 335

Arg Val Val Ser Val Leu Thr Val Leu His Gln Asp Trp Leu Asn Gly
            340                 345                 350

Lys Glu Tyr Lys Cys Lys Val Ser Asn Lys Ala Leu Pro Ala Pro Ile
            355                 360                 365

Glu Lys Thr Ile Ser Lys Ala Lys Gly Gln Pro Arg Glu Pro Gln Val
            370                 375                 380

Tyr Thr Leu Pro Pro Ser Arg Asp Glu Leu Thr Lys Asn Gln Val Ser
385                 390                 395                 400

Leu Thr Cys Leu Val Lys Gly Phe Tyr Pro Ser Asp Ile Ala Val Glu
                405                 410                 415

Trp Glu Ser Asn Gly Gln Pro Glu Asn Asn Tyr Lys Thr Thr Pro Pro
            420                 425                 430

Val Leu Asp Ser Asp Gly Ser Phe Phe Leu Tyr Ser Lys Leu Thr Val
            435                 440                 445

Asp Lys Ser Arg Trp Gln Gln Gly Asn Val Phe Ser Cys Ser Val Met
450                 455                 460

His Glu Ala Leu His Asn His Tyr Thr Gln Lys Ser Leu Ser Leu Ser
465                 470                 475                 480

Pro Gly Lys Gly Ser Gly Asp Tyr Lys Asp Asp Asp Lys Gly Ser
                485                 490                 495

Gly His His His His His His
```

-continued

500

<210> SEQ ID NO 221
<211> LENGTH: 503
<212> TYPE: PRT
<213> ORGANISM: Artificial Sequence
<220> FEATURE:
<223> OTHER INFORMATION: Synthetic: 1557-F03, scFv-Fc

<400> SEQUENCE: 221

```
Met Glu Val Gln Leu Leu Glu Ser Gly Gly Gly Leu Val Gln Pro Gly
1               5                   10                  15

Gly Ser Leu Arg Leu Ser Cys Ala Ala Ser Gly Phe Thr Phe Ser Gly
            20                  25                  30

Ser Ser Met Ser Trp Val Arg Gln Ala Pro Gly Lys Gly Leu Glu Trp
        35                  40                  45

Val Gly Ala Ile Ala Gly Gly Gly Ser Thr Gly Tyr Ala Asp Ser
    50                  55                  60

Val Lys Gly Arg Phe Thr Ile Ser Arg Asp Asn Ser Lys Asn Thr Leu
65                  70                  75                  80

Tyr Leu Gln Met Asn Ser Leu Arg Ala Glu Asp Thr Ala Val Tyr Tyr
                85                  90                  95

Cys Ala Lys Gly Trp His Pro Gln Thr Leu Tyr Asp Leu Asp Tyr Trp
            100                 105                 110

Gly Gln Gly Thr Leu Val Thr Val Ser Ser Gly Gly Gly Gly Ser Gly
        115                 120                 125

Gly Gly Gly Ser Gly Gly Gly Ser Glu Ile Val Leu Thr Gln Ser
    130                 135                 140

Pro Gly Thr Leu Ser Leu Ser Pro Gly Glu Arg Ala Thr Leu Ser Cys
145                 150                 155                 160

Arg Ala Ser Gln Ser Val Lys Thr Ser Asp Leu Ala Trp Tyr Gln Gln
                165                 170                 175

Lys Pro Gly Gln Ala Pro Arg Leu Leu Ile Tyr Gly Ala Ser Ser Arg
            180                 185                 190

Ala Thr Gly Ile Pro Asp Arg Phe Ser Gly Ser Gly Ser Gly Thr Asp
        195                 200                 205

Phe Thr Leu Thr Ile Ser Arg Leu Glu Pro Glu Asp Phe Ala Val Tyr
    210                 215                 220

Tyr Cys Gln Gln Leu Val Ser Lys Pro Pro Thr Phe Gly Gln Gly Thr
225                 230                 235                 240

Lys Val Glu Ile Lys Ala Ala Gly Ser Asp Gln Glu Pro Lys Ser Ser
                245                 250                 255

Asp Lys Thr His Thr Cys Pro Pro Cys Ser Ala Pro Glu Leu Leu Gly
            260                 265                 270

Gly Ser Ser Val Phe Leu Phe Pro Pro Lys Pro Lys Asp Thr Leu Met
        275                 280                 285

Ile Ser Arg Thr Pro Glu Val Thr Cys Val Val Val Asp Val Ser His
    290                 295                 300

Glu Asp Pro Glu Val Lys Phe Asn Trp Tyr Val Asp Gly Val Glu Val
305                 310                 315                 320

His Asn Ala Lys Thr Lys Pro Arg Glu Glu Gln Tyr Asn Ser Thr Tyr
                325                 330                 335

Arg Val Val Ser Val Leu Thr Val Leu His Gln Asp Trp Leu Asn Gly
            340                 345                 350

Lys Glu Tyr Lys Cys Lys Val Ser Asn Lys Ala Leu Pro Ala Pro Ile
```

```
                355                 360                 365
Glu Lys Thr Ile Ser Lys Ala Lys Gly Gln Pro Arg Glu Pro Gln Val
        370                 375                 380

Tyr Thr Leu Pro Pro Ser Arg Asp Glu Leu Thr Lys Asn Gln Val Ser
385                 390                 395                 400

Leu Thr Cys Leu Val Lys Gly Phe Tyr Pro Ser Asp Ile Ala Val Glu
                405                 410                 415

Trp Glu Ser Asn Gly Gln Pro Glu Asn Asn Tyr Lys Thr Thr Pro Pro
            420                 425                 430

Val Leu Asp Ser Asp Gly Ser Phe Phe Leu Tyr Ser Lys Leu Thr Val
                435                 440                 445

Asp Lys Ser Arg Trp Gln Gln Gly Asn Val Phe Ser Cys Ser Val Met
        450                 455                 460

His Glu Ala Leu His Asn His Tyr Thr Gln Lys Ser Leu Ser Leu Ser
465                 470                 475                 480

Pro Gly Lys Gly Ser Gly Asp Tyr Lys Asp Asp Asp Asp Lys Gly Ser
                485                 490                 495

Gly His His His His His His
            500

<210> SEQ ID NO 222
<211> LENGTH: 503
<212> TYPE: PRT
<213> ORGANISM: Artificial Sequence
<220> FEATURE:
<223> OTHER INFORMATION: Synthetic: 1557-F05, scFv-Fc

<400> SEQUENCE: 222

Met Glu Val Gln Leu Leu Glu Ser Gly Gly Gly Leu Val Gln Pro Gly
1               5                   10                  15

Gly Ser Leu Arg Leu Ser Cys Ala Ala Ser Gly Phe Thr Phe Arg Gly
            20                  25                  30

Ser Ser Met Ser Trp Val Arg Gln Ala Pro Gly Lys Gly Leu Glu Trp
        35                  40                  45

Val Gly Ala Ile Asp Gly Glu Gly Ser Thr Gly Tyr Ala Asp Ser
50                  55                  60

Val Lys Gly Arg Phe Thr Ile Ser Arg Asp Asn Ser Lys Asn Thr Leu
65                  70                  75                  80

Tyr Leu Gln Met Asn Ser Leu Arg Ala Glu Asp Thr Ala Val Tyr Tyr
                85                  90                  95

Cys Ala Lys Asp Trp His Pro Gln Thr Leu Tyr Asp Leu Asp Tyr Trp
                100                 105                 110

Gly Gln Gly Thr Leu Val Thr Val Ser Ser Gly Gly Gly Gly Ser Gly
            115                 120                 125

Gly Gly Gly Ser Gly Gly Gly Gly Ser Glu Ile Val Leu Thr Gln Ser
        130                 135                 140

Pro Gly Thr Leu Ser Leu Ser Pro Gly Glu Arg Ala Thr Leu Ser Cys
145                 150                 155                 160

Arg Ala Ser Gln Thr Val Ser Pro Ser Val Leu Ala Trp Tyr Gln Gln
                165                 170                 175

Lys Pro Gly Gln Ala Pro Arg Leu Leu Ile Tyr Gly Ala Ser Ser Arg
                180                 185                 190

Ala Thr Gly Ile Pro Gly Arg Phe Ser Gly Ser Gly Ser Gly Thr Asp
            195                 200                 205

Phe Thr Leu Thr Ile Ser Arg Leu Glu Pro Glu Asp Phe Ala Val Tyr
```

```
            210                 215                 220
Tyr Cys Gln Gln Leu Val Thr Asn Pro Pro Thr Phe Gly Gln Gly Thr
225                 230                 235                 240

Lys Val Glu Ile Lys Ala Ala Gly Ser Asp Gln Glu Pro Lys Ser Ser
                245                 250                 255

Asp Lys Thr His Thr Cys Pro Pro Cys Ser Ala Pro Glu Leu Leu Gly
            260                 265                 270

Gly Ser Ser Val Phe Leu Phe Pro Pro Lys Pro Lys Asp Thr Leu Met
        275                 280                 285

Ile Ser Arg Thr Pro Glu Val Thr Cys Val Val Val Asp Val Ser His
    290                 295                 300

Glu Asp Pro Glu Val Lys Phe Asn Trp Tyr Val Asp Gly Val Glu Val
305                 310                 315                 320

His Asn Ala Lys Thr Lys Pro Arg Glu Glu Gln Tyr Asn Ser Thr Tyr
                325                 330                 335

Arg Val Val Ser Val Leu Thr Val Leu His Gln Asp Trp Leu Asn Gly
            340                 345                 350

Lys Glu Tyr Lys Cys Lys Val Ser Asn Lys Ala Leu Pro Ala Pro Ile
        355                 360                 365

Glu Lys Thr Ile Ser Lys Ala Lys Gly Gln Pro Arg Glu Pro Gln Val
    370                 375                 380

Tyr Thr Leu Pro Pro Ser Arg Asp Glu Leu Thr Lys Asn Gln Val Ser
385                 390                 395                 400

Leu Thr Cys Leu Val Lys Gly Phe Tyr Pro Ser Asp Ile Ala Val Glu
                405                 410                 415

Trp Glu Ser Asn Gly Gln Pro Glu Asn Asn Tyr Lys Thr Thr Pro Pro
            420                 425                 430

Val Leu Asp Ser Asp Gly Ser Phe Phe Leu Tyr Ser Lys Leu Thr Val
        435                 440                 445

Asp Lys Ser Arg Trp Gln Gln Gly Asn Val Phe Ser Cys Ser Val Met
    450                 455                 460

His Glu Ala Leu His Asn His Tyr Thr Gln Lys Ser Leu Ser Leu Ser
465                 470                 475                 480

Pro Gly Lys Gly Ser Gly Asp Tyr Lys Asp Asp Asp Lys Gly Ser
                485                 490                 495

Gly His His His His His His
            500

<210> SEQ ID NO 223
<211> LENGTH: 503
<212> TYPE: PRT
<213> ORGANISM: Artificial Sequence
<220> FEATURE:
<223> OTHER INFORMATION: Synthetic: 1557-G01, scFv-Fc

<400> SEQUENCE: 223

Met Glu Val Gln Leu Leu Glu Ser Gly Gly Gly Leu Val Gln Pro Gly
1               5                   10                  15

Gly Ser Leu Arg Leu Ser Cys Ala Ala Ser Gly Phe Thr Phe Ser Val
            20                  25                  30

Thr Ser Met Ser Trp Met Arg Gln Ala Pro Gly Lys Gly Leu Glu Trp
        35                  40                  45

Val Gly Ala Ile Ala Gly Gly Glu Gly Ser Thr Gly Tyr Ala Asp Ser
    50                  55                  60

Val Lys Gly Arg Phe Thr Ile Ser Arg Asp Asn Ser Lys Asn Thr Leu
```

```
            65                  70                  75                  80
Tyr Leu Gln Met Asn Ser Leu Arg Ala Glu Asp Thr Ala Val Tyr Tyr
                    85                  90                  95

Cys Ala Lys Gly Trp His Pro Gln Thr Leu Tyr Asp Leu Asp Tyr Trp
                100                 105                 110

Gly Gln Gly Thr Leu Val Thr Val Ser Ser Gly Gly Gly Gly Ser Gly
                115                 120                 125

Gly Gly Gly Ser Gly Gly Gly Ser Glu Ile Val Leu Thr Gln Ser
            130                 135                 140

Pro Gly Thr Leu Ser Leu Ser Pro Gly Glu Arg Ala Thr Met Ser Cys
145                 150                 155                 160

Arg Ala Ser Gln Val Leu Ser Ser Ser Leu Ala Trp Tyr Gln Gln
                165                 170                 175

Lys Pro Gly Gln Ala Pro Arg Leu Leu Ile Tyr Gly Ala Ser Ser Arg
                180                 185                 190

Ala Thr Gly Ile Pro Asp Arg Phe Ser Gly Ser Gly Ser Gly Thr Asp
                195                 200                 205

Phe Thr Leu Thr Ile Ser Arg Leu Glu Pro Glu Asp Phe Ala Val Tyr
                210                 215                 220

Tyr Cys Gln Gln Leu Val Thr Ser Pro Pro Thr Phe Gly Gln Gly Thr
225                 230                 235                 240

Lys Val Glu Ile Lys Ala Ala Gly Ser Asp Gln Glu Pro Lys Ser Ser
                245                 250                 255

Asp Lys Thr His Thr Cys Pro Pro Cys Ser Ala Pro Glu Leu Leu Gly
                260                 265                 270

Gly Ser Ser Val Phe Leu Phe Pro Pro Lys Pro Lys Asp Thr Leu Met
                275                 280                 285

Ile Ser Arg Thr Pro Glu Val Thr Cys Val Val Val Asp Val Ser His
                290                 295                 300

Glu Asp Pro Glu Val Lys Phe Asn Trp Tyr Val Asp Gly Val Glu Val
305                 310                 315                 320

His Asn Ala Lys Thr Lys Pro Arg Glu Glu Gln Tyr Asn Ser Thr Tyr
                325                 330                 335

Arg Val Val Ser Val Leu Thr Val Leu His Gln Asp Trp Leu Asn Gly
                340                 345                 350

Lys Glu Tyr Lys Cys Lys Val Ser Asn Lys Ala Leu Pro Ala Pro Ile
                355                 360                 365

Glu Lys Thr Ile Ser Lys Ala Lys Gly Gln Pro Arg Glu Pro Gln Val
                370                 375                 380

Tyr Thr Leu Pro Pro Ser Arg Asp Glu Leu Thr Lys Asn Gln Val Ser
385                 390                 395                 400

Leu Thr Cys Leu Val Lys Gly Phe Tyr Pro Ser Asp Ile Ala Val Glu
                405                 410                 415

Trp Glu Ser Asn Gly Gln Pro Glu Asn Asn Tyr Lys Thr Thr Pro Pro
                420                 425                 430

Val Leu Asp Ser Asp Gly Ser Phe Phe Leu Tyr Ser Lys Leu Thr Val
                435                 440                 445

Asp Lys Ser Arg Trp Gln Gln Gly Asn Val Phe Ser Cys Ser Val Met
                450                 455                 460

His Glu Ala Leu His Asn His Tyr Thr Gln Lys Ser Leu Ser Leu Ser
465                 470                 475                 480

Pro Gly Lys Gly Ser Gly Asp Tyr Lys Asp Asp Asp Lys Gly Ser
                485                 490                 495
```

Gly His His His His His His
              500

<210> SEQ ID NO 224
<211> LENGTH: 503
<212> TYPE: PRT
<213> ORGANISM: Artificial Sequence
<220> FEATURE:
<223> OTHER INFORMATION: Synthetic: 1557-G03, scFv-Fc

<400> SEQUENCE: 224

Met Glu Val Gln Leu Leu Glu Ser Gly Gly Gly Leu Val Gln Pro Gly
1               5                   10                  15

Gly Ser Leu Arg Leu Ser Cys Ala Ala Ser Gly Phe Thr Phe Gly Gly
            20                  25                  30

Ser Ser Met Ser Trp Val Arg Gln Ala Pro Gly Lys Gly Leu Glu Trp
        35                  40                  45

Val Gly Ala Ile Gly Gly Glu Gly Tyr Thr Gly Tyr Ala Asp Ser
    50                  55                  60

Val Lys Gly Arg Phe Thr Ile Ser Arg Asp Asn Ser Lys Asn Thr Leu
65                  70                  75                  80

Tyr Leu Gln Met Asn Ser Leu Arg Ala Glu Asp Thr Ala Val Tyr Tyr
                85                  90                  95

Cys Ala Lys Gly Trp His Pro Gln Thr Leu Tyr Asp Leu Asp Tyr Trp
            100                 105                 110

Gly Gln Gly Thr Leu Val Thr Val Ser Ser Gly Gly Gly Gly Ser Gly
        115                 120                 125

Gly Gly Gly Ser Gly Gly Gly Ser Glu Ile Val Leu Thr Gln Ser
    130                 135                 140

Pro Gly Thr Leu Ser Leu Ser Pro Gly Glu Arg Ala Thr Leu Ser Cys
145                 150                 155                 160

Arg Ala Ser Gln Ser Val His Ser Ser Tyr Leu Ala Trp Tyr Gln Gln
                165                 170                 175

Lys Pro Gly Gln Ala Pro Arg Leu Leu Ile Tyr Gly Ala Ser Ser Arg
            180                 185                 190

Ala Thr Gly Ile Pro Asp Arg Phe Ser Gly Ser Gly Ser Gly Thr Asp
        195                 200                 205

Phe Thr Leu Thr Ile Ser Arg Leu Glu Pro Glu Asp Phe Ala Val Tyr
    210                 215                 220

Tyr Cys Gln Gln Leu Leu Ser Ser Pro Pro Thr Phe Gly Gln Gly Thr
225                 230                 235                 240

Lys Val Glu Ile Lys Ala Ala Gly Ser Asp Gln Glu Pro Lys Ser Ser
                245                 250                 255

Asp Lys Thr His Thr Cys Pro Pro Cys Ser Ala Pro Glu Leu Leu Gly
            260                 265                 270

Gly Ser Ser Val Phe Leu Phe Pro Pro Lys Pro Lys Asp Thr Leu Met
        275                 280                 285

Ile Ser Arg Thr Pro Glu Val Thr Cys Val Val Val Asp Val Ser His
    290                 295                 300

Glu Asp Pro Glu Val Lys Phe Asn Trp Tyr Val Asp Gly Val Glu Val
305                 310                 315                 320

His Asn Ala Lys Thr Lys Pro Arg Glu Glu Gln Tyr Asn Ser Thr Tyr
                325                 330                 335

Arg Val Val Ser Val Leu Thr Val Leu His Gln Asp Trp Leu Asn Gly
            340                 345                 350

Lys Glu Tyr Lys Cys Lys Val Ser Asn Lys Ala Leu Pro Ala Pro Ile
            355                 360                 365

Glu Lys Thr Ile Ser Lys Ala Lys Gly Gln Pro Arg Glu Pro Gln Val
        370                 375                 380

Tyr Thr Leu Pro Pro Ser Arg Asp Glu Leu Thr Lys Asn Gln Val Ser
385                 390                 395                 400

Leu Thr Cys Leu Val Lys Gly Phe Tyr Pro Ser Asp Ile Ala Val Glu
                405                 410                 415

Trp Glu Ser Asn Gly Gln Pro Glu Asn Asn Tyr Lys Thr Thr Pro Pro
            420                 425                 430

Val Leu Asp Ser Asp Gly Ser Phe Phe Leu Tyr Ser Lys Leu Thr Val
        435                 440                 445

Asp Lys Ser Arg Trp Gln Gln Gly Asn Val Phe Ser Cys Ser Val Met
450                 455                 460

His Glu Ala Leu His Asn His Tyr Thr Gln Lys Ser Leu Ser Leu Ser
465                 470                 475                 480

Pro Gly Lys Gly Ser Gly Asp Tyr Lys Asp Asp Asp Lys Gly Ser
                485                 490                 495

Gly His His His His His His
            500

<210> SEQ ID NO 225
<211> LENGTH: 503
<212> TYPE: PRT
<213> ORGANISM: Artificial Sequence
<220> FEATURE:
<223> OTHER INFORMATION: Synthetic: 1557-G04, scFv-Fc

<400> SEQUENCE: 225

Met Glu Val Gln Leu Leu Glu Ser Gly Gly Gly Leu Val Gln Pro Gly
1               5                   10                  15

Gly Ser Leu Arg Leu Ser Cys Ala Ala Ser Gly Phe Thr Phe Cys Gly
            20                  25                  30

Ser Ser Met Ser Trp Val Arg Gln Ala Pro Gly Lys Gly Leu Glu Trp
        35                  40                  45

Val Gly Ala Ile Asp Gly Gly Val Gly Ser Thr Gly Tyr Ala Asp Ser
    50                  55                  60

Val Lys Gly Arg Phe Thr Ile Ser Arg Asp Asn Ser Lys Asn Thr Leu
65                  70                  75                  80

Tyr Leu Gln Met Asn Ser Leu Arg Ala Glu Asp Thr Ala Val Tyr Tyr
                85                  90                  95

Cys Ala Lys Gly Trp His Pro Gln Thr Leu Tyr Asp Leu Asp Tyr Trp
            100                 105                 110

Gly Gln Gly Thr Leu Val Thr Val Ser Ser Gly Gly Asp Ser Gly
        115                 120                 125

Gly Gly Gly Ser Gly Gly Gly Ser Glu Ile Val Leu Thr Gln Ser
    130                 135                 140

Pro Gly Thr Leu Ser Leu Ser Pro Gly Glu Arg Ala Thr Leu Ser Cys
145                 150                 155                 160

Arg Ala Ser Gln Ser Val Ser Ser Ser Tyr Leu Ala Trp Tyr Gln Gln
                165                 170                 175

Lys Pro Gly Gln Ala Pro Arg Leu Leu Ile Tyr Gly Ala Ser Ser Arg
            180                 185                 190

Ala Thr Gly Ile Pro Asp Arg Phe Ser Gly Ser Gly Ser Gly Thr Asp
        195                 200                 205

-continued

Phe Thr Leu Thr Ile Ser Arg Leu Glu Pro Glu Asp Phe Ala Val Tyr
                210                 215                 220

Tyr Cys Gln Gln Asp Ser Phe Val Pro Pro Thr Phe Gly Gln Gly Thr
225                 230                 235                 240

Lys Val Glu Ile Lys Ala Ala Gly Ser Asp Gln Glu Pro Lys Ser Ser
                245                 250                 255

Asp Lys Thr His Thr Cys Pro Pro Cys Ser Ala Pro Glu Leu Leu Gly
                260                 265                 270

Gly Ser Ser Val Phe Leu Phe Pro Pro Lys Pro Lys Asp Thr Leu Met
                275                 280                 285

Ile Ser Arg Thr Pro Glu Val Thr Cys Val Val Val Asp Val Ser His
                290                 295                 300

Glu Asp Pro Glu Val Lys Phe Asn Trp Tyr Val Asp Gly Val Glu Val
305                 310                 315                 320

His Asn Ala Lys Thr Lys Pro Arg Glu Glu Gln Tyr Asn Ser Thr Tyr
                325                 330                 335

Arg Val Val Ser Val Leu Thr Val Leu His Gln Asp Trp Leu Asn Gly
                340                 345                 350

Lys Glu Tyr Lys Cys Lys Val Ser Asn Lys Ala Leu Pro Ala Pro Ile
                355                 360                 365

Glu Lys Thr Ile Ser Lys Ala Lys Gly Gln Pro Arg Glu Pro Gln Val
                370                 375                 380

Tyr Thr Leu Pro Pro Ser Arg Asp Glu Leu Thr Lys Asn Gln Val Ser
385                 390                 395                 400

Leu Thr Cys Leu Val Lys Gly Phe Tyr Pro Ser Asp Ile Ala Val Glu
                405                 410                 415

Trp Glu Ser Asn Gly Gln Pro Glu Asn Asn Tyr Lys Thr Thr Pro Pro
                420                 425                 430

Val Leu Asp Ser Asp Gly Ser Phe Phe Leu Tyr Ser Lys Leu Thr Val
                435                 440                 445

Asp Lys Ser Arg Trp Gln Gln Gly Asn Val Phe Ser Cys Ser Val Met
                450                 455                 460

His Glu Ala Leu His Asn His Tyr Thr Gln Lys Ser Leu Ser Leu Ser
465                 470                 475                 480

Pro Gly Lys Gly Ser Gly Asp Tyr Lys Asp Asp Asp Asp Lys Gly Ser
                485                 490                 495

Gly His His His His His His
            500

<210> SEQ ID NO 226
<211> LENGTH: 503
<212> TYPE: PRT
<213> ORGANISM: Artificial Sequence
<220> FEATURE:
<223> OTHER INFORMATION: Synthetic: 1557-G06, scFv-Fc

<400> SEQUENCE: 226

Met Glu Val Gln Leu Leu Glu Ser Gly Gly Gly Leu Val Gln Pro Gly
1               5                   10                  15

Gly Ser Leu Arg Leu Ser Cys Ala Ala Ser Gly Phe Thr Phe Ser Gly
                20                  25                  30

Phe Ser Met Ser Trp Val Arg Gln Ala Pro Gly Lys Gly Leu Glu Trp
            35                  40                  45

Val Gly Ala Ile Asp Gly Gly Glu Gly Ser Thr Gly Tyr Ala Asp Ser
        50                  55                  60

```
Val Lys Gly Arg Phe Thr Ile Ser Arg Asp Asn Ser Lys Asn Thr Leu
 65                  70                  75                  80

Tyr Leu Gln Met Asn Ser Leu Arg Ala Glu Asp Thr Ala Val Tyr Tyr
                 85                  90                  95

Cys Ala Lys Gly Trp His Pro Gln Thr Leu Tyr His Leu Asp Tyr Trp
            100                 105                 110

Gly Gln Gly Thr Leu Val Thr Val Ser Ser Gly Gly Gly Gly Ser Gly
            115                 120                 125

Gly Gly Gly Ser Gly Gly Gly Ser Glu Ile Val Leu Thr Gln Ser
        130                 135                 140

Pro Gly Thr Leu Ser Leu Ser Pro Gly Glu Arg Ala Thr Leu Ser Cys
145                 150                 155                 160

Arg Ala Ser Gln Ser Ile Pro Ser Ser Tyr Leu Ala Trp Tyr Gln Gln
                165                 170                 175

Glu Pro Gly Gln Ala Pro Arg Leu Leu Ile Tyr Gly Ala Ser Ser Arg
            180                 185                 190

Ala Thr Gly Ile Pro Asp Arg Phe Ser Gly Ser Gly Ser Gly Thr Asp
            195                 200                 205

Phe Thr Leu Thr Ile Ser Arg Leu Glu Pro Glu Asp Phe Ala Val Tyr
            210                 215                 220

Tyr Cys Gln Gln Leu Ala Thr Ser Pro Pro Thr Phe Gly Gln Gly Thr
225                 230                 235                 240

Lys Val Glu Ile Lys Ala Ala Gly Ser Asp Gln Glu Pro Lys Ser Ser
                245                 250                 255

Asp Lys Thr His Thr Cys Pro Pro Cys Ser Ala Pro Glu Leu Leu Gly
            260                 265                 270

Gly Ser Ser Val Phe Leu Phe Pro Pro Lys Pro Lys Asp Thr Leu Met
            275                 280                 285

Ile Ser Arg Thr Pro Glu Val Thr Cys Val Val Val Asp Val Ser His
            290                 295                 300

Glu Asp Pro Glu Val Lys Phe Asn Trp Tyr Val Asp Gly Val Glu Val
305                 310                 315                 320

His Asn Ala Lys Thr Lys Pro Arg Glu Glu Gln Tyr Asn Ser Thr Tyr
                325                 330                 335

Arg Val Val Ser Val Leu Thr Val Leu His Gln Asp Trp Leu Asn Gly
            340                 345                 350

Lys Glu Tyr Lys Cys Lys Val Ser Asn Lys Ala Leu Pro Ala Pro Ile
            355                 360                 365

Glu Lys Thr Ile Ser Lys Ala Lys Gly Gln Pro Arg Glu Pro Gln Val
            370                 375                 380

Tyr Thr Leu Pro Pro Ser Arg Asp Glu Leu Thr Lys Asn Gln Val Ser
385                 390                 395                 400

Leu Thr Cys Leu Val Lys Gly Phe Tyr Pro Ser Asp Ile Ala Val Glu
                405                 410                 415

Trp Glu Ser Asn Gly Gln Pro Glu Asn Asn Tyr Lys Thr Thr Pro Pro
            420                 425                 430

Val Leu Asp Ser Asp Gly Ser Phe Phe Leu Tyr Ser Lys Leu Thr Val
            435                 440                 445

Asp Lys Ser Arg Trp Gln Gln Gly Asn Val Phe Ser Cys Ser Val Met
            450                 455                 460

His Glu Ala Leu His Asn His Tyr Thr Gln Lys Ser Leu Ser Leu Ser
465                 470                 475                 480
```

```
Pro Gly Lys Gly Ser Gly Asp Tyr Lys Asp Asp Asp Lys Gly Ser
            485                 490                 495
Gly His His His His His His
            500

<210> SEQ ID NO 227
<211> LENGTH: 503
<212> TYPE: PRT
<213> ORGANISM: Artificial Sequence
<220> FEATURE:
<223> OTHER INFORMATION: Synthetic: 1557-H04, scFv-Fc

<400> SEQUENCE: 227

Met Glu Val Gln Leu Leu Glu Ser Gly Gly Gly Leu Val Gln Pro Gly
1               5                   10                  15

Gly Ser Leu Arg Leu Ser Cys Ala Ala Ser Gly Phe Thr Phe Ser Val
            20                  25                  30

Thr Ser Met Ser Trp Met Arg Gln Ala Pro Gly Lys Gly Leu Glu Trp
        35                  40                  45

Val Gly Ala Ile Ala Gly Gly Glu Gly Ser Thr Gly Tyr Ala Asp Ser
    50                  55                  60

Val Lys Gly Arg Phe Thr Ile Ser Arg Asp Asn Ser Lys Asn Thr Leu
65                  70                  75                  80

Tyr Leu Gln Met Asn Ser Leu Arg Ala Glu Asp Thr Ala Val Tyr Tyr
                85                  90                  95

Cys Ala Lys Gly Trp His Pro Gln Thr Leu Tyr Asp Leu Asp Tyr Trp
            100                 105                 110

Gly Gln Gly Thr Leu Val Thr Val Ser Ser Gly Gly Gly Ser Asp
        115                 120                 125

Gly Gly Gly Ser Gly Gly Gly Ser Glu Ile Val Leu Thr Gln Gly
    130                 135                 140

Pro Ser Thr Leu Ser Leu Ser Pro Gly Glu Arg Ala Thr Leu Ser Cys
145                 150                 155                 160

Arg Ala Ser Gln Ser Val Ser Thr Gly Tyr Leu Ala Trp Tyr Gln Gln
                165                 170                 175

Lys Pro Gly Gln Ala Pro Arg Leu Leu Ile Tyr Gly Ala Ser Ser Arg
            180                 185                 190

Ala Thr Gly Ile Pro Asp Arg Phe Ser Gly Ser Gly Ser Gly Thr Asp
        195                 200                 205

Phe Thr Leu Thr Ile Ser Arg Leu Glu Pro Glu Asp Phe Ala Val Tyr
    210                 215                 220

Tyr Cys Gln Gln Leu Val Thr Arg Pro Pro Thr Phe Gly Gln Gly Thr
225                 230                 235                 240

Lys Val Glu Ile Lys Ala Ala Gly Ser Asp Gln Glu Pro Lys Ser Ser
                245                 250                 255

Asp Lys Thr His Thr Cys Pro Pro Cys Ser Ala Pro Glu Leu Leu Gly
            260                 265                 270

Gly Ser Ser Val Phe Leu Phe Pro Pro Lys Pro Lys Asp Thr Leu Met
        275                 280                 285

Ile Ser Arg Thr Pro Glu Val Thr Cys Val Val Val Asp Val Ser His
    290                 295                 300

Glu Asp Pro Glu Val Lys Phe Asn Trp Tyr Val Asp Gly Val Glu Val
305                 310                 315                 320

His Asn Ala Lys Thr Lys Pro Arg Glu Glu Gln Tyr Asn Ser Thr Tyr
                325                 330                 335
```

```
Arg Val Val Ser Val Leu Thr Val Leu His Gln Asp Trp Leu Asn Gly
            340                 345                 350

Lys Glu Tyr Lys Cys Lys Val Ser Asn Lys Ala Leu Pro Ala Pro Ile
        355                 360                 365

Glu Lys Thr Ile Ser Lys Ala Lys Gly Gln Pro Arg Glu Pro Gln Val
    370                 375                 380

Tyr Thr Leu Pro Pro Ser Arg Asp Glu Leu Thr Lys Asn Gln Val Ser
385                 390                 395                 400

Leu Thr Cys Leu Val Lys Gly Phe Tyr Pro Ser Asp Ile Ala Val Glu
            405                 410                 415

Trp Glu Ser Asn Gly Gln Pro Glu Asn Asn Tyr Lys Thr Thr Pro Pro
        420                 425                 430

Val Leu Asp Ser Asp Gly Ser Phe Phe Leu Tyr Ser Lys Leu Thr Val
    435                 440                 445

Asp Lys Ser Arg Trp Gln Gln Gly Asn Val Phe Ser Cys Ser Val Met
450                 455                 460

His Glu Ala Leu His Asn His Tyr Thr Gln Lys Ser Leu Ser Leu Ser
465                 470                 475                 480

Pro Gly Lys Gly Ser Gly Asp Tyr Lys Asp Asp Asp Asp Lys Gly Ser
            485                 490                 495

Gly His His His His His His
            500

<210> SEQ ID NO 228
<211> LENGTH: 503
<212> TYPE: PRT
<213> ORGANISM: Artificial Sequence
<220> FEATURE:
<223> OTHER INFORMATION: Synthetic: 1557-H10, scFv-Fc

<400> SEQUENCE: 228

Met Glu Val Gln Leu Leu Glu Ser Gly Gly Gly Leu Val Gln Pro Gly
1               5                   10                  15

Gly Ser Leu Arg Leu Ser Cys Ala Ala Ser Gly Phe Thr Phe Ser Gly
            20                  25                  30

Ser Ser Met Ser Trp Val Arg Gln Ala Pro Gly Lys Gly Leu Glu Trp
        35                  40                  45

Val Gly Ala Ile Asp Gly Gly Glu Gly Ser Thr Gly Tyr Ala Asp Ser
    50                  55                  60

Val Lys Gly Arg Phe Thr Ile Ser Arg Asp Asn Ser Lys Asn Thr Leu
65                  70                  75                  80

Tyr Leu Gln Met Asn Ser Leu Arg Ala Glu Asp Thr Ala Val Tyr Tyr
                85                  90                  95

Cys Ala Lys Gly Trp His Pro Gln Ser Met Tyr Asp Leu Asp Tyr Trp
            100                 105                 110

Gly Gln Gly Thr Leu Val Thr Val Ser Ser Gly Gly Gly Gly Ser Gly
        115                 120                 125

Gly Gly Gly Ser Gly Gly Gly Gly Ser Glu Ile Val Leu Thr Gln Ser
    130                 135                 140

Pro Gly Thr Leu Ser Leu Ser Pro Gly Glu Arg Ala Thr Met Ser Cys
145                 150                 155                 160

Arg Ala Ser Gln Val Leu Ser Ser Ser Leu Ala Trp Tyr Gln Gln
                165                 170                 175

Lys Pro Gly Gln Ala Pro Arg Leu Leu Ile Tyr Gly Ala Ser Ser Arg
            180                 185                 190
```

```
Ala Thr Gly Ile Pro Asp Arg Phe Ser Gly Ser Gly Ser Gly Thr Asp
            195                 200                 205

Phe Thr Leu Thr Ile Ser Arg Leu Glu Pro Glu Asp Phe Ala Val Tyr
            210                 215                 220

Tyr Cys Gln Gln Leu Val Thr Ala Pro Pro Thr Phe Gly Gln Gly Thr
225                 230                 235                 240

Lys Val Glu Ile Lys Ala Ala Gly Ser Asp Gln Glu Pro Lys Ser Ser
            245                 250                 255

Asp Lys Thr His Thr Cys Pro Pro Cys Ser Ala Pro Glu Leu Leu Gly
            260                 265                 270

Gly Ser Ser Val Phe Leu Phe Pro Pro Lys Pro Lys Asp Thr Leu Met
            275                 280                 285

Ile Ser Arg Thr Pro Glu Val Thr Cys Val Val Val Asp Val Ser His
            290                 295                 300

Glu Asp Pro Glu Val Lys Phe Asn Trp Tyr Val Asp Gly Val Glu Val
305                 310                 315                 320

His Asn Ala Lys Thr Lys Pro Arg Glu Glu Gln Tyr Asn Ser Thr Tyr
            325                 330                 335

Arg Val Val Ser Val Leu Thr Val Leu His Gln Asp Trp Leu Asn Gly
            340                 345                 350

Lys Glu Tyr Lys Cys Lys Val Ser Asn Lys Ala Leu Pro Ala Pro Ile
            355                 360                 365

Glu Lys Thr Ile Ser Lys Ala Lys Gly Gln Pro Arg Glu Pro Gln Val
            370                 375                 380

Tyr Thr Leu Pro Pro Ser Arg Asp Glu Leu Thr Lys Asn Gln Val Ser
385                 390                 395                 400

Leu Thr Cys Leu Val Lys Gly Phe Tyr Pro Ser Asp Ile Ala Val Glu
            405                 410                 415

Trp Glu Ser Asn Gly Gln Pro Glu Asn Asn Tyr Lys Thr Thr Pro Pro
            420                 425                 430

Val Leu Asp Ser Asp Gly Ser Phe Phe Leu Tyr Ser Lys Leu Thr Val
            435                 440                 445

Asp Lys Ser Arg Trp Gln Gln Gly Asn Val Phe Ser Cys Ser Val Met
450                 455                 460

His Glu Ala Leu His Asn His Tyr Thr Gln Lys Ser Leu Ser Leu Ser
465                 470                 475                 480

Pro Gly Lys Gly Ser Gly Asp Tyr Lys Asp Asp Asp Lys Gly Ser
            485                 490                 495

Gly His His His His His
            500

<210> SEQ ID NO 229
<211> LENGTH: 121
<212> TYPE: PRT
<213> ORGANISM: Artificial Sequence
<220> FEATURE:
<223> OTHER INFORMATION: Synthetic: 1304-G11, VH

<400> SEQUENCE: 229

Glu Val Gln Leu Leu Glu Ser Gly Gly Gly Leu Val Arg Pro Gly Gly
1               5                   10                  15

Ser Leu Arg Leu Ser Cys Ala Ala Ser Gly Phe Thr Phe Ser Gly Ser
            20                  25                  30

Ser Met Ser Trp Val Arg Gln Ala Pro Gly Lys Gly Leu Glu Trp Val
            35                  40                  45
```

Gly Ala Ile Asp Gly Gly Gly Tyr Thr Asn Tyr Ala Asp Ser Val
    50                  55                  60

Arg Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Trp His Pro Gln Thr Tyr Tyr Gly Leu Asp Tyr Trp Gly
            100                 105                 110

Gln Gly Thr Leu Val Thr Val Ser Ser
            115                 120

<210> SEQ ID NO 230
<211> LENGTH: 120
<212> TYPE: PRT
<213> ORGANISM: Artificial Sequence
<220> FEATURE:
<223> OTHER INFORMATION: Synthetic: 1332-A05, VH

<400> SEQUENCE: 230

Glu Val Gln Leu Leu Glu Gln Ser Gly Ala Glu Leu Val Arg Pro Gly
1               5                   10                  15

Thr Ser Val Lys Ile Ser Cys Lys Ala Ser Asp Tyr Ala Phe Ala Asn
                20                  25                  30

Arg Trp Leu Gly Trp Val Lys Gln Arg Pro Gly His Gly Leu Glu Trp
            35                  40                  45

Ile Gly Asp Ile Phe Pro Gly Ser Gly Asn Ile His Tyr Asn Glu Lys
    50                  55                  60

Phe Lys Gly Lys Ala Thr Leu Thr Ala Asp Lys Ser Ser Ser Thr Ala
65                  70                  75                  80

Tyr Met Gln Leu Ser Ser Leu Thr Phe Glu Asp Ser Ala Val Tyr Phe
                85                  90                  95

Cys Ala Arg Leu Arg Asn Trp Glu Gly Pro Met Asp Tyr Trp Gly Gln
            100                 105                 110

Gly Thr Thr Val Thr Val Ser Ser
            115                 120

<210> SEQ ID NO 231
<211> LENGTH: 120
<212> TYPE: PRT
<213> ORGANISM: Artificial Sequence
<220> FEATURE:
<223> OTHER INFORMATION: Synthetic: 1332-C01, VH

<400> SEQUENCE: 231

Glu Val Gln Leu Leu Glu Gln Ser Gly Ala Glu Leu Val Arg Pro Gly
1               5                   10                  15

Thr Ser Val Lys Ile Ser Cys Lys Ala Ser Gly Tyr Ala Phe Thr Asn
                20                  25                  30

Ser Trp Leu Gly Trp Val Lys Gln Arg Pro Gly His Gly Leu Glu Trp
            35                  40                  45

Ile Gly Asp Ile Phe Pro Gly Ser Gly Asn Ile His Tyr Asn Glu Lys
    50                  55                  60

Phe Lys Gly Lys Ala Thr Leu Thr Ala Asp Lys Ser Ser Ser Thr Ala
65                  70                  75                  80

Tyr Met Gln Leu Ser Ser Leu Thr Phe Glu Asp Ser Ala Val Tyr Phe
                85                  90                  95

Cys Ala Arg Leu Arg Asn Trp Asp Met Pro Met Asp Tyr Trp Gly Gln
            100                 105                 110

```
Gly Thr Thr Val Thr Val Ser Ser
        115                 120

<210> SEQ ID NO 232
<211> LENGTH: 120
<212> TYPE: PRT
<213> ORGANISM: Artificial Sequence
<220> FEATURE:
<223> OTHER INFORMATION: Synthetic: 1332-F11, VH

<400> SEQUENCE: 232

Glu Val Gln Leu Leu Glu Gln Ser Gly Ala Glu Leu Val Arg Pro Gly
1               5                   10                  15

Thr Ser Val Lys Ile Ser Cys Lys Ala Ser Gly Tyr Ala Phe Ala Asn
            20                  25                  30

Arg Trp Leu Gly Trp Val Lys Gln Arg Pro Gly His Gly Leu Glu Trp
        35                  40                  45

Ile Gly Asp Ile Phe Pro Gly Ser Gly Asn Ile His Tyr Asn Glu Lys
    50                  55                  60

Phe Lys Gly Lys Ala Thr Leu Thr Ala Asp Lys Ser Ser Ser Thr Ala
65                  70                  75                  80

Tyr Met Gln Leu Ser Ser Leu Thr Phe Glu Asp Ser Ala Val Tyr Phe
                85                  90                  95

Cys Ala Arg Leu Arg Asn Trp Glu Gly Pro Met Asp Tyr Trp Gly Gln
            100                 105                 110

Gly Thr Thr Val Thr Val Ser Ser
        115                 120

<210> SEQ ID NO 233
<211> LENGTH: 121
<212> TYPE: PRT
<213> ORGANISM: Artificial Sequence
<220> FEATURE:
<223> OTHER INFORMATION: Synthetic: 1464-A02, VH

<400> SEQUENCE: 233

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Gly Val Glu
            20                  25                  30

Ser Met Ser Trp Val Arg Gln Ala Pro Gly Lys Gly Leu Glu Trp Val
        35                  40                  45

Gly Ala Ile Asp Gly Gly Asp Gly Tyr Thr Gly Tyr Ala Asp Ser Val
    50                  55                  60

Lys Asp Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ala Trp His Pro Gln Thr Tyr Tyr Gly Val Asp Tyr Trp Gly
            100                 105                 110

Gln Gly Thr Leu Val Thr Val Ser Ser
        115                 120

<210> SEQ ID NO 234
<211> LENGTH: 121
<212> TYPE: PRT
<213> ORGANISM: Artificial Sequence
<220> FEATURE:
<223> OTHER INFORMATION: Synthetic: 1464-A08, VH
```

<400> SEQUENCE: 234

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Gly Ser
            20                  25                  30

Ser Met Ser Trp Val Arg Gln Ala Pro Gly Lys Gly Leu Glu Trp Val
        35                  40                  45

Gly Ala Ile Ala Gly Gly Asp Gly Tyr Thr Gly Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Trp His Arg Gln Asp Tyr Tyr Gly Gln Asp Tyr Trp Gly
            100                 105                 110

Gln Gly Thr Leu Val Thr Val Ser Ser
        115                 120
```

<210> SEQ ID NO 235
<211> LENGTH: 121
<212> TYPE: PRT
<213> ORGANISM: Artificial Sequence
<220> FEATURE:
<223> OTHER INFORMATION: Synthetic: 1464-B04, VH

<400> SEQUENCE: 235

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Gly Ser
            20                  25                  30

Ser Met Ser Trp Val Arg Gln Ala Pro Gly Lys Gly Leu Glu Trp Val
        35                  40                  45

Gly Ala Ile Asp Gly Gly Glu Gly Tyr Thr Ser Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Trp His Pro Gln Thr Leu Tyr Asp Leu Asp Tyr Trp Gly
            100                 105                 110

Gln Gly Thr Leu Val Thr Val Ser Ser
        115                 120
```

<210> SEQ ID NO 236
<211> LENGTH: 121
<212> TYPE: PRT
<213> ORGANISM: Artificial Sequence
<220> FEATURE:
<223> OTHER INFORMATION: Synthetic: 1557-A04, VH

<400> SEQUENCE: 236

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Gly Ser
            20                  25                  30

Ser Met Ser Trp Val Arg Gln Ala Pro Gly Lys Gly Leu Glu Trp Val
        35                  40                  45
```

```
Gly Ala Ile Asp Gly Gly Glu Gly Ser Thr Ala Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Trp His Pro Gln Thr Met Tyr Asp Leu Asp Tyr Trp Gly
            100                 105                 110

Gln Gly Thr Leu Val Thr Val Ser Ser
            115                 120

<210> SEQ ID NO 237
<211> LENGTH: 121
<212> TYPE: PRT
<213> ORGANISM: Artificial Sequence
<220> FEATURE:
<223> OTHER INFORMATION: Synthetic: 1557-A05, VH

<400> SEQUENCE: 237

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Gly Gly Ser
            20                  25                  30

Ser Met Ser Trp Val Arg Gln Ala Pro Gly Lys Gly Leu Glu Trp Val
        35                  40                  45

Gly Ala Ile Gly Gly Gly Glu Gly Ser Thr Gly Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Trp His Asp Gln Ser Leu Tyr Asp Arg Asp Tyr Trp Gly
            100                 105                 110

Gln Gly Thr Leu Val Thr Val Ser Ser
            115                 120

<210> SEQ ID NO 238
<211> LENGTH: 121
<212> TYPE: PRT
<213> ORGANISM: Artificial Sequence
<220> FEATURE:
<223> OTHER INFORMATION: Synthetic: 1557-B03, VH

<400> SEQUENCE: 238

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Arg Ser Ser
            20                  25                  30

Ser Met Ser Trp Val Arg Gln Ala Pro Gly Lys Gly Leu Glu Trp Val
        35                  40                  45

Gly Ala Ile Gly Gly His Glu Gly Tyr Thr Gly Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Trp Asn Pro Gln Thr Leu Tyr His Leu Asp Tyr Trp Gly
```

100                 105                 110

Gln Gly Thr Leu Val Thr Val Ser Ser
        115                 120

<210> SEQ ID NO 239
<211> LENGTH: 121
<212> TYPE: PRT
<213> ORGANISM: Artificial Sequence
<220> FEATURE:
<223> OTHER INFORMATION: Synthetic: 1557-B10, VH

<400> SEQUENCE: 239

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Gly Cys
            20                  25                  30

Ser Met Ser Trp Val Arg Gln Ala Pro Gly Lys Gly Leu Glu Trp Val
        35                  40                  45

Gly Ala Ile Ala Gly Gly Glu Gly Asn Thr Gly Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Trp His Pro Gln Thr Leu Tyr Asp Leu Asp Tyr Trp Gly
            100                 105                 110

Gln Gly Thr Leu Val Thr Val Ser Ser
        115                 120

<210> SEQ ID NO 240
<211> LENGTH: 121
<212> TYPE: PRT
<213> ORGANISM: Artificial Sequence
<220> FEATURE:
<223> OTHER INFORMATION: Synthetic: 1557-C06, VH

<400> SEQUENCE: 240

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Arg Gly Ala
            20                  25                  30

Ser Met Ser Trp Val Arg Gln Ala Pro Gly Lys Gly Leu Glu Trp Val
        35                  40                  45

Gly Ala Ile Asp Gly Ser Gln Gly Ser Thr Gly Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Trp His Pro Gln Thr Met Tyr Asp Leu Asp Tyr Trp Gly
            100                 105                 110

Gln Gly Thr Leu Val Thr Val Ser Ser
        115                 120

<210> SEQ ID NO 241
<211> LENGTH: 121
<212> TYPE: PRT
<213> ORGANISM: Artificial Sequence
<220> FEATURE:

<223> OTHER INFORMATION: Synthetic: 1557-E07, VH

<400> SEQUENCE: 241

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Gly Ser
            20                  25                  30

Ser Met Ser Trp Val Arg Gln Ala Pro Gly Lys Gly Leu Glu Trp Val
        35                  40                  45

Gly Ala Ile Asp Gly Gly Glu Gly Ser Thr Gly Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Trp His Pro Gln Thr Leu Tyr Asp Leu Asp Tyr Trp Gly
            100                 105                 110

Gln Gly Thr Leu Val Thr Val Ser Ser
        115                 120

<210> SEQ ID NO 242
<211> LENGTH: 121
<212> TYPE: PRT
<213> ORGANISM: Artificial Sequence
<220> FEATURE:
<223> OTHER INFORMATION: Synthetic: 1557-E08, VH

<400> SEQUENCE: 242

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Arg Ala Ser
            20                  25                  30

Ser Met Ser Trp Met Arg Gln Ala Pro Gly Lys Gly Leu Glu Trp Val
        35                  40                  45

Gly Ala Ile Asp Gly Gly Val Gly Ser Thr Gly Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Trp His Pro Gln Thr Leu Tyr Asp Leu Asp Tyr Trp Gly
            100                 105                 110

Gln Gly Thr Leu Val Thr Val Ser Ser
        115                 120

<210> SEQ ID NO 243
<211> LENGTH: 121
<212> TYPE: PRT
<213> ORGANISM: Artificial Sequence
<220> FEATURE:
<223> OTHER INFORMATION: Synthetic: 1557-E11, VH

<400> SEQUENCE: 243

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Arg Gly Ser
            20                  25                  30

Ser Met Ser Trp Val Arg Gln Ala Pro Gly Lys Gly Leu Glu Trp Val

```
                35                  40                  45

Gly Ala Ile Asp Gly Gly Glu Gly Ser Thr Gly Tyr Ala Asp Ser Val
        50                  55                  60

Lys Gly Arg Phe Thr Ile Asn Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Lys Gly Trp His Pro Gln Ser Leu Tyr Asp Leu Tyr Trp Gly
                100                 105                 110

Gln Gly Thr Leu Val Thr Val Ser Ser
        115                 120

<210> SEQ ID NO 244
<211> LENGTH: 121
<212> TYPE: PRT
<213> ORGANISM: Artificial Sequence
<220> FEATURE:
<223> OTHER INFORMATION: Synthetic: 1557-F01, VH

<400> SEQUENCE: 244

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Gly Ser
                20                  25                  30

Ser Met Ser Trp Val Arg Gln Ala Pro Gly Lys Gly Leu Glu Trp Val
                35                  40                  45

Gly Ala Ile Asp Gly Gly Glu Gly Ser Thr Gly Tyr Ala Asp Ser Val
        50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Lys Gly Trp His Pro Gln Thr Leu Tyr Asp Leu Tyr Trp Gly
                100                 105                 110

Gln Gly Thr Leu Val Thr Val Ser Ser
        115                 120

<210> SEQ ID NO 245
<211> LENGTH: 121
<212> TYPE: PRT
<213> ORGANISM: Artificial Sequence
<220> FEATURE:
<223> OTHER INFORMATION: Synthetic: 1557-F02, VH

<400> SEQUENCE: 245

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Arg Gly Ser
                20                  25                  30

Ser Met Ser Trp Val Arg Gln Ala Pro Gly Lys Gly Leu Glu Trp Val
                35                  40                  45

Gly Ala Ile Asp Gly Gly Glu Gly Ser Thr Gly Tyr Ala Asp Ser Val
        50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95
```

Ala Lys Gly Trp His Pro Gln Thr Met Tyr Asn Leu Asp Tyr Trp Gly
            100                 105                 110

Gln Gly Thr Leu Val Thr Val Ser Ser
        115                 120

<210> SEQ ID NO 246
<211> LENGTH: 121
<212> TYPE: PRT
<213> ORGANISM: Artificial Sequence
<220> FEATURE:
<223> OTHER INFORMATION: Synthetic: 1557-F03, VH

<400> SEQUENCE: 246

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Gly Ser
            20                  25                  30

Ser Met Ser Trp Val Arg Gln Ala Pro Gly Lys Gly Leu Glu Trp Val
        35                  40                  45

Gly Ala Ile Ala Gly Gly Gly Ser Thr Gly Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Trp His Pro Gln Thr Leu Tyr Asp Leu Asp Tyr Trp Gly
            100                 105                 110

Gln Gly Thr Leu Val Thr Val Ser Ser
        115                 120

<210> SEQ ID NO 247
<211> LENGTH: 121
<212> TYPE: PRT
<213> ORGANISM: Artificial Sequence
<220> FEATURE:
<223> OTHER INFORMATION: Synthetic: 1557-F05, VH

<400> SEQUENCE: 247

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Arg Gly Ser
            20                  25                  30

Ser Met Ser Trp Val Arg Gln Ala Pro Gly Lys Gly Leu Glu Trp Val
        35                  40                  45

Gly Ala Ile Asp Gly Gly Glu Gly Ser Thr Gly Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Trp His Pro Gln Thr Leu Tyr Asp Leu Asp Tyr Trp Gly
            100                 105                 110

Gln Gly Thr Leu Val Thr Val Ser Ser
        115                 120

<210> SEQ ID NO 248
<211> LENGTH: 121
<212> TYPE: PRT
<213> ORGANISM: Artificial Sequence
<220> FEATURE:
<223> OTHER INFORMATION: Synthetic: 1557-G01, VH

<400> SEQUENCE: 248

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Val Thr
            20                  25                  30

Ser Met Ser Trp Met Arg Gln Ala Pro Gly Lys Gly Leu Glu Trp Val
        35                  40                  45

Gly Ala Ile Ala Gly Gly Glu Gly Ser Thr Gly Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Trp His Pro Gln Thr Leu Tyr Asp Leu Asp Tyr Trp Gly
            100                 105                 110

Gln Gly Thr Leu Val Thr Val Ser Ser
        115                 120

<210> SEQ ID NO 249
<211> LENGTH: 121
<212> TYPE: PRT
<213> ORGANISM: Artificial Sequence
<220> FEATURE:
<223> OTHER INFORMATION: Synthetic: 1557-G03, VH

<400> SEQUENCE: 249

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Gly Gly Ser
            20                  25                  30

Ser Met Ser Trp Val Arg Gln Ala Pro Gly Lys Gly Leu Glu Trp Val
        35                  40                  45

Gly Ala Ile Gly Gly Gly Glu Gly Tyr Thr Gly Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Trp His Pro Gln Thr Leu Tyr Asp Leu Asp Tyr Trp Gly
            100                 105                 110

Gln Gly Thr Leu Val Thr Val Ser Ser
        115                 120

<210> SEQ ID NO 250
<211> LENGTH: 121
<212> TYPE: PRT
<213> ORGANISM: Artificial Sequence
<220> FEATURE:
<223> OTHER INFORMATION: Synthetic: 1557-G04, VH

<400> SEQUENCE: 250

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Cys Gly Ser
            20                  25                  30

```
Ser Met Ser Trp Val Arg Gln Ala Pro Gly Lys Gly Leu Glu Trp Val
            35                  40                  45

Gly Ala Ile Asp Gly Gly Val Gly Ser Thr Gly Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Trp His Pro Gln Thr Leu Tyr Asp Leu Asp Tyr Trp Gly
            100                 105                 110

Gln Gly Thr Leu Val Thr Val Ser Ser
        115                 120

<210> SEQ ID NO 251
<211> LENGTH: 121
<212> TYPE: PRT
<213> ORGANISM: Artificial Sequence
<220> FEATURE:
<223> OTHER INFORMATION: Synthetic: 1557-G06, VH

<400> SEQUENCE: 251

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Gly Phe
            20                  25                  30

Ser Met Ser Trp Val Arg Gln Ala Pro Gly Lys Gly Leu Glu Trp Val
            35                  40                  45

Gly Ala Ile Asp Gly Gly Glu Gly Ser Thr Gly Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Trp His Pro Gln Thr Leu Tyr His Leu Asp Tyr Trp Gly
            100                 105                 110

Gln Gly Thr Leu Val Thr Val Ser Ser
        115                 120

<210> SEQ ID NO 252
<211> LENGTH: 121
<212> TYPE: PRT
<213> ORGANISM: Artificial Sequence
<220> FEATURE:
<223> OTHER INFORMATION: Synthetic: 1557-H04, VH

<400> SEQUENCE: 252

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Val Thr
            20                  25                  30

Ser Met Ser Trp Met Arg Gln Ala Pro Gly Lys Gly Leu Glu Trp Val
            35                  40                  45

Gly Ala Ile Ala Gly Gly Glu Gly Ser Thr Gly Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95
```

Ala Lys Gly Trp His Pro Gln Thr Leu Tyr Asp Leu Asp Tyr Trp Gly
            100                 105                 110

Gln Gly Thr Leu Val Thr Val Ser Ser
        115                 120

<210> SEQ ID NO 253
<211> LENGTH: 121
<212> TYPE: PRT
<213> ORGANISM: Artificial Sequence
<220> FEATURE:
<223> OTHER INFORMATION: Synthetic: 1557-H10, VH

<400> SEQUENCE: 253

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Gly Ser
            20                  25                  30

Ser Met Ser Trp Val Arg Gln Ala Pro Gly Lys Gly Leu Glu Trp Val
        35                  40                  45

Gly Ala Ile Asp Gly Gly Glu Gly Ser Thr Gly Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Trp His Pro Gln Ser Met Tyr Asp Leu Asp Tyr Trp Gly
            100                 105                 110

Gln Gly Thr Leu Val Thr Val Ser Ser
        115                 120

<210> SEQ ID NO 254
<211> LENGTH: 108
<212> TYPE: PRT
<213> ORGANISM: Artificial Sequence
<220> FEATURE:
<223> OTHER INFORMATION: Synthetic: 1304-G11, VL

<400> SEQUENCE: 254

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Ser Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Trp Tyr Gly Pro
                85                  90                  95

Pro Thr Phe Gly Gln Gly Thr Lys Val Glu Ile Lys
            100                 105

<210> SEQ ID NO 255
<211> LENGTH: 113
<212> TYPE: PRT
<213> ORGANISM: Artificial Sequence
<220> FEATURE:
<223> OTHER INFORMATION: Synthetic: 1332-A05, VL

<400> SEQUENCE: 255

Glu Leu Val Met Thr Gln Ser Pro Ser Ser Leu Thr Val Thr Ala Gly
1               5                   10                  15

Glu Lys Val Thr Met Ser Cys Lys Ser Gln Ser Leu Leu Asn Ser
            20                  25                  30

Gly Asn Gln Lys Asn Tyr Leu Thr Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Gln Asn
                85                  90                  95

Asp Leu Ser Tyr Pro Leu Thr Phe Gly Ala Gly Thr Lys Leu Glu Ile
            100                 105                 110

Lys

<210> SEQ ID NO 256
<211> LENGTH: 113
<212> TYPE: PRT
<213> ORGANISM: Artificial Sequence
<220> FEATURE:
<223> OTHER INFORMATION: Synthetic: 1332-C01, VL

<400> SEQUENCE: 256

Glu Leu Val Met Thr Gln Ser Pro Ser Ser Leu Thr Val Thr Ala Gly
1               5                   10                  15

Glu Lys Val Thr Met Ser Cys Lys Ser Gln Ser Leu Leu Asn Ser
            20                  25                  30

Gly Asn Gln Lys Asn Tyr Leu Thr Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Gln Asn
                85                  90                  95

Asp Tyr Arg Tyr Pro Leu Thr Phe Gly Ala Gly Thr Lys Leu Glu Ile
            100                 105                 110

Lys

<210> SEQ ID NO 257
<211> LENGTH: 113
<212> TYPE: PRT
<213> ORGANISM: Artificial Sequence
<220> FEATURE:
<223> OTHER INFORMATION: Synthetic: 1332-F11, VL

<400> SEQUENCE: 257

Glu Leu Val Met Thr Gln Ser Pro Ser Ser Leu Thr Val Thr Ala Gly
1               5                   10                  15

Glu Lys Val Thr Met Ser Cys Lys Ser Gln Ser Leu Leu Asn Ser
            20                  25                  30

Gly Asn Gln Lys Asn Tyr Leu Thr Trp Tyr Gln Gln Lys Pro Gly Gln
        35                  40                  45

Pro Pro Lys Leu Leu Ile Tyr Arg Ala Ser Thr Arg Glu Ser Gly Val

```
                     50                  55                  60
Pro Asp Arg Phe Thr Gly Ser Gly Ser Gly Thr Asp Phe Thr Leu Thr
 65                  70                  75                  80

Ile Ser Ser Val Gln Ala Glu Asp Leu Ala Val Tyr Tyr Cys Gln Asn
                 85                  90                  95

Asp Ser Ser Tyr Pro Leu Thr Phe Gly Ala Gly Thr Lys Leu Glu Ile
                100                 105                 110

Lys
```

<210> SEQ ID NO 258
<211> LENGTH: 108
<212> TYPE: PRT
<213> ORGANISM: Artificial Sequence
<220> FEATURE:
<223> OTHER INFORMATION: Synthetic: 1464-A02, VL

<400> SEQUENCE: 258

```
Glu Ile Val Leu Thr Gln Ser Pro Gly Thr Leu Ser Leu Ser Pro Gly
  1               5                  10                  15

Glu Arg Ala Thr Leu Ser Cys Arg Ala Ser Gln Ser Val Ser Ser Ser
                 20                  25                  30

Tyr Leu Ala Trp Tyr Gln Gln Lys Pro Gly Gln Ala Pro Arg Leu Leu
             35                  40                  45

Ile Tyr Gly Ala Ser Ser Arg Ala Thr Gly Ile Pro Asp Arg Phe Ser
 50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Thr Ser Glu Ala Pro
                 85                  90                  95

Pro Thr Phe Gly Gln Gly Thr Lys Val Glu Ile Lys
                100                 105
```

<210> SEQ ID NO 259
<211> LENGTH: 108
<212> TYPE: PRT
<213> ORGANISM: Artificial Sequence
<220> FEATURE:
<223> OTHER INFORMATION: Synthetic: 1464-A08, VL

<400> SEQUENCE: 259

```
Glu Ile Val Leu Thr Gln Ser Pro Gly Thr Leu Ser Leu Ser Pro Gly
  1               5                  10                  15

Glu Arg Ala Thr Leu Gly Cys Arg Ala Ser Gln Ser Val Ser Ser Ser
                 20                  25                  30

Tyr Leu Ala Trp Tyr Gln Gln Lys Pro Gly Gln Ala Pro Arg Leu Leu
             35                  40                  45

Ile Tyr Gly Ala Ser Ser Arg Ala Thr Gly Ile Pro Asp Arg Phe Ser
 50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Asn Gln Ala Ala Pro
                 85                  90                  95

Ala Thr Phe Gly Gln Gly Thr Lys Val Glu Ile Lys
                100                 105
```

<210> SEQ ID NO 260
<211> LENGTH: 108
<212> TYPE: PRT

<213> ORGANISM: Artificial Sequence
<220> FEATURE:
<223> OTHER INFORMATION: Synthetic: 1464-B04, VL

<400> SEQUENCE: 260

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Leu Val Thr Ser Pro
                85                  90                  95

Pro Thr Phe Gly Gln Gly Thr Lys Val Glu Ile Lys
            100                 105
```

<210> SEQ ID NO 261
<211> LENGTH: 108
<212> TYPE: PRT
<213> ORGANISM: Artificial Sequence
<220> FEATURE:
<223> OTHER INFORMATION: Synthetic: 1557-A04, VL

<400> SEQUENCE: 261

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Asn Val Ser Thr Asn
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Leu Val Thr Asn Pro
                85                  90                  95

Pro Thr Phe Gly Gln Gly Thr Lys Val Glu Ile Lys
            100                 105
```

<210> SEQ ID NO 262
<211> LENGTH: 108
<212> TYPE: PRT
<213> ORGANISM: Artificial Sequence
<220> FEATURE:
<223> OTHER INFORMATION: Synthetic: 1557-A05, VL

<400> SEQUENCE: 262

```
Glu Ile Val Leu Thr Gln Ser Pro Gly Thr Leu Ser Leu Ser Pro Gly
1               5                   10                  15

Glu Arg Ala Thr Leu Ser Cys Ser Ala Ser Gln Thr Val Ser Ser Ser
            20                  25                  30

Tyr Ile Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Gly
50                  55                  60
```

```
Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Leu Leu Thr Ser Pro
                 85                  90                  95

Pro Thr Phe Gly Gln Gly Thr Lys Val Glu Ile Lys
            100                 105

<210> SEQ ID NO 263
<211> LENGTH: 108
<212> TYPE: PRT
<213> ORGANISM: Artificial Sequence
<220> FEATURE:
<223> OTHER INFORMATION: Synthetic: 1557-B03, VL

<400> SEQUENCE: 263

Glu Ile Val Leu Thr Gln Ser Pro Gly Thr Leu Ser Leu Ser Pro Gly
 1               5                  10                  15

Glu Arg Ala Thr Leu Ser Cys Arg Ala Ser Gln Lys Cys Ser Ser Ser
                 20                  25                  30

Ser Met Ala Trp Tyr Gln Gln Lys Pro Gly Gln Ala Pro Arg Leu Leu
             35                  40                  45

Ile Tyr Gly Ala Ser Ser Arg Ala Thr Gly Ile Pro Asp Arg Phe Ser
         50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Leu Gln Thr Ser Pro
                 85                  90                  95

Pro Thr Phe Gly Gln Gly Thr Lys Val Glu Ile Lys
            100                 105

<210> SEQ ID NO 264
<211> LENGTH: 108
<212> TYPE: PRT
<213> ORGANISM: Artificial Sequence
<220> FEATURE:
<223> OTHER INFORMATION: Synthetic: 1557-B10, VL

<400> SEQUENCE: 264

Glu Ile Val Leu Thr Gln Ser Pro Gly Thr Leu Ser Leu Ser Pro Gly
 1               5                  10                  15

Glu Arg Ala Thr Leu Ser Cys Arg Ala Ser Gln Gly Leu Ala Ser Arg
                 20                  25                  30

Tyr Met Ala Trp Tyr Gln Gln Lys Pro Gly Gln Ala Pro Arg Leu Leu
             35                  40                  45

Ile Tyr Gly Ala Ser Ser Arg Ala Thr Gly Ile Pro Asp Arg Phe Ser
         50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Val Met Thr Ile Pro
                 85                  90                  95

Pro Thr Phe Gly Gln Gly Thr Lys Val Glu Ile Lys
            100                 105

<210> SEQ ID NO 265
<211> LENGTH: 108
<212> TYPE: PRT
<213> ORGANISM: Artificial Sequence
<220> FEATURE:
<223> OTHER INFORMATION: Synthetic: 1557-C06, VL
```

<400> SEQUENCE: 265

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Arg Gly Thr Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln His Val Thr Ser Pro
                85                  90                  95

Pro Thr Phe Gly Gln Gly Thr Lys Val Glu Ile Lys
            100                 105

<210> SEQ ID NO 266
<211> LENGTH: 108
<212> TYPE: PRT
<213> ORGANISM: Artificial Sequence
<220> FEATURE:
<223> OTHER INFORMATION: Synthetic: 1557-E07, VL

<400> SEQUENCE: 266

Glu Ile Val Leu Thr Gln Ser Pro Gly Thr Leu Ser Leu Ser Pro Gly
1               5                   10                  15

Glu Arg Ala Thr Met Ser Cys Arg Ala Ser Gln Val Leu Ser Ser Ser
            20                  25                  30

Ser Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Ala Leu Thr Ile Ser Arg Leu Glu
65                  70                  75                  80

Pro Glu Asp Phe Ala Val Tyr Tyr Cys Gln Gln Arg Ala Ala Pro Pro
                85                  90                  95

Pro Thr Phe Gly Gln Gly Thr Lys Val Glu Ile Lys
            100                 105

<210> SEQ ID NO 267
<211> LENGTH: 108
<212> TYPE: PRT
<213> ORGANISM: Artificial Sequence
<220> FEATURE:
<223> OTHER INFORMATION: Synthetic: 1557-E08, VL

<400> SEQUENCE: 267

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Gly Asp Ser Ser Ser
            20                  25                  30

Val Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Leu Val Pro Ser Pro
             85                  90                  95

Pro Thr Phe Gly Gln Gly Thr Lys Val Glu Ile Lys
            100                 105

<210> SEQ ID NO 268
<211> LENGTH: 108
<212> TYPE: PRT
<213> ORGANISM: Artificial Sequence
<220> FEATURE:
<223> OTHER INFORMATION: Synthetic: 1557-E11, VL

<400> SEQUENCE: 268

Glu Ile Val Leu Thr Gln Ser Pro Gly Thr Leu Ser Leu Ser Pro Gly
1               5                  10                  15

Glu Arg Ala Thr Leu Ser Cys Arg Ala Ser Gln Pro Val Pro Asn Thr
            20                  25                  30

Thr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Ala Tyr Tyr Cys Gln Gln Leu Val Pro Ser Pro
                85                  90                  95

Pro Thr Phe Gly Gln Gly Thr Lys Val Glu Ile Lys
            100                 105

<210> SEQ ID NO 269
<211> LENGTH: 108
<212> TYPE: PRT
<213> ORGANISM: Artificial Sequence
<220> FEATURE:
<223> OTHER INFORMATION: Synthetic: 1557-F01, VL

<400> SEQUENCE: 269

Glu Ile Val Leu Thr Gln Ser Pro Gly Thr Leu Ser Leu Ser Pro Gly
1               5                  10                  15

Glu Arg Ala Thr Leu Ser Cys Arg Ala Ser Gln Ser Val Ser Ser Ser
            20                  25                  30

Lys Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Tyr Gly Ser Gly Thr Asp Phe Thr Leu Thr Ile Ser Arg Leu Glu
65                  70                  75                  80

Pro Glu Asp Phe Ala Val Tyr Tyr Cys Gln Gln Leu Glu Thr Ile Pro
                85                  90                  95

Pro Thr Phe Gly Gln Gly Thr Lys Val Glu Ile Lys
            100                 105

<210> SEQ ID NO 270
<211> LENGTH: 108
<212> TYPE: PRT
<213> ORGANISM: Artificial Sequence
<220> FEATURE:
<223> OTHER INFORMATION: Synthetic: 1557-F02, VL

<400> SEQUENCE: 270

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Leu Phe Asn Ser Pro
            85                  90                  95

Pro Thr Phe Gly Gln Gly Thr Lys Val Glu Ile Lys
            100                 105

<210> SEQ ID NO 271
<211> LENGTH: 108
<212> TYPE: PRT
<213> ORGANISM: Artificial Sequence
<220> FEATURE:
<223> OTHER INFORMATION: Synthetic: 1557-F03, VL

<400> SEQUENCE: 271

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Lys Thr Ser
            20                  25                  30

Asp Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Leu Val Ser Lys Pro
            85                  90                  95

Pro Thr Phe Gly Gln Gly Thr Lys Val Glu Ile Lys
            100                 105

<210> SEQ ID NO 272
<211> LENGTH: 108
<212> TYPE: PRT
<213> ORGANISM: Artificial Sequence
<220> FEATURE:
<223> OTHER INFORMATION: Synthetic: 1557-F05, VL

<400> SEQUENCE: 272

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Thr Val Ser Pro Ser
            20                  25                  30

Val Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Gly Arg Phe Ser
50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Leu Val Thr Asn Pro
            85                  90                  95

```
Pro Thr Phe Gly Gln Gly Thr Lys Val Glu Ile Lys
            100                 105
```

<210> SEQ ID NO 273
<211> LENGTH: 108
<212> TYPE: PRT
<213> ORGANISM: Artificial Sequence
<220> FEATURE:
<223> OTHER INFORMATION: Synthetic: 1557-G01, VL

<400> SEQUENCE: 273

```
Glu Ile Val Leu Thr Gln Ser Pro Gly Thr Leu Ser Leu Ser Pro Gly
1               5                   10                  15

Glu Arg Ala Thr Met Ser Cys Arg Ala Ser Gln Val Leu Ser Ser Ser
            20                  25                  30

Ser Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Leu Val Thr Ser Pro
                85                  90                  95

Pro Thr Phe Gly Gln Gly Thr Lys Val Glu Ile Lys
            100                 105
```

<210> SEQ ID NO 274
<211> LENGTH: 108
<212> TYPE: PRT
<213> ORGANISM: Artificial Sequence
<220> FEATURE:
<223> OTHER INFORMATION: Synthetic: 1557-G03, VL

<400> SEQUENCE: 274

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val His Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Leu Leu Ser Ser Pro
                85                  90                  95

Pro Thr Phe Gly Gln Gly Thr Lys Val Glu Ile Lys
            100                 105
```

<210> SEQ ID NO 275
<211> LENGTH: 108
<212> TYPE: PRT
<213> ORGANISM: Artificial Sequence
<220> FEATURE:
<223> OTHER INFORMATION: Synthetic: 1557-G04, VL

<400> SEQUENCE: 275

```
Glu Ile Val Leu Thr Gln Ser Pro Gly Thr Leu Ser Leu Ser Pro Gly
1               5                   10                  15
```

Glu Arg Ala Thr Leu Ser Cys Arg Ala Ser Gln Ser Val Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Asp Ser Phe Val Pro
                85                  90                  95

Pro Thr Phe Gly Gln Gly Thr Lys Val Glu Ile Lys
            100                 105

<210> SEQ ID NO 276
<211> LENGTH: 108
<212> TYPE: PRT
<213> ORGANISM: Artificial Sequence
<220> FEATURE:
<223> OTHER INFORMATION: Synthetic: 1557-G06, VL

<400> SEQUENCE: 276

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Ile Pro Ser Ser
            20                  25                  30

Tyr Leu Ala Trp Tyr Gln Gln Glu Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Leu Ala Thr Ser Pro
                85                  90                  95

Pro Thr Phe Gly Gln Gly Thr Lys Val Glu Ile Lys
            100                 105

<210> SEQ ID NO 277
<211> LENGTH: 108
<212> TYPE: PRT
<213> ORGANISM: Artificial Sequence
<220> FEATURE:
<223> OTHER INFORMATION: Synthetic: 1557-H04, VL

<400> SEQUENCE: 277

Glu Ile Val Leu Thr Gln Gly Pro Ser Thr Leu Ser Leu Ser Pro Gly
1               5                   10                  15

Glu Arg Ala Thr Leu Ser Cys Arg Ala Ser Gln Ser Val Ser Thr Gly
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Leu Val Thr Arg Pro
                85                  90                  95

Pro Thr Phe Gly Gln Gly Thr Lys Val Glu Ile Lys
            100                 105

```
<210> SEQ ID NO 278
<211> LENGTH: 108
<212> TYPE: PRT
<213> ORGANISM: Artificial Sequence
<220> FEATURE:
<223> OTHER INFORMATION: Synthetic: 1557-H10, VL

<400> SEQUENCE: 278
```

Glu Ile Val Leu Thr Gln Ser Pro Gly Thr Leu Ser Leu Ser Pro Gly
1               5                   10                  15

Glu Arg Ala Thr Met Ser Cys Arg Ala Ser Gln Val Leu Ser Ser Ser
            20                  25                  30

Ser Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Leu Val Thr Ala Pro
                85                  90                  95

Pro Thr Phe Gly Gln Gly Thr Lys Val Glu Ile Lys
            100                 105

```
<210> SEQ ID NO 279
<211> LENGTH: 330
<212> TYPE: PRT
<213> ORGANISM: Artificial Sequence
<220> FEATURE:
<223> OTHER INFORMATION: Synthetic: IgG1 Constant Region

<400> SEQUENCE: 279
```

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn

|     |     |     |     | 195 |     |     |     |     | 200 |     |     |     |     | 205 |     |
| --- | --- | --- | --- | --- | --- | --- | --- | --- | --- | --- | --- | --- | --- | --- | --- |

Lys Ala Leu Pro Ala Pro Ile Glu Lys Thr Ile Ser Lys Ala Lys Gly
210 215 220

Gln Pro Arg Glu Pro Gln Val Tyr Thr Leu Pro Pro Ser Arg Glu Glu
225 230 235 240

Met Thr Lys Asn Gln Val Ser Leu Thr Cys Leu Val Lys Gly Phe Tyr
245 250 255

Pro Ser Asp Ile Ala Val Glu Trp Glu Ser Asn Gly Gln Pro Glu Asn
260 265 270

Asn Tyr Lys Thr Thr Pro Pro Val Leu Asp Ser Asp Gly Ser Phe Phe
275 280 285

Leu Tyr Ser Lys Leu Thr Val Asp Lys Ser Arg Trp Gln Gln Gly Asn
290 295 300

Val Phe Ser Cys Ser Val Met His Glu Ala Leu His Asn His Tyr Thr
305 310 315 320

Gln Lys Ser Leu Ser Leu Ser Pro Gly Lys
325 330

<210> SEQ ID NO 280
<211> LENGTH: 252
<212> TYPE: PRT
<213> ORGANISM: Artificial Sequence
<220> FEATURE:
<223> OTHER INFORMATION: Synthetic: IgG1 Fc from scFv-Fc

<400> SEQUENCE: 280

Ala Ala Gly Ser Asp Gln Glu Pro Lys Ser Ser Asp Lys Thr His Thr
1               5                   10                  15

Cys Pro Pro Cys Ser Ala Pro Glu Leu Leu Gly Gly Ser Ser Val Phe
                20                  25                  30

Leu Phe Pro Pro Lys Pro Lys Asp Thr Leu Met Ile Ser Arg Thr Pro
            35                  40                  45

Glu Val Thr Cys Val Val Val Asp Val Ser His Glu Asp Pro Glu Val
    50                  55                  60

Lys Phe Asn Trp Tyr Val Asp Gly Val Glu Val His Asn Ala Lys Thr
65                  70                  75                  80

Lys Pro Arg Glu Glu Gln Tyr Asn Ser Thr Tyr Arg Val Val Ser Val
                85                  90                  95

Leu Thr Val Leu His Gln Asp Trp Leu Asn Gly Lys Glu Tyr Lys Cys
            100                 105                 110

Lys Val Ser Asn Lys Ala Leu Pro Ala Pro Ile Glu Lys Thr Ile Ser
        115                 120                 125

Lys Ala Lys Gly Gln Pro Arg Glu Pro Gln Val Tyr Thr Leu Pro Pro
    130                 135                 140

Ser Arg Asp Glu Leu Thr Lys Asn Gln Val Ser Leu Thr Cys Leu Val
145                 150                 155                 160

Lys Gly Phe Tyr Pro Ser Asp Ile Ala Val Glu Trp Glu Ser Asn Gly
                165                 170                 175

Gln Pro Glu Asn Asn Tyr Lys Thr Thr Pro Pro Val Leu Asp Ser Asp
            180                 185                 190

Gly Ser Phe Phe Leu Tyr Ser Lys Leu Thr Val Asp Lys Ser Arg Trp
        195                 200                 205

Gln Gln Gly Asn Val Phe Ser Cys Ser Val Met His Glu Ala Leu His
    210                 215                 220

Asn His Tyr Thr Gln Lys Ser Leu Ser Leu Ser Pro Gly Lys Gly Ser

```
                225                 230                 235                 240
Gly Asp Tyr Lys Asp Asp Asp Lys Gly Ser Gly
                245                 250
```

<210> SEQ ID NO 281
<211> LENGTH: 106
<212> TYPE: PRT
<213> ORGANISM: Artificial Sequence
<220> FEATURE:
<223> OTHER INFORMATION: Synthetic: Lambda Constant Region

<400> SEQUENCE: 281

```
Gly Gln Pro Lys Ala Ala Pro Ser Val Thr Leu Phe Pro Pro Ser Ser
1               5                   10                  15

Glu Glu Leu Gln Ala Asn Lys Ala Thr Leu Val Cys Leu Ile Ser Asp
                20                  25                  30

Phe Tyr Pro Gly Ala Val Thr Val Ala Trp Lys Ala Asp Ser Ser Pro
            35                  40                  45

Val Lys Ala Gly Val Glu Thr Thr Thr Pro Ser Lys Gln Ser Asn Asn
    50                  55                  60

Lys Tyr Ala Ala Ser Ser Tyr Leu Ser Leu Thr Pro Glu Gln Trp Lys
65                  70                  75                  80

Ser His Arg Ser Tyr Ser Cys Gln Val Thr His Glu Gly Ser Thr Val
                85                  90                  95

Glu Lys Thr Val Ala Pro Thr Glu Cys Ser
            100                 105
```

<210> SEQ ID NO 282
<211> LENGTH: 107
<212> TYPE: PRT
<213> ORGANISM: Artificial Sequence
<220> FEATURE:
<223> OTHER INFORMATION: Synthetic: Kappa Constant Region

<400> SEQUENCE: 282

```
Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
                20                  25                  30

Tyr Pro Arg Glu Ala Lys Val Gln Trp Lys Val Asp Asn Ala Leu Gln
            35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105
```

<210> SEQ ID NO 283
<211> LENGTH: 15
<212> TYPE: PRT
<213> ORGANISM: Artificial Sequence
<220> FEATURE:
<223> OTHER INFORMATION: Synthetic: Linker

<400> SEQUENCE: 283

```
Gly Gly Gly Gly Ser Gly Gly Gly Ser Gly Gly Gly Gly Ser
1               5                   10                  15
```

<210> SEQ ID NO 284
<211> LENGTH: 6
<212> TYPE: PRT
<213> ORGANISM: Artificial Sequence
<220> FEATURE:
<223> OTHER INFORMATION: Synthetic: Linker

<400> SEQUENCE: 284

Ala Ala Gly Ser Asp Gln
1               5

<210> SEQ ID NO 285
<211> LENGTH: 20
<212> TYPE: PRT
<213> ORGANISM: Artificial Sequence
<220> FEATURE:
<223> OTHER INFORMATION: Synthetic: His Tag with Linker

<400> SEQUENCE: 285

Gly Ser Gly Asp Tyr Lys Asp Asp Asp Lys Gly Ser Gly His His
1               5                   10                  15

His His His His
            20

<210> SEQ ID NO 286
<211> LENGTH: 7
<212> TYPE: PRT
<213> ORGANISM: Artificial Sequence
<220> FEATURE:
<223> OTHER INFORMATION: Synthetic: mAb_3-1, CDR-H1

<400> SEQUENCE: 286

Gly Tyr Ala Phe Thr Asn Tyr
1               5

<210> SEQ ID NO 287
<211> LENGTH: 7
<212> TYPE: PRT
<213> ORGANISM: Artificial Sequence
<220> FEATURE:
<223> OTHER INFORMATION: Synthetic: mAb_3-5, CDR-H1

<400> SEQUENCE: 287

Gly Tyr Thr Phe Thr Ser Tyr
1               5

<210> SEQ ID NO 288
<211> LENGTH: 7
<212> TYPE: PRT
<213> ORGANISM: Artificial Sequence
<220> FEATURE:
<223> OTHER INFORMATION: Synthetic: mAb_4-1, CDR-H1

<400> SEQUENCE: 288

Gly Tyr Ala Phe Thr Asn Tyr
1               5

<210> SEQ ID NO 289
<211> LENGTH: 7
<212> TYPE: PRT
<213> ORGANISM: Artificial Sequence
<220> FEATURE:
<223> OTHER INFORMATION: Synthetic: mAb_4-7, CDR-H1

<400> SEQUENCE: 289

Gly Tyr Thr Phe Thr Asn Tyr
1               5

<210> SEQ ID NO 290
<211> LENGTH: 7
<212> TYPE: PRT
<213> ORGANISM: Artificial Sequence
<220> FEATURE:
<223> OTHER INFORMATION: Synthetic: mAb_5-10, CDR-H1

<400> SEQUENCE: 290

Gly Tyr Ala Phe Thr Asn Tyr
1               5

<210> SEQ ID NO 291
<211> LENGTH: 5
<212> TYPE: PRT
<213> ORGANISM: Artificial Sequence
<220> FEATURE:
<223> OTHER INFORMATION: Synthetic: mAb_3-1, CDR-H1

<400> SEQUENCE: 291

Asn Tyr Trp Leu Gly
1               5

<210> SEQ ID NO 292
<211> LENGTH: 5
<212> TYPE: PRT
<213> ORGANISM: Artificial Sequence
<220> FEATURE:
<223> OTHER INFORMATION: Synthetic: mAb_3-5, CDR-H1

<400> SEQUENCE: 292

Ser Tyr Gly Leu Ser
1               5

<210> SEQ ID NO 293
<211> LENGTH: 5
<212> TYPE: PRT
<213> ORGANISM: Artificial Sequence
<220> FEATURE:
<223> OTHER INFORMATION: Synthetic: mAb_4-1, CDR-H1

<400> SEQUENCE: 293

Asn Tyr Trp Leu Gly
1               5

<210> SEQ ID NO 294
<211> LENGTH: 5
<212> TYPE: PRT
<213> ORGANISM: Artificial Sequence
<220> FEATURE:
<223> OTHER INFORMATION: Synthetic: mAb_4-7, CDR-H1

<400> SEQUENCE: 294

Asn Tyr Gly Leu Ser
1               5

<210> SEQ ID NO 295
<211> LENGTH: 5
<212> TYPE: PRT
<213> ORGANISM: Artificial Sequence
<220> FEATURE:
<223> OTHER INFORMATION: Synthetic: mAb_5-10, CDR-H1

<400> SEQUENCE: 295

Asn Tyr Trp Leu Gly

-continued

```
1               5

<210> SEQ ID NO 296
<211> LENGTH: 6
<212> TYPE: PRT
<213> ORGANISM: Artificial Sequence
<220> FEATURE:
<223> OTHER INFORMATION: Synthetic: mAb_3-1, CDR-H2

<400> SEQUENCE: 296

Phe Pro Gly Ser Gly Asn
1               5

<210> SEQ ID NO 297
<211> LENGTH: 6
<212> TYPE: PRT
<213> ORGANISM: Artificial Sequence
<220> FEATURE:
<223> OTHER INFORMATION: Synthetic: mAb_3-5, CDR-H2

<400> SEQUENCE: 297

Tyr Pro Arg Ile Gly Asn
1               5

<210> SEQ ID NO 298
<211> LENGTH: 6
<212> TYPE: PRT
<213> ORGANISM: Artificial Sequence
<220> FEATURE:
<223> OTHER INFORMATION: Synthetic: mAb_4-1, CDR-H2

<400> SEQUENCE: 298

Phe Pro Gly Ser Gly Asn
1               5

<210> SEQ ID NO 299
<211> LENGTH: 6
<212> TYPE: PRT
<213> ORGANISM: Artificial Sequence
<220> FEATURE:
<223> OTHER INFORMATION: Synthetic: mAb_4-7, CDR-H2

<400> SEQUENCE: 299

Tyr Pro Arg Ile Gly Asn
1               5

<210> SEQ ID NO 300
<211> LENGTH: 6
<212> TYPE: PRT
<213> ORGANISM: Artificial Sequence
<220> FEATURE:
<223> OTHER INFORMATION: Synthetic: mAb_5-10, CDR-H2

<400> SEQUENCE: 300

Phe Pro Gly Ser Gly Asn
1               5

<210> SEQ ID NO 301
<211> LENGTH: 17
<212> TYPE: PRT
<213> ORGANISM: Artificial Sequence
<220> FEATURE:
<223> OTHER INFORMATION: Synthetic: mAb_3-1, CDR-H2

<400> SEQUENCE: 301

Asp Leu Phe Pro Gly Ser Gly Asn Thr His Tyr Asn Glu Arg Phe Arg
1               5                   10                  15
```

<210> SEQ ID NO 302
<211> LENGTH: 17
<212> TYPE: PRT
<213> ORGANISM: Artificial Sequence
<220> FEATURE:
<223> OTHER INFORMATION: Synthetic: mAb_3-5, CDR-H2

<400> SEQUENCE: 302

Glu Val Tyr Pro Arg Ile Gly Asn Ala Tyr Tyr Asn Glu Lys Phe Lys
1               5                   10                  15
Gly

<210> SEQ ID NO 303
<211> LENGTH: 17
<212> TYPE: PRT
<213> ORGANISM: Artificial Sequence
<220> FEATURE:
<223> OTHER INFORMATION: Synthetic: mAb_4-1, CDR-H2

<400> SEQUENCE: 303

Asp Ile Phe Pro Gly Ser Gly Asn Ala His Tyr Asn Glu Lys Phe Lys
1               5                   10                  15
Gly

<210> SEQ ID NO 304
<211> LENGTH: 17
<212> TYPE: PRT
<213> ORGANISM: Artificial Sequence
<220> FEATURE:
<223> OTHER INFORMATION: Synthetic: mAb_4-7, CDR-H2

<400> SEQUENCE: 304

Glu Val Tyr Pro Arg Ile Gly Asn Ala Tyr Tyr Asn Glu Lys Phe Lys
1               5                   10                  15
Gly

<210> SEQ ID NO 305
<211> LENGTH: 17
<212> TYPE: PRT
<213> ORGANISM: Artificial Sequence
<220> FEATURE:
<223> OTHER INFORMATION: Synthetic: mAb_5-10, CDR-H2

<400> SEQUENCE: 305

Asp Ile Phe Pro Gly Ser Gly Asn Ile His Tyr Asn Glu Lys Phe Lys
1               5                   10                  15
Gly

<210> SEQ ID NO 306
<211> LENGTH: 10
<212> TYPE: PRT
<213> ORGANISM: Artificial Sequence
<220> FEATURE:
<223> OTHER INFORMATION: Synthetic: mAb_3-1, CDR-H3

<400> SEQUENCE: 306

Leu Arg Asn Trp Asp Glu Ala Met Asp Tyr
1               5                   10

<210> SEQ ID NO 307
<211> LENGTH: 14

```
<212> TYPE: PRT
<213> ORGANISM: Artificial Sequence
<220> FEATURE:
<223> OTHER INFORMATION: Synthetic: mAb_3-5, CDR-H3

<400> SEQUENCE: 307

Arg Gly Ser Tyr Gly Ser Asn Tyr Asp Trp Tyr Phe Asp Val
1               5                   10

<210> SEQ ID NO 308
<211> LENGTH: 10
<212> TYPE: PRT
<213> ORGANISM: Artificial Sequence
<220> FEATURE:
<223> OTHER INFORMATION: Synthetic: mAb_4-1, CDR-H3

<400> SEQUENCE: 308

Leu Arg Asn Trp Asp Glu Ala Met Asp Tyr
1               5                   10

<210> SEQ ID NO 309
<211> LENGTH: 14
<212> TYPE: PRT
<213> ORGANISM: Artificial Sequence
<220> FEATURE:
<223> OTHER INFORMATION: Synthetic: mAb_4-7, CDR-H3

<400> SEQUENCE: 309

Arg Gly Ser Tyr Asp Thr Asn Tyr Asp Trp Tyr Phe Asp Val
1               5                   10

<210> SEQ ID NO 310
<211> LENGTH: 10
<212> TYPE: PRT
<213> ORGANISM: Artificial Sequence
<220> FEATURE:
<223> OTHER INFORMATION: Synthetic: mAb_5-10, CDR-H3

<400> SEQUENCE: 310

Leu Arg Asn Trp Asp Glu Pro Met Asp Tyr
1               5                   10

<210> SEQ ID NO 311
<211> LENGTH: 11
<212> TYPE: PRT
<213> ORGANISM: Artificial Sequence
<220> FEATURE:
<223> OTHER INFORMATION: Synthetic: mAb_3-1, CDR-L1

<400> SEQUENCE: 311

Arg Ala Ser Lys Ser Ile Ser Lys Tyr Leu Ala
1               5                   10

<210> SEQ ID NO 312
<211> LENGTH: 16
<212> TYPE: PRT
<213> ORGANISM: Artificial Sequence
<220> FEATURE:
<223> OTHER INFORMATION: Synthetic: mAb_3-5, CDR-L1

<400> SEQUENCE: 312

Arg Ser Ser Gln Ser Leu Val His Ser Asn Gly Asn Thr Tyr Leu His
1               5                   10                  15

<210> SEQ ID NO 313
<211> LENGTH: 17
<212> TYPE: PRT
```

```
<213> ORGANISM: Artificial Sequence
<220> FEATURE:
<223> OTHER INFORMATION: Synthetic: mAb_4-1, CDR-L1

<400> SEQUENCE: 313

Lys Ser Ser Gln Ser Leu Leu Asn Ser Gly Asn Gln Lys Asn Tyr Leu
1               5                   10                  15

Ala

<210> SEQ ID NO 314
<211> LENGTH: 16
<212> TYPE: PRT
<213> ORGANISM: Artificial Sequence
<220> FEATURE:
<223> OTHER INFORMATION: Synthetic: mAb_4-7, CDR-L1

<400> SEQUENCE: 314

Arg Ser Ser Gln Ser Leu Val His Ser Asn Gly Asn Thr Tyr Leu His
1               5                   10                  15

<210> SEQ ID NO 315
<211> LENGTH: 17
<212> TYPE: PRT
<213> ORGANISM: Artificial Sequence
<220> FEATURE:
<223> OTHER INFORMATION: Synthetic: mAb_5-10, CDR-L1

<400> SEQUENCE: 315

Lys Ser Ser Gln Ser Leu Leu Asn Ser Gly Asn Gln Lys Asn Tyr Leu
1               5                   10                  15

Thr

<210> SEQ ID NO 316
<211> LENGTH: 7
<212> TYPE: PRT
<213> ORGANISM: Artificial Sequence
<220> FEATURE:
<223> OTHER INFORMATION: Synthetic: mAb_3-1, CDR-L2

<400> SEQUENCE: 316

Ser Gly Ser Thr Leu Gln Ser
1               5

<210> SEQ ID NO 317
<211> LENGTH: 7
<212> TYPE: PRT
<213> ORGANISM: Artificial Sequence
<220> FEATURE:
<223> OTHER INFORMATION: Synthetic: mAb_3-5, CDR-L2

<400> SEQUENCE: 317

Lys Val Ser Asn Arg Phe Ser
1               5

<210> SEQ ID NO 318
<211> LENGTH: 7
<212> TYPE: PRT
<213> ORGANISM: Artificial Sequence
<220> FEATURE:
<223> OTHER INFORMATION: Synthetic: mAb_4-1, CDR-L2

<400> SEQUENCE: 318

Gly Ala Ser Thr Arg Glu Ser
1               5
```

<210> SEQ ID NO 319
<211> LENGTH: 7
<212> TYPE: PRT
<213> ORGANISM: Artificial Sequence
<220> FEATURE:
<223> OTHER INFORMATION: Synthetic: mAb_4-7, CDR-L2

<400> SEQUENCE: 319

Lys Val Ser Asn Arg Phe Ser
1               5

<210> SEQ ID NO 320
<211> LENGTH: 7
<212> TYPE: PRT
<213> ORGANISM: Artificial Sequence
<220> FEATURE:
<223> OTHER INFORMATION: Synthetic: mAb_5-10, CDR-L2

<400> SEQUENCE: 320

Trp Ala Ser Thr Arg Glu Ser
1               5

<210> SEQ ID NO 321
<211> LENGTH: 9
<212> TYPE: PRT
<213> ORGANISM: Artificial Sequence
<220> FEATURE:
<223> OTHER INFORMATION: Synthetic: mAb_3-1, CDR-L3

<400> SEQUENCE: 321

Gln Gln His Asn Glu Tyr Pro Tyr Thr
1               5

<210> SEQ ID NO 322
<211> LENGTH: 9
<212> TYPE: PRT
<213> ORGANISM: Artificial Sequence
<220> FEATURE:
<223> OTHER INFORMATION: Synthetic: mAb_3-5, CDR-L3

<400> SEQUENCE: 322

Ser Gln Ser Thr His Val Pro Tyr Thr
1               5

<210> SEQ ID NO 323
<211> LENGTH: 9
<212> TYPE: PRT
<213> ORGANISM: Artificial Sequence
<220> FEATURE:
<223> OTHER INFORMATION: Synthetic: mAb_4-1, CDR-L3

<400> SEQUENCE: 323

Gln Asn Asp Tyr Ser Tyr Pro Tyr Thr
1               5

<210> SEQ ID NO 324
<211> LENGTH: 9
<212> TYPE: PRT
<213> ORGANISM: Artificial Sequence
<220> FEATURE:
<223> OTHER INFORMATION: Synthetic: mAb_4-7, CDR-L3

<400> SEQUENCE: 324

Ser Gln Ser Thr His Val Pro Tyr Thr
1               5

<210> SEQ ID NO 325

```
<211> LENGTH: 9
<212> TYPE: PRT
<213> ORGANISM: Artificial Sequence
<220> FEATURE:
<223> OTHER INFORMATION: Synthetic: mAb_5-10, CDR-L3

<400> SEQUENCE: 325

Gln Asn Asp Tyr Ser Tyr Pro Leu Thr
1               5

<210> SEQ ID NO 326
<211> LENGTH: 120
<212> TYPE: PRT
<213> ORGANISM: Artificial Sequence
<220> FEATURE:
<223> OTHER INFORMATION: Synthetic: mAb_3-1, VH

<400> SEQUENCE: 326

Glu Val Gln Leu Leu Glu Gln Ser Gly Ala Glu Leu Val Lys Pro Gly
1               5                   10                  15

Ala Ser Val Lys Ile Ser Cys Lys Ala Ser Gly Tyr Ala Phe Thr Asn
            20                  25                  30

Tyr Trp Leu Gly Trp Val Lys Gln Arg Pro Gly His Gly Leu Glu Trp
        35                  40                  45

Ile Gly Asp Leu Phe Pro Gly Ser Gly Asn Thr His Tyr Asn Glu Arg
    50                  55                  60

Phe Arg Gly Lys Ala Thr Leu Thr Ala Asp Lys Ser Ser Ser Thr Ala
65                  70                  75                  80

Phe Met Gln Leu Ser Ser Leu Thr Ser Glu Asp Ser Ala Val Tyr Phe
                85                  90                  95

Cys Ala Arg Leu Arg Asn Trp Asp Glu Ala Met Asp Tyr Trp Gly Gln
            100                 105                 110

Gly Thr Thr Val Thr Val Ser Ser
        115                 120

<210> SEQ ID NO 327
<211> LENGTH: 124
<212> TYPE: PRT
<213> ORGANISM: Artificial Sequence
<220> FEATURE:
<223> OTHER INFORMATION: Synthetic: mAb_3-5, VH

<400> SEQUENCE: 327

Glu Val Gln Leu Leu Glu Gln Ser Gly Ala Glu Leu Val Arg Pro Gly
1               5                   10                  15

Thr Ser Val Lys Leu Ser Cys Lys Ala Ser Gly Tyr Thr Phe Thr Ser
            20                  25                  30

Tyr Gly Leu Ser Trp Val Lys Gln Arg Thr Gly Gln Gly Leu Glu Trp
        35                  40                  45

Ile Gly Glu Val Tyr Pro Arg Ile Gly Asn Ala Tyr Tyr Asn Glu Lys
    50                  55                  60

Phe Lys Gly Lys Ala Thr Leu Thr Ala Asp Lys Ser Ser Ser Thr Ala
65                  70                  75                  80

Ser Met Glu Leu Arg Ser Leu Thr Ser Glu Asp Ser Ala Val Tyr Phe
                85                  90                  95

Cys Ala Arg Arg Gly Ser Tyr Gly Ser Asn Tyr Asp Trp Tyr Phe Asp
            100                 105                 110

Val Trp Gly Gln Gly Thr Thr Val Thr Val Ser Ser
        115                 120
```

<210> SEQ ID NO 328
<211> LENGTH: 120
<212> TYPE: PRT
<213> ORGANISM: Artificial Sequence
<220> FEATURE:
<223> OTHER INFORMATION: Synthetic: mAb_4-1, VH

<400> SEQUENCE: 328

Glu Val Gln Leu Leu Glu Gln Ser Gly Ala Glu Leu Val Arg Pro Gly
1               5                   10                  15

Thr Ser Val Lys Ile Ser Cys Lys Ala Ser Gly Tyr Ala Phe Thr Asn
            20                  25                  30

Tyr Trp Leu Gly Trp Val Lys Gln Arg Pro Gly His Gly Leu Glu Trp
        35                  40                  45

Val Gly Asp Ile Phe Pro Gly Ser Gly Asn Ala His Tyr Asn Glu Lys
    50                  55                  60

Phe Lys Gly Lys Ala Thr Leu Thr Ala Asp Lys Ser Ser Tyr Thr Ala
65                  70                  75                  80

Tyr Met Gln Leu Ser Ser Leu Thr Ser Glu Asp Ser Ala Val Tyr Phe
                85                  90                  95

Cys Ala Arg Leu Arg Asn Trp Asp Glu Ala Met Asp Tyr Trp Gly Gln
            100                 105                 110

Gly Thr Thr Val Thr Val Ser Ser
        115                 120

<210> SEQ ID NO 329
<211> LENGTH: 124
<212> TYPE: PRT
<213> ORGANISM: Artificial Sequence
<220> FEATURE:
<223> OTHER INFORMATION: Synthetic: mAb_4-7, VH

<400> SEQUENCE: 329

Glu Val Gln Leu Leu Glu Gln Ser Gly Ala Glu Leu Ala Arg Pro Gly
1               5                   10                  15

Ala Ser Val Lys Leu Ser Cys Lys Ala Ser Gly Tyr Thr Phe Thr Asn
            20                  25                  30

Tyr Gly Leu Ser Trp Val Lys Gln Arg Pro Gly Gln Val Leu Glu Trp
        35                  40                  45

Ile Gly Glu Val Tyr Pro Arg Ile Gly Asn Ala Tyr Tyr Asn Glu Lys
    50                  55                  60

Phe Lys Gly Lys Ala Thr Leu Thr Ala Asp Lys Ser Ser Thr Ala
65                  70                  75                  80

Ser Met Glu Leu Arg Ser Leu Thr Ser Glu Asp Ser Ala Val Tyr Phe
                85                  90                  95

Cys Ala Arg Arg Gly Ser Tyr Asp Thr Asn Tyr Asp Tyr Phe Asp
            100                 105                 110

Val Trp Gly Gln Gly Thr Thr Val Thr Val Ser Ser
        115                 120

<210> SEQ ID NO 330
<211> LENGTH: 120
<212> TYPE: PRT
<213> ORGANISM: Artificial Sequence
<220> FEATURE:
<223> OTHER INFORMATION: Synthetic: mAb_5-10, VH

<400> SEQUENCE: 330

Glu Val Gln Leu Leu Glu Gln Ser Gly Ala Glu Leu Val Arg Pro Gly

```
1               5                   10                  15
Thr Ser Val Lys Ile Ser Cys Lys Ala Ser Gly Tyr Ala Phe Thr Asn
                20                  25                  30

Tyr Trp Leu Gly Trp Val Lys Gln Arg Pro Gly His Gly Leu Glu Trp
            35                  40                  45

Ile Gly Asp Ile Phe Pro Ser Gly Asn Ile His Tyr Asn Glu Lys
        50                  55                  60

Phe Lys Gly Lys Ala Thr Leu Thr Ala Asp Lys Ser Ser Ser Thr Ala
65                  70                  75                  80

Tyr Met Gln Leu Ser Ser Leu Thr Phe Glu Asp Ser Ala Val Tyr Phe
                85                  90                  95

Cys Ala Arg Leu Arg Asn Trp Asp Glu Pro Met Asp Tyr Trp Gly Gln
            100                 105                 110

Gly Thr Thr Val Thr Val Ser Ser
            115                 120

<210> SEQ ID NO 331
<211> LENGTH: 107
<212> TYPE: PRT
<213> ORGANISM: Artificial Sequence
<220> FEATURE:
<223> OTHER INFORMATION: Synthetic: mAb_3-1, VL

<400> SEQUENCE: 331

Glu Leu Val Met Thr Gln Ser Pro Ser Tyr Leu Ala Ala Ser Pro Gly
1               5                   10                  15

Glu Thr Ile Thr Ile Asn Cys Arg Ala Ser Lys Ser Ile Ser Lys Tyr
                20                  25                  30

Leu Ala Trp Tyr Gln Glu Lys Pro Gly Lys Thr Asn Lys Leu Leu Ile
            35                  40                  45

Tyr Ser Gly Ser Thr Leu Gln Ser Gly Ile Pro Ser Arg Phe Ser Gly
        50                  55                  60

Ser Gly Ser Gly Thr Asp Phe Thr Leu Thr Ile Ser Ser Leu Glu Pro
65                  70                  75                  80

Glu Asp Phe Ala Met Tyr Tyr Cys Gln Gln His Asn Glu Tyr Pro Tyr
                85                  90                  95

Thr Phe Gly Gly Gly Thr Lys Leu Glu Ile Lys
            100                 105

<210> SEQ ID NO 332
<211> LENGTH: 112
<212> TYPE: PRT
<213> ORGANISM: Artificial Sequence
<220> FEATURE:
<223> OTHER INFORMATION: Synthetic: mAb_3-5, VL

<400> SEQUENCE: 332

Glu Leu Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser
                20                  25                  30

Asn Gly Asn Thr Tyr Leu His Trp Tyr Leu Gln Lys Pro Gly Gln Ser
            35                  40                  45

Pro Lys Leu Leu Ile Tyr Lys Val Ser Asn Arg Phe Ser Gly Val Pro
        50                  55                  60

Asp Arg Phe Ser Gly Ser Gly Ser Gly Thr Asp Phe Thr Leu Lys Ile
65                  70                  75                  80
```

Ser Arg Val Glu Ala Glu Asp Leu Gly Val Tyr Phe Cys Ser Gln Ser
                85                  90                  95

Thr His Val Pro Tyr Thr Phe Gly Gly Gly Thr Lys Leu Glu Ile Lys
            100                 105                 110

<210> SEQ ID NO 333
<211> LENGTH: 113
<212> TYPE: PRT
<213> ORGANISM: Artificial Sequence
<220> FEATURE:
<223> OTHER INFORMATION: Synthetic: mAb_4-1, VL

<400> SEQUENCE: 333

Glu Leu Val Met Thr Gln Ser Pro Ser Ser Leu Ser Val Ser Ala Gly
1               5                   10                  15

Glu Lys Val Thr Met Ser Cys Lys Ser Ser Gln Ser Leu Leu Asn Ser
            20                  25                  30

Gly Asn Gln Lys Asn Tyr Leu Ala Trp Tyr Gln Gln Lys Pro Gly Gln
        35                  40                  45

Pro Pro Lys Leu Leu Ile Tyr Gly Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Gln Asn
                85                  90                  95

Asp Tyr Ser Tyr Pro Tyr Thr Phe Gly Gly Gly Thr Lys Leu Glu Ile
            100                 105                 110

Lys

<210> SEQ ID NO 334
<211> LENGTH: 112
<212> TYPE: PRT
<213> ORGANISM: Artificial Sequence
<220> FEATURE:
<223> OTHER INFORMATION: Synthetic: mAb_4-7, VL

<400> SEQUENCE: 334

Glu Leu Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr His Val Pro Tyr Thr Phe Gly Gly Gly Thr Lys Leu Glu Ile Lys
            100                 105                 110

<210> SEQ ID NO 335
<211> LENGTH: 113
<212> TYPE: PRT
<213> ORGANISM: Artificial Sequence
<220> FEATURE:
<223> OTHER INFORMATION: Synthetic: mAb_5-10, VL

<400> SEQUENCE: 335

Glu Leu Val Met Thr Gln Ser Pro Ser Ser Leu Thr Val Thr Ala Gly
1               5                   10                  15

Glu Lys Val Thr Met Ser Cys Lys Ser Ser Gln Ser Leu Leu Asn Ser
            20                  25                  30

Gly Asn Gln Lys Asn Tyr Leu Thr Trp Tyr Gln Lys Pro Gly Gln
        35                  40                  45

Pro Pro Lys Leu Leu Ile Tyr Trp Ala Ser Thr Arg Glu Ser Gly Val
50                      55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Gln Asn
                85                  90                  95

Asp Tyr Ser Tyr Pro Leu Thr Phe Gly Ala Gly Thr Lys Leu Glu Ile
            100                 105                 110

Lys

<210> SEQ ID NO 336
<211> LENGTH: 248
<212> TYPE: PRT
<213> ORGANISM: Artificial Sequence
<220> FEATURE:
<223> OTHER INFORMATION: Synthetic: mAB_5-10, scFv

<400> SEQUENCE: 336

Glu Leu Val Met Thr Gln Ser Pro Ser Ser Leu Thr Val Thr Ala Gly
1               5                   10                  15

Glu Lys Val Thr Met Ser Cys Lys Ser Ser Gln Ser Leu Leu Asn Ser
            20                  25                  30

Gly Asn Gln Lys Asn Tyr Leu Thr Trp Tyr Gln Lys Pro Gly Gln
        35                  40                  45

Pro Pro Lys Leu Leu Ile Tyr Trp Ala Ser Thr Arg Glu Ser Gly Val
50                      55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Gln Asn
                85                  90                  95

Asp Tyr Ser Tyr Pro Leu Thr Phe Gly Ala Gly Thr Lys Leu Glu Ile
            100                 105                 110

Lys Gly Gly Gly Gly Ser Gly Gly Gly Ser Gly Gly Gly Ser
        115                 120                 125

Glu Val Gln Leu Leu Glu Gln Ser Gly Ala Glu Leu Val Arg Pro Gly
        130                 135                 140

Thr Ser Val Lys Ile Ser Cys Lys Ala Ser Gly Tyr Ala Phe Thr Asn
145                 150                 155                 160

Tyr Trp Leu Gly Trp Val Lys Gln Arg Pro Gly His Gly Leu Glu Trp
                165                 170                 175

Ile Gly Asp Ile Phe Pro Gly Ser Gly Asn Ile His Tyr Asn Glu Lys
            180                 185                 190

Phe Lys Gly Lys Ala Thr Leu Thr Ala Asp Lys Ser Ser Ser Thr Ala
        195                 200                 205

Tyr Met Gln Leu Ser Ser Leu Thr Phe Glu Asp Ser Ala Val Tyr Phe
    210                 215                 220

Cys Ala Arg Leu Arg Asn Trp Asp Glu Pro Met Asp Tyr Trp Gly Gln
225                 230                 235                 240

```
Gly Thr Thr Val Thr Val Ser Ser
            245

<210> SEQ ID NO 337
<211> LENGTH: 245
<212> TYPE: PRT
<213> ORGANISM: Artificial Sequence
<220> FEATURE:
<223> OTHER INFORMATION: Synthetic: 1304-G11, scFv

<400> SEQUENCE: 337

Met Glu Val Gln Leu Leu Glu Ser Gly Gly Gly Leu Val Arg Pro Gly
1               5                   10                  15

Gly Ser Leu Arg Leu Ser Cys Ala Ala Ser Gly Phe Thr Phe Ser Gly
            20                  25                  30

Ser Ser Met Ser Trp Val Arg Gln Ala Pro Gly Lys Gly Leu Glu Trp
        35                  40                  45

Val Gly Ala Ile Asp Gly Gly Asp Tyr Thr Asn Tyr Ala Asp Ser
    50                  55                  60

Val Arg Gly Arg Phe Thr Ile Ser Arg Asp Asn Ser Lys Asn Thr Leu
65                  70                  75                  80

Tyr Leu Gln Met Asn Ser Leu Arg Ala Glu Asp Thr Ala Val Tyr Tyr
                85                  90                  95

Cys Ala Lys Gly Trp His Pro Gln Thr Tyr Tyr Gly Leu Asp Tyr Trp
            100                 105                 110

Gly Gln Gly Thr Leu Val Thr Val Ser Ser Gly Gly Gly Ser Gly
        115                 120                 125

Gly Gly Gly Ser Gly Gly Gly Ser Glu Ile Val Leu Thr Gln Ser
    130                 135                 140

Pro Gly Thr Leu Ser Leu Ser Pro Gly Glu Arg Ala Thr Leu Ser Cys
145                 150                 155                 160

Arg Ala Ser Gln Ser Val Ser Ser Ser Tyr Leu Ala Trp Tyr Gln Gln
                165                 170                 175

Lys Pro Gly Gln Ala Pro Arg Leu Leu Ile Tyr Gly Ala Ser Ser Arg
            180                 185                 190

Ala Thr Gly Ile Pro Asp Arg Phe Ser Gly Ser Ser Gly Thr Asp
        195                 200                 205

Phe Thr Leu Thr Ile Ser Arg Leu Glu Pro Glu Asp Phe Ala Val Tyr
    210                 215                 220

Tyr Cys Gln Gln Tyr Trp Tyr Gly Pro Pro Thr Phe Gly Gln Gly Thr
225                 230                 235                 240

Lys Val Glu Ile Lys
            245

<210> SEQ ID NO 338
<211> LENGTH: 249
<212> TYPE: PRT
<213> ORGANISM: Artificial Sequence
<220> FEATURE:
<223> OTHER INFORMATION: Synthetic: 1332-A05, scFv

<400> SEQUENCE: 338

Met Glu Leu Val Met Thr Gln Ser Pro Ser Ser Leu Val Thr Ala
1               5                   10                  15

Gly Glu Lys Val Thr Met Ser Cys Lys Ser Ser Gln Ser Leu Leu Asn
            20                  25                  30

Ser Gly Asn Gln Lys Asn Tyr Leu Thr Trp Tyr Gln Gln Lys Pro Gly
        35                  40                  45
```

Gln Pro Pro Lys Leu Leu Ile Tyr Trp Ala Ser Thr Arg Glu Ser Gly
            50                  55                  60

Val Pro Asp Arg Phe Thr Gly Ser Gly Ser Gly Thr Asp Phe Thr Leu
 65                  70                  75                  80

Thr Ile Ser Ser Val Gln Ala Glu Asp Leu Ala Val Tyr Tyr Cys Gln
                 85                  90                  95

Asn Asp Leu Ser Tyr Pro Leu Thr Phe Gly Ala Gly Thr Lys Leu Glu
            100                 105                 110

Ile Lys Gly Gly Gly Gly Ser Gly Gly Gly Ser Gly Gly Gly Gly
            115                 120                 125

Ser Glu Val Gln Leu Leu Glu Gln Ser Gly Ala Glu Leu Val Arg Pro
            130                 135                 140

Gly Thr Ser Val Lys Ile Ser Cys Lys Ala Ser Asp Tyr Ala Phe Ala
145                 150                 155                 160

Asn Arg Trp Leu Gly Trp Val Lys Gln Arg Pro Gly His Gly Leu Glu
                165                 170                 175

Trp Ile Gly Asp Ile Phe Pro Gly Ser Gly Asn Ile His Tyr Asn Glu
            180                 185                 190

Lys Phe Lys Gly Lys Ala Thr Leu Thr Ala Asp Lys Ser Ser Ser Thr
            195                 200                 205

Ala Tyr Met Gln Leu Ser Ser Leu Thr Phe Glu Asp Ser Ala Val Tyr
            210                 215                 220

Phe Cys Ala Arg Leu Arg Asn Trp Glu Gly Pro Met Asp Tyr Trp Gly
225                 230                 235                 240

Gln Gly Thr Thr Val Thr Val Ser Ser
                245

<210> SEQ ID NO 339
<211> LENGTH: 249
<212> TYPE: PRT
<213> ORGANISM: Artificial Sequence
<220> FEATURE:
<223> OTHER INFORMATION: Synthetic: 1332-C01, scFv

<400> SEQUENCE: 339

Met Glu Leu Val Met Thr Gln Ser Pro Ser Ser Leu Thr Val Thr Ala
 1               5                  10                  15

Gly Glu Lys Val Thr Met Ser Cys Lys Ser Ser Gln Ser Leu Leu Asn
             20                  25                  30

Ser Gly Asn Gln Lys Asn Tyr Leu Thr Trp Tyr Gln Gln Lys Pro Gly
         35                  40                  45

Gln Pro Pro Lys Leu Leu Ile Tyr Trp Ala Ser Thr Arg Glu Ser Gly
     50                  55                  60

Val Pro Asp Arg Phe Thr Gly Ser Gly Ser Gly Thr Asp Phe Thr Leu
 65                  70                  75                  80

Thr Ile Ser Ser Val Gln Ala Glu Asp Leu Ala Val Tyr Tyr Cys Gln
                 85                  90                  95

Asn Asp Tyr Arg Tyr Pro Leu Thr Phe Gly Ala Gly Thr Lys Leu Glu
            100                 105                 110

Ile Lys Gly Gly Gly Gly Ser Gly Gly Gly Gly Ser Gly Gly Gly Gly
            115                 120                 125

Ser Glu Val Gln Leu Leu Glu Gln Ser Gly Ala Glu Leu Val Arg Pro
            130                 135                 140

Gly Thr Ser Val Lys Ile Ser Cys Lys Ala Ser Gly Tyr Ala Phe Thr
145                 150                 155                 160

```
Asn Ser Trp Leu Gly Trp Val Lys Gln Arg Pro Gly His Gly Leu Glu
                165                 170                 175

Trp Ile Gly Asp Ile Phe Pro Gly Ser Gly Asn Ile His Tyr Asn Glu
            180                 185                 190

Lys Phe Lys Gly Lys Ala Thr Leu Thr Ala Asp Lys Ser Ser Ser Thr
        195                 200                 205

Ala Tyr Met Gln Leu Ser Ser Leu Thr Phe Glu Asp Ser Ala Val Tyr
    210                 215                 220

Phe Cys Ala Arg Leu Arg Asn Trp Asp Met Pro Met Asp Tyr Trp Gly
225                 230                 235                 240

Gln Gly Thr Thr Val Thr Val Ser Ser
                245

<210> SEQ ID NO 340
<211> LENGTH: 249
<212> TYPE: PRT
<213> ORGANISM: Artificial Sequence
<220> FEATURE:
<223> OTHER INFORMATION: Synthetic: 1332-F11, scFv

<400> SEQUENCE: 340

Met Glu Leu Val Met Thr Gln Ser Pro Ser Ser Leu Thr Val Thr Ala
1               5                   10                  15

Gly Glu Lys Val Thr Met Ser Cys Lys Ser Ser Gln Ser Leu Leu Asn
            20                  25                  30

Ser Gly Asn Gln Lys Asn Tyr Leu Thr Trp Tyr Gln Gln Lys Pro Gly
        35                  40                  45

Gln Pro Pro Lys Leu Leu Ile Tyr Arg Ala Ser Thr Arg Glu Ser Gly
    50                  55                  60

Val Pro Asp Arg Phe Thr Gly Ser Gly Ser Gly Thr Asp Phe Thr Leu
65                  70                  75                  80

Thr Ile Ser Ser Val Gln Ala Glu Asp Leu Ala Val Tyr Tyr Cys Gln
                85                  90                  95

Asn Asp Ser Ser Tyr Pro Leu Thr Phe Gly Ala Gly Thr Lys Leu Glu
                100                 105                 110

Ile Lys Gly Gly Gly Gly Ser Gly Gly Gly Ser Gly Gly Gly Gly Gly
            115                 120                 125

Ser Glu Val Gln Leu Leu Glu Gln Ser Gly Ala Glu Leu Val Arg Pro
        130                 135                 140

Gly Thr Ser Val Lys Ile Ser Cys Lys Ala Ser Gly Tyr Ala Phe Ala
145                 150                 155                 160

Asn Arg Trp Leu Gly Trp Val Lys Gln Arg Pro Gly His Gly Leu Glu
                165                 170                 175

Trp Ile Gly Asp Ile Phe Pro Gly Ser Gly Asn Ile His Tyr Asn Glu
            180                 185                 190

Lys Phe Lys Gly Lys Ala Thr Leu Thr Ala Asp Lys Ser Ser Ser Thr
        195                 200                 205

Ala Tyr Met Gln Leu Ser Ser Leu Thr Phe Glu Asp Ser Ala Val Tyr
    210                 215                 220

Phe Cys Ala Arg Leu Arg Asn Trp Glu Gly Pro Met Asp Tyr Trp Gly
225                 230                 235                 240

Gln Gly Thr Thr Val Thr Val Ser Ser
                245

<210> SEQ ID NO 341
```

```
<211> LENGTH: 245
<212> TYPE: PRT
<213> ORGANISM: Artificial Sequence
<220> FEATURE:
<223> OTHER INFORMATION: Synthetic: 1464-A02, scFv

<400> SEQUENCE: 341

Met Glu Val Gln Leu Leu Glu Ser Gly Gly Gly Leu Val Gln Pro Gly
1               5                   10                  15

Gly Ser Leu Arg Leu Ser Cys Ala Ala Ser Gly Phe Thr Phe Gly Val
            20                  25                  30

Glu Ser Met Ser Trp Val Arg Gln Ala Pro Gly Lys Gly Leu Glu Trp
        35                  40                  45

Val Gly Ala Ile Asp Gly Gly Asp Gly Tyr Thr Gly Tyr Ala Asp Ser
    50                  55                  60

Val Lys Asp Arg Phe Thr Ile Ser Arg Asp Asn Ser Lys Asn Thr Leu
65                  70                  75                  80

Tyr Leu Gln Met Asn Ser Leu Arg Ala Glu Asp Thr Ala Val Tyr Tyr
                85                  90                  95

Cys Ala Lys Ala Trp His Pro Gln Thr Tyr Tyr Gly Val Asp Tyr Trp
            100                 105                 110

Gly Gln Gly Thr Leu Val Thr Val Ser Ser Gly Gly Gly Gly Ser Gly
        115                 120                 125

Gly Gly Gly Ser Gly Gly Gly Ser Glu Ile Val Leu Thr Gln Ser
    130                 135                 140

Pro Gly Thr Leu Ser Leu Ser Pro Gly Glu Arg Ala Thr Leu Ser Cys
145                 150                 155                 160

Arg Ala Ser Gln Ser Val Ser Ser Ser Tyr Leu Ala Trp Tyr Gln Gln
                165                 170                 175

Lys Pro Gly Gln Ala Pro Arg Leu Leu Ile Tyr Gly Ala Ser Ser Arg
            180                 185                 190

Ala Thr Gly Ile Pro Asp Arg Phe Ser Gly Ser Gly Ser Gly Thr Asp
        195                 200                 205

Phe Thr Leu Thr Ile Ser Arg Leu Glu Pro Glu Asp Phe Ala Val Tyr
    210                 215                 220

Tyr Cys Gln Gln Thr Ser Glu Ala Pro Pro Thr Phe Gly Gln Gly Thr
225                 230                 235                 240

Lys Val Glu Ile Lys
                245

<210> SEQ ID NO 342
<211> LENGTH: 245
<212> TYPE: PRT
<213> ORGANISM: Artificial Sequence
<220> FEATURE:
<223> OTHER INFORMATION: Synthetic: 1464-A08, scFv

<400> SEQUENCE: 342

Met Glu Val Gln Leu Leu Glu Ser Gly Gly Gly Leu Val Gln Pro Gly
1               5                   10                  15

Gly Ser Leu Arg Leu Ser Cys Ala Ala Ser Gly Phe Thr Phe Ser Gly
            20                  25                  30

Ser Ser Met Ser Trp Val Arg Gln Ala Pro Gly Lys Gly Leu Glu Trp
        35                  40                  45

Val Gly Ala Ile Ala Gly Gly Asp Gly Tyr Thr Gly Tyr Ala Asp Ser
    50                  55                  60

Val Lys Gly Arg Phe Thr Ile Ser Arg Asp Asn Ser Lys Asn Thr Leu
```

```
            65                  70                  75                  80
Tyr Leu Gln Met Asn Ser Leu Arg Ala Glu Asp Thr Ala Val Tyr Tyr
                    85                  90                  95

Cys Ala Lys Gly Trp His Arg Gln Asp Tyr Tyr Gly Gln Asp Tyr Trp
                100                 105                 110

Gly Gln Gly Thr Leu Val Thr Val Ser Ser Gly Gly Gly Ser Gly
            115                 120                 125

Gly Gly Gly Ser Gly Gly Gly Ser Glu Ile Val Leu Thr Gln Ser
130                 135                 140

Pro Gly Thr Leu Ser Leu Ser Pro Gly Glu Arg Ala Thr Leu Gly Cys
145                 150                 155                 160

Arg Ala Ser Gln Ser Val Ser Ser Ser Tyr Leu Ala Trp Tyr Gln Gln
                165                 170                 175

Lys Pro Gly Gln Ala Pro Arg Leu Leu Ile Tyr Gly Ala Ser Ser Arg
            180                 185                 190

Ala Thr Gly Ile Pro Asp Arg Phe Ser Gly Ser Gly Ser Gly Thr Asp
            195                 200                 205

Phe Thr Leu Thr Ile Ser Arg Leu Glu Pro Glu Asp Phe Ala Val Tyr
            210                 215                 220

Tyr Cys Gln Gln Asn Gln Ala Ala Pro Ala Thr Phe Gly Gln Gly Thr
225                 230                 235                 240

Lys Val Glu Ile Lys
            245

<210> SEQ ID NO 343
<211> LENGTH: 245
<212> TYPE: PRT
<213> ORGANISM: Artificial Sequence
<220> FEATURE:
<223> OTHER INFORMATION: Synthetic: 1464-B04, scFv

<400> SEQUENCE: 343

Met Glu Val Gln Leu Leu Glu Ser Gly Gly Gly Leu Val Gln Pro Gly
1               5                   10                  15

Gly Ser Leu Arg Leu Ser Cys Ala Ala Ser Gly Phe Thr Phe Ser Gly
            20                  25                  30

Ser Ser Met Ser Trp Val Arg Gln Ala Pro Gly Lys Gly Leu Glu Trp
        35                  40                  45

Val Gly Ala Ile Asp Gly Gly Glu Gly Tyr Thr Ser Tyr Ala Asp Ser
    50                  55                  60

Val Lys Gly Arg Phe Thr Ile Ser Arg Asp Asn Ser Lys Asn Thr Leu
65                  70                  75                  80

Tyr Leu Gln Met Asn Ser Leu Arg Ala Glu Asp Thr Ala Val Tyr Tyr
                85                  90                  95

Cys Ala Lys Gly Trp His Pro Gln Thr Leu Tyr Asp Leu Asp Tyr Trp
                100                 105                 110

Gly Gln Gly Thr Leu Val Thr Val Ser Ser Gly Gly Gly Ser Gly
            115                 120                 125

Gly Gly Gly Ser Gly Gly Gly Ser Glu Ile Val Leu Thr Gln Ser
130                 135                 140

Pro Gly Thr Leu Ser Leu Ser Pro Gly Glu Arg Ala Thr Leu Ser Cys
145                 150                 155                 160

Arg Ala Ser Gln Ser Val Ser Ser Ser Tyr Leu Ala Trp Tyr Gln Gln
                165                 170                 175

Lys Pro Gly Gln Ala Pro Arg Leu Leu Ile Tyr Gly Ala Ser Ser Arg
```

```
                180                 185                 190
Ala Thr Gly Ile Pro Asp Arg Phe Ser Gly Ser Gly Ser Gly Thr Asp
            195                 200                 205

Phe Thr Leu Thr Ile Ser Arg Leu Glu Pro Glu Asp Phe Ala Val Tyr
        210                 215                 220

Tyr Cys Gln Gln Leu Val Thr Ser Pro Pro Thr Phe Gly Gln Gly Thr
225                 230                 235                 240

Lys Val Glu Ile Lys
            245

<210> SEQ ID NO 344
<211> LENGTH: 245
<212> TYPE: PRT
<213> ORGANISM: Artificial Sequence
<220> FEATURE:
<223> OTHER INFORMATION: Synthetic: 1557-A04, scFv

<400> SEQUENCE: 344

Met Glu Val Gln Leu Leu Glu Ser Gly Gly Gly Leu Val Gln Pro Gly
1               5                   10                  15

Gly Ser Leu Arg Leu Ser Cys Ala Ala Ser Gly Phe Thr Phe Ser Gly
            20                  25                  30

Ser Ser Met Ser Trp Val Arg Gln Ala Pro Gly Lys Gly Leu Glu Trp
        35                  40                  45

Val Gly Ala Ile Asp Gly Glu Gly Ser Thr Ala Tyr Ala Asp Ser
    50                  55                  60

Val Lys Gly Arg Phe Thr Ile Ser Arg Asp Asn Ser Lys Asn Thr Leu
65                  70                  75                  80

Tyr Leu Gln Met Asn Ser Leu Arg Ala Glu Asp Thr Ala Val Tyr Tyr
                85                  90                  95

Cys Ala Lys Gly Trp His Pro Gln Thr Met Tyr Asp Leu Asp Tyr Trp
            100                 105                 110

Gly Gln Gly Thr Leu Val Thr Val Ser Ser Gly Gly Gly Gly Ser Gly
        115                 120                 125

Gly Gly Gly Ser Gly Gly Gly Gly Asn Glu Ile Val Leu Thr Gln Ser
    130                 135                 140

Pro Gly Thr Leu Ser Leu Ser Pro Gly Glu Arg Ala Thr Leu Ser Cys
145                 150                 155                 160

Arg Ala Ser Gln Asn Val Ser Thr Asn Tyr Leu Ala Trp Tyr Gln Gln
                165                 170                 175

Lys Pro Gly Gln Ala Pro Arg Leu Leu Ile Tyr Gly Ala Ser Ser Arg
            180                 185                 190

Ala Thr Gly Ile Pro Asp Arg Phe Ser Gly Ser Gly Ser Gly Thr Asp
        195                 200                 205

Phe Thr Leu Thr Ile Ser Arg Leu Glu Pro Glu Asp Phe Ala Val Tyr
    210                 215                 220

Tyr Cys Gln Gln Leu Val Thr Asn Pro Pro Thr Phe Gly Gln Gly Thr
225                 230                 235                 240

Lys Val Glu Ile Lys
            245

<210> SEQ ID NO 345
<211> LENGTH: 245
<212> TYPE: PRT
<213> ORGANISM: Artificial Sequence
<220> FEATURE:
<223> OTHER INFORMATION: Synthetic: 1557-A05, scFv
```

<400> SEQUENCE: 345

```
Met Glu Val Gln Leu Leu Glu Ser Gly Gly Gly Leu Val Gln Pro Gly
1               5                   10                  15

Gly Ser Leu Arg Leu Ser Cys Ala Ala Ser Gly Phe Thr Phe Gly Gly
            20                  25                  30

Ser Ser Met Ser Trp Val Arg Gln Ala Pro Gly Lys Gly Leu Glu Trp
        35                  40                  45

Val Gly Ala Ile Gly Gly Glu Gly Ser Thr Gly Tyr Ala Asp Ser
    50                  55                  60

Val Lys Gly Arg Phe Thr Ile Ser Arg Asp Asn Ser Lys Asn Thr Leu
65                  70                  75                  80

Tyr Leu Gln Met Asn Ser Leu Arg Ala Glu Asp Thr Ala Val Tyr Tyr
                85                  90                  95

Cys Ala Lys Gly Trp His Asp Gln Ser Leu Tyr Asp Arg Asp Tyr Trp
            100                 105                 110

Gly Gln Gly Thr Leu Val Thr Val Ser Ser Gly Gly Gly Gly Ser Gly
            115                 120                 125

Gly Gly Ser Gly Gly Gly Ser Glu Ile Val Leu Thr Gln Ser
            130                 135                 140

Pro Gly Thr Leu Ser Leu Ser Pro Gly Glu Arg Ala Thr Leu Ser Cys
145                 150                 155                 160

Ser Ala Ser Gln Thr Val Ser Ser Tyr Ile Ala Trp Tyr Gln Gln
                165                 170                 175

Lys Pro Gly Gln Ala Pro Arg Leu Leu Ile Tyr Gly Ala Ser Ser Arg
            180                 185                 190

Ala Thr Gly Ile Pro Asp Arg Phe Gly Gly Ser Gly Ser Gly Thr Asp
            195                 200                 205

Phe Thr Leu Thr Ile Ser Arg Leu Glu Pro Glu Asp Phe Ala Val Tyr
            210                 215                 220

Tyr Cys Gln Gln Leu Leu Thr Ser Pro Pro Thr Phe Gly Gln Gly Thr
225                 230                 235                 240

Lys Val Glu Ile Lys
            245
```

<210> SEQ ID NO 346
<211> LENGTH: 245
<212> TYPE: PRT
<213> ORGANISM: Artificial Sequence
<220> FEATURE:
<223> OTHER INFORMATION: Synthetic: 1557-B03, scFv

<400> SEQUENCE: 346

```
Met Glu Val Gln Leu Leu Glu Ser Gly Gly Gly Leu Val Gln Pro Gly
1               5                   10                  15

Gly Ser Leu Arg Leu Ser Cys Ala Ala Ser Gly Phe Thr Phe Arg Ser
            20                  25                  30

Ser Ser Met Ser Trp Val Arg Gln Ala Pro Gly Lys Gly Leu Glu Trp
        35                  40                  45

Val Gly Ala Ile Gly Gly His Glu Gly Tyr Thr Gly Tyr Ala Asp Ser
    50                  55                  60

Val Lys Gly Arg Phe Thr Ile Ser Arg Asp Asn Ser Lys Asn Thr Leu
65                  70                  75                  80

Tyr Leu Gln Met Asn Ser Leu Arg Ala Glu Asp Thr Ala Val Tyr Tyr
                85                  90                  95
```

```
Cys Ala Lys Gly Trp Asn Pro Gln Thr Leu Tyr His Leu Asp Tyr Trp
                100                 105                 110
Gly Gln Gly Thr Leu Val Thr Val Ser Ser Gly Gly Gly Gly Ser Gly
            115                 120                 125
Gly Gly Gly Ser Gly Gly Gly Ser Glu Ile Val Leu Thr Gln Ser
        130                 135                 140
Pro Gly Thr Leu Ser Leu Ser Pro Gly Glu Arg Ala Thr Leu Ser Cys
145                 150                 155                 160
Arg Ala Ser Gln Lys Cys Ser Ser Ser Met Ala Trp Tyr Gln Gln
                165                 170                 175
Lys Pro Gly Gln Ala Pro Arg Leu Leu Ile Tyr Gly Ala Ser Ser Arg
                180                 185                 190
Ala Thr Gly Ile Pro Asp Arg Phe Ser Gly Ser Gly Ser Gly Thr Asp
            195                 200                 205
Phe Thr Leu Thr Ile Ser Arg Leu Glu Pro Glu Asp Phe Ala Val Tyr
        210                 215                 220
Tyr Cys Gln Gln Leu Gln Thr Ser Pro Pro Thr Phe Gly Gln Gly Thr
225                 230                 235                 240
Lys Val Glu Ile Lys
                245

<210> SEQ ID NO 347
<211> LENGTH: 245
<212> TYPE: PRT
<213> ORGANISM: Artificial Sequence
<220> FEATURE:
<223> OTHER INFORMATION: Synthetic: 1557-B10, scFv

<400> SEQUENCE: 347

Met Glu Val Gln Leu Leu Glu Ser Gly Gly Gly Leu Val Gln Pro Gly
1               5                   10                  15
Gly Ser Leu Arg Leu Ser Cys Ala Ala Ser Gly Phe Thr Phe Ser Gly
            20                  25                  30
Cys Ser Met Ser Trp Val Arg Gln Ala Pro Gly Lys Gly Leu Glu Trp
        35                  40                  45
Val Gly Ala Ile Ala Gly Glu Gly Asn Thr Gly Tyr Ala Asp Ser
    50                  55                  60
Val Lys Gly Arg Phe Thr Ile Ser Arg Asp Asn Ser Lys Asn Thr Leu
65                  70                  75                  80
Tyr Leu Gln Met Asn Ser Leu Arg Ala Glu Asp Thr Ala Val Tyr Tyr
                85                  90                  95
Cys Ala Lys Gly Trp His Pro Gln Thr Leu Tyr Asp Leu Asp Tyr Trp
                100                 105                 110
Gly Gln Gly Thr Leu Val Thr Val Ser Ser Gly Gly Gly Gly Ser Gly
            115                 120                 125
Gly Gly Gly Ser Gly Gly Gly Ser Glu Ile Val Leu Thr Gln Ser
        130                 135                 140
Pro Gly Thr Leu Ser Leu Ser Pro Gly Glu Arg Ala Thr Leu Ser Cys
145                 150                 155                 160
Arg Ala Ser Gln Gly Leu Ala Ser Arg Tyr Met Ala Trp Tyr Gln Gln
                165                 170                 175
Lys Pro Gly Gln Ala Pro Arg Leu Leu Ile Tyr Gly Ala Ser Ser Arg
                180                 185                 190
Ala Thr Gly Ile Pro Asp Arg Phe Ser Gly Ser Gly Ser Gly Thr Asp
            195                 200                 205
```

Phe Thr Leu Thr Ile Ser Arg Leu Glu Pro Glu Asp Phe Ala Val Tyr
    210                 215                 220

Tyr Cys Gln Gln Val Met Thr Ile Pro Pro Thr Phe Gly Gln Gly Thr
225                 230                 235                 240

Lys Val Glu Ile Lys
            245

<210> SEQ ID NO 348
<211> LENGTH: 245
<212> TYPE: PRT
<213> ORGANISM: Artificial Sequence
<220> FEATURE:
<223> OTHER INFORMATION: Synthetic: 1557-C06, scFv

<400> SEQUENCE: 348

Met Glu Val Gln Leu Leu Glu Ser Gly Gly Gly Leu Val Gln Pro Gly
1               5                   10                  15

Gly Ser Leu Arg Leu Ser Cys Ala Ala Ser Gly Phe Thr Phe Arg Gly
            20                  25                  30

Ala Ser Met Ser Trp Val Arg Gln Ala Pro Gly Lys Gly Leu Glu Trp
        35                  40                  45

Val Gly Ala Ile Asp Gly Ser Gln Gly Ser Thr Gly Tyr Ala Asp Ser
    50                  55                  60

Val Lys Gly Arg Phe Thr Ile Ser Arg Asp Asn Ser Lys Asn Thr Leu
65                  70                  75                  80

Tyr Leu Gln Met Asn Ser Leu Arg Ala Glu Asp Thr Ala Val Tyr Tyr
                85                  90                  95

Cys Ala Lys Gly Trp His Pro Gln Thr Met Tyr Asp Leu Asp Tyr Trp
            100                 105                 110

Gly Gln Gly Thr Leu Val Thr Val Ser Ser Gly Gly Cys Gly Ser Gly
        115                 120                 125

Gly Gly Gly Ser Gly Gly Gly Ser Glu Ile Val Leu Thr Gln Ser
    130                 135                 140

Pro Gly Thr Leu Ser Leu Ser Pro Gly Glu Arg Ala Thr Leu Ser Cys
145                 150                 155                 160

Arg Ala Ser Gln Arg Gly Thr Ser Ser Tyr Leu Ala Trp Tyr Gln Gln
                165                 170                 175

Lys Pro Gly Gln Ala Pro Arg Leu Leu Ile Tyr Gly Ala Ser Ser Arg
            180                 185                 190

Ala Thr Gly Ile Pro Asp Arg Phe Ser Gly Ser Gly Ser Gly Thr Asp
        195                 200                 205

Phe Thr Leu Thr Ile Ser Arg Leu Glu Pro Glu Asp Phe Ala Val Tyr
    210                 215                 220

Tyr Cys Gln Gln His Val Thr Ser Pro Pro Thr Phe Gly Gln Gly Thr
225                 230                 235                 240

Lys Val Glu Ile Lys
            245

<210> SEQ ID NO 349
<211> LENGTH: 245
<212> TYPE: PRT
<213> ORGANISM: Artificial Sequence
<220> FEATURE:
<223> OTHER INFORMATION: Synthetic: 1557-E07, scFv

<400> SEQUENCE: 349

Met Glu Val Gln Leu Leu Glu Ser Gly Gly Gly Leu Val Gln Pro Gly
1               5                   10                  15

```
Gly Ser Leu Arg Leu Ser Cys Ala Ala Ser Gly Phe Thr Phe Ser Gly
            20                  25                  30

Ser Ser Met Ser Trp Val Arg Gln Ala Pro Gly Lys Gly Leu Glu Trp
        35                  40                  45

Val Gly Ala Ile Asp Gly Gly Glu Gly Ser Thr Gly Tyr Ala Asp Ser
50                  55                  60

Val Lys Gly Arg Phe Thr Ile Ser Arg Asp Asn Ser Lys Asn Thr Leu
65                  70                  75                  80

Tyr Leu Gln Met Asn Ser Leu Arg Ala Glu Asp Thr Ala Val Tyr Tyr
                85                  90                  95

Cys Ala Lys Gly Trp His Pro Gln Thr Leu Tyr Asp Leu Asp Tyr Trp
            100                 105                 110

Gly Gln Gly Thr Leu Val Thr Val Ser Ser Gly Gly Gly Gly Ser Gly
        115                 120                 125

Gly Gly Ser Gly Gly Gly Ser Glu Ile Val Leu Thr Gln Ser
130                 135                 140

Pro Gly Thr Leu Ser Leu Ser Pro Gly Glu Arg Ala Thr Met Ser Cys
145                 150                 155                 160

Arg Ala Ser Gln Val Leu Ser Ser Ser Leu Ala Trp Tyr Gln Gln
                165                 170                 175

Lys Pro Gly Gln Ala Pro Arg Leu Leu Ile Tyr Gly Ala Ser Ser Arg
            180                 185                 190

Ala Thr Gly Ile Pro Asp Arg Phe Ser Gly Ser Gly Ser Gly Thr Asp
        195                 200                 205

Phe Ala Leu Thr Ile Ser Arg Leu Glu Pro Glu Asp Phe Ala Val Tyr
210                 215                 220

Tyr Cys Gln Gln Arg Ala Ala Pro Pro Thr Phe Gly Gln Gly Thr
225                 230                 235                 240

Lys Val Glu Ile Lys
            245

<210> SEQ ID NO 350
<211> LENGTH: 245
<212> TYPE: PRT
<213> ORGANISM: Artificial Sequence
<220> FEATURE:
<223> OTHER INFORMATION: Synthetic: 1557-E08, scFv

<400> SEQUENCE: 350

Met Glu Val Gln Leu Leu Glu Ser Gly Gly Gly Leu Val Gln Pro Gly
1               5                   10                  15

Gly Ser Leu Arg Leu Ser Cys Ala Ala Ser Gly Phe Thr Phe Arg Ala
            20                  25                  30

Ser Ser Met Ser Trp Met Arg Gln Ala Pro Gly Lys Gly Leu Glu Trp
        35                  40                  45

Val Gly Ala Ile Asp Gly Gly Val Gly Ser Thr Gly Tyr Ala Asp Ser
50                  55                  60

Val Lys Gly Arg Phe Thr Ile Ser Arg Asp Asn Ser Lys Asn Thr Leu
65                  70                  75                  80

Tyr Leu Gln Met Asn Ser Leu Arg Ala Glu Asp Thr Ala Val Tyr Tyr
                85                  90                  95

Cys Ala Lys Gly Trp His Pro Gln Thr Leu Tyr Asp Leu Asp Tyr Trp
            100                 105                 110

Gly Gln Gly Thr Leu Val Thr Val Ser Ser Gly Gly Gly Gly Ser Gly
        115                 120                 125
```

Gly Gly Gly Ser Gly Gly Gly Ser Glu Ile Val Leu Thr Gln Ser
            130             135                 140

Pro Gly Thr Leu Ser Leu Ser Pro Gly Glu Arg Ala Thr Leu Ser Cys
145                 150                 155                 160

Arg Ala Ser Gln Gly Asp Ser Ser Val Leu Ala Trp Tyr Gln Gln
                165                 170                 175

Lys Pro Gly Gln Ala Pro Arg Leu Leu Ile Tyr Gly Ala Ser Ser Arg
                180                 185                 190

Ala Thr Gly Ile Pro Asp Arg Phe Ser Gly Ser Gly Ser Gly Thr Asp
            195                 200                 205

Phe Thr Leu Thr Ile Ser Arg Leu Glu Pro Glu Asp Phe Ala Val Tyr
            210                 215                 220

Tyr Cys Gln Gln Leu Val Pro Ser Pro Pro Thr Phe Gly Gln Gly Thr
225                 230                 235                 240

Lys Val Glu Ile Lys
            245

<210> SEQ ID NO 351
<211> LENGTH: 245
<212> TYPE: PRT
<213> ORGANISM: Artificial Sequence
<220> FEATURE:
<223> OTHER INFORMATION: Synthetic: 1557-E11, scFv

<400> SEQUENCE: 351

Met Glu Val Gln Leu Leu Glu Ser Gly Gly Gly Leu Val Gln Pro Gly
1               5                   10                  15

Gly Ser Leu Arg Leu Ser Cys Ala Ala Ser Gly Phe Thr Phe Arg Gly
            20                  25                  30

Ser Ser Met Ser Trp Val Arg Gln Ala Pro Gly Lys Gly Leu Glu Trp
        35                  40                  45

Val Gly Ala Ile Asp Gly Gly Glu Gly Ser Thr Gly Tyr Ala Asp Ser
    50                  55                  60

Val Lys Gly Arg Phe Thr Ile Asn Arg Asp Asn Ser Lys Asn Thr Leu
65                  70                  75                  80

Tyr Leu Gln Met Asn Ser Leu Arg Ala Glu Asp Thr Ala Val Tyr Tyr
                85                  90                  95

Cys Ala Lys Gly Trp His Pro Gln Ser Leu Tyr Asp Leu Asp Tyr Trp
            100                 105                 110

Gly Gln Gly Thr Leu Val Thr Val Ser Ser Gly Gly Gly Gly Ser Gly
        115                 120                 125

Gly Gly Asp Ser Gly Gly Gly Ser Glu Ile Val Leu Thr Gln Ser
    130                 135                 140

Pro Gly Thr Leu Ser Leu Ser Pro Gly Glu Arg Ala Thr Leu Ser Cys
145                 150                 155                 160

Arg Ala Ser Gln Pro Val Pro Asn Thr Thr Leu Ala Trp Tyr Gln Gln
                165                 170                 175

Lys Pro Gly Gln Ala Pro Arg Leu Leu Ile Tyr Gly Ala Ser Ser Arg
                180                 185                 190

Ala Thr Gly Ile Pro Asp Arg Phe Ser Gly Ser Gly Ser Gly Thr Asp
            195                 200                 205

Phe Thr Leu Thr Ile Ser Arg Leu Glu Pro Glu Asp Phe Ala Ala Tyr
            210                 215                 220

Tyr Cys Gln Gln Leu Val Pro Ser Pro Pro Thr Phe Gly Gln Gly Thr
225                 230                 235                 240

Lys Val Glu Ile Lys
            245

<210> SEQ ID NO 352
<211> LENGTH: 245
<212> TYPE: PRT
<213> ORGANISM: Artificial Sequence
<220> FEATURE:
<223> OTHER INFORMATION: Synthetic: 1557-F01, scFv

<400> SEQUENCE: 352

Met Glu Val Gln Leu Leu Glu Ser Gly Gly Gly Leu Val Gln Pro Gly
1               5                   10                  15

Gly Ser Leu Arg Leu Ser Cys Ala Ala Ser Gly Phe Thr Phe Ser Gly
            20                  25                  30

Ser Ser Met Ser Trp Val Arg Gln Ala Pro Gly Lys Gly Leu Glu Trp
        35                  40                  45

Val Gly Ala Ile Asp Gly Glu Gly Ser Thr Gly Tyr Ala Asp Ser
    50                  55                  60

Val Lys Gly Arg Phe Thr Ile Ser Arg Asp Asn Ser Lys Asn Thr Leu
65                  70                  75                  80

Tyr Leu Gln Met Asn Ser Leu Arg Ala Glu Asp Thr Ala Val Tyr Tyr
                85                  90                  95

Cys Ala Lys Gly Trp His Pro Gln Thr Leu Tyr Asp Leu Asp Tyr Trp
            100                 105                 110

Gly Gln Gly Thr Leu Val Thr Val Ser Ser Gly Gly Gly Gly Ser Gly
        115                 120                 125

Gly Gly Gly Ser Gly Gly Gly Ser Glu Ile Val Leu Thr Gln Ser
    130                 135                 140

Pro Gly Thr Leu Ser Leu Ser Pro Gly Glu Arg Ala Thr Leu Ser Cys
145                 150                 155                 160

Arg Ala Ser Gln Ser Val Ser Ser Ser Lys Leu Ala Trp Tyr Gln Gln
                165                 170                 175

Lys Pro Gly Gln Ala Pro Arg Leu Leu Ile Tyr Gly Ala Ser Ser Arg
            180                 185                 190

Ala Thr Gly Ile Pro Asp Arg Phe Ser Gly Tyr Gly Ser Gly Thr Asp
        195                 200                 205

Phe Thr Leu Thr Ile Ser Arg Leu Glu Pro Glu Asp Phe Ala Val Tyr
    210                 215                 220

Tyr Cys Gln Gln Leu Glu Thr Ile Pro Pro Thr Phe Gly Gln Gly Thr
225                 230                 235                 240

Lys Val Glu Ile Lys
            245

<210> SEQ ID NO 353
<211> LENGTH: 245
<212> TYPE: PRT
<213> ORGANISM: Artificial Sequence
<220> FEATURE:
<223> OTHER INFORMATION: Synthetic: 1557-F02, scFv

<400> SEQUENCE: 353

Met Glu Val Gln Leu Leu Glu Ser Gly Gly Gly Leu Val Gln Pro Gly
1               5                   10                  15

Gly Ser Leu Arg Leu Ser Cys Ala Ala Ser Gly Phe Thr Phe Arg Gly
            20                  25                  30

Ser Ser Met Ser Trp Val Arg Gln Ala Pro Gly Lys Gly Leu Glu Trp

```
               35                  40                  45
Val Gly Ala Ile Asp Gly Gly Glu Gly Ser Thr Gly Tyr Ala Asp Ser
 50                  55                  60

Val Lys Gly Arg Phe Thr Ile Ser Arg Asp Asn Ser Lys Asn Thr Leu
 65                  70                  75                  80

Tyr Leu Gln Met Asn Ser Leu Arg Ala Glu Asp Thr Ala Val Tyr Tyr
                 85                  90                  95

Cys Ala Lys Gly Trp His Pro Gln Thr Met Tyr Asn Leu Asp Tyr Trp
                100                 105                 110

Gly Gln Gly Thr Leu Val Thr Val Ser Ser Gly Gly Gly Ser Gly
                115                 120                 125

Gly Gly Gly Ser Gly Gly Gly Ser Glu Ile Val Leu Thr Gln Ser
            130                 135                 140

Pro Gly Thr Leu Ser Leu Ser Pro Gly Glu Arg Ala Thr Leu Ser Cys
145                 150                 155                 160

Arg Ala Ser Gln Ser Val Ser Ser Ser Tyr Leu Ala Trp Tyr Gln Gln
                165                 170                 175

Lys Pro Gly Gln Ala Pro Arg Leu Leu Ile Tyr Gly Ala Ser Ser Arg
                180                 185                 190

Ala Thr Gly Ile Pro Asp Arg Phe Ser Gly Ser Gly Ser Gly Thr Asp
                195                 200                 205

Phe Thr Leu Thr Ile Ser Arg Leu Glu Pro Glu Asp Phe Ala Val Tyr
                210                 215                 220

Tyr Cys Gln Gln Leu Phe Asn Ser Pro Pro Thr Phe Gly Gln Gly Thr
225                 230                 235                 240

Lys Val Glu Ile Lys
                245

<210> SEQ ID NO 354
<211> LENGTH: 245
<212> TYPE: PRT
<213> ORGANISM: Artificial Sequence
<220> FEATURE:
<223> OTHER INFORMATION: Synthetic: 1557-F03, scFv

<400> SEQUENCE: 354

Met Glu Val Gln Leu Leu Glu Ser Gly Gly Gly Leu Val Gln Pro Gly
  1               5                  10                  15

Gly Ser Leu Arg Leu Ser Cys Ala Ala Ser Gly Phe Thr Phe Ser Gly
                 20                  25                  30

Ser Ser Met Ser Trp Val Arg Gln Ala Pro Gly Lys Gly Leu Glu Trp
                 35                  40                  45

Val Gly Ala Ile Ala Gly Gly Gly Ser Thr Gly Tyr Ala Asp Ser
 50                  55                  60

Val Lys Gly Arg Phe Thr Ile Ser Arg Asp Asn Ser Lys Asn Thr Leu
 65                  70                  75                  80

Tyr Leu Gln Met Asn Ser Leu Arg Ala Glu Asp Thr Ala Val Tyr Tyr
                 85                  90                  95

Cys Ala Lys Gly Trp His Pro Gln Thr Leu Tyr Asp Leu Asp Tyr Trp
                100                 105                 110

Gly Gln Gly Thr Leu Val Thr Val Ser Ser Gly Gly Gly Gly Ser Gly
                115                 120                 125

Gly Gly Gly Ser Gly Gly Gly Gly Ser Glu Ile Val Leu Thr Gln Ser
            130                 135                 140

Pro Gly Thr Leu Ser Leu Ser Pro Gly Glu Arg Ala Thr Leu Ser Cys
```

```
                145                 150                 155                 160
Arg Ala Ser Gln Ser Val Lys Thr Ser Asp Leu Ala Trp Tyr Gln Gln
                    165                 170                 175

Lys Pro Gly Gln Ala Pro Arg Leu Leu Ile Tyr Gly Ala Ser Ser Arg
                180                 185                 190

Ala Thr Gly Ile Pro Asp Arg Phe Ser Gly Ser Gly Ser Gly Thr Asp
                195                 200                 205

Phe Thr Leu Thr Ile Ser Arg Leu Glu Pro Glu Asp Phe Ala Val Tyr
            210                 215                 220

Tyr Cys Gln Gln Leu Val Ser Lys Pro Pro Thr Phe Gly Gln Gly Thr
225                 230                 235                 240

Lys Val Glu Ile Lys
                245

<210> SEQ ID NO 355
<211> LENGTH: 245
<212> TYPE: PRT
<213> ORGANISM: Artificial Sequence
<220> FEATURE:
<223> OTHER INFORMATION: Synthetic: 1557-F05, scFv

<400> SEQUENCE: 355

Met Glu Val Gln Leu Leu Glu Ser Gly Gly Gly Leu Val Gln Pro Gly
1               5                   10                  15

Gly Ser Leu Arg Leu Ser Cys Ala Ala Ser Gly Phe Thr Phe Arg Gly
                20                  25                  30

Ser Ser Met Ser Trp Val Arg Gln Ala Pro Gly Lys Gly Leu Glu Trp
            35                  40                  45

Val Gly Ala Ile Asp Gly Gly Glu Gly Ser Thr Gly Tyr Ala Asp Ser
        50                  55                  60

Val Lys Gly Arg Phe Thr Ile Ser Arg Asp Asn Ser Lys Asn Thr Leu
65                  70                  75                  80

Tyr Leu Gln Met Asn Ser Leu Arg Ala Glu Asp Thr Ala Val Tyr Tyr
                85                  90                  95

Cys Ala Lys Asp Trp His Pro Gln Thr Leu Tyr Asp Leu Asp Tyr Trp
                100                 105                 110

Gly Gln Gly Thr Leu Val Thr Val Ser Ser Gly Gly Gly Gly Ser Gly
            115                 120                 125

Gly Gly Gly Ser Gly Gly Gly Gly Ser Glu Ile Val Leu Thr Gln Ser
        130                 135                 140

Pro Gly Thr Leu Ser Leu Ser Pro Gly Glu Arg Ala Thr Leu Ser Cys
145                 150                 155                 160

Arg Ala Ser Gln Thr Val Ser Pro Ser Val Leu Ala Trp Tyr Gln Gln
                165                 170                 175

Lys Pro Gly Gln Ala Pro Arg Leu Leu Ile Tyr Gly Ala Ser Ser Arg
                180                 185                 190

Ala Thr Gly Ile Pro Gly Arg Phe Ser Gly Ser Gly Ser Gly Thr Asp
                195                 200                 205

Phe Thr Leu Thr Ile Ser Arg Leu Glu Pro Glu Asp Phe Ala Val Tyr
            210                 215                 220

Tyr Cys Gln Gln Leu Val Thr Asn Pro Pro Thr Phe Gly Gln Gly Thr
225                 230                 235                 240

Lys Val Glu Ile Lys
                245
```

<210> SEQ ID NO 356
<211> LENGTH: 245
<212> TYPE: PRT
<213> ORGANISM: Artificial Sequence
<220> FEATURE:
<223> OTHER INFORMATION: Synthetic: 1557-G01, scFv

<400> SEQUENCE: 356

```
Met Glu Val Gln Leu Leu Glu Ser Gly Gly Gly Leu Val Gln Pro Gly
1               5                   10                  15

Gly Ser Leu Arg Leu Ser Cys Ala Ala Ser Gly Phe Thr Phe Ser Val
            20                  25                  30

Thr Ser Met Ser Trp Met Arg Gln Ala Pro Gly Lys Gly Leu Glu Trp
        35                  40                  45

Val Gly Ala Ile Ala Gly Gly Glu Gly Ser Thr Gly Tyr Ala Asp Ser
    50                  55                  60

Val Lys Gly Arg Phe Thr Ile Ser Arg Asp Asn Ser Lys Asn Thr Leu
65                  70                  75                  80

Tyr Leu Gln Met Asn Ser Leu Arg Ala Glu Asp Thr Ala Val Tyr Tyr
                85                  90                  95

Cys Ala Lys Gly Trp His Pro Gln Thr Leu Tyr Asp Leu Asp Tyr Trp
            100                 105                 110

Gly Gln Gly Thr Leu Val Thr Val Ser Ser Gly Gly Gly Gly Ser Gly
        115                 120                 125

Gly Gly Gly Ser Gly Gly Gly Gly Ser Glu Ile Val Leu Thr Gln Ser
    130                 135                 140

Pro Gly Thr Leu Ser Leu Ser Pro Gly Glu Arg Ala Thr Met Ser Cys
145                 150                 155                 160

Arg Ala Ser Gln Val Leu Ser Ser Ser Leu Ala Trp Tyr Gln Gln
                165                 170                 175

Lys Pro Gly Gln Ala Pro Arg Leu Leu Ile Tyr Gly Ala Ser Ser Arg
            180                 185                 190

Ala Thr Gly Ile Pro Asp Arg Phe Ser Gly Ser Gly Ser Gly Thr Asp
        195                 200                 205

Phe Thr Leu Thr Ile Ser Arg Leu Glu Pro Glu Asp Phe Ala Val Tyr
    210                 215                 220

Tyr Cys Gln Gln Leu Val Thr Ser Pro Pro Thr Phe Gly Gln Gly Thr
225                 230                 235                 240

Lys Val Glu Ile Lys
            245
```

<210> SEQ ID NO 357
<211> LENGTH: 245
<212> TYPE: PRT
<213> ORGANISM: Artificial Sequence
<220> FEATURE:
<223> OTHER INFORMATION: Synthetic: 1557-G03, scFv

<400> SEQUENCE: 357

```
Met Glu Val Gln Leu Leu Glu Ser Gly Gly Gly Leu Val Gln Pro Gly
1               5                   10                  15

Gly Ser Leu Arg Leu Ser Cys Ala Ala Ser Gly Phe Thr Phe Gly Gly
            20                  25                  30

Ser Ser Met Ser Trp Val Arg Gln Ala Pro Gly Lys Gly Leu Glu Trp
        35                  40                  45

Val Gly Ala Ile Gly Gly Gly Glu Gly Tyr Thr Gly Tyr Ala Asp Ser
    50                  55                  60
```

Val Lys Gly Arg Phe Thr Ile Ser Arg Asp Asn Ser Lys Asn Thr Leu
65                  70                  75                  80

Tyr Leu Gln Met Asn Ser Leu Arg Ala Glu Asp Thr Ala Val Tyr Tyr
                85                  90                  95

Cys Ala Lys Gly Trp His Pro Gln Thr Leu Tyr Asp Leu Asp Tyr Trp
            100                 105                 110

Gly Gln Gly Thr Leu Val Thr Val Ser Ser Gly Gly Gly Ser Gly
            115                 120                 125

Gly Gly Gly Ser Gly Gly Gly Ser Glu Ile Val Leu Thr Gln Ser
        130                 135                 140

Pro Gly Thr Leu Ser Leu Ser Pro Gly Glu Arg Ala Thr Leu Ser Cys
145                 150                 155                 160

Arg Ala Ser Gln Ser Val His Ser Ser Tyr Leu Ala Trp Tyr Gln Gln
                165                 170                 175

Lys Pro Gly Gln Ala Pro Arg Leu Leu Ile Tyr Gly Ala Ser Ser Arg
            180                 185                 190

Ala Thr Gly Ile Pro Asp Arg Phe Ser Gly Ser Gly Ser Gly Thr Asp
        195                 200                 205

Phe Thr Leu Thr Ile Ser Arg Leu Glu Pro Glu Asp Phe Ala Val Tyr
210                 215                 220

Tyr Cys Gln Gln Leu Leu Ser Ser Pro Pro Thr Phe Gly Gln Gly Thr
225                 230                 235                 240

Lys Val Glu Ile Lys
                245

<210> SEQ ID NO 358
<211> LENGTH: 245
<212> TYPE: PRT
<213> ORGANISM: Artificial Sequence
<220> FEATURE:
<223> OTHER INFORMATION: Synthetic: 1557-G04, scFv

<400> SEQUENCE: 358

Met Glu Val Gln Leu Leu Glu Ser Gly Gly Gly Leu Val Gln Pro Gly
1               5                   10                  15

Gly Ser Leu Arg Leu Ser Cys Ala Ala Ser Gly Phe Thr Phe Cys Gly
            20                  25                  30

Ser Ser Met Ser Trp Val Arg Gln Ala Pro Gly Lys Gly Leu Glu Trp
        35                  40                  45

Val Gly Ala Ile Asp Gly Gly Val Gly Ser Thr Gly Tyr Ala Asp Ser
    50                  55                  60

Val Lys Gly Arg Phe Thr Ile Ser Arg Asp Asn Ser Lys Asn Thr Leu
65                  70                  75                  80

Tyr Leu Gln Met Asn Ser Leu Arg Ala Glu Asp Thr Ala Val Tyr Tyr
                85                  90                  95

Cys Ala Lys Gly Trp His Pro Gln Thr Leu Tyr Asp Leu Asp Tyr Trp
            100                 105                 110

Gly Gln Gly Thr Leu Val Thr Val Ser Ser Gly Gly Asp Ser Gly
            115                 120                 125

Gly Gly Gly Ser Gly Gly Gly Ser Glu Ile Val Leu Thr Gln Ser
        130                 135                 140

Pro Gly Thr Leu Ser Leu Ser Pro Gly Glu Arg Ala Thr Leu Ser Cys
145                 150                 155                 160

Arg Ala Ser Gln Ser Val Ser Ser Ser Tyr Leu Ala Trp Tyr Gln Gln
                165                 170                 175

```
Lys Pro Gly Gln Ala Pro Arg Leu Leu Ile Tyr Gly Ala Ser Ser Arg
            180                 185                 190

Ala Thr Gly Ile Pro Asp Arg Phe Ser Gly Ser Gly Ser Gly Thr Asp
            195                 200                 205

Phe Thr Leu Thr Ile Ser Arg Leu Glu Pro Glu Asp Phe Ala Val Tyr
            210                 215                 220

Tyr Cys Gln Gln Asp Ser Phe Val Pro Pro Thr Phe Gly Gln Gly Thr
225                 230                 235                 240

Lys Val Glu Ile Lys
            245

<210> SEQ ID NO 359
<211> LENGTH: 245
<212> TYPE: PRT
<213> ORGANISM: Artificial Sequence
<220> FEATURE:
<223> OTHER INFORMATION: Synthetic: 1557-G06, scFv

<400> SEQUENCE: 359

Met Glu Val Gln Leu Leu Glu Ser Gly Gly Gly Leu Val Gln Pro Gly
1               5                   10                  15

Gly Ser Leu Arg Leu Ser Cys Ala Ala Ser Gly Phe Thr Phe Ser Gly
            20                  25                  30

Phe Ser Met Ser Trp Val Arg Gln Ala Pro Gly Lys Gly Leu Glu Trp
        35                  40                  45

Val Gly Ala Ile Asp Gly Gly Glu Ser Thr Gly Tyr Ala Asp Ser
    50                  55                  60

Val Lys Gly Arg Phe Thr Ile Ser Arg Asp Asn Ser Lys Asn Thr Leu
65                  70                  75                  80

Tyr Leu Gln Met Asn Ser Leu Arg Ala Glu Asp Thr Ala Val Tyr Tyr
                85                  90                  95

Cys Ala Lys Gly Trp His Pro Gln Thr Leu Tyr His Leu Asp Tyr Trp
            100                 105                 110

Gly Gln Gly Thr Leu Val Thr Val Ser Ser Gly Gly Gly Gly Ser Gly
        115                 120                 125

Gly Gly Gly Ser Gly Gly Gly Ser Glu Ile Val Leu Thr Gln Ser
    130                 135                 140

Pro Gly Thr Leu Ser Leu Ser Pro Gly Glu Arg Ala Thr Leu Ser Cys
145                 150                 155                 160

Arg Ala Ser Gln Ser Ile Pro Ser Ser Tyr Leu Ala Trp Tyr Gln Gln
                165                 170                 175

Glu Pro Gly Gln Ala Pro Arg Leu Leu Ile Tyr Gly Ala Ser Ser Arg
            180                 185                 190

Ala Thr Gly Ile Pro Asp Arg Phe Ser Gly Ser Gly Ser Gly Thr Asp
            195                 200                 205

Phe Thr Leu Thr Ile Ser Arg Leu Glu Pro Glu Asp Phe Ala Val Tyr
            210                 215                 220

Tyr Cys Gln Gln Leu Ala Thr Ser Pro Pro Thr Phe Gly Gln Gly Thr
225                 230                 235                 240

Lys Val Glu Ile Lys
            245

<210> SEQ ID NO 360
<211> LENGTH: 245
<212> TYPE: PRT
<213> ORGANISM: Artificial Sequence
<220> FEATURE:
```

<223> OTHER INFORMATION: Synthetic: 1557-H04, scFv

<400> SEQUENCE: 360

Met Glu Val Gln Leu Leu Glu Ser Gly Gly Gly Leu Val Gln Pro Gly
1               5                   10                  15

Gly Ser Leu Arg Leu Ser Cys Ala Ala Ser Gly Phe Thr Phe Ser Val
            20                  25                  30

Thr Ser Met Ser Trp Met Arg Gln Ala Pro Gly Lys Gly Leu Glu Trp
        35                  40                  45

Val Gly Ala Ile Ala Gly Gly Glu Gly Ser Thr Gly Tyr Ala Asp Ser
    50                  55                  60

Val Lys Gly Arg Phe Thr Ile Ser Arg Asp Asn Ser Lys Asn Thr Leu
65                  70                  75                  80

Tyr Leu Gln Met Asn Ser Leu Arg Ala Glu Asp Thr Ala Val Tyr Tyr
                85                  90                  95

Cys Ala Lys Gly Trp His Pro Gln Thr Leu Tyr Asp Leu Asp Tyr Trp
            100                 105                 110

Gly Gln Gly Thr Leu Val Thr Val Ser Ser Gly Gly Gly Gly Ser Asp
        115                 120                 125

Gly Gly Gly Ser Gly Gly Gly Ser Glu Ile Val Leu Thr Gln Gly
    130                 135                 140

Pro Ser Thr Leu Ser Leu Ser Pro Gly Glu Arg Ala Thr Leu Ser Cys
145                 150                 155                 160

Arg Ala Ser Gln Ser Val Ser Thr Gly Tyr Leu Ala Trp Tyr Gln Gln
                165                 170                 175

Lys Pro Gly Gln Ala Pro Arg Leu Leu Ile Tyr Gly Ala Ser Ser Arg
            180                 185                 190

Ala Thr Gly Ile Pro Asp Arg Phe Ser Gly Ser Gly Ser Gly Thr Asp
        195                 200                 205

Phe Thr Leu Thr Ile Ser Arg Leu Glu Pro Glu Asp Phe Ala Val Tyr
    210                 215                 220

Tyr Cys Gln Gln Leu Val Thr Arg Pro Pro Thr Phe Gly Gln Gly Thr
225                 230                 235                 240

Lys Val Glu Ile Lys
            245

<210> SEQ ID NO 361
<211> LENGTH: 245
<212> TYPE: PRT
<213> ORGANISM: Artificial Sequence
<220> FEATURE:
<223> OTHER INFORMATION: Synthetic: 1557-H10, scFv

<400> SEQUENCE: 361

Met Glu Val Gln Leu Leu Glu Ser Gly Gly Gly Leu Val Gln Pro Gly
1               5                   10                  15

Gly Ser Leu Arg Leu Ser Cys Ala Ala Ser Gly Phe Thr Phe Ser Gly
            20                  25                  30

Ser Ser Met Ser Trp Val Arg Gln Ala Pro Gly Lys Gly Leu Glu Trp
        35                  40                  45

Val Gly Ala Ile Asp Gly Gly Glu Gly Ser Thr Gly Tyr Ala Asp Ser
    50                  55                  60

Val Lys Gly Arg Phe Thr Ile Ser Arg Asp Asn Ser Lys Asn Thr Leu
65                  70                  75                  80

Tyr Leu Gln Met Asn Ser Leu Arg Ala Glu Asp Thr Ala Val Tyr Tyr
                85                  90                  95

Cys Ala Lys Gly Trp His Pro Gln Ser Met Tyr Asp Leu Asp Tyr Trp
                100                 105                 110

Gly Gln Gly Thr Leu Val Thr Val Ser Ser Gly Gly Gly Ser Gly
            115                 120                 125

Gly Gly Gly Ser Gly Gly Gly Ser Glu Ile Val Leu Thr Gln Ser
130                 135                 140

Pro Gly Thr Leu Ser Leu Ser Pro Gly Glu Arg Ala Thr Met Ser Cys
145                 150                 155                 160

Arg Ala Ser Gln Val Leu Ser Ser Ser Leu Ala Trp Tyr Gln Gln
                165                 170                 175

Lys Pro Gly Gln Ala Pro Arg Leu Leu Ile Tyr Gly Ala Ser Ser Arg
            180                 185                 190

Ala Thr Gly Ile Pro Asp Arg Phe Ser Gly Ser Gly Ser Gly Thr Asp
                195                 200                 205

Phe Thr Leu Thr Ile Ser Arg Leu Glu Pro Glu Asp Phe Ala Val Tyr
            210                 215                 220

Tyr Cys Gln Gln Leu Val Thr Ala Pro Pro Thr Phe Gly Gln Gly Thr
225                 230                 235                 240

Lys Val Glu Ile Lys
            245

<210> SEQ ID NO 362
<211> LENGTH: 496
<212> TYPE: PRT
<213> ORGANISM: Artificial Sequence
<220> FEATURE:
<223> OTHER INFORMATION: Synthetic: mAB_5-10, scFv-Fc

<400> SEQUENCE: 362

Met Glu Leu Val Met Thr Gln Ser Pro Ser Ser Leu Thr Val Thr Ala
1               5                   10                  15

Gly Glu Lys Val Thr Met Ser Cys Lys Ser Ser Gln Ser Leu Leu Asn
            20                  25                  30

Ser Gly Asn Gln Lys Asn Tyr Leu Thr Trp Tyr Gln Gln Lys Pro Gly
        35                  40                  45

Gln Pro Pro Lys Leu Leu Ile Tyr Trp Ala Ser Thr Arg Glu Ser Gly
    50                  55                  60

Val Pro Asp Arg Phe Thr Gly Ser Gly Ser Gly Thr Asp Phe Thr Leu
65                  70                  75                  80

Thr Ile Ser Ser Val Gln Ala Glu Asp Leu Ala Val Tyr Tyr Cys Gln
                85                  90                  95

Asn Asp Tyr Ser Tyr Pro Leu Thr Phe Gly Ala Gly Thr Lys Leu Glu
            100                 105                 110

Ile Lys Gly Gly Gly Gly Ser Gly Gly Gly Gly Ser Gly Gly Gly Gly
        115                 120                 125

Ser Glu Val Gln Leu Leu Glu Gln Ser Gly Ala Glu Leu Val Arg Pro
    130                 135                 140

Gly Thr Ser Val Lys Ile Ser Cys Lys Ala Ser Gly Tyr Ala Phe Thr
145                 150                 155                 160

Asn Tyr Trp Leu Gly Trp Val Lys Gln Arg Pro Gly His Gly Leu Glu
                165                 170                 175

Trp Ile Gly Asp Ile Phe Pro Gly Ser Gly Asn Ile His Tyr Asn Glu
            180                 185                 190

Lys Phe Lys Gly Lys Ala Thr Leu Thr Ala Asp Lys Ser Ser Ser Thr
        195                 200                 205

```
Ala Tyr Met Gln Leu Ser Ser Leu Thr Phe Glu Asp Ser Ala Val Tyr
    210                 215                 220

Phe Cys Ala Arg Leu Arg Asn Trp Asp Glu Pro Met Asp Tyr Trp Gly
225                 230                 235                 240

Gln Gly Thr Thr Val Thr Val Ser Ser Ala Ala Gly Ser Asp Gln Glu
                245                 250                 255

Pro Lys Ser Ser Asp Lys Thr His Thr Cys Pro Pro Cys Ser Ala Pro
                260                 265                 270

Glu Leu Leu Gly Gly Ser Ser Val Phe Leu Phe Pro Pro Lys Pro Lys
            275                 280                 285

Asp Thr Leu Met Ile Ser Arg Thr Pro Glu Val Thr Cys Val Val Val
    290                 295                 300

Asp Val Ser His Glu Asp Pro Glu Val Lys Phe Asn Trp Tyr Val Asp
305                 310                 315                 320

Gly Val Glu Val His Asn Ala Lys Thr Lys Pro Arg Glu Glu Gln Tyr
                325                 330                 335

Asn Ser Thr Tyr Arg Val Val Ser Val Leu Thr Val Leu His Gln Asp
                340                 345                 350

Trp Leu Asn Gly Lys Glu Tyr Lys Cys Lys Val Ser Asn Lys Ala Leu
            355                 360                 365

Pro Ala Pro Ile Glu Lys Thr Ile Ser Lys Ala Lys Gly Gln Pro Arg
    370                 375                 380

Glu Pro Gln Val Tyr Thr Leu Pro Pro Ser Arg Asp Glu Leu Thr Lys
385                 390                 395                 400

Asn Gln Val Ser Leu Thr Cys Leu Val Lys Gly Phe Tyr Pro Ser Asp
                405                 410                 415

Ile Ala Val Glu Trp Glu Ser Asn Gly Gln Pro Glu Asn Asn Tyr Lys
                420                 425                 430

Thr Thr Pro Pro Val Leu Asp Ser Asp Gly Ser Phe Phe Leu Tyr Ser
            435                 440                 445

Lys Leu Thr Val Asp Lys Ser Arg Trp Gln Gln Gly Asn Val Phe Ser
    450                 455                 460

Cys Ser Val Met His Glu Ala Leu His Asn His Tyr Thr Gln Lys Ser
465                 470                 475                 480

Leu Ser Leu Ser Pro Gly Lys Gly Gly Ser His His His His His His
                485                 490                 495
```

ANTI-EPCAM ANTIBODIES, COMPOSITIONS COMPRISING ANTI-EPCAM ANTIBODIES AND METHODS OF MAKING AND USING ANTI-EPCAM ANTIBODIES

FIELD

Provided herein are antibodies with binding specificity for epithelial cell adhesion molecule (EpCAM) and compositions comprising the antibodies, including pharmaceutical compositions, diagnostic compositions, and kits. Also provided are methods of making anti-EpCAM antibodies, and methods of using anti-EpCAM antibodies, for example, for therapeutic, diagnostic purposes, and research purposes.

BACKGROUND

EpCAM is a type I transmembrane glycoprotein that mediates calcium-independent homotypic epithelial cell-cell adhesion. See Litvinov et al., *J. Cell. Biol.*, 1994, 125:437-446, incorporated by reference in its entirety. EpCAM is also involved in cell signaling, migration, proliferation, and differentiation. See Maetzel et al., *Nature Cell Biol.*, 2009, 11:162-171; Osta et al., *Cancer Res.*, 2004, 64:5818-5824; and Litvinov et al., *Am. J. Pathol.*, 1996, 148:865-875, each of which is incorporated by reference in its entirety.

EpCAM has oncogenic potential via its capacity to upregulate at least c-Myc, E-FABP, and cyclins A and E. See Munz et al., *Oncogene*, 2004, 23:5748-5758, incorporated by reference in its entirety. Because EpCAM is expressed exclusively in epithelia and epithelial-derived neoplasms, it can be used as diagnostic marker for some cancers. It may also be a useful prognostic marker for certain tumor types. See Munz et al., *Cancer Res.*, 2009, 69:5627-5629 and Baeuerle and Gires, *Br. J. Cancer*, 2007, 96:417-423, each of which is incorporated by reference in its entirety.

EpCAM is known to be overexpressed in some cancers, and therefore represents a potential target for cancer therapy. See Osta et al., supra.; Haisma et al., *Gene Therapy*, 1999, 6:1469-1474; Heideman et al., *Cancer Gene Ther.*, 2001, 8:342-351; and Seimetz et al., *Cancer Treatment Reviews*, 2010, 36:458-467, each of which is incorporated by reference in its entirety. Most known EpCAM antibodies bind an epitope encoded by EpCAM exon 2. See Münz et al., *Cancer Cell Int*, 2010, 10:44. One known EpCAM antibody, adecatumumab, binds outside exon 2 at an epitope encoded by EpCAM exon 5. See id. However, adecatumumab does not have significant binding affinity for cynomolgus EpCAM. See id. Cynomolgous cross-reactivity is advantageous because it facilitates evaluation of the potential toxicity of antibodies in a primate model, without exposing human subjects to molecules of unknown toxicity.

There is a need for targeted delivery of therapeutics to tumor cells in a manner that provides a localized therapeutic effect while minimizing or eliminating systemic side-effects. More particularly, in light of the overexpression of EpCAM in various cancers, there is a need for therapeutics that specifically target cancer cells over expressing EpCAM. Particularly advantageous therapeutics would bind epitopes outside those encoded by exon 2 of EpCAM and would cross-react with cynomolgus EpCAM.

SUMMARY

Provided herein are antibodies that specifically bind to EpCAM. In some embodiments, the antibodies bind human EpCAM. In some embodiments, the antibodies also bind homologs of human EpCAM. In some aspects, the homolog is a cynomolgus monkey homolog. In some aspects, the antibodies do not bind a murine homolog. In some embodiments, the antibodies bind to human EpCAM and a cynomolgus monkey homolog, but not a murine homolog.

In some embodiments, the antibodies comprise at least one CDR sequence defined by a consensus sequence provided in this disclosure. In some embodiments, the antibodies comprise an illustrative CDR, $V_H$, or $V_L$ sequence provided in this disclosure, or a variant thereof. In some aspects, the variant is a variant with one or more conservative amino acid substitutions.

Also provided are compositions comprising the antibodies. In some embodiments, the composition is a pharmaceutical composition. In some embodiments, the pharmaceutical composition is for the treatment or diagnosis of a disease or condition, as described further elsewhere in this disclosure. In some embodiments, the pharmaceutical composition is a composition for parenteral administration.

This disclosure also provides methods of making the anti-EpCAM antibodies provided herein. The antibodies can be made, for example, in any suitable cell or organism. The antibodies can also be made in a cell-free reaction mixture.

Also provided are methods of using the anti-EpCAM antibodies provided herein. In some embodiments, the method of use is a method of treatment. In some embodiments, the method of use is a diagnostic method. In some embodiments, the method of use is an analytical method. In some embodiments, the method of use is a method of purifying and/or quantifying EpCAM.

In some embodiments, the antibodies are used to treat a disease or condition. In some aspects, the disease or condition is a cancer.

BRIEF DESCRIPTION OF THE DRAWINGS

FIG. 1 (A-C) provides an alignment of the "1304," "1464," and "1557" $V_H$ sequences provided herein.

FIG. 2 (A, B) provides an alignment of the "1332" $V_H$ sequences provided herein.

FIG. 3 (A, B) provides an alignment of the "1304," "1464," and "1557" $V_L$ sequences provided herein.

FIG. 4 (A, B) provides an alignment of the "1332" $V_L$ sequences provided herein.

DETAILED DESCRIPTION

1. Definitions

Unless otherwise defined, all terms of art, notations and other scientific terminology used herein are intended to have the meanings commonly understood by those of skill in the art to which this invention pertains. In some cases, terms with commonly understood meanings are defined herein for clarity and/or for ready reference, and the inclusion of such definitions herein should not necessarily be construed to represent a difference over what is generally understood in the art. The techniques and procedures described or referenced herein are generally well understood and commonly employed using conventional methodologies by those skilled in the art, such as, for example, the widely utilized molecular cloning methodologies described in Sambrook et al., *Molecular Cloning: A Laboratory Manual* 2nd ed. (1989) Cold Spring Harbor Laboratory Press, Cold Spring Harbor, N.Y. As appropriate, procedures involving the use of commercially available kits and reagents are generally carried out in accordance with manufacturer-defined protocols and conditions unless otherwise noted.

As used herein, the singular forms "a," "an," and "the" include the plural referents unless the context clearly indicates otherwise.

The term "about" indicates and encompasses an indicated value and a range above and below that value. In certain embodiments, the term "about" indicates the designated value±10%, ±5%, or ±1%. In certain embodiments, the term "about" indicates the designated value±one standard deviation of that value.

The term "combinations thereof" includes every possible combination of elements to which the term refers to. For example, a sentence stating that "if $\alpha_2$ is A, then $\alpha_3$ is not D; $\alpha_5$ is not S; or $\alpha_6$ is not S; or combinations thereof" includes the following combinations when $\alpha_2$ is A: (1) $\alpha_3$ is not D; (2) $\alpha_5$ is not S; (3) $\alpha_6$ is not S; (4) $\alpha_3$ is not D; $\alpha_5$ is not S; and $\alpha_6$ is not S; (5) $\alpha_3$ is not D and $\alpha_5$ is not S; (6) $\alpha_3$ is not D and $\alpha_6$ is not S; and (7) $\alpha_5$ is not S and $\alpha_6$ is not S.

The terms "EpCAM" and "EpCAM antigen" are used interchangeably herein. EpCAM is also known by a variety of synonyms, including CD326, Ep-CAM, 17-1A, HEA125, MK-1, GA733-2, EGP-2, EGP34, KSA, TROP-1, ESA, and KS1/4, among others. Unless specified otherwise, the terms include any variants, isoforms and species homologs of human EpCAM that are naturally expressed by cells, or that are expressed by cells transfected with an EpCAM gene. EpCAM proteins include, for example, human EpCAM (GI: 15928632; SEQ ID NO: 1). In some embodiments, EpCAM proteins include cynomolgus monkey EpCAM (GI: 544483249; SEQ ID NO: 2). In some embodiments, EpCAM proteins include murine EpCAM (GI: 112293275; SEQ ID NO: 3). However, as discussed in detail elsewhere in this disclosure, in some embodiments the antibodies provided herein do not bind murine EpCAM proteins. The antibodies provided herein bind to an extracellular domain of EpCAM.

The term "immunoglobulin" refers to a class of structurally related proteins generally comprising two pairs of polypeptide chains: one pair of light (L) chains and one pair of heavy (H) chains. In an "intact immunoglobulin," all four of these chains are interconnected by disulfide bonds. The structure of immunoglobulins has been well characterized. See, e.g., Paul, *Fundamental Immunology* 7th ed., Ch. 5 (2013) Lippincott Williams & Wilkins, Philadelphia, Pa. Briefly, each heavy chain typically comprises a heavy chain variable region ($V_H$) and a heavy chain constant region ($C_H$). The heavy chain constant region typically comprises three domains, abbreviated $C_{H1}$, $C_{H2}$, and $C_{H3}$. Each light chain typically comprises a light chain variable region ($V_L$) and a light chain constant region. The light chain constant region typically comprises one domain, abbreviated $C_L$.

The term "antibody" describes a type of immunoglobulin molecule and is used herein in its broadest sense. An antibody specifically includes intact antibodies (e.g., intact immunoglobulins), and antibody fragments. Antibodies comprise at least one antigen-binding domain. One example of an antigen-binding domain is an antigen binding domain formed by a $V_H$-$V_L$ dimer. An "EpCAM antibody," "anti-EpCAM antibody," "EpCAM Ab," "EpCAM-specific antibody" or "anti-EpCAM Ab" is an antibody, as described herein, which binds specifically to the antigen EpCAM. In some embodiments, the antibody binds the extracellular domain of EpCAM.

The $V_H$ and $V_L$ regions may be further subdivided into regions of hypervariability ("hypervariable regions (HVRs);" also called "complementarity determining regions" (CDRs)) interspersed with regions that are more conserved. The more conserved regions are called framework regions (FRs). Each $V_H$ and $V_L$ generally comprises three CDRs and four FRs, arranged in the following order (from N-terminus to C-terminus): FR1-CDR1-FR2-CDR2-FR3-CDR3-FR4. The CDRs are involved in antigen binding, and influence antigen specificity and binding affinity of the antibody. See Kabat et al., *Sequences of Proteins of Immunological Interest* 5th ed. (1991) Public Health Service, National Institutes of Health, Bethesda, Md., incorporated by reference in its entirety.

The light chain from any vertebrate species can be assigned to one of two types, called kappa and lambda, based on the sequence of the constant domain.

The heavy chain from any vertebrate species can be assigned to one of five different classes (or isotypes): IgA, IgD, IgE, IgG, and IgM. These classes are also designated α, δ, ε, γ, and μ, respectively. The IgG and IgA classes are further divided into subclasses on the basis of differences in sequence and function. Humans express the following subclasses: IgG1, IgG2, IgG3, IgG4, IgA1, and IgA2.

The amino acid sequence boundaries of a CDR can be determined by one of skill in the art using any of a number of known numbering schemes, including those described by Kabat et al., supra ("Kabat" numbering scheme); Al-Lazikani et al., 1997, *J. Mol. Biol.*, 273:927-948 ("Chothia" numbering scheme); MacCallum et al., 1996, *J. Mol. Biol.* 262:732-745 ("Contact" numbering scheme); Lefranc et al., *Dev. Comp. Immunol.*, 2003, 27:55-77 ("IMGT" numbering scheme); and Honegge and Plückthun, *J. Mol. Biol.*, 2001, 309:657-70 ("AHo" numbering scheme), each of which is incorporated by reference in its entirety.

Table 1 provides the positions of CDR-L1, CDR-L2, CDR-L3, CDR-H1, CDR-H2, and CDR-H3 as identified by the Kabat and Chothia schemes. For CDR-H1, residue numbering is provided using both the Kabat and Chothia numbering schemes.

Unless otherwise specified, the numbering scheme used for identification of a particular CDR herein is the Kabat/Chothia numbering scheme. Where the residues encompassed by these two numbering schemes diverge (e.g., CDR-H1 and/or CDR-H2), the numbering scheme is specified as either Kabat or Chothia. For convenience, CDR-H3 is sometimes referred to herein as either Kabat or Chothia. However, this is not intended to imply differences in sequence where they do not exist, and one of skill in the art can readily confirm whether the sequences are the same or different by examining the sequences.

CDRs may be assigned, for example, using antibody numbering software, such as Abnum, available at http://www.bioinf.org.uk/abs/abnum/, and described in Abhinandan and Martin, *Immunology*, 2008, 45:3832-3839, incorporated by reference in its entirety.

TABLE 1

Residues in CDRs according to Kabat and Chothia numbering schemes.

| CDR | Kabat | Chothia |
|---|---|---|
| L1 | L24-L34 | L24-L34 |
| L2 | L50-L56 | L50-L56 |
| L3 | L89-L97 | L89-L97 |
| H1 (Kabat Numbering) | H31-H35B | H26-H32 or H34* |
| H1 (Chothia Numbering) | H31-H35 | H26-H32 |

TABLE 1-continued

Residues in CDRs according to Kabat
and Chothia numbering schemes.

| CDR | Kabat | Chothia |
|-----|-------|---------|
| H2  | H50-H65 | H52-H56 |
| H3  | H95-H102 | H95-H102 |

*The C-terminus of CDR-H1, when numbered using the Kabat numbering convention, varies between H32 and H34, depending on the length of the CDR, as illustrated in FIG. 1.

The "EU numbering scheme" is generally used when referring to a residue in an antibody heavy chain constant region (e.g., as reported in Kabat et al., supra). Unless stated otherwise, the EU numbering scheme is used to refer to residues in antibody heavy chain constant regions described herein.

An "antibody fragment" comprises a portion of an intact antibody, such as the antigen binding or variable region of an intact antibody. Antibody fragments include, for example, Fv fragments, Fab fragments, F(ab')$_2$ fragments, Fab' fragments, scFv (sFv) fragments, and scFv-Fc fragments.

"Fv" fragments comprise a non-covalently-linked dimer of one heavy chain variable domain and one light chain variable domain.

"Fab" fragments comprise, in addition to the heavy and light chain variable domains, the constant domain of the light chain and the first constant domain ($C_{H1}$) of the heavy chain. Fab fragments may be generated, for example, by recombinant methods or by papain digestion of a full-length antibody.

"F(ab')$_2$" fragments contain two Fab' fragments joined, near the hinge region, by disulfide bonds. F(ab')$_2$ fragments may be generated, for example, by recombinant methods or by pepsin digestion of an intact antibody. The F(ab') fragments can be dissociated, for example, by treatment with β-mercaptoethanol.

"Single-chain Fv" or "sFv" or "scFv" antibody fragments comprise a $V_H$ domain and a $V_L$ domain in a single polypeptide chain. The $V_H$ and $V_L$ are generally linked by a peptide linker. See Plückthun A. (1994). In some embodiments, the linker is SEQ ID NO: 283. Antibodies from *Escherichia coli*. In Rosenberg M. & Moore G. P. (Eds.), *The Pharmacology of Monoclonal Antibodies* vol. 113 (pp. 269-315). Springer-Verlag, New York, incorporated by reference in its entirety.

"scFv-Fc" fragments comprise an scFv attached to an Fc domain. For example, an Fc domain may be attached to the C-terminal of the scFv. The Fc domain may follow the $V_H$ or $V_L$, depending on the orientation of the variable domains in the scFv (i.e., $V_H$-$V_L$ or $V_L$-$V_H$). Any suitable Fc domain known in the art or described herein may be used. In some cases, the Fc domain comprises an IgG1 Fc domain. In some embodiments, the IgG1 Fc domain comprises SEQ ID NO: 279, or a portion thereof, or SEQ ID NO: 280. SEQ ID NO: 279 provides the sequence of $C_{H1}$, $C_{H2}$, and $C_{H3}$ of the human IgG1 constant region. SEQ ID NO: 280 provides the sequence of the constant region used in the illustrative scFv-Fc antibodies provided herein.

The term "monoclonal antibody" refers to an antibody from a population of substantially homogeneous antibodies. A population of substantially homogeneous antibodies comprises antibodies that are substantially similar and that bind the same epitope(s), except for variants that may normally arise during production of the monoclonal antibody. Such variants are generally present in only minor amounts. A monoclonal antibody is typically obtained by a process that includes the selection of a single antibody from a plurality of antibodies. For example, the selection process can be the selection of a unique clone from a plurality of clones, such as a pool of hybridoma clones, phage clones, yeast clones, bacterial clones, or other recombinant DNA clones. The selected antibody can be further altered, for example, to improve affinity for the target ("affinity maturation"), to humanize the antibody, to improve its production in cell culture, and/or to reduce its immunogenicity in a subject.

The term "chimeric antibody" refers to an antibody in which a portion of the heavy and/or light chain is derived from a particular source or species, while the remainder of the heavy and/or light chain is derived from a different source or species.

"Humanized" forms of non-human antibodies are chimeric antibodies that contain minimal sequence derived from the non-human antibody. A humanized antibody is generally a human immunoglobulin (recipient antibody) in which residues from one or more CDRs are replaced by residues from one or more CDRs of a non-human antibody (donor antibody). The donor antibody can be any suitable non-human antibody, such as a mouse, rat, rabbit, chicken, or non-human primate antibody having a desired specificity, affinity, or biological effect. In some instances, selected framework region residues of the recipient antibody are replaced by the corresponding framework region residues from the donor antibody. Humanized antibodies may also comprise residues that are not found in either the recipient antibody or the donor antibody. Such modifications may be made to further refine antibody function. For further details, see Jones et al., *Nature*, 1986, 321:522-525; Riechmann et al., *Nature*, 1988, 332:323-329; and Presta, *Curr. Op. Struct. Biol.*, 1992, 2:593-596, each of which is incorporated by reference in its entirety.

A "human antibody" is one which possesses an amino acid sequence corresponding to that of an antibody produced by a human or a human cell, or derived from a non-human source that utilizes a human antibody repertoire or human antibody-encoding sequences (e.g., obtained from human sources or designed de novo). Human antibodies specifically exclude humanized antibodies.

An "isolated antibody" is one that has been separated and/or recovered from a component of its natural environment. Components of the natural environment may include enzymes, hormones, and other proteinaceous or nonproteinaceous materials. In some embodiments, an isolated antibody is purified to a degree sufficient to obtain at least 15 residues of N-terminal or internal amino acid sequence, for example by use of a spinning cup sequenator. In some embodiments, an isolated antibody is purified to homogeneity by gel electrophoresis (e.g., SDS-PAGE) under reducing or nonreducing conditions, with detection by Coomassie blue or silver stain. An isolated antibody includes an antibody in situ within recombinant cells, since at least one component of the antibody's natural environment is not present. In some aspects, an isolated antibody is prepared by at least one purification step.

In some embodiments, an isolated antibody is purified to at least 80%, 85%, 90%, 95%, or 99% by weight. In some embodiments, an isolated antibody is purified to at least 80%, 85%, 90%, 95%, or 99% by volume. In some embodiments, an isolated antibody is provided as a solution comprising at least 85%, 90%, 95%, 98%, 99% to 100% by weight. In some embodiments, an isolated antibody is provided as a solution comprising at least 85%, 90%, 95%, 98%, 99% to 100% by volume.

"Affinity" refers to the strength of the sum total of non-covalent interactions between a single binding site of a molecule (e.g., an antibody) and its binding partner (e.g., an antigen). Unless indicated otherwise, as used herein, "binding affinity" refers to intrinsic binding affinity, which reflects a 1:1 interaction between members of a binding pair (e.g., antibody and antigen). The affinity of a molecule X for its partner Y can be represented by the dissociation constant ($K_D$). Affinity can be measured by common methods known in the art, including those described herein. Affinity can be determined, for example, using surface plasmon resonance (SPR) technology, such as a Biacore® instrument. In some embodiments, the affinity is determined at 25° C.

With regard to the binding of an antibody to a target molecule, the terms "specific binding," "specifically binds to," "specific for," "selectively binds," and "selective for" a particular antigen (e.g., a polypeptide target) or an epitope on a particular antigen mean binding that is measurably different from a non-specific or non-selective interaction. Specific binding can be measured, for example, by determining binding of a molecule compared to binding of a control molecule. Specific binding can also be determined by competition with a control molecule that mimics the antibody binding site on the target. In that case, specific binding is indicated if the binding of the antibody to the target is competitively inhibited by the control molecule.

The term "$k_d$" (sec$^{-1}$), as used herein, refers to the dissociation rate constant of a particular antibody-antigen interaction. This value is also referred to as the $k_{off}$ value.

The term "$k_a$" (M$^{-1}$×sec$^{-1}$), as used herein, refers to the association rate constant of a particular antibody-antigen interaction. This value is also referred to as the $k_{on}$ value.

The term "$K_D$" (M), as used herein, refers to the dissociation equilibrium constant of a particular antibody-antigen interaction. $K_D = k_d/k_a$.

The term "$K_A$" (M$^{-1}$), as used herein, refers to the association equilibrium constant of a particular antibody-antigen interaction. $K_A = k_a/k_d$.

An "affinity matured" antibody is one with one or more alterations in one or more CDRs or FRs that result in an improvement in the affinity of the antibody for its antigen, compared to a parent antibody which does not possess the alteration(s). In one embodiment, an affinity matured antibody has nanomolar or picomolar affinity for the target antigen. Affinity matured antibodies may be produced using a variety of methods known in the art. For example, Marks et al. (*Bio/Technology*, 1992, 10:779-783, incorporated by reference in its entirety) describes affinity maturation by $V_H$ and $V_L$ domain shuffling. Random mutagenesis of CDR and/or framework residues is described by, for example, Barbas et al. (*Proc. Nat. Acad. Sci. U.S.A.*, 1994, 91:3809-3813); Schier et al., *Gene*, 1995, 169:147-155; Yelton et al., *J. Immunol.*, 1995, 155:1994-2004; Jackson et al., *J. Immunol.*, 1995, 154:3310-33199; and Hawkins et al, *J. Mol. Biol.*, 1992, 226:889-896, each of which is incorporated by reference in its entirety.

When used herein in the context of two or more antibodies, the term "competes with" or "cross-competes with" indicates that the two or more antibodies compete for binding to an antigen (e.g., EpCAM). In one exemplary assay, EpCAM is coated on a plate and allowed to bind a first antibody, after which a second, labeled antibody is added. If the presence of the first antibody reduces binding of the second antibody, then the antibodies compete. In another exemplary assay, a first antibody is coated on a plate and allowed to bind the antigen, and then the second antibody is added. The term "competes with" also includes combinations of antibodies where one antibody reduces binding of another antibody, but where no competition is observed when the antibodies are added in the reverse order. However, in some embodiments, the first and second antibodies inhibit binding of each other, regardless of the order in which they are added. In some embodiments, one antibody reduces binding of another antibody to its antigen by at least 50%, at least 60%, at least 70%, at least 80%, or at least 90%.

The term "epitope" means a portion of an antigen capable of specific binding to an antibody. Epitopes frequently consist of surface-accessible amino acid residues and/or sugar side chains and may have specific three dimensional structural characteristics, as well as specific charge characteristics. Conformational and non-conformational epitopes are distinguished in that the binding to the former but not the latter is lost in the presence of denaturing solvents. An epitope may comprise amino acid residues that are directly involved in the binding, and other amino acid residues, which are not directly involved in the binding. The epitope to which an antibody binds can be determined using known techniques for epitope determination such as, for example, testing for antibody binding to EpCAM variants with different point-mutations, or to chimeric EpCAM variants as described further in the Examples provided herein.

Percent "identity" between a polypeptide sequence and a reference sequence, is defined as the percentage of amino acid residues in the polypeptide sequence that are identical to the amino acid residues in the reference sequence, after aligning the sequences and introducing gaps, if necessary, to achieve the maximum percent sequence identity. Alignment for purposes of determining percent amino acid sequence identity can be achieved in various ways that are within the skill in the art, for instance, using publicly available computer software such as BLAST, BLAST-2, ALIGN, MEGALIGN (DNASTAR), CLUSTALW, CLUSTAL OMEGA, or MUSCLE software. Those skilled in the art can determine appropriate parameters for aligning sequences, including any algorithms needed to achieve maximal alignment over the full length of the sequences being compared.

A "conservative substitution" or a "conservative amino acid substitution," refers to the substitution an amino acid with a chemically or functionally similar amino acid. Conservative substitution tables providing similar amino acids are well known in the art. Polypeptide sequences having such substitutions are known as "conservatively modified variants." By way of example, the groups of amino acids provided in Tables 2-4 are, in some embodiments, considered conservative substitutions for one another.

TABLE 2

Selected groups of amino acids that are considered conservative substitutions for one another, in certain embodiments.

| | |
|---|---|
| Acidic Residues | D and E |
| Basic Residues | K, R, and H |
| Hydrophilic Uncharged Residues | S, T, N, and Q |
| Aliphatic Uncharged Residues | G, A, V, L, and I |
| Non-polar Uncharged Residues | C, M, and P |
| Aromatic Residues | F, Y, and W |

TABLE 3

Additional selected groups of amino acids that are considered conservative substitutions for one another, in certain embodiments.

| | |
|---|---|
| Group 1 | A, S, and T |
| Group 2 | D and E |

TABLE 3-continued

Additional selected groups of amino acids that are considered conservative substitutions for one another, in certain embodiments.

| Group 3 | N and Q |
| Group 4 | R and K |
| Group 5 | I, L, and M |
| Group 6 | F, Y, and W |

TABLE 4

Further selected groups of amino acids that are considered conservative substitutions for one another, in certain embodiments.

| Group A | A and G |
| Group B | D and E |
| Group C | S and Q |
| Group D | R, K, and H |
| Group E | I, L, M, V |
| Group F | F, Y, and W |
| Group G | S and T |
| Group H | C and M |

Additional conservative substitutions may be found, for example, in Creighton, *Proteins: Structures and Molecular Properties* 2nd ed. (1993) W. H. Freeman & Co., New York, N.Y. An antibody generated by making one or more conservative substitutions of amino acid residues in a parent antibody is referred to as a "conservatively modified variant."

The term "amino acid" refers to the twenty common naturally occurring amino acids. Naturally occurring amino acids include alanine (Ala; A), arginine (Arg; R), asparagine (Asn; N), aspartic acid (Asp; D), cysteine (Cys; C); glutamic acid (Glu; E), glutamine (Gln; Q), Glycine (Gly; G); histidine (His; H), isoleucine (Ile; I), leucine (Leu; L), lysine (Lys; K), methionine (Met; M), phenylalanine (Phe; F), proline (Pro; P), serine (Ser; S), threonine (Thr; T), tryptophan (Trp; W), tyrosine (Tyr; Y), and valine (Val; V).

"Treating" or "treatment" of any disease or disorder refers, in certain embodiments, to ameliorating a disease or disorder that exists in a subject. In another embodiment, "treating" or "treatment" includes ameliorating at least one physical parameter, which may be indiscernible by the subject. In yet another embodiment, "treating" or "treatment" includes modulating the disease or disorder, either physically (e.g., stabilization of a discernible symptom) or physiologically (e.g., stabilization of a physical parameter) or both. In yet another embodiment, "treating" or "treatment" includes delaying or preventing the onset of the disease or disorder.

As used herein, the term "therapeutically effective amount" or "effective amount" refers to an amount of an antibody or composition that when administered to a subject is effective to treat a disease or disorder.

As used herein, the term "subject" means a mammalian subject. Exemplary subjects include, but are not limited to humans, monkeys, dogs, cats, mice, rats, cows, horses, camels, avians, goats, and sheep. In certain embodiments, the subject is a human. In some embodiments, the subject has a cancer that can be treated or diagnosed with an antibody provided herein. In some embodiments, the cancer is a cancer of epithelial origin.

2. Antibodies

Provided herein are antibodies that selectively bind human EpCAM. In some aspects, the antibody selectively binds to the extracellular domain of human EpCAM. In some embodiments, the antibody selectively binds to a portion of the EpCAM protein encoded by an exon selected from exons 4-7 of the EpCAM gene. In some embodiments, the antibody does not bind the portion of the EpCAM protein encoded by exon 2 of the EpCAM gene.

In some embodiments, the antibody binds to a homolog of human EpCAM. In some aspects, the antibody binds to a homolog of human EpCAM from a species selected from monkeys, mice, dogs, cats, rats, cows, horses, goats and sheep. In some aspects, the homolog is a cynomolgus monkey homolog. In some aspects, the antibody does not bind a murine homolog.

In some embodiments, the antibody has one or more CDRs having particular lengths, in terms of the number of amino acid residues. In some embodiments, the Chothia CDR-H1 of the antibody is 6, 7, or 8 residues in length. In some embodiments, the Kabat CDR-H1 of the antibody is 4, 5, or 6 residues in length. In some embodiments, the Chothia CDR-H2 of the antibody is 5, 6, or 7 residues in length. In some embodiments, the Kabat CDR-H2 of the antibody is 16, 17, or 18 residues in length. In some embodiments, the Kabat/Chothia CDR-H3 of the antibody is 9, 10, 11, 12, or 13 residues in length.

In some aspects, the Kabat/Chothia CDR-L1 of the antibody is 11, 12, 13, 14, 15, 16, 17, or 18 residues in length. In some aspects, the Kabat/Chothia CDR-L2 of the antibody is 6, 7, or 8 residues in length. In some aspects, the Kabat/Chothia CDR-L3 of the antibody is 8, 9, or 10 residues in length.

In some embodiments, the antibody comprises a light chain. In some aspects, the light chain is a kappa light chain. In some aspects, the light chain is a lambda light chain.

In some embodiments, the antibody comprises a heavy chain. In some aspects, the heavy chain is an IgA. In some aspects, the heavy chain is an IgD. In some aspects, the heavy chain is an IgE. In some aspects, the heavy chain is an IgG. In some aspects, the heavy chain is an IgM. In some aspects, the heavy chain is an IgG1. In some aspects, the heavy chain is an IgG2. In some aspects, the heavy chain is an IgG3. In some aspects, the heavy chain is an IgG4. In some aspects, the heavy chain is an IgA1. In some aspects, the heavy chain is an IgA2.

In some embodiments, the antibody is an antibody fragment. In some aspects, the antibody fragment is an Fv fragment. In some aspects, the antibody fragment is a Fab fragment. In some aspects, the antibody fragment is a F(ab')$_2$ fragment. In some aspects, the antibody fragment is a Fab' fragment. In some aspects, the antibody fragment is an scFv (sFv) fragment. In some aspects, the antibody fragment is an scFv-Fc fragment.

In some embodiments, the scFv-Fc fragment comprises a constant region wherein the constant region comprises SEQ ID NO: 280. The constant region in SEQ ID NO: 280 differs from the human IgG1 constant region of SEQ ID NO: 279 in several respects. First, the sequence in SEQ ID NO: 280 comprises the linker AAGSDQ (SEQ ID NO: 284). SEQ ID NO: 280 also does not comprise the CH1 domain of the IgG1 constant region. SEQ ID NO: 280 further comprises a C220S (EU numbering system) mutation, which removes an unpaired cysteine reside that is not needed when the light chain constant region is not present (e.g., in an scFv-Fc format). SEQ ID NO: 280 further comprises two, optional, P to S mutations (P230S and P238S by the EU numbering system). Either or both of these serine residues can be reverted to the naturally occurring proline residues. Finally, SEQ ID NO: 280 comprises an aspartic acid (D) residue at EU position 356 and a leucine (L) residue at EU position 358. In contrast, SEQ ID NO: 279 comprises glutamic acid (E) in EU position 356 and methionine (M) in EU position 358. In some embodiments, the antibodies provided herein comprise constant regions comprising D356/L358, E356/M358, D356/M358, or E356/L358 (EU numbering). However, a skilled person will recognize that the antibodies provide herein may comprise any suitable constant region and that the constant region sequences provided herein are for illustrative purposes.

In some embodiments, the antibody is a monoclonal antibody. In some embodiments, the antibody is a polyclonal antibody.

In some embodiments, the antibody is a chimeric antibody. In some embodiments, the antibody is a humanized antibody. In some embodiments, the antibody is a human antibody.

In some embodiments, the antibody is an affinity matured antibody. In some aspects, the antibody is an affinity matured antibody derived from an illustrative sequence provided in this disclosure.

In some embodiments, the antibody inhibits the binding of EpCAM to one or more of its ligands. In some aspects, the antibody inhibits the binding of EpCAM to a ligand selected from a second EpCAM molecule, claudin-7, CD44v4-v7, E-cadherin, and CD9.

The antibodies provided herein may be useful for the treatment of a variety of diseases and conditions including cancers. In particular, the antibodies provided herein may be useful for the treatment of cancers of epithelial origin.

2.1. CDR-H3 Sequences

In some embodiments, the antibody comprises a CDR-H3 sequence comprising, consisting of, or consisting essentially of a CDR-H3 sequence of an illustrative antibody or $V_H$ sequence provided herein. In some aspects, the CDR-H3 sequence is a CDR-H3 sequence of an scFv-Fc sequence provided in SEQ ID NOs.: 204-228 or of an scFv sequence provided in SEQ ID NOs.: 337-361. In some aspects, the CDR-H3 sequence is a CDR-H3 sequence of a $V_H$ sequence provided in SEQ ID NOs.: 229-253.

In some embodiments, the antibody comprises a CDR-H3 sequence comprising, consisting of, or consisting essentially of a sequence selected from SEQ ID NOs: 104-128. In some aspects, the antibody comprises a CDR-H3 sequence comprising, consisting of, or consisting essentially of SEQ ID NO: 104. In some aspects, the antibody comprises a CDR-H3 sequence comprising, consisting of, or consisting essentially of SEQ ID NO: 105. In some aspects, the antibody comprises a CDR-H3 sequence comprising, consisting of, or consisting essentially of SEQ ID NO: 106. In some aspects, the antibody comprises a CDR-H3 sequence comprising, consisting of, or consisting essentially of SEQ ID NO: 107. In some aspects, the antibody comprises a CDR-H3 sequence comprising, consisting of, or consisting essentially of SEQ ID NO: 108. In some aspects, the antibody comprises a CDR-H3 sequence comprising, consisting of, or consisting essentially of SEQ ID NO: 109. In some aspects, the antibody comprises a CDR-H3 sequence comprising, consisting of, or consisting essentially of SEQ ID NO: 110. In some aspects, the antibody comprises a CDR-H3 sequence comprising, consisting of, or consisting essentially of SEQ ID NO: 111. In some aspects, the antibody comprises a CDR-H3 sequence comprising, consisting of, or consisting essentially of SEQ ID NO: 112. In some aspects, the antibody comprises a CDR-H3 sequence comprising, consisting of, or consisting essentially of SEQ ID NO: 113. In some aspects, the antibody comprises a CDR-H3 sequence comprising, consisting of, or consisting essentially of SEQ ID NO: 114. In some aspects, the antibody comprises a CDR-H3 sequence comprising, consisting of, or consisting essentially of SEQ ID NO: 115. In some aspects, the antibody comprises a CDR-H3 sequence comprising, consisting of, or consisting essentially of SEQ ID NO: 116. In some aspects, the antibody comprises a CDR-H3 sequence comprising, consisting of, or consisting essentially of SEQ ID NO: 117. In some aspects, the antibody comprises a CDR-H3 sequence comprising, consisting of, or consisting essentially of SEQ ID NO: 118. In some aspects, the antibody comprises a CDR-H3 sequence comprising, consisting of, or consisting essentially of SEQ ID NO: 119. In some aspects, the antibody comprises a CDR-H3 sequence comprising, consisting of, or consisting essentially of SEQ ID NO: 120. In some aspects, the antibody comprises a CDR-H3 sequence comprising, consisting of, or consisting essentially of SEQ ID NO: 121. In some aspects, the antibody comprises a CDR-H3 sequence comprising, consisting of, or consisting essentially of SEQ ID NO: 122. In some aspects, the antibody comprises a CDR-H3 sequence comprising, consisting of, or consisting essentially of SEQ ID NO: 123. In some aspects, the antibody comprises a CDR-H3 sequence comprising, consisting of, or consisting essentially of SEQ ID NO: 124. In some aspects, the antibody comprises a CDR-H3 sequence comprising, consisting of, or consisting essentially of SEQ ID NO: 125. In some aspects, the antibody comprises a CDR-H3 sequence comprising, consisting of, or consisting essentially of SEQ ID NO: 126. In some aspects, the antibody comprises a CDR-H3 sequence comprising, consisting of, or consisting essentially of SEQ ID NO: 127. In some aspects, the antibody comprises a CDR-H3 sequence comprising, consisting of, or consisting essentially of SEQ ID NO: 128.

In some aspects, the CDR-H3 sequence comprises, consists of, or consists essentially of a variant of an illustrative CDR-H3 sequence provided in this disclosure. In some aspects, the CDR-H3 sequence comprises, consists of, or consists essentially of a sequence having at least 70%, 75%, 80%, 85%, 90%, or 95% identity with any of the illustrative CDR-H3 sequences provided in this disclosure. In some aspects, the CDR-H3 sequence comprises, consists of, or consists essentially of any of the illustrative CDR-H3 sequences provided in this disclosure, with 1, 2, or 3 amino acid substitutions. In some aspects, the amino acid substitutions are conservative amino acid substitutions.

In some aspects, the CDR-H3 sequence does not comprise, consist of, or consist essentially of a sequence selected from SEQ ID NOs: 306-310. In some aspects, the CDR-H3 sequence does not comprise, consist of, or consist essentially of SEQ ID NO: 306. In some aspects, the CDR-H3 sequence does not comprise, consist of, or consist essentially of SEQ ID NO: 307. In some aspects, the CDR-H3 sequence does not comprise, consist of, or consist essentially of SEQ ID NO: 308. In some aspects, the CDR-H3 sequence does not comprise, consist of, or consist essentially of SEQ ID NO: 309. In some aspects, the CDR-H3 sequence does not comprise, consist of, or consist essentially of SEQ ID NO: 310.

2.2. $V_H$ Sequences Comprising Illustrative CDRs

In some embodiments, the antibody comprises a $V_H$ sequence comprising one or more CDR-H sequences comprising, consisting of, or consisting essentially of one or more illustrative CDR-H sequences provided in this disclosure, and variants thereof. In some embodiments, the CDR-H sequences comprise, consist of, or consist essentially of one or more CDR-H sequences provided in a $V_H$ sequence selected from SEQ ID NOs: 229-253.

2.2.1. $V_H$ Sequences Comprising Illustrative Kabat CDRs

In some embodiments, the antibody comprises a $V_H$ sequence comprising one or more Kabat CDR-H sequences comprising, consisting of, or consisting essentially of one or more illustrative Kabat CDR-H sequences provided in this disclosure, and variants thereof.

2.2.1.1. Kabat CDR-H3

In some embodiments, the antibody comprises a $V_H$ sequence comprising a CDR-H3 sequence, wherein the CDR-H3 sequence comprises, consists of, or consists essentially of a Kabat CDR-H3 sequence of an illustrative antibody or $V_H$ sequence provided herein. In some aspects, the Kabat CDR-H3 sequence is a Kabat CDR-H3 sequence of a scFv-Fc sequence provided in SEQ ID NOs.: 204-228 or of a scFv sequence provided in SEQ ID NOs.: 337-361. In some aspects, the Kabat CDR-H3 sequence is a Kabat CDR-H3 sequence of a $V_H$ sequence provided in SEQ ID NOs.: 229-253.

In some embodiments, the antibody comprises a $V_H$ sequence comprising a Kabat CDR-H3 sequence comprising, consisting of, or consisting essentially of a sequence selected from SEQ ID NOs: 104-128. In some aspects, the antibody comprises a $V_H$ sequence comprising a Kabat CDR-H3 sequence comprising, consisting of, or consisting essentially of SEQ ID NO: 104. In some aspects, the antibody comprises a $V_H$ sequence comprising a Kabat CDR-H3 sequence comprising, consisting of, or consisting essentially of SEQ ID NO: 105. In some aspects, the antibody comprises a $V_H$ sequence comprising a Kabat CDR-H3 sequence comprising, consisting of, or consisting essentially of SEQ ID NO: 106. In some aspects, the antibody comprises a $V_H$ sequence comprising a Kabat CDR-H3 sequence comprising, consisting of, or consisting essentially of SEQ ID NO: 107. In some aspects, the antibody comprises a $V_H$ sequence comprising a Kabat CDR-H3 sequence comprising, consisting of, or consisting essentially of SEQ ID NO: 108. In some aspects, the antibody comprises a $V_H$ sequence comprising a Kabat CDR-H3 sequence comprising, consisting of, or consisting essentially of SEQ ID NO: 109. In some aspects, the antibody comprises a $V_H$ sequence comprising a Kabat CDR-H3 sequence comprising, consisting of, or consisting essentially of SEQ ID NO: 110. In some aspects, the antibody comprises a $V_H$ sequence comprising a Kabat CDR-H3 sequence comprising, consisting of, or consisting essentially of SEQ ID NO: 111. In some aspects, the antibody comprises a $V_H$ sequence comprising a Kabat CDR-H3 sequence comprising, consisting of, or consisting essentially of SEQ ID NO: 112. In some aspects, the antibody comprises a $V_H$ sequence comprising a Kabat CDR-H3 sequence comprising, consisting of, or consisting essentially of SEQ ID NO: 113. In some aspects, the antibody comprises a $V_H$ sequence comprising a Kabat CDR-H3 sequence comprising, consisting of, or consisting essentially of SEQ ID NO: 114. In some aspects, the antibody comprises a $V_H$ sequence comprising a Kabat CDR-H3 sequence comprising, consisting of, or consisting essentially of SEQ ID NO: 115. In some aspects, the antibody comprises a $V_H$ sequence comprising a Kabat CDR-H3 sequence comprising, consisting of, or consisting essentially of SEQ ID NO: 116. In some aspects, the antibody comprises a $V_H$ sequence comprising a Kabat CDR-H3 sequence comprising, consisting of, or consisting essentially of SEQ ID NO: 117. In some aspects, the antibody comprises a $V_H$ sequence comprising a Kabat CDR-H3 sequence comprising, consisting of, or consisting essentially of SEQ ID NO: 118. In some aspects, the antibody comprises a $V_H$ sequence comprising a Kabat CDR-H3 sequence comprising, consisting of, or consisting essentially of SEQ ID NO: 119. In some aspects, the antibody comprises a $V_H$ sequence comprising a Kabat CDR-H3 sequence comprising, consisting of, or consisting essentially of SEQ ID NO: 120. In some aspects, the antibody comprises a $V_H$ sequence comprising a Kabat CDR-H3 sequence comprising, consisting of, or consisting essentially of SEQ ID NO: 121. In some aspects, the antibody comprises a $V_H$ sequence comprising a Kabat CDR-H3 sequence comprising, consisting of, or consisting essentially of SEQ ID NO: 122. In some aspects, the antibody comprises a $V_H$ sequence comprising a Kabat CDR-H3 sequence comprising, consisting of, or consisting essentially of SEQ ID NO: 123. In some aspects, the antibody comprises a $V_H$ sequence comprising a Kabat CDR-H3 sequence comprising, consisting of, or consisting essentially of SEQ ID NO: 124. In some aspects, the antibody comprises a $V_H$ sequence comprising a Kabat CDR-H3 sequence comprising, consisting of, or consisting essentially of SEQ ID NO: 125. In some aspects, the antibody comprises a $V_H$ sequence comprising a Kabat CDR-H3 sequence comprising, consisting of, or consisting essentially of SEQ ID NO: 126. In some aspects, the antibody comprises a $V_H$ sequence comprising a Kabat CDR-H3 sequence comprising, consisting of, or consisting essentially of SEQ ID NO: 127. In some aspects, the antibody comprises a $V_H$ sequence comprising a Kabat CDR-H3 sequence comprising, consisting of, or consisting essentially of SEQ ID NO: 128.

2.2.1.2. Kabat CDR-H2

In some embodiments, the antibody comprises a $V_H$ sequence comprising a CDR-H2 sequence, wherein the CDR-H2 sequence comprises, consists of, or consists essentially of a Kabat CDR-H2 sequence of an illustrative antibody or $V_H$ sequence provided herein. In some aspects, the Kabat CDR-H2 sequence is a Kabat CDR-H2 sequence of an scFv-Fc sequence provided in SEQ ID NOs.: 204-228 or of an scFv sequence provided in SEQ ID NOs.: 337-361. In some aspects, the Kabat CDR-H3 sequence is a Kabat CDR-H3 sequence of a $V_H$ sequence provided in SEQ ID NOs.: 229-253.

In some embodiments, the antibody comprises a $V_H$ sequence comprising a Kabat CDR-H2 sequence comprising, consisting of, or consisting essentially of a sequence selected from SEQ ID NOs: 79-103. In some aspects, the antibody comprises a $V_H$ sequence comprising a Kabat CDR-H2 sequence comprising, consisting of, or consisting essentially of SEQ ID NO: 79. In some aspects, the antibody comprises a $V_H$ sequence comprising a Kabat CDR-H2 sequence comprising, consisting of, or consisting essentially of SEQ ID NO: 80. In some aspects, the antibody comprises a $V_H$ sequence comprising a Kabat CDR-H2 sequence comprising, consisting of, or consisting essentially of SEQ ID NO: 81. In some aspects, the antibody comprises a $V_H$ sequence comprising a Kabat CDR-H2 sequence comprising, consisting of, or consisting essentially of SEQ ID NO: 82. In some aspects, the antibody comprises a $V_H$ sequence comprising a Kabat CDR-H2 sequence comprising, consisting of, or consisting essentially of SEQ ID NO: 83. In some aspects, the antibody comprises a $V_H$ sequence comprising a Kabat CDR-H2 sequence comprising, consisting of, or consisting essentially of SEQ ID NO: 84. In some aspects, the antibody comprises a $V_H$ sequence comprising a Kabat CDR-H2 sequence comprising, consisting of, or consisting essentially of SEQ ID NO: 85. In some aspects, the antibody comprises a $V_H$ sequence comprising a Kabat CDR-H2 sequence comprising, consisting of, or consisting essentially of SEQ ID NO: 86. In some aspects, the antibody comprises a $V_H$ sequence comprising a Kabat CDR-H2 sequence comprising, consisting of, or consisting essentially of SEQ ID NO: 87. In some aspects, the antibody comprises a $V_H$ sequence comprising a Kabat CDR-H2 sequence comprising, consisting of, or consisting essentially of SEQ ID NO: 88. In some aspects, the antibody comprises a $V_H$ sequence comprising a Kabat CDR-H2 sequence comprising, consisting of, or consisting essentially of SEQ ID NO: 89. In some aspects, the antibody comprises a $V_H$ sequence comprising a Kabat CDR-H2 sequence comprising, consisting of, or consisting essentially of SEQ ID NO: 90. In some aspects, the antibody comprises a $V_H$ sequence comprising a Kabat CDR-H2 sequence comprising, consisting of, or consisting essentially of SEQ ID NO: 91. In some aspects, the antibody comprises a $V_H$ sequence comprising a Kabat CDR-H2 sequence comprising, consisting of, or consisting essentially of SEQ ID NO: 92. In some aspects, the antibody comprises a $V_H$ sequence comprising a Kabat CDR-H2 sequence comprising, consisting of, or consisting essentially of SEQ ID NO: 93. In some aspects, the antibody comprises a $V_H$ sequence comprising a Kabat CDR-H2 sequence comprising, consisting of, or consisting essentially of SEQ ID NO: 94. In some aspects, the antibody comprises a $V_H$ sequence comprising a Kabat CDR-H2 sequence comprising, consisting of, or consisting essentially of SEQ ID NO: 95. In some aspects, the antibody comprises a $V_H$ sequence comprising a Kabat CDR-H2 sequence comprising, consisting of, or consisting essentially of SEQ ID NO: 96. In some aspects, the antibody comprises a $V_H$ sequence comprising a Kabat CDR-H2 sequence comprising, consisting of, or consisting essentially of SEQ ID NO: 97. In some aspects, the antibody comprises a $V_H$ sequence comprising a Kabat CDR-H2 sequence comprising, consisting of, or consisting essentially of SEQ ID NO: 98. In some aspects, the antibody comprises a $V_H$ sequence comprising a Kabat CDR-H2 sequence comprising, consisting of, or consisting essentially of SEQ ID NO: 99. In some aspects, the antibody comprises a $V_H$ sequence comprising a Kabat CDR-H2 sequence comprising, consisting of, or consisting essentially of SEQ ID NO: 100. In some aspects, the antibody comprises a $V_H$ sequence comprising a Kabat CDR-H2 sequence comprising, consisting of, or consisting essentially of SEQ ID NO: 101. In some aspects, the antibody comprises a $V_H$ sequence comprising a Kabat CDR-H2 sequence comprising, consisting of, or consisting essentially of SEQ ID NO: 102. In some aspects, the antibody comprises a $V_H$ sequence comprising a Kabat CDR-H2 sequence comprising, consisting of, or consisting essentially of SEQ ID NO: 103.

2.2.1.3. Kabat CDR-H1

In some embodiments, the antibody comprises a $V_H$ sequence comprising a CDR-H1 sequence, wherein the CDR-H1 sequence comprises, consists of, or consists essentially of a Kabat CDR-H1 sequence of an illustrative antibody or $V_H$ sequence provided herein. In some aspects, the Kabat CDR-H1 sequence is a Kabat CDR-H1 sequence of an scFv-Fc sequence provided in SEQ ID NOs.: 204-228 or of an scFv sequence provided in SEQ ID NOs.: 337-361. In some aspects, the Kabat CDR-H3 sequence is a Kabat CDR-H1 sequence of a $V_H$ sequence provided in SEQ ID NOs.: 229-253.

In some embodiments, the antibody comprises a $V_H$ sequence comprising a Kabat CDR-H1 sequence comprising, consisting of, or consisting essentially of a sequence selected from SEQ ID NOs: 29-53. In some aspects, the antibody comprises a $V_H$ sequence comprising a Kabat CDR-H1 sequence comprising, consisting of, or consisting essentially of SEQ ID NO: 29. In some aspects, the antibody comprises a $V_H$ sequence comprising a Kabat CDR-H1 sequence comprising, consisting of, or consisting essentially of SEQ ID NO: 30. In some aspects, the antibody comprises a $V_H$ sequence comprising a Kabat CDR-H1 sequence comprising, consisting of, or consisting essentially of SEQ ID NO: 31. In some aspects, the antibody comprises a $V_H$ sequence comprising a Kabat CDR-H1 sequence comprising, consisting of, or consisting essentially of SEQ ID NO: 32. In some aspects, the antibody comprises a $V_H$ sequence comprising a Kabat CDR-H1 sequence comprising, consisting of, or consisting essentially of SEQ ID NO: 33. In some aspects, the antibody comprises a $V_H$ sequence comprising a Kabat CDR-H1 sequence comprising, consisting of, or consisting essentially of SEQ ID NO: 34. In some aspects, the antibody comprises a $V_H$ sequence comprising a Kabat CDR-H1 sequence comprising, consisting of, or consisting essentially of SEQ ID NO: 35. In some aspects, the antibody comprises a $V_H$ sequence comprising a Kabat CDR-H1 sequence comprising, consisting of, or consisting essentially of SEQ ID NO: 36. In some aspects, the antibody comprises a $V_H$ sequence comprising a Kabat CDR-H1 sequence comprising, consisting of, or consisting essentially of SEQ ID NO: 37. In some aspects, the antibody comprises a $V_H$ sequence comprising a Kabat CDR-H1 sequence comprising, consisting of, or consisting essentially of SEQ ID NO: 38. In some aspects, the antibody comprises a $V_H$ sequence comprising a Kabat CDR-H1 sequence comprising, consisting of, or consisting essentially of SEQ ID NO: 39. In some aspects, the antibody comprises a $V_H$ sequence comprising a Kabat CDR-H1 sequence comprising, consisting of, or consisting essentially of SEQ ID NO: 40. In some aspects, the antibody comprises a $V_H$ sequence comprising a Kabat CDR-H1 sequence comprising, consisting of, or consisting essentially of SEQ ID NO: 41. In some aspects, the antibody comprises a $V_H$ sequence comprising a Kabat CDR-H1 sequence comprising, consisting of, or consisting essentially of SEQ ID NO: 42. In some aspects, the antibody comprises a $V_H$ sequence comprising a Kabat CDR-H1 sequence comprising, consisting of, or consisting essentially of SEQ ID NO: 43. In some aspects, the antibody comprises a $V_H$ sequence comprising a Kabat CDR-H1 sequence comprising, consisting of, or consisting essentially of SEQ ID NO: 44. In some aspects, the antibody comprises a $V_H$ sequence comprising a Kabat CDR-H1 sequence comprising, consisting of, or consisting essentially of SEQ ID NO: 45. In some aspects, the antibody comprises a $V_H$ sequence comprising a Kabat CDR-H1 sequence comprising, consisting of, or consisting essentially of SEQ ID NO: 46. In some aspects, the antibody comprises a $V_H$ sequence comprising a Kabat CDR-H1 sequence comprising, consisting of, or consisting essentially of SEQ ID NO: 47. In some aspects, the antibody comprises a $V_H$ sequence comprising a Kabat CDR-H1 sequence comprising, consisting of, or consisting essentially of SEQ ID NO: 48. In some aspects, the antibody comprises a $V_H$ sequence comprising a Kabat CDR-H1 sequence comprising, consisting of, or consisting essentially of SEQ ID NO: 49. In some aspects, the antibody comprises a $V_H$ sequence comprising a Kabat CDR-H1 sequence comprising, consisting of, or consisting essentially of SEQ ID NO: 50. In some aspects, the antibody comprises a $V_H$ sequence comprising a Kabat CDR-H1 sequence comprising, consisting of, or consisting essentially of SEQ ID NO: 51. In some aspects, the antibody comprises a $V_H$ sequence comprising a Kabat CDR-H1 sequence comprising, consisting of, or consisting essentially of SEQ ID NO: 52. In some aspects, the antibody comprises a $V_H$ sequence comprising a Kabat CDR-H1 sequence comprising, consisting of, or consisting essentially of SEQ ID NO: 53.

2.2.1.4. Kabat CDR-H3+Kabat CDR-H2

In some embodiments, the antibody comprises a $V_H$ sequence comprising a Kabat CDR-H3 sequence comprising, consisting of, or consisting essentially of a sequence selected from SEQ ID NOs: 104-128, and a Kabat CDR-H2 sequence comprising, consisting of, or consisting essentially of a sequence selected from SEQ ID NOs: 79-103. In some aspects, the Kabat CDR-H3 sequence and the Kabat CDR-H2 sequence are both from a single illustrative $V_H$ sequence provided in this disclosure. For example, in some aspects, the Kabat CDR-H3 and Kabat CDR-H2 are both from a single illustrative $V_H$ sequence selected from SEQ ID NOs: 229-253.

2.2.1.5. Kabat CDR-H3+Kabat CDR-H1

In some embodiments, the antibody comprises a $V_H$ sequence comprising a Kabat CDR-H3 sequence comprising, consisting of, or consisting essentially of a sequence selected from SEQ ID NOs: 104-128, and a Kabat CDR-H1 sequence comprising, consisting of, or consisting essentially of a sequence selected from SEQ ID NOs: 29-53. In some aspects, the Kabat CDR-H3 sequence and the Kabat CDR-H1 sequence are both from a single illustrative $V_H$ sequence provided in this disclosure. For example, in some aspects, the Kabat CDR-H3 and Kabat CDR-H1 are both from a single illustrative $V_H$ sequence selected from SEQ ID NOs: 229-253.

2.2.1.6. Kabat CDR-H1+Kabat CDR-H2

In some embodiments, the antibody comprises a $V_H$ sequence comprising a Kabat CDR-H1 sequence comprising, consisting of, or consisting essentially of a sequence selected from SEQ ID NOs: 29-53 and a Kabat CDR-H2 sequence comprising, consisting of, or consisting essentially of a sequence selected from SEQ ID NOs: 79-103. In some aspects, the Kabat CDR-H1 sequence and the Kabat CDR-H2 sequence are both from a single illustrative $V_H$ sequence provided in this disclosure. For example, in some aspects, the Kabat CDR-H1 and Kabat CDR-H2 are both from a single illustrative $V_H$ sequence selected from SEQ ID NOs: 229-253.

2.2.1.7. Kabat CDR-H1+Kabat CDR-H2+Kabat CDR-H3

In some embodiments, the antibody comprises a $V_H$ sequence comprising a Kabat CDR-H1 sequence comprising, consisting of, or consisting essentially of a sequence selected from SEQ ID NOs: 29-53, a Kabat CDR-H2 sequence comprising, consisting of, or consisting essentially of a sequence selected from SEQ ID NOs: 79-103, and a Kabat CDR-H3 sequence comprising, consisting of, or consisting essentially of a sequence selected from SEQ ID NOs: 104-128. In some aspects, the Kabat CDR-H1 sequence, Kabat CDR-H2 sequence, and Kabat CDR-H3 sequence are all from a single illustrative $V_H$ sequence provided in this disclosure. For example, in some aspects, the Kabat CDR-H1, Kabat CDR-H2, and Kabat CDR-H3 are all from a single illustrative $V_H$ sequence selected from SEQ ID NOs: 229-253.

2.2.1.8. Variants of $V_H$ Sequences Comprising Illustrative Kabat CDRs

In some embodiments, the $V_H$ sequences provided herein comprise a variant of an illustrative Kabat CDR-H3, CDR-H2, and/or CDR-H1 sequence provided in this disclosure.

In some aspects, the Kabat CDR-H3 sequence comprises, consists of, or consists essentially of a variant of an illustrative Kabat CDR-H3 sequence provided in this disclosure. In some aspects, the Kabat CDR-H3 sequence comprises, consists of, or consists essentially of a sequence having at least 70%, 75%, 80%, 85%, 90%, or 95% identity with any of the illustrative Kabat CDR-H3 sequences provided in this disclosure. In some aspects, the Kabat CDR-H3 sequence comprises, consists of, or consists essentially of any of the illustrative Kabat CDR-H3 sequences provided in this disclosure, with 1, 2, or 3 amino acid substitutions. In some aspects, the amino acid substitutions are conservative amino acid substitutions.

In some aspects, the Kabat CDR-H2 sequence comprises, consists of, or consists essentially of a variant of an illustrative Kabat CDR-H2 sequence provided in this disclosure. In some aspects, the Kabat CDR-H2 sequence comprises, consists of, or consists essentially of a sequence having at least 70%, 75%, 80%, 85%, 90%, or 95% identity with any of the illustrative Kabat CDR-H2 sequences provided in this disclosure. In some aspects, the Kabat CDR-H2 sequence comprises, consists of, or consists essentially of any of the illustrative Kabat CDR-H2 sequences provided in this disclosure, with 1, 2, or 3 amino acid substitutions. In some aspects, the amino acid substitutions are conservative amino acid substitutions.

In some aspects, the Kabat CDR-H1 sequence comprises, consists of, or consists essentially of a variant of an illustrative Kabat CDR-H1 sequence provided in this disclosure. In some aspects, the Kabat CDR-H1 sequence comprises, consists of, or consists essentially of a sequence having at least 70%, 75%, 80%, 85%, 90%, or 95% identity with any of the illustrative Kabat CDR-H1 sequences provided in this disclosure. In some aspects, the Kabat CDR-H1 sequence comprises, consists of, or consists essentially of any of the illustrative Kabat CDR-H1 sequences provided in this disclosure, with 1, 2, or 3 amino acid substitutions. In some aspects, the amino acid substitutions are conservative amino acid substitutions.

2.2.1.9. Excluded $V_H$ Sequences Comprising Kabat CDRs

In some embodiments, the $V_H$ sequences provided herein do not comprise certain Kabat CDR-H3, CDR-H2, and/or CDR-H1 sequences.

In some aspects, the Kabat CDR-H3 sequence does not comprise, consist of, or consist essentially of a sequence selected from SEQ ID NOs: 306-310. In some aspects, the Kabat CDR-H3 sequence does not comprise, consist of, or consist essentially of SEQ ID NO: 306. In some aspects, the Kabat CDR-H3 sequence does not comprise, consist of, or consist essentially of SEQ ID NO: 307. In some aspects, the Kabat CDR-H3 sequence does not comprise, consist of, or consist essentially of SEQ ID NO: 308. In some aspects, the Kabat CDR-H3 sequence does not comprise, consist of, or consist essentially of SEQ ID NO: 309. In some aspects, the Kabat CDR-H3 sequence does not comprise, consist of, or consist essentially of SEQ ID NO: 310.

In some aspects, the Kabat CDR-H2 sequence does not comprise, consist of, or consist essentially of a sequence selected from SEQ ID NOs: 301-305. In some aspects, the Kabat CDR-H2 sequence does not comprise, consist of, or consist essentially of SEQ ID NO: 301. In some aspects, the Kabat CDR-H2 sequence does not comprise, consist of, or consist essentially of SEQ ID NO: 302. In some aspects, the Kabat CDR-H2 sequence does not comprise, consist of, or consist essentially of SEQ ID NO: 303. In some aspects, the Kabat CDR-H2 sequence does not comprise, consist of, or consist essentially of SEQ ID NO: 304. In some aspects, the Kabat CDR-H2 sequence does not comprise, consist of, or consist essentially of SEQ ID NO: 305.

In some aspects, the Kabat CDR-H1 sequence does not comprise, consist of, or consist essentially of a sequence selected from SEQ ID NOs: 291-295. In some aspects, the Kabat CDR-H1 sequence does not comprise, consist of, or consist essentially of SEQ ID NO: 291. In some aspects, the Kabat CDR-H1 sequence does not comprise, consist of, or consist essentially of SEQ ID NO: 292. In some aspects, the Kabat CDR-H1 sequence does not comprise, consist of, or consist essentially of SEQ ID NO: 293. In some aspects, the Kabat CDR-H1 sequence does not comprise, consist of, or consist essentially of SEQ ID NO: 294. In some aspects, the Kabat CDR-H1 sequence does not comprise, consist of, or consist essentially of SEQ ID NO: 295.

2.2.2. $V_H$ Sequences Comprising Illustrative Chothia CDRs

In some embodiments, the antibody comprises a $V_H$ sequence comprising one or more Chothia CDR-H sequences comprising, consisting of, or consisting essentially of one or more illustrative Chothia CDR-H sequences provided in this disclosure, and variants thereof.

2.2.2.1. Chothia CDR-H3

In some embodiments, the antibody comprises a $V_H$ sequence comprising a CDR-H3 sequence, wherein the CDR-H3 sequence comprises, consists of, or consists essentially of a Chothia CDR-H3 sequence of an illustrative antibody or $V_H$ sequence provided herein. In some aspects, the Chothia CDR-H3 sequence is a Chothia CDR-H3 sequence of an scFv-Fc sequence provided in SEQ ID NOs.: 204-228 or of an scFv sequence provided in SEQ ID NOs.: 337-361. In some aspects, the Chothia CDR-H3 sequence is a Chothia CDR-H3 sequence of a $V_H$ sequence provided in SEQ ID NOs.: 229-253.

In some embodiments, the antibody comprises a $V_H$ sequence comprising a Chothia CDR-H3 sequence comprising, consisting of, or consisting essentially of a sequence selected from SEQ ID NOs: 104-128. In some aspects, the antibody comprises a $V_H$ sequence comprising a Chothia CDR-H3 sequence comprising, consisting of, or consisting essentially of SEQ ID NO: 104. In some aspects, the antibody comprises a $V_H$ sequence comprising a Chothia CDR-H3 sequence comprising, consisting of, or consisting essentially of SEQ ID NO: 105. In some aspects, the antibody comprises a $V_H$ sequence comprising a Chothia CDR-H3 sequence comprising, consisting of, or consisting essentially of SEQ ID NO: 106. In some aspects, the antibody comprises a $V_H$ sequence comprising a Chothia CDR-H3 sequence comprising, consisting of, or consisting essentially of SEQ ID NO: 107. In some aspects, the antibody comprises a $V_H$ sequence comprising a Chothia CDR-H3 sequence comprising, consisting of, or consisting essentially of SEQ ID NO: 108. In some aspects, the antibody comprises a $V_H$ sequence comprising a Chothia CDR-H3 sequence comprising, consisting of, or consisting essentially of SEQ ID NO: 109. In some aspects, the antibody comprises a $V_H$ sequence comprising a Chothia CDR-H3 sequence comprising, consisting of, or consisting essentially of SEQ ID NO: 110. In some aspects, the antibody comprises a $V_H$ sequence comprising a Chothia CDR-H3 sequence comprising, consisting of, or consisting essentially of SEQ ID NO: 111. In some aspects, the antibody comprises a $V_H$ sequence comprising a Chothia CDR-H3 sequence comprising, consisting of, or consisting essentially of SEQ ID NO: 112. In some aspects, the antibody comprises a $V_H$ sequence comprising a Chothia CDR-H3 sequence comprising, consisting of, or consisting essentially of SEQ ID NO: 113. In some aspects, the antibody comprises a $V_H$ sequence comprising a Chothia CDR-H3 sequence comprising, consisting of, or consisting essentially of SEQ ID NO: 114. In some aspects, the antibody comprises a $V_H$ sequence comprising a Chothia CDR-H3 sequence comprising, consisting of, or consisting essentially of SEQ ID NO: 115. In some aspects, the antibody comprises a $V_H$ sequence comprising a Chothia CDR-H3 sequence comprising, consisting of, or consisting essentially of SEQ ID NO: 116. In some aspects, the antibody comprises a $V_H$ sequence comprising a Chothia CDR-H3 sequence comprising, consisting of, or consisting essentially of SEQ ID NO: 117. In some aspects, the antibody comprises a $V_H$ sequence comprising a Chothia CDR-H3 sequence comprising, consisting of, or consisting essentially of SEQ ID NO: 118. In some aspects, the antibody comprises a $V_H$ sequence comprising a Chothia CDR-H3 sequence comprising, consisting of, or consisting essentially of SEQ ID NO: 119. In some aspects, the antibody comprises a $V_H$ sequence comprising a Chothia CDR-H3 sequence comprising, consisting of, or consisting essentially of SEQ ID NO: 120. In some aspects, the antibody comprises a $V_H$ sequence comprising a Chothia CDR-H3 sequence comprising, consisting of, or consisting essentially of SEQ ID NO: 121. In some aspects, the antibody comprises a $V_H$ sequence comprising a Chothia CDR-H3 sequence comprising, consisting of, or consisting essentially of SEQ ID NO: 122. In some aspects, the antibody comprises a $V_H$ sequence comprising a Chothia CDR-H3 sequence comprising, consisting of, or consisting essentially of SEQ ID NO: 123. In some aspects, the antibody comprises a $V_H$ sequence comprising a Chothia CDR-H3 sequence comprising, consisting of, or consisting essentially of SEQ ID NO: 124. In some aspects, the antibody comprises a $V_H$ sequence comprising a Chothia CDR-H3 sequence comprising, consisting of, or consisting essentially of SEQ ID NO: 125. In some aspects, the antibody comprises a $V_H$ sequence comprising a Chothia CDR-H3 sequence comprising, consisting of, or consisting essentially of SEQ ID NO: 126. In some aspects, the antibody comprises a $V_H$ sequence comprising a Chothia CDR-H3 sequence comprising, consisting of, or consisting essentially of SEQ ID NO: 127. In some aspects, the antibody comprises a $V_H$ sequence comprising a Chothia CDR-H3 sequence comprising, consisting of, or consisting essentially of SEQ ID NO: 128.

2.2.2.2. Chothia CDR-H2

In some embodiments, the antibody comprises a $V_H$ sequence comprising a CDR-H2 sequence, wherein the CDR-H2 sequence comprises, consists of, or consists essentially of a Chothia CDR-H2 sequence of an illustrative antibody or $V_H$ sequence provided herein. In some aspects, the Chothia CDR-H2 sequence is a Chothia CDR-H2 sequence of an scFv-Fc sequence provided in SEQ ID NOs.: 204-228 or of an scFv sequence provided in SEQ ID NOs.: 337-361. In some aspects, the Chothia CDR-H2 sequence is a Chothia CDR-H2 sequence of a $V_H$ sequence provided in SEQ ID NOs.: 229-253.

In some embodiments, the antibody comprises a $V_H$ sequence comprising a Chothia CDR-H2 sequence comprising, consisting of, or consisting essentially of a sequence selected from SEQ ID NOs: 54-78. In some aspects, the antibody comprises a $V_H$ sequence comprising a Chothia CDR-H2 sequence comprising, consisting of, or consisting essentially of SEQ ID NO: 54. In some aspects, the antibody comprises a $V_H$ sequence comprising a Chothia CDR-H2 sequence comprising, consisting of, or consisting essentially of SEQ ID NO: 55. In some aspects, the antibody comprises a $V_H$ sequence comprising a Chothia CDR-H2 sequence comprising, consisting of, or consisting essentially of SEQ ID NO: 56. In some aspects, the antibody comprises a $V_H$ sequence comprising a Chothia CDR-H2 sequence comprising, consisting of, or consisting essentially of SEQ ID NO: 57. In some aspects, the antibody comprises a $V_H$ sequence comprising a Chothia CDR-H2 sequence comprising, consisting of, or consisting essentially of SEQ ID NO: 58. In some aspects, the antibody comprises a $V_H$ sequence comprising a Chothia CDR-H2 sequence comprising, consisting of, or consisting essentially of SEQ ID NO: 59. In some aspects, the antibody comprises a $V_H$ sequence comprising a Chothia CDR-H2 sequence comprising, consisting of, or consisting essentially of SEQ ID NO: 60. In some aspects, the antibody comprises a $V_H$ sequence comprising a Chothia CDR-H2 sequence comprising, consisting of, or consisting essentially of SEQ ID NO: 61. In some aspects, the antibody comprises a $V_H$ sequence comprising a Chothia CDR-H2 sequence comprising, consisting of, or consisting essentially of SEQ ID NO: 62. In some aspects, the antibody comprises a $V_H$ sequence comprising a Chothia CDR-H2 sequence comprising, consisting of, or consisting essentially of SEQ ID NO: 63. In some aspects, the antibody comprises a $V_H$ sequence comprising a Chothia CDR-H2 sequence comprising, consisting of, or consisting essentially of SEQ ID NO: 64. In some aspects, the antibody comprises a $V_H$ sequence comprising a Chothia CDR-H2 sequence comprising, consisting of, or consisting essentially of SEQ ID NO: 65. In some aspects, the antibody comprises a $V_H$ sequence comprising a Chothia CDR-H2 sequence comprising, consisting of, or consisting essentially of SEQ ID NO: 66. In some aspects, the antibody comprises a $V_H$ sequence comprising a Chothia CDR-H2 sequence comprising, consisting of, or consisting essentially of SEQ ID NO: 67. In some aspects, the antibody comprises a $V_H$ sequence comprising a Chothia CDR-H2 sequence comprising, consisting of, or consisting essentially of SEQ ID NO: 68. In some aspects, the antibody comprises a $V_H$ sequence comprising a Chothia CDR-H2 sequence comprising, consisting of, or consisting essentially of SEQ ID NO: 69. In some aspects, the antibody comprises a $V_H$ sequence comprising a Chothia CDR-H2 sequence comprising, consisting of, or consisting essentially of SEQ ID NO: 70. In some aspects, the antibody comprises a $V_H$ sequence comprising a Chothia CDR-H2 sequence comprising, consisting of, or consisting essentially of SEQ ID NO: 71. In some aspects, the antibody comprises a $V_H$ sequence comprising a Chothia CDR-H2 sequence comprising, consisting of, or consisting essentially of SEQ ID NO: 72. In some aspects, the antibody comprises a $V_H$ sequence comprising a Chothia CDR-H2 sequence comprising, consisting of, or consisting essentially of SEQ ID NO: 73. In some aspects, the antibody comprises a $V_H$ sequence comprising a Chothia CDR-H2 sequence comprising, consisting of, or consisting essentially of SEQ ID NO: 74. In some aspects, the antibody comprises a $V_H$ sequence comprising a Chothia CDR-H2 sequence comprising, consisting of, or consisting essentially of SEQ ID NO: 75. In some aspects, the antibody comprises a $V_H$ sequence comprising a Chothia CDR-H2 sequence comprising, consisting of, or consisting essentially of SEQ ID NO: 76. In some aspects, the antibody comprises a $V_H$ sequence comprising a Chothia CDR-H2 sequence comprising, consisting of, or consisting essentially of SEQ ID NO: 77. In some aspects, the antibody comprises a $V_H$ sequence comprising a Chothia CDR-H2 sequence comprising, consisting of, or consisting essentially of SEQ ID NO: 78.

2.2.2.3. Chothia CDR-H1

In some embodiments, the antibody comprises a $V_H$ sequence comprising a CDR-H1 sequence, wherein the CDR-H1 sequence comprises, consists of, or consists essentially of a Chothia CDR-H1 sequence of an illustrative antibody or $V_H$ sequence provided herein. In some aspects, the Chothia CDR-H1 sequence is a Chothia CDR-H1 sequence of an scFv-Fc sequence provided in SEQ ID NOs.: 204-228 or of an scFv sequence provided in SEQ ID NOs.: 337-361. In some aspects, the Chothia CDR-H1 sequence is a Chothia CDR-H1 sequence of a $V_H$ sequence provided in SEQ ID NOs.: 229-253.

In some embodiments, the antibody comprises a $V_H$ sequence comprising a Chothia CDR-H1 sequence comprising, consisting of, or consisting essentially of a sequence selected from SEQ ID NOs: 4-28. In some aspects, the antibody comprises a $V_H$ sequence comprising a Chothia CDR-H1 sequence comprising, consisting of, or consisting essentially of SEQ ID NO: 4. In some aspects, the antibody comprises a $V_H$ sequence comprising a Chothia CDR-H1 sequence comprising, consisting of, or consisting essentially of SEQ ID NO: 5. In some aspects, the antibody comprises a $V_H$ sequence comprising a Chothia CDR-H1 sequence comprising, consisting of, or consisting essentially of SEQ ID NO: 6. In some aspects, the antibody comprises a $V_H$ sequence comprising a Chothia CDR-H1 sequence comprising, consisting of, or consisting essentially of SEQ ID NO: 7. In some aspects, the antibody comprises a $V_H$ sequence comprising a Chothia CDR-H1 sequence comprising, consisting of, or consisting essentially of SEQ ID NO: 8. In some aspects, the antibody comprises a $V_H$ sequence comprising a Chothia CDR-H1 sequence comprising, consisting of, or consisting essentially of SEQ ID NO: 9. In some aspects, the antibody comprises a $V_H$ sequence comprising a Chothia CDR-H1 sequence comprising, consisting of, or consisting essentially of SEQ ID NO: 10. In some aspects, the antibody comprises a $V_H$ sequence comprising a Chothia CDR-H1 sequence comprising, consisting of, or consisting essentially of SEQ ID NO: 11. In some aspects, the antibody comprises a $V_H$ sequence comprising a Chothia CDR-H1 sequence comprising, consisting of, or consisting essentially of SEQ ID NO: 12. In some aspects, the antibody comprises a $V_H$ sequence comprising a Chothia CDR-H1 sequence comprising, consisting of, or consisting essentially of SEQ ID NO: 13. In some aspects, the antibody comprises a $V_H$ sequence comprising a Chothia CDR-H1 sequence comprising, consisting of, or consisting essentially of SEQ ID NO: 14. In some aspects, the antibody comprises a $V_H$ sequence comprising a Chothia CDR-H1 sequence comprising, consisting of, or consisting essentially of SEQ ID NO: 15. In some aspects, the antibody comprises a $V_H$ sequence comprising a Chothia CDR-H1 sequence comprising, consisting of, or consisting essentially of SEQ ID NO: 16. In some aspects, the antibody comprises a $V_H$ sequence comprising a Chothia CDR-H1 sequence comprising, consisting of, or consisting essentially of SEQ ID NO: 17. In some aspects, the antibody comprises a $V_H$ sequence comprising a Chothia CDR-H1 sequence comprising, consisting of, or consisting essentially of SEQ ID NO: 18. In some aspects, the antibody comprises a $V_H$ sequence comprising a Chothia CDR-H1 sequence comprising, consisting of, or consisting essentially of SEQ ID NO: 19. In some aspects, the antibody comprises a $V_H$ sequence comprising a Chothia CDR-H1 sequence comprising, consisting of, or consisting essentially of SEQ ID NO: 20. In some aspects, the antibody comprises a $V_H$ sequence comprising a Chothia CDR-H1 sequence comprising, consisting of, or consisting essentially of SEQ ID NO: 21. In some aspects, the antibody comprises a $V_H$ sequence comprising a Chothia CDR-H1 sequence comprising, consisting of, or consisting essentially of SEQ ID NO: 22. In some aspects, the antibody comprises a $V_H$ sequence comprising a Chothia CDR-H1 sequence comprising, consisting of, or consisting essentially of SEQ ID NO: 23. In some aspects, the antibody comprises a $V_H$ sequence comprising a Chothia CDR-H1 sequence comprising, consisting of, or consisting essentially of SEQ ID NO: 24. In some aspects, the antibody comprises a $V_H$ sequence comprising a Chothia CDR-H1 sequence comprising, consisting of, or consisting essentially of SEQ ID NO: 25. In some aspects, the antibody comprises a $V_H$ sequence comprising a Chothia CDR-H1 sequence comprising, consisting of, or consisting essentially of SEQ ID NO: 26. In some aspects, the antibody comprises a $V_H$ sequence comprising a Chothia CDR-H1 sequence comprising, consisting of, or consisting essentially of SEQ ID NO: 27. In some aspects, the antibody comprises a $V_H$ sequence comprising a Chothia CDR-H1 sequence comprising, consisting of, or consisting essentially of SEQ ID NO: 28.

2.2.2.4. Chothia CDR-H3+Chothia CDR-H2

In some embodiments, the antibody comprises a $V_H$ sequence comprising a Chothia CDR-H3 sequence comprising, consisting of, or consisting essentially of a sequence selected from SEQ ID NOs: 104-128, and a Chothia CDR-H2 sequence comprising, consisting of, or consisting essentially of a sequence selected from SEQ ID NOs: 54-78. In some aspects, the Chothia CDR-H3 sequence and the Chothia CDR-H2 sequence are both from a single illustrative $V_H$ sequence provided in this disclosure. For example, in some aspects, the Chothia CDR-H3 and Chothia CDR-H2 are both from a single illustrative $V_H$ sequence selected from SEQ ID NOs: 229-253.

2.2.2.5. Chothia CDR-H3+Chothia CDR-H1

In some embodiments, the antibody comprises a $V_H$ sequence comprising a Chothia CDR-H3 sequence comprising, consisting of, or consisting essentially of a sequence selected from SEQ ID NOs: 104-128, and a Chothia CDR-H1 sequence comprising, consisting of, or consisting essentially of a sequence selected from SEQ ID NOs: 4-28. In some aspects, the Chothia CDR-H3 sequence and the Chothia CDR-H1 sequence are both from a single illustrative $V_H$ sequence provided in this disclosure. For example, in some aspects, the Chothia CDR-H3 and Chothia CDR-H1 are both from a single illustrative $V_H$ sequence selected from SEQ ID NOs: 229-253.

2.2.2.6. Chothia CDR-H1+Chothia CDR-H2

In some embodiments, the antibody comprises a $V_H$ sequence comprising a Chothia CDR-H1 sequence comprising, consisting of, or consisting essentially of a sequence selected from SEQ ID NOs: 4-28 and a Chothia CDR-H2 sequence comprising, consisting of, or consisting essentially of a sequence selected from SEQ ID NOs: 54-78. In some aspects, the Chothia CDR-H1 sequence and the Chothia CDR-H2 sequence are both from a single illustrative $V_H$ sequence provided in this disclosure. For example, in some aspects, the Chothia CDR-H1 and Chothia CDR-H2 are both from a single illustrative $V_H$ sequence selected from SEQ ID NOs: 229-253.

2.2.2.7. Chothia CDR-H1+Chothia CDR-H2+Chothia CDR-H3

In some embodiments, the antibody comprises a $V_H$ sequence comprising a Chothia CDR-H1 sequence comprising, consisting of, or consisting essentially of a sequence selected from SEQ ID NOs: 4-28, a Chothia CDR-H2 sequence comprising, consisting of, or consisting essentially of a sequence selected from SEQ ID NOs: 54-78, and a Chothia CDR-H3 sequence comprising, consisting of, or consisting essentially of a sequence selected from SEQ ID NOs: 104-128. In some aspects, the Chothia CDR-H1 sequence, Chothia CDR-H2 sequence, and Chothia CDR-H3 sequence are all from a single illustrative $V_H$ sequence provided in this disclosure. For example, in some aspects, the Chothia CDR-H1, Chothia CDR-H2, and Chothia CDR-H3 are all from a single illustrative $V_H$ sequence selected from SEQ ID NOs: 229-253.

2.2.2.8. Variants of $V_H$ Sequences Comprising Illustrative Chothia CDRs

In some embodiments, the $V_H$ sequences provided herein comprise a variant of an illustrative Chothia CDR-H3, CDR-H2, and/or CDR-H1 sequence provided in this disclosure.

In some aspects, the Chothia CDR-H3 sequence comprises, consists of, or consists essentially of a variant of an illustrative Chothia CDR-H3 sequence provided in this disclosure. In some aspects, the Chothia CDR-H3 sequence comprises, consists of, or consists essentially of a sequence having at least 70%, 75%, 80%, 85%, 90%, or 95% identity with any of the illustrative Chothia CDR-H3 sequences provided in this disclosure. In some aspects, the Chothia CDR-H3 sequence comprises, consists of, or consists essentially of any of the illustrative Chothia CDR-H3 sequences provided in this disclosure, with 1, 2, or 3 amino acid substitutions. In some aspects, the amino acid substitutions are conservative amino acid substitutions.

In some aspects, the Chothia CDR-H2 sequence comprises, consists of, or consists essentially of a variant of an illustrative Chothia CDR-H2 sequence provided in this disclosure. In some aspects, the Chothia CDR-H2 sequence comprises, consists of, or consists essentially of a sequence having at least 70%, 75%, 80%, 85%, 90%, or 95% identity with any of the illustrative Chothia CDR-H2 sequences provided in this disclosure. In some aspects, the Chothia CDR-H2 sequence comprises, consists of, or consists essentially of any of the illustrative Chothia CDR-H2 sequences provided in this disclosure, with 1, 2, or 3 amino acid substitutions. In some aspects, the amino acid substitutions are conservative amino acid substitutions.

In some aspects, the Chothia CDR-H1 sequence comprises, consists of, or consists essentially of a variant of an illustrative Chothia CDR-H1 sequence provided in this disclosure. In some aspects, the Chothia CDR-H1 sequence comprises, consists of, or consists essentially of a sequence having at least 70%, 75%, 80%, 85%, 90%, or 95% identity with any of the illustrative Chothia CDR-H1 sequences provided in this disclosure. In some aspects, the Chothia CDR-H1 sequence comprises, consists of, or consists essentially of any of the illustrative Chothia CDR-H1 sequences provided in this disclosure, with 1, 2, or 3 amino acid substitutions. In some aspects, the amino acid substitutions are conservative amino acid substitutions.

2.2.2.9. Excluded $V_H$ Sequences Comprising Chothia CDRs

In some embodiments, the $V_H$ sequences provided herein do not comprise certain Chothia CDR-H3, CDR-H2, and/or CDR-H1 sequences.

In some aspects, the Chothia CDR-H3 sequence does not comprise, consist of, or consist essentially of a sequence selected from SEQ ID NOs: 306-310. In some aspects, the Chothia CDR-H3 sequence does not comprise, consist of, or consist essentially of SEQ ID NO: 306. In some aspects, the Chothia CDR-H3 sequence does not comprise, consist of, or consist essentially of SEQ ID NO: 307. In some aspects, the Chothia CDR-H3 sequence does not comprise, consist of, or consist essentially of SEQ ID NO: 308. In some aspects, the Chothia CDR-H3 sequence does not comprise, consist of, or consist essentially of SEQ ID NO: 309. In some aspects, the Chothia CDR-H3 sequence does not comprise, consist of, or consist essentially of SEQ ID NO: 310.

In some aspects, the Chothia CDR-H2 sequence does not comprise, consist of, or consist essentially of a sequence selected from SEQ ID NOs: 296-300. In some aspects, the Chothia CDR-H2 sequence does not comprise, consist of, or consist essentially of SEQ ID NO: 296. In some aspects, the Chothia CDR-H2 sequence does not comprise, consist of, or consist essentially of SEQ ID NO: 297. In some aspects, the Chothia CDR-H2 sequence does not comprise, consist of, or consist essentially of SEQ ID NO: 298. In some aspects, the Chothia CDR-H2 sequence does not comprise, consist of, or consist essentially of SEQ ID NO: 299. In some aspects, the Chothia CDR-H2 sequence does not comprise, consist of, or consist essentially of SEQ ID NO: 300.

In some aspects, the Chothia CDR-H1 sequence does not comprise, consist of, or consist essentially of a sequence selected from SEQ ID NOs: 286-290. In some aspects, the Chothia CDR-H1 sequence does not comprise, consist of, or consist essentially of SEQ ID NO: 286. In some aspects, the Chothia CDR-H1 sequence does not comprise, consist of, or consist essentially of SEQ ID NO: 287. In some aspects, the Chothia CDR-H1 sequence does not comprise, consist of, or consist essentially of SEQ ID NO: 288. In some aspects, the Chothia CDR-H1 sequence does not comprise, consist of, or consist essentially of SEQ ID NO: 289. In some aspects, the Chothia CDR-H1 sequence does not comprise, consist of, or consist essentially of SEQ ID NO: 290.

2.3. $V_H$ Sequences

In some embodiments, the antibody comprises, consists of, or consists essentially of a $V_H$ sequence of an scFv-Fc sequence provided in SEQ ID NOs.: 204-228 or of an scFv sequence provided in SEQ ID NOs.: 337-361. In some embodiments, the antibody comprises, consists of, or consists essentially of a $V_H$ sequence provided in SEQ ID NOs.: 229-253.

In some embodiments, the antibody comprises a $V_H$ sequence comprising, consisting of, or consisting essentially of a sequence selected from SEQ ID NOs: 229-253. In some aspects, the antibody comprises a $V_H$ sequence comprising, consisting of, or consisting essentially of SEQ ID NO: 229. In some aspects, the antibody comprises a $V_H$ sequence comprising, consisting of, or consisting essentially of SEQ ID NO: 230. In some aspects, the antibody comprises a $V_H$ sequence comprising, consisting of, or consisting essentially of SEQ ID NO: 231. In some aspects, the antibody comprises a $V_H$ sequence comprising, consisting of, or consisting essentially of SEQ ID NO: 232. In some aspects, the antibody comprises a $V_H$ sequence comprising, consisting of, or consisting essentially of SEQ ID NO: 233. In some aspects, the antibody comprises a $V_H$ sequence comprising, consisting of, or consisting essentially of SEQ ID NO: 234. In some aspects, the antibody comprises a $V_H$ sequence comprising, consisting of, or consisting essentially of SEQ ID NO: 235. In some aspects, the antibody comprises a $V_H$ sequence comprising, consisting of, or consisting essentially of SEQ ID NO: 236. In some aspects, the antibody comprises a $V_H$ sequence comprising, consisting of, or consisting essentially of SEQ ID NO: 237. In some aspects, the antibody comprises a $V_H$ sequence comprising, consisting of, or consisting essentially of SEQ ID NO: 238. In some aspects, the antibody comprises a $V_H$ sequence comprising, consisting of, or consisting essentially of SEQ ID NO: 239. In some aspects, the antibody comprises a $V_H$ sequence comprising, consisting of, or consisting essentially of SEQ ID NO: 240. In some aspects, the antibody comprises a $V_H$ sequence comprising, consisting of, or consisting essentially of SEQ ID NO: 241. In some aspects, the antibody comprises a $V_H$ sequence comprising, consisting of, or consisting essentially of SEQ ID NO: 242. In some aspects, the antibody comprises a $V_H$ sequence comprising, consisting of, or consisting essentially of SEQ ID NO: 243. In some aspects, the antibody comprises a $V_H$ sequence comprising, consisting of, or consisting essentially of SEQ ID NO: 244. In some aspects, the antibody comprises a $V_H$ sequence comprising, consisting of, or consisting essentially of SEQ ID NO: 245. In some aspects, the antibody comprises a $V_H$ sequence comprising, consisting of, or consisting essentially of SEQ ID NO: 246. In some aspects, the antibody comprises a $V_H$ sequence comprising, consisting of, or consisting essentially of SEQ ID NO: 247. In some aspects, the antibody comprises a $V_H$ sequence comprising, consisting of, or consisting essentially of SEQ ID NO: 248. In some aspects, the antibody comprises a $V_H$ sequence comprising, consisting of, or consisting essentially of SEQ ID NO: 249. In some aspects, the antibody comprises a $V_H$ sequence comprising, consisting of, or consisting essentially of SEQ ID NO: 250. In some aspects, the antibody comprises a $V_H$ sequence comprising, consisting of, or consisting essentially of SEQ ID NO: 251. In some aspects, the antibody comprises a $V_H$ sequence comprising, consisting of, or consisting essentially of SEQ ID NO: 252. In some aspects, the antibody comprises a $V_H$ sequence comprising, consisting of, or consisting essentially of SEQ ID NO: 253.

2.3.1. Variants of $V_H$ Sequences

In some embodiments, the $V_H$ sequences provided herein comprise, consist of, or consist essentially of a variant of an illustrative $V_H$ sequence provided in this disclosure.

In some aspects, the $V_H$ sequence comprises, consists of, or consists essentially of a variant of an illustrative $V_H$ sequence provided in this disclosure. In some aspects, the $V_H$ sequence comprises, consists of, or consists essentially of a sequence having at least 85%, 90%, 95%, 96%, 97%, 98%, 99%, or 99.5% identity with any of the illustrative $V_H$ sequences provided in this disclosure.

In some embodiments, the $V_H$ sequence comprises, consists of, or consists essentially of any of the illustrative $V_H$ sequences provided in this disclosure having 20 or fewer, 19 or fewer, 18 or fewer, 17 or fewer, 16 or fewer, 15 or fewer, 14 or fewer, 13 or fewer, 12 or fewer, 11 or fewer, 10 or fewer, 9 or fewer, 8 or fewer, 7 or fewer, 6 or fewer, 5 or fewer, 4 or fewer, 3 or fewer, 2 or fewer, or 1 or fewer amino acid substitutions. In some aspects, the amino acid substitutions are conservative amino acid substitutions.

2.3.2. Excluded $V_H$ Sequences

In some embodiments, the $V_H$ sequences provided herein do not comprise certain $V_H$ sequences.

In some aspects, the $V_H$ sequence does not comprise, consist of, or consist essentially of a sequence selected from SEQ ID NOs: 326-330. In some aspects, the $V_H$ sequence does not comprise, consist of, or consist essentially of SEQ ID NO: 326. In some aspects, the $V_H$ sequence does not comprise, consist of, or consist essentially of SEQ ID NO: 327. In some aspects, the $V_H$ sequence does not comprise, consist of, or consist essentially of SEQ ID NO: 328. In some aspects, the $V_H$ sequence does not comprise, consist of, or consist essentially of SEQ ID NO: 329. In some aspects, the $V_H$ sequence does not comprise, consist of, or consist essentially of SEQ ID NO: 330.

2.4. CDR-L3 Sequences

In some embodiments, the antibody comprises a CDR-L3 sequence comprising, consisting of, or consisting essentially of a CDR-L3 sequence of an illustrative antibody or $V_L$ sequence provided herein. In some aspects, the CDR-L3 sequence is a CDR-L3 sequence of an scFv-Fc sequence provided in SEQ ID NOs.: 204-228 or of an scFv sequence provided in SEQ ID NOs.: 337-361. In some aspects, the CDR-L3 sequence is a CDR-L3 sequence of a $V_L$ sequence provided in SEQ ID NOs.: 254-278.

In some embodiments, the antibody comprises a CDR-L3 sequence comprising, consisting of, or consisting essentially of a sequence selected from SEQ ID NOs: 179-203. In some aspects, the antibody comprises a CDR-L3 sequence comprising, consisting of, or consisting essentially of SEQ ID NO: 179. In some aspects, the antibody comprises a CDR-L3 sequence comprising, consisting of, or consisting essentially of SEQ ID NO: 180. In some aspects, the antibody comprises a CDR-L3 sequence comprising, consisting of, or consisting essentially of SEQ ID NO: 181. In some aspects, the antibody comprises a CDR-L3 sequence comprising, consisting of, or consisting essentially of SEQ ID NO: 182. In some aspects, the antibody comprises a CDR-L3 sequence comprising, consisting of, or consisting essentially of SEQ ID NO: 183. In some aspects, the antibody comprises a CDR-L3 sequence comprising, consisting of, or consisting essentially of SEQ ID NO: 184. In some aspects, the antibody comprises a CDR-L3 sequence comprising, consisting of, or consisting essentially of SEQ ID NO: 185. In some aspects, the antibody comprises a CDR-L3 sequence comprising, consisting of, or consisting essentially of SEQ ID NO: 186. In some aspects, the antibody comprises a CDR-L3 sequence comprising, consisting of, or consisting essentially of SEQ ID NO: 187. In some aspects, the antibody comprises a CDR-L3 sequence comprising, consisting of, or consisting essentially of SEQ ID NO: 188. In some aspects, the antibody comprises a CDR-L3 sequence comprising, consisting of, or consisting essentially of SEQ ID NO: 189. In some aspects, the antibody comprises a CDR-L3 sequence comprising, consisting of, or consisting essentially of SEQ ID NO: 190. In some aspects, the antibody comprises a CDR-L3 sequence comprising, consisting of, or consisting essentially of SEQ ID NO: 191. In some aspects, the antibody comprises a CDR-L3 sequence comprising, consisting of, or consisting essentially of SEQ ID NO: 192. In some aspects, the antibody comprises a CDR-L3 sequence comprising, consisting of, or consisting essentially of SEQ ID NO: 193. In some aspects, the antibody comprises a CDR-L3 sequence comprising, consisting of, or consisting essentially of SEQ ID NO: 194. In some aspects, the antibody comprises a CDR-L3 sequence comprising, consisting of, or consisting essentially of SEQ ID NO: 195. In some aspects, the antibody comprises a CDR-L3 sequence comprising, consisting of, or consisting essentially of SEQ ID NO: 196. In some aspects, the antibody comprises a CDR-L3 sequence comprising, consisting of, or consisting essentially of SEQ ID NO: 197. In some aspects, the antibody comprises a CDR-L3 sequence comprising, consisting of, or consisting essentially of SEQ ID NO: 198. In some aspects, the antibody comprises a CDR-L3 sequence comprising, consisting of, or consisting essentially of SEQ ID NO: 199. In some aspects, the antibody comprises a CDR-L3 sequence comprising, consisting of, or consisting essentially of SEQ ID NO: 200. In some aspects, the antibody comprises a CDR-L3 sequence comprising, consisting of, or consisting essentially of SEQ ID NO: 201. In some aspects, the antibody comprises a CDR-L3 sequence comprising, consisting of, or consisting essentially of SEQ ID NO: 202. In some aspects, the antibody comprises a CDR-L3 sequence comprising, consisting of, or consisting essentially of SEQ ID NO: 203.

In some aspects, the CDR-L3 sequence comprises, consists of, or consists essentially of a variant of an illustrative CDR-L3 sequence provided in this disclosure. In some aspects, the CDR-L3 sequence comprises, consists of, or consists essentially of a sequence having at least 70%, 75%, 80%, 85%, 90%, or 95% identity with any of the illustrative CDR-L3 sequences provided in this disclosure. In some aspects, the CDR-L3 sequence comprises, consists of, or consists essentially of any of the illustrative CDR-L3 sequences provided in this disclosure, with 1, 2, or 3 amino acid substitutions. In some aspects, the amino acid substitutions are conservative amino acid substitutions.

In some aspects, the CDR-L3 sequence does not comprise, consist of, or consist essentially of a sequence selected from SEQ ID NOs: 321-325. In some aspects the CDR-L3 sequence does not comprise, consist of, or consist essentially of SEQ ID NO: 321. In some aspects the CDR-L3 sequence does not comprise, consist of, or consist essentially of SEQ ID NO: 322. In some aspects the CDR-L3 sequence does not comprise, consist of, or consist essentially of SEQ ID NO: 323. In some aspects the CDR-L3 sequence does not comprise, consist of, or consist essentially of SEQ ID NO: 324. In some aspects the CDR-L3 sequence does not comprise, consist of, or consist essentially of SEQ ID NO: 325.

2.5. $V_L$ Sequences Comprising Illustrative CDRs

In some embodiments, the antibody comprises a $V_L$ sequence comprising one or more CDR-L sequences comprising, consisting of, or consisting essentially of one or more illustrative CDR-L sequences provided in this disclosure, and variants thereof.

2.5.1. CDR-L3

In some embodiments, the antibody comprises a $V_L$ sequence comprising a CDR-L3 sequence, wherein the CDR-L3 sequence comprises, consists of, or consists essentially of a CDR-L3 sequence of an illustrative antibody or $V_L$ sequence provided herein. In some aspects, the CDR-L3 sequence is a CDR-L3 sequence of an scFv-Fc sequence provided in SEQ ID NOs.: 204-228 or of an scFv sequence provided in SEQ ID NOs.: 337-361. In some aspects, the CDR-L3 sequence is a CDR-L3 sequence of a $V_L$ sequence provided in SEQ ID NOs.: 254-278.

In some embodiments, the antibody comprises a $V_L$ sequence comprising a CDR-L3 sequence comprising, consisting of, or consisting essentially of a sequence selected from SEQ ID NOs: 179-203. In some aspects, the antibody comprises a $V_L$ sequence comprising a CDR-L3 sequence comprising, consisting of, or consisting essentially of SEQ ID NO: 179. In some aspects, the antibody comprises a $V_L$ sequence comprising a CDR-L3 sequence comprising, consisting of, or consisting essentially of SEQ ID NO: 180. In some aspects, the antibody comprises a $V_L$ sequence comprising a CDR-L3 sequence comprising, consisting of, or consisting essentially of SEQ ID NO: 181. In some aspects, the antibody comprises a $V_L$ sequence comprising a CDR-L3 sequence comprising, consisting of, or consisting essentially of SEQ ID NO: 182. In some aspects, the antibody comprises a $V_L$ sequence comprising a CDR-L3 sequence comprising, consisting of, or consisting essentially of SEQ ID NO: 183. In some aspects, the antibody comprises a $V_L$ sequence comprising a CDR-L3 sequence comprising, consisting of, or consisting essentially of SEQ ID NO: 184. In some aspects, the antibody comprises a $V_L$ sequence comprising a CDR-L3 sequence comprising, consisting of, or consisting essentially of SEQ ID NO: 185. In some aspects, the antibody comprises a $V_L$ sequence comprising a CDR-L3 sequence comprising, consisting of, or consisting essentially of SEQ ID NO: 186. In some aspects, the antibody comprises a $V_L$ sequence comprising a CDR-L3 sequence comprising, consisting of, or consisting essentially of SEQ ID NO: 187. In some aspects, the antibody comprises a $V_L$ sequence comprising a CDR-L3 sequence comprising, consisting of, or consisting essentially of SEQ ID NO: 188. In some aspects, the antibody comprises a $V_L$ sequence comprising a CDR-L3 sequence comprising, consisting of, or consisting essentially of SEQ ID NO: 189. In some aspects, the antibody comprises a $V_L$ sequence comprising a CDR-L3 sequence comprising, consisting of, or consisting essentially of SEQ ID NO: 190. In some aspects, the antibody comprises a $V_L$ sequence comprising a CDR-L3 sequence comprising, consisting of, or consisting essentially of SEQ ID NO: 191. In some aspects, the antibody comprises a $V_L$ sequence comprising a CDR-L3 sequence comprising, consisting of, or consisting essentially of SEQ ID NO: 192. In some aspects, the antibody comprises a $V_L$ sequence comprising a CDR-L3 sequence comprising, consisting of, or consisting essentially of SEQ ID NO: 193. In some aspects, the antibody comprises a $V_L$ sequence comprising a CDR-L3 sequence comprising, consisting of, or consisting essentially of SEQ ID NO: 194. In some aspects, the antibody comprises a $V_L$ sequence comprising a CDR-L3 sequence comprising, consisting of, or consisting essentially of SEQ ID NO: 195. In some aspects, the antibody comprises a $V_L$ sequence comprising a CDR-L3 sequence comprising, consisting of, or consisting essentially of SEQ ID NO: 196. In some aspects, the antibody comprises a $V_L$ sequence comprising a CDR-L3 sequence comprising, consisting of, or consisting essentially of SEQ ID NO: 197. In some aspects, the antibody comprises a $V_L$ sequence comprising a CDR-L3 sequence comprising, consisting of, or consisting essentially of SEQ ID NO: 198. In some aspects, the antibody comprises a $V_L$ sequence comprising a CDR-L3 sequence comprising, consisting of, or consisting essentially of SEQ ID NO: 199. In some aspects, the antibody comprises a $V_L$ sequence comprising a CDR-L3 sequence comprising, consisting of, or consisting essentially of SEQ ID NO: 200. In some aspects, the antibody comprises a $V_L$ sequence comprising a CDR-L3 sequence comprising, consisting of, or consisting essentially of SEQ ID NO: 201. In some aspects, the antibody comprises a $V_L$ sequence comprising a CDR-L3 sequence comprising, consisting of, or consisting essentially of SEQ ID NO: 202. In some aspects, the antibody comprises a $V_L$ sequence comprising a CDR-L3 sequence comprising, consisting of, or consisting essentially of SEQ ID NO: 203.

2.5.2. CDR-L2

In some embodiments, the antibody comprises a $V_L$ sequence comprising a CDR-L2 sequence, wherein the CDR-L2 sequence comprises, consists of, or consists essentially of a CDR-L2 sequence of an illustrative antibody or $V_L$ sequence provided herein. In some aspects, the CDR-L2 sequence is a CDR-L2 sequence of an scFv-Fc sequence provided in SEQ ID NOs.: 204-228 or of an scFv sequence provided in SEQ ID NOs.: 337-361. In some aspects, the CDR-L2 sequence is a CDR-L2 sequence of a $V_L$ sequence provided in SEQ ID NOs.: 254-278.

In some embodiments, the antibody comprises a $V_L$ sequence comprising a CDR-L2 sequence comprising, consisting of, or consisting essentially of a sequence selected from SEQ ID NOs: 154-178. In some aspects, the antibody comprises a $V_L$ sequence comprising a CDR-L2 sequence comprising, consisting of, or consisting essentially of SEQ ID NO: 154. In some aspects, the antibody comprises a $V_L$ sequence comprising a CDR-L2 sequence comprising, consisting of, or consisting essentially of SEQ ID NO: 155. In some aspects, the antibody comprises a $V_L$ sequence comprising a CDR-L2 sequence comprising, consisting of, or consisting essentially of SEQ ID NO: 156. In some aspects, the antibody comprises a $V_L$ sequence comprising a CDR-L2 sequence comprising, consisting of, or consisting essentially of SEQ ID NO: 157. In some aspects, the antibody comprises a $V_L$ sequence comprising a CDR-L2 sequence comprising, consisting of, or consisting essentially of SEQ ID NO: 158. In some aspects, the antibody comprises a $V_L$ sequence comprising a CDR-L2 sequence comprising, consisting of, or consisting essentially of SEQ ID NO: 159. In some aspects, the antibody comprises a $V_L$ sequence comprising a CDR-L2 sequence comprising, consisting of, or consisting essentially of SEQ ID NO: 160. In some aspects, the antibody comprises a $V_L$ sequence comprising a CDR-L2 sequence comprising, consisting of, or consisting essentially of SEQ ID NO: 161. In some aspects, the antibody comprises a $V_L$ sequence comprising a CDR-L2 sequence comprising, consisting of, or consisting essentially of SEQ ID NO: 162. In some aspects, the antibody comprises a $V_L$ sequence comprising a CDR-L2 sequence comprising, consisting of, or consisting essentially of SEQ ID NO: 163. In some aspects, the antibody comprises a $V_L$ sequence comprising a CDR-L2 sequence comprising, consisting of, or consisting essentially of SEQ ID NO: 164. In some aspects, the antibody comprises a $V_L$ sequence comprising a CDR-L2 sequence comprising, consisting of, or consisting essentially of SEQ ID NO: 165. In some aspects, the antibody comprises a $V_L$ sequence comprising a CDR-L2 sequence comprising, consisting of, or consisting essentially of SEQ ID NO: 166. In some aspects, the antibody comprises a $V_L$ sequence comprising a CDR-L2 sequence comprising, consisting of, or consisting essentially of SEQ ID NO: 167. In some aspects, the antibody comprises a $V_L$ sequence comprising a CDR-L2 sequence comprising, consisting of, or consisting essentially of SEQ ID NO: 168. In some aspects, the antibody comprises a $V_L$ sequence comprising a CDR-L2 sequence comprising, consisting of, or consisting essentially of SEQ ID NO: 169. In some aspects, the antibody comprises a $V_L$ sequence comprising a CDR-L2 sequence comprising, consisting of, or consisting essentially of SEQ ID NO: 170. In some aspects, the antibody comprises a $V_L$ sequence comprising a CDR-L2 sequence comprising, consisting of, or consisting essentially of SEQ ID NO: 171. In some aspects, the antibody comprises a $V_L$ sequence comprising a CDR-L2 sequence comprising, consisting of, or consisting essentially of SEQ ID NO: 172. In some aspects, the antibody comprises a $V_L$ sequence comprising a CDR-L2 sequence comprising, consisting of, or consisting essentially of SEQ ID NO: 173. In some aspects, the antibody comprises a $V_L$ sequence comprising a CDR-L2 sequence comprising, consisting of, or consisting essentially of SEQ ID NO: 174. In some aspects, the antibody comprises a $V_L$ sequence comprising a CDR-L2 sequence comprising, consisting of, or consisting essentially of SEQ ID NO: 175. In some aspects, the antibody comprises a $V_L$ sequence comprising a CDR-L2 sequence comprising, consisting of, or consisting essentially of SEQ ID NO: 176. In some aspects, the antibody comprises a $V_L$ sequence comprising a CDR-L2 sequence comprising, consisting of, or consisting essentially of SEQ ID NO: 177. In some aspects, the antibody comprises a $V_L$ sequence comprising a CDR-L2 sequence comprising, consisting of, or consisting essentially of SEQ ID NO: 178.

2.5.3. CDR-L1

In some embodiments, the antibody comprises a $V_L$ sequence comprising a CDR-L1 sequence, wherein the CDR-L1 sequence comprises, consists of, or consists essentially of a CDR-L1 sequence of an illustrative antibody or $V_L$ sequence provided herein. In some aspects, the CDR-L1 sequence is a CDR-L1 sequence of an scFv-Fc sequence provided in SEQ ID NOs.: 204-228 or of an scFv sequence provided in SEQ ID NOs.: 337-361. In some aspects, the CDR-L1 sequence is a CDR-L1 sequence of a $V_L$ sequence provided in SEQ ID NOs.: 254-278.

In some embodiments, the antibody comprises a $V_L$ sequence comprising a CDR-L1 sequence comprising, consisting of, or consisting essentially of a sequence selected from SEQ ID NOs: 129-153. In some aspects, the antibody comprises a $V_L$ sequence comprising a CDR-L1 sequence comprising, consisting of, or consisting essentially of SEQ ID NO: 129. In some aspects, the antibody comprises a $V_L$ sequence comprising a CDR-L1 sequence comprising, consisting of, or consisting essentially of SEQ ID NO: 130. In some aspects, the antibody comprises a $V_L$ sequence comprising a CDR-L1 sequence comprising, consisting of, or consisting essentially of SEQ ID NO: 131. In some aspects, the antibody comprises a $V_L$ sequence comprising a CDR-L1 sequence comprising, consisting of, or consisting essentially of SEQ ID NO: 132. In some aspects, the antibody comprises a $V_L$ sequence comprising a CDR-L1 sequence comprising, consisting of, or consisting essentially of SEQ ID NO: 133. In some aspects, the antibody comprises a $V_L$ sequence comprising a CDR-L1 sequence comprising, consisting of, or consisting essentially of SEQ ID NO: 134. In some aspects, the antibody comprises a $V_L$ sequence comprising a CDR-L1 sequence comprising, consisting of, or consisting essentially of SEQ ID NO: 135. In some aspects, the antibody comprises a $V_L$ sequence comprising a CDR-L1 sequence comprising, consisting of, or consisting essentially of SEQ ID NO: 136. In some aspects, the antibody comprises a $V_L$ sequence comprising a CDR-L1 sequence comprising, consisting of, or consisting essentially of SEQ ID NO: 137. In some aspects, the antibody comprises a $V_L$ sequence comprising a CDR-L1 sequence comprising, consisting of, or consisting essentially of SEQ ID NO: 138. In some aspects, the antibody comprises a $V_L$ sequence comprising a CDR-L1 sequence comprising, consisting of, or consisting essentially of SEQ ID NO: 139. In some aspects, the antibody comprises a $V_L$ sequence comprising a CDR-L1 sequence comprising, consisting of, or consisting essentially of SEQ ID NO: 140. In some aspects, the antibody comprises a $V_L$ sequence comprising a CDR-L1 sequence comprising, consisting of, or consisting essentially of SEQ ID NO: 141. In some aspects, the antibody comprises a $V_L$ sequence comprising a CDR-L1 sequence comprising, consisting of, or consisting essentially of SEQ ID NO: 142. In some aspects, the antibody comprises a $V_L$ sequence comprising a CDR-L1 sequence comprising, consisting of, or consisting essentially of SEQ ID NO: 143. In some aspects, the antibody comprises a $V_L$ sequence comprising a CDR-L1 sequence comprising, consisting of, or consisting essentially of SEQ ID NO: 144. In some aspects, the antibody comprises a $V_L$ sequence comprising a CDR-L1 sequence comprising, consisting of, or consisting essentially of SEQ ID NO: 145. In some aspects, the antibody comprises a $V_L$ sequence comprising a CDR-L1 sequence comprising, consisting of, or consisting essentially of SEQ ID NO: 146. In some aspects, the antibody comprises a $V_L$ sequence comprising a CDR-L1 sequence comprising, consisting of, or consisting essentially of SEQ ID NO: 147. In some aspects, the antibody comprises a $V_L$ sequence comprising a CDR-L1 sequence comprising, consisting of, or consisting essentially of SEQ ID NO: 148. In some aspects, the antibody comprises a $V_L$ sequence comprising a CDR-L1 sequence comprising, consisting of, or consisting essentially of SEQ ID NO: 149. In some aspects, the antibody comprises a $V_L$ sequence comprising a CDR-L1 sequence comprising, consisting of, or consisting essentially of SEQ ID NO: 150. In some aspects, the antibody comprises a $V_L$ sequence comprising a CDR-L1 sequence comprising, consisting of, or consisting essentially of SEQ ID NO: 151. In some aspects, the antibody comprises a $V_L$ sequence comprising a CDR-L1 sequence comprising, consisting of, or consisting essentially of SEQ ID NO: 152. In some aspects, the antibody comprises a $V_L$ sequence comprising a CDR-L1 sequence comprising, consisting of, or consisting essentially of SEQ ID NO: 153.

2.5.4. CDR-L3+CDR-L2

In some embodiments, the antibody comprises a $V_L$ sequence comprising a CDR-L3 sequence comprising, consisting of, or consisting essentially of a sequence selected from SEQ ID NOs: 179-203 and a CDR-L2 sequence comprising, consisting of, or consisting essentially of a sequence selected from SEQ ID NOs: 154-178. In some aspects, the CDR-L3 sequence and the CDR-L2 sequence are both from a single illustrative $V_L$ sequence provided in this disclosure. For example, in some aspects, the CDR-L3 and CDR-L2 are both from a single illustrative $V_L$ sequence selected from SEQ ID NOs: 254-278.

2.5.5. CDR-L3+CDR-L1

In some embodiments, the antibody comprises a $V_L$ sequence comprising a CDR-L3 sequence comprising, consisting of, or consisting essentially of a sequence selected from SEQ ID NOs: 179-203 and a CDR-L1 sequence comprising, consisting of, or consisting essentially of a sequence selected from SEQ ID NOs: 129-153. In some aspects, the CDR-L3 sequence and the CDR-L1 sequence are both from a single illustrative $V_L$ sequence provided in this disclosure. For example, in some aspects, the CDR-L3 and CDR-L1 are both from a single illustrative $V_L$ sequence selected from SEQ ID NOs: 254-278.

2.5.6. CDR-L1+CDR-L2

In some embodiments, the antibody comprises a $V_L$ sequence comprising a CDR-L1 sequence comprising, consisting of, or consisting essentially of a sequence selected from SEQ ID NOs: 129-153 and a CDR-L2 sequence comprising, consisting of, or consisting essentially of a sequence selected from SEQ ID NOs: 154-178. In some aspects, the CDR-L1 sequence and the CDR-L2 sequence are both from a single illustrative $V_L$ sequence provided in this disclosure. For example, in some aspects, the CDR-L1 and CDR-L2 are both from a single illustrative $V_L$ sequence selected from SEQ ID NOs: 254-278.

2.5.7. CDR-L1+CDR-L2+CDR-L3

In some embodiments, the antibody comprises a $V_L$ sequence comprising a CDR-L1 sequence comprising, consisting of, or consisting essentially of a sequence selected from SEQ ID NOs: 129-153, a CDR-L2 sequence comprising, consisting of, or consisting essentially of a sequence selected from SEQ ID NOs: 154-178, and a CDR-L3 sequence comprising, consisting of, or consisting essentially of a sequence selected from SEQ ID NOs: 179-203. In some aspects, the CDR-L1 sequence, CDR-L2 sequence, and CDR-L3 sequence are all from a single illustrative $V_L$ sequence provided in this disclosure. For example, in some aspects, the CDR-L1, CDR-L2, and CDR-L3 are all from a single illustrative $V_L$ sequence selected from SEQ ID NOs: 254-278.

2.5.8. Variants of $V_L$ Sequences Comprising Illustrative CDR-Ls

In some embodiments, the $V_L$ sequences provided herein comprise a variant of an illustrative CDR-L3, CDR-L2, and/or CDR-L1 sequence provided in this disclosure.

In some aspects, the CDR-L3 sequence comprises, consists of, or consists essentially of a variant of an illustrative CDR-L3 sequence provided in this disclosure. In some aspects, the CDR-L3 sequence comprises, consists of, or consists essentially of a sequence having at least 70%, 75%, 80%, 85%, 90%, or 95% identity with any of the illustrative CDR-L3 sequences provided in this disclosure. In some aspects, the CDR-L3 sequence comprises, consists of, or consists essentially of any of the illustrative CDR-L3 sequences provided in this disclosure, with 1, 2, or 3 amino acid substitutions. In some aspects, the amino acid substitutions are conservative amino acid substitutions.

In some aspects, the CDR-L2 sequence comprises, consists of, or consists essentially of a variant of an illustrative CDR-L2 sequence provided in this disclosure. In some aspects, the CDR-L2 sequence comprises, consists of, or consists essentially of a sequence having at least 70%, 75%, 80%, 85%, 90%, or 95% identity with any of the illustrative CDR-L2 sequences provided in this disclosure. In some aspects, the CDR-L2 sequence comprises, consists of, or consists essentially of any of the illustrative CDR-L2 sequences provided in this disclosure, with 1, 2, or 3 amino acid substitutions. In some aspects, the amino acid substitutions are conservative amino acid substitutions.

In some aspects, the CDR-L1 sequence comprises, consists of, or consists essentially of a variant of an illustrative CDR-L1 sequence provided in this disclosure. In some aspects, the CDR-L1 sequence comprises, consists of, or consists essentially of a sequence having at least 70%, 75%, 80%, 85%, 90%, or 95% identity with any of the illustrative CDR-L1 sequences provided in this disclosure. In some aspects, the CDR-L1 sequence comprises, consists of, or consists essentially of any of the illustrative CDR-L1 sequences provided in this disclosure, with 1, 2, or 3 amino acid substitutions. In some aspects, the amino acid substitutions are conservative amino acid substitutions.

2.5.9. Excluded $V_L$ Sequences Comprising CDR-Ls

In some embodiments, the $V_L$ sequences provided herein do not comprise certain CDR-L3, CDR-L2, and/or CDR-L1 sequences.

In some aspects, the CDR-L3 sequence does not comprise, consist of, or consist essentially of a sequence selected from SEQ ID NOs: 321-325. In some aspects, the CDR-L3 sequence does not comprise, consist of, or consist essentially of SEQ ID NOs: 321. In some aspects, the CDR-L3 sequence does not comprise, consist of, or consist essentially of SEQ ID NOs: 322. In some aspects, the CDR-L3 sequence does not comprise, consist of, or consist essentially of SEQ ID NOs: 323. In some aspects, the CDR-L3 sequence does not comprise, consist of, or consist essentially of SEQ ID NOs: 324. In some aspects, the CDR-L3 sequence does not comprise, consist of, or consist essentially of SEQ ID NOs: 325.

In some aspects, the CDR-L2 sequence does not comprise, consist of, or consist essentially of a sequence selected from SEQ ID NOs: 316-320. In some aspects, the CDR-L2 sequence does not comprise, consist of, or consist essentially of SEQ ID NO: 316. In some aspects, the CDR-L2 sequence does not comprise, consist of, or consist essentially of SEQ ID NO: 317. In some aspects, the CDR-L2 sequence does not comprise, consist of, or consist essentially of SEQ ID NO: 318. In some aspects, the CDR-L2 sequence does not comprise, consist of, or consist essentially of SEQ ID NO: 319. In some aspects, the CDR-L2 sequence does not comprise, consist of, or consist essentially of SEQ ID NO: 320.

In some aspects, the CDR-L1 sequence does not comprise, consist of, or consist essentially of a sequence selected from SEQ ID NOs: 311-315. In some aspects, the CDR-L1 sequence does not comprise, consist of, or consist essentially of SEQ ID NO: 311. In some aspects, the CDR-L1 sequence does not comprise, consist of, or consist essentially of SEQ ID NO: 312. In some aspects, the CDR-L1 sequence does not comprise, consist of, or consist essentially of SEQ ID NO: 313. In some aspects, the CDR-L1 sequence does not comprise, consist of, or consist essentially of SEQ ID NO: 314. In some aspects, the CDR-L1 sequence does not comprise, consist of, or consist essentially of SEQ ID NO: 315.

2.6. $V_L$ Sequences

In some embodiments, the antibody comprises, consists of, or consists essentially of a $V_L$ sequence of an scFv-Fc sequence provided in SEQ ID NOs.: 204-228 or of an scFv sequence provided in SEQ ID NOs.: 337-361. In some embodiments, the antibody comprises, consists of, or consists essentially of a $V_L$ sequence provided in SEQ ID NOs.: 254-278.

In some embodiments, the antibody comprises a $V_L$ sequence comprising, consisting of, or consisting essentially of a sequence selected from SEQ ID NOs: 254-278. In some aspects, the antibody comprises a $V_L$ sequence comprising, consisting of, or consisting essentially of SEQ ID NO: 254. In some aspects, the antibody comprises a $V_L$ sequence comprising, consisting of, or consisting essentially of SEQ ID NO: 255. In some aspects, the antibody comprises a $V_L$ sequence comprising, consisting of, or consisting essentially of SEQ ID NO: 256. In some aspects, the antibody comprises a $V_L$ sequence comprising, consisting of, or consisting essentially of SEQ ID NO: 257. In some aspects, the antibody comprises a $V_L$ sequence comprising, consisting of, or consisting essentially of SEQ ID NO: 258. In some aspects, the antibody comprises a $V_L$ sequence comprising, consisting of, or consisting essentially of SEQ ID NO: 259. In some aspects, the antibody comprises a $V_L$ sequence comprising, consisting of, or consisting essentially of SEQ ID NO: 260. In some aspects, the antibody comprises a $V_L$ sequence comprising, consisting of, or consisting essentially of SEQ ID NO: 261. In some aspects, the antibody comprises a $V_L$ sequence comprising, consisting of, or consisting essentially of SEQ ID NO: 262. In some aspects, the antibody comprises a $V_L$ sequence comprising, consisting of, or consisting essentially of SEQ ID NO: 263. In some aspects, the antibody comprises a $V_L$ sequence comprising, consisting of, or consisting essentially of SEQ ID NO: 264. In some aspects, the antibody comprises a $V_L$ sequence comprising, consisting of, or consisting essentially of SEQ ID NO: 265. In some aspects, the antibody comprises a $V_L$ sequence comprising, consisting of, or consisting essentially of SEQ ID NO: 266. In some aspects, the antibody comprises a $V_L$ sequence comprising, consisting of, or consisting essentially of SEQ ID NO: 267. In some aspects, the antibody comprises a $V_L$ sequence comprising, consisting of, or consisting essentially of SEQ ID NO: 268. In some aspects, the antibody comprises a $V_L$ sequence comprising, consisting of, or consisting essentially of SEQ ID NO: 269. In some aspects, the antibody comprises a $V_L$ sequence comprising, consisting of, or consisting essentially of SEQ ID NO: 270. In some aspects, the antibody comprises a $V_L$ sequence comprising, consisting of, or consisting essentially of SEQ ID NO: 271. In some aspects, the antibody comprises a $V_L$ sequence comprising, consisting of, or consisting essentially of SEQ ID NO: 272. In some aspects, the antibody comprises a $V_L$ sequence comprising, consisting of, or consisting essentially of SEQ ID NO: 273. In some aspects, the antibody comprises a $V_L$ sequence comprising, consisting of, or consisting essentially of SEQ ID NO: 274. In some aspects, the antibody comprises a $V_L$ sequence comprising, consisting of, or consisting essentially of SEQ ID NO: 275. In some aspects, the antibody comprises a $V_L$ sequence comprising, consisting of, or consisting essentially of SEQ ID NO: 276. In some aspects, the antibody comprises a $V_L$ sequence comprising, consisting of, or consisting essentially of SEQ ID NO: 277. In some aspects, the antibody comprises a $V_L$ sequence comprising, consisting of, or consisting essentially of SEQ ID NO: 278.

2.6.1. Variants of $V_L$ Sequences

In some embodiments, the $V_L$ sequences provided herein comprise, consist of, or consist essentially of a variant of an illustrative $V_L$ sequence provided in this disclosure.

In some aspects, the $V_L$ sequence comprises, consists of, or consists essentially of a variant of an illustrative $V_L$ sequence provided in this disclosure. In some aspects, the $V_L$ sequence comprises, consists of, or consists essentially of a sequence having at least 85%, 90%, 95%, 96%, 97%, 98%, 99%, or 99.5% identity with any of the illustrative $V_L$ sequences provided in this disclosure.

In some embodiments, the $V_L$ sequence comprises, consists of, or consists essentially of any of the illustrative $V_L$ sequences provided in this disclosure having 20 or fewer, 19 or fewer, 18 or fewer, 17 or fewer, 16 or fewer, 15 or fewer, 14 or fewer, 13 or fewer, 12 or fewer, 11 or fewer, 10 or fewer, 9 or fewer, 8 or fewer, 7 or fewer, 6 or fewer, 5 or fewer, 4 or fewer, 3 or fewer, 2 or fewer, or 1 or fewer amino acid substitutions. In some aspects, the amino acid substitutions are conservative amino acid substitutions.

2.6.2. Excluded $V_L$ Sequences

In some embodiments, the $V_L$ sequences provided herein do not comprise certain $V_L$ sequences.

In some aspects, the $V_L$ sequence does not comprise, consist of, or consist essentially of a sequence selected from SEQ ID NOs: 331-335. In some aspects, the $V_L$ sequence does not comprise, consist of, or consist essentially of SEQ ID NO: 331. In some aspects, the $V_L$ sequence does not comprise, consist of, or consist essentially of SEQ ID NO: 332. In some aspects, the $V_L$ sequence does not comprise, consist of, or consist essentially of SEQ ID NO: 333. In some aspects, the $V_L$ sequence does not comprise, consist of, or consist essentially of SEQ ID NO: 334. In some aspects, the $V_L$ sequence does not comprise, consist of, or consist essentially of SEQ ID NO: 335.

2.7. Pairs 2.7.1. CDR-H3-CDR-L3 Pairs

In some embodiments, the antibody comprises a CDR-H3 sequence and a CDR-L3 sequence. In some aspects, the CDR-H3 sequence is part of a $V_H$ and the CDR-L3 sequence is part of a $V_L$.

In some aspects, the CDR-H3 sequence is a CDR-H3 sequence comprising, consisting of, or consisting essentially of SEQ ID NOs: 104-128, and the CDR-L3 sequence is a CDR-L3 sequence comprising, consisting of, or consisting essentially of SEQ ID NOs: 179-203.

In some aspects, the CDR-H3-CDR-L3 pairs are selected from SEQ ID NO: 104 and SEQ ID NO: 179; SEQ ID NO: 104 and SEQ ID NO: 180; SEQ ID NO: 104 and SEQ ID NO: 181; SEQ ID NO: 104 and SEQ ID NO: 182; SEQ ID NO: 104 and SEQ ID NO: 183; SEQ ID NO: 104 and SEQ ID NO: 184; SEQ ID NO: 104 and SEQ ID NO: 185; SEQ ID NO: 104 and SEQ ID NO: 186; SEQ ID NO: 104 and SEQ ID NO: 187; SEQ ID NO: 104 and SEQ ID NO: 188; SEQ ID NO: 104 and SEQ ID NO: 189; SEQ ID NO: 104 and SEQ ID NO: 190; SEQ ID NO: 104 and SEQ ID NO: 191; SEQ ID NO: 104 and SEQ ID NO: 192; SEQ ID NO: 104 and SEQ ID NO: 193; SEQ ID NO: 104 and SEQ ID NO: 194; SEQ ID NO: 104 and SEQ ID NO: 195; SEQ ID NO: 104 and SEQ ID NO: 196; SEQ ID NO: 104 and SEQ ID NO: 197; SEQ ID NO: 104 and SEQ ID NO: 198; SEQ ID NO: 104 and SEQ ID NO: 199; SEQ ID NO: 104 and SEQ ID NO: 200; SEQ ID NO: 104 and SEQ ID NO: 201; SEQ ID NO: 104 and SEQ ID NO: 202; and SEQ ID NO: 104 and SEQ ID NO: 203.

In some aspects, the CDR-H3-CDR-L3 pairs are selected from SEQ ID NO: 105 and SEQ ID NO: 179; SEQ ID NO: 105 and SEQ ID NO: 180; SEQ ID NO: 105 and SEQ ID NO: 181; SEQ ID NO: 105 and SEQ ID NO: 182; SEQ ID NO: 105 and SEQ ID NO: 183; SEQ ID NO: 105 and SEQ ID NO: 184; SEQ ID NO: 105 and SEQ ID NO: 185; SEQ ID NO: 105 and SEQ ID NO: 186; SEQ ID NO: 105 and SEQ ID NO: 187; SEQ ID NO: 105 and SEQ ID NO: 188; SEQ ID NO: 105 and SEQ ID NO: 189; SEQ ID NO: 105 and SEQ ID NO: 190; SEQ ID NO: 105 and SEQ ID NO: 191; SEQ ID NO: 105 and SEQ ID NO: 192; SEQ ID NO: 105 and SEQ ID NO: 193; SEQ ID NO: 105 and SEQ ID NO: 194; SEQ ID NO: 105 and SEQ ID NO: 195; SEQ ID NO: 105 and SEQ ID NO: 196; SEQ ID NO: 105 and SEQ ID NO: 197; SEQ ID NO: 105 and SEQ ID NO: 198; SEQ ID NO: 105 and SEQ ID NO: 199; SEQ ID NO: 105 and SEQ ID NO: 200; SEQ ID NO: 105 and SEQ ID NO: 201; SEQ ID NO: 105 and SEQ ID NO: 202; and SEQ ID NO: 105 and SEQ ID NO: 203.

In some aspects, the CDR-H3-CDR-L3 pairs are selected from SEQ ID NO: 106 and SEQ ID NO: 179; SEQ ID NO: 106 and SEQ ID NO: 180; SEQ ID NO: 106 and SEQ ID NO: 181; SEQ ID NO: 106 and SEQ ID NO: 182; SEQ ID NO: 106 and SEQ ID NO: 183; SEQ ID NO: 106 and SEQ ID NO: 184; SEQ ID NO: 106 and SEQ ID NO: 185; SEQ ID NO: 106 and SEQ ID NO: 186; SEQ ID NO: 106 and SEQ ID NO: 187; SEQ ID NO: 106 and SEQ ID NO: 188; SEQ ID NO: 106 and SEQ ID NO: 189; SEQ ID NO: 106 and SEQ ID NO: 190; SEQ ID NO: 106 and SEQ ID NO: 191; SEQ ID NO: 106 and SEQ ID NO: 192; SEQ ID NO: 106 and SEQ ID NO: 193; SEQ ID NO: 106 and SEQ ID NO: 194; SEQ ID NO: 106 and SEQ ID NO: 195; SEQ ID NO: 106 and SEQ ID NO: 196; SEQ ID NO: 106 and SEQ ID NO: 197; SEQ ID NO: 106 and SEQ ID NO: 198; SEQ ID NO: 106 and SEQ ID NO: 199; SEQ ID NO: 106 and SEQ ID NO: 200; SEQ ID NO: 106 and SEQ ID NO: 201; SEQ ID NO: 106 and SEQ ID NO: 202; and SEQ ID NO: 106 and SEQ ID NO: 203.

In some aspects, the CDR-H3-CDR-L3 pairs are selected from SEQ ID NO: 107 and SEQ ID NO: 179; SEQ ID NO: 107 and SEQ ID NO: 180; SEQ ID NO: 107 and SEQ ID NO: 181; SEQ ID NO: 107 and SEQ ID NO: 182; SEQ ID NO: 107 and SEQ ID NO: 183; SEQ ID NO: 107 and SEQ ID NO: 184; SEQ ID NO: 107 and SEQ ID NO: 185; SEQ ID NO: 107 and SEQ ID NO: 186; SEQ ID NO: 107 and SEQ ID NO: 187; SEQ ID NO: 107 and SEQ ID NO: 188; SEQ ID NO: 107 and SEQ ID NO: 189; SEQ ID NO: 107 and SEQ ID NO: 190; SEQ ID NO: 107 and SEQ ID NO: 191; SEQ ID NO: 107 and SEQ ID NO: 192; SEQ ID NO: 107 and SEQ ID NO: 193; SEQ ID NO: 107 and SEQ ID NO: 194; SEQ ID NO: 107 and SEQ ID NO: 195; SEQ ID NO: 107 and SEQ ID NO: 196; SEQ ID NO: 107 and SEQ ID NO: 197; SEQ ID NO: 107 and SEQ ID NO: 198; SEQ ID NO: 107 and SEQ ID NO: 199; SEQ ID NO: 107 and SEQ ID NO: 200; SEQ ID NO: 107 and SEQ ID NO: 201; SEQ ID NO: 107 and SEQ ID NO: 202; and SEQ ID NO: 107 and SEQ ID NO: 203.

In some aspects, the CDR-H3-CDR-L3 pairs are selected from SEQ ID NO: 108 and SEQ ID NO: 179; SEQ ID NO: 108 and SEQ ID NO: 180; SEQ ID NO: 108 and SEQ ID NO: 181; SEQ ID NO: 108 and SEQ ID NO: 182; SEQ ID NO: 108 and SEQ ID NO: 183; SEQ ID NO: 108 and SEQ ID NO: 184; SEQ ID NO: 108 and SEQ ID NO: 185; SEQ ID NO: 108 and SEQ ID NO: 186; SEQ ID NO: 108 and SEQ ID NO: 187; SEQ ID NO: 108 and SEQ ID NO: 188; SEQ ID NO: 108 and SEQ ID NO: 189; SEQ ID NO: 108 and SEQ ID NO: 190; SEQ ID NO: 108 and SEQ ID NO: 191; SEQ ID NO: 108 and SEQ ID NO: 192; SEQ ID NO: 108 and SEQ ID NO: 193; SEQ ID NO: 108 and SEQ ID NO: 194; SEQ ID NO: 108 and SEQ ID NO: 195; SEQ ID NO: 108 and SEQ ID NO: 196; SEQ ID NO: 108 and SEQ ID NO: 197; SEQ ID NO: 108 and SEQ ID NO: 198; SEQ ID NO: 108 and SEQ ID NO: 199; SEQ ID NO: 108 and SEQ ID NO: 200; SEQ ID NO: 108 and SEQ ID NO: 201; SEQ ID NO: 108 and SEQ ID NO: 202; and SEQ ID NO: 108 and SEQ ID NO: 203.

In some aspects, the CDR-H3-CDR-L3 pairs are selected from SEQ ID NO: 109 and SEQ ID NO: 179; SEQ ID NO: 109 and SEQ ID NO: 180; SEQ ID NO: 109 and SEQ ID NO: 181; SEQ ID NO: 109 and SEQ ID NO: 182; SEQ ID NO: 109 and SEQ ID NO: 183; SEQ ID NO: 109 and SEQ ID NO: 184; SEQ ID NO: 109 and SEQ ID NO: 185; SEQ ID NO: 109 and SEQ ID NO: 186; SEQ ID NO: 109 and SEQ ID NO: 187; SEQ ID NO: 109 and SEQ ID NO: 188; SEQ ID NO: 109 and SEQ ID NO: 189; SEQ ID NO: 109 and SEQ ID NO: 190; SEQ ID NO: 109 and SEQ ID NO: 191; SEQ ID NO: 109 and SEQ ID NO: 192; SEQ ID NO: 109 and SEQ ID NO: 193; SEQ ID NO: 109 and SEQ ID NO: 194; SEQ ID NO: 109 and SEQ ID NO: 195; SEQ ID NO: 109 and SEQ ID NO: 196; SEQ ID NO: 109 and SEQ ID NO: 197; SEQ ID NO: 109 and SEQ ID NO: 198; SEQ ID NO: 109 and SEQ ID NO: 199; SEQ ID NO: 109 and SEQ ID NO: 200; SEQ ID NO: 109 and SEQ ID NO: 201; SEQ ID NO: 109 and SEQ ID NO: 202; and SEQ ID NO: 109 and SEQ ID NO: 203.

In some aspects, the CDR-H3-CDR-L3 pairs are selected from SEQ ID NO: 110 and SEQ ID NO: 179; SEQ ID NO: 110 and SEQ ID NO: 180; SEQ ID NO: 110 and SEQ ID NO: 181; SEQ ID NO: 110 and SEQ ID NO: 182; SEQ ID NO: 110 and SEQ ID NO: 183; SEQ ID NO: 110 and SEQ ID NO: 184; SEQ ID NO: 110 and SEQ ID NO: 185; SEQ ID NO: 110 and SEQ ID NO: 186; SEQ ID NO: 110 and SEQ ID NO: 187; SEQ ID NO: 110 and SEQ ID NO: 188; SEQ ID NO: 110 and SEQ ID NO: 189; SEQ ID NO: 110 and SEQ ID NO: 190; SEQ ID NO: 110 and SEQ ID NO: 191; SEQ ID NO: 110 and SEQ ID NO: 192; SEQ ID NO: 110 and SEQ ID NO: 193; SEQ ID NO: 110 and SEQ ID NO: 194; SEQ ID NO: 110 and SEQ ID NO: 195; SEQ ID NO: 110 and SEQ ID NO: 196; SEQ ID NO: 110 and SEQ ID NO: 197; SEQ ID NO: 110 and SEQ ID NO: 198; SEQ ID NO: 110 and SEQ ID NO: 199; SEQ ID NO: 110 and SEQ ID NO: 200; SEQ ID NO: 110 and SEQ ID NO: 201; SEQ ID NO: 110 and SEQ ID NO: 202; and SEQ ID NO: 110 and SEQ ID NO: 203.

In some aspects, the CDR-H3-CDR-L3 pairs are selected from SEQ ID NO: 111 and SEQ ID NO: 179; SEQ ID NO: 111 and SEQ ID NO: 180; SEQ ID NO: 111 and SEQ ID NO: 181; SEQ ID NO: 111 and SEQ ID NO: 182; SEQ ID NO: 111 and SEQ ID NO: 183; SEQ ID NO: 111 and SEQ ID NO: 184; SEQ ID NO: 111 and SEQ ID NO: 185; SEQ ID NO: 111 and SEQ ID NO: 186; SEQ ID NO: 111 and SEQ ID NO: 187; SEQ ID NO: 111 and SEQ ID NO: 188; SEQ ID NO: 111 and SEQ ID NO: 189; SEQ ID NO: 111 and SEQ ID NO: 190; SEQ ID NO: 111 and SEQ ID NO: 191; SEQ ID NO: 111 and SEQ ID NO: 192; SEQ ID NO: 111 and SEQ ID NO: 193; SEQ ID NO: 111 and SEQ ID NO: 194; SEQ ID NO: 111 and SEQ ID NO: 195; SEQ ID NO: 111 and SEQ ID NO: 196; SEQ ID NO: 111 and SEQ ID NO: 197; SEQ ID NO: 111 and SEQ ID NO: 198; SEQ ID NO: 111 and SEQ ID NO: 199; SEQ ID NO: 111 and SEQ ID NO: 200; SEQ ID NO: 111 and SEQ ID NO: 201; SEQ ID NO: 111 and SEQ ID NO: 202; and SEQ ID NO: 111 and SEQ ID NO: 203.

In some aspects, the CDR-H3-CDR-L3 pairs are selected from SEQ ID NO: 112 and SEQ ID NO: 179; SEQ ID NO: 112 and SEQ ID NO: 180; SEQ ID NO: 112 and SEQ ID NO: 181; SEQ ID NO: 112 and SEQ ID NO: 182; SEQ ID NO: 112 and SEQ ID NO: 183; SEQ ID NO: 112 and SEQ ID NO: 184; SEQ ID NO: 112 and SEQ ID NO: 185; SEQ ID NO: 112 and SEQ ID NO: 186; SEQ ID NO: 112 and SEQ ID NO: 187; SEQ ID NO: 112 and SEQ ID NO: 188; SEQ ID NO: 112 and SEQ ID NO: 189; SEQ ID NO: 112 and SEQ ID NO: 190; SEQ ID NO: 112 and SEQ ID NO: 191; SEQ ID NO: 112 and SEQ ID NO: 192; SEQ ID NO: 112 and SEQ ID NO: 193; SEQ ID NO: 112 and SEQ ID NO: 194; SEQ ID NO: 112 and SEQ ID NO: 195; SEQ ID NO: 112 and SEQ ID NO: 196; SEQ ID NO: 112 and SEQ ID NO: 197; SEQ ID NO: 112 and SEQ ID NO: 198; SEQ ID NO: 112 and SEQ ID NO: 199; SEQ ID NO: 112 and SEQ ID NO: 200; SEQ ID NO: 112 and SEQ ID NO: 201; SEQ ID NO: 112 and SEQ ID NO: 202; and SEQ ID NO: 112 and SEQ ID NO: 203.

In some aspects, the CDR-H3-CDR-L3 pairs are selected from SEQ ID NO: 113 and SEQ ID NO: 179; SEQ ID NO: 113 and SEQ ID NO: 180; SEQ ID NO: 113 and SEQ ID NO: 181; SEQ ID NO: 113 and SEQ ID NO: 182; SEQ ID NO: 113 and SEQ ID NO: 183; SEQ ID NO: 113 and SEQ ID NO: 184; SEQ ID NO: 113 and SEQ ID NO: 185; SEQ ID NO: 113 and SEQ ID NO: 186; SEQ ID NO: 113 and SEQ ID NO: 187; SEQ ID NO: 113 and SEQ ID NO: 188; SEQ ID NO: 113 and SEQ ID NO: 189; SEQ ID NO: 113 and SEQ ID NO: 190; SEQ ID NO: 113 and SEQ ID NO: 191; SEQ ID NO: 113 and SEQ ID NO: 192; SEQ ID NO: 113 and SEQ ID NO: 193; SEQ ID NO: 113 and SEQ ID NO: 194; SEQ ID NO: 113 and SEQ ID NO: 195; SEQ ID NO: 113 and SEQ ID NO: 196; SEQ ID NO: 113 and SEQ ID NO: 197; SEQ ID NO: 113 and SEQ ID NO: 198; SEQ ID NO: 113 and SEQ ID NO: 199; SEQ ID NO: 113 and SEQ ID NO: 200; SEQ ID NO: 113 and SEQ ID NO: 201; SEQ ID NO: 113 and SEQ ID NO: 202; and SEQ ID NO: 113 and SEQ ID NO: 203.

In some aspects, the CDR-H3-CDR-L3 pairs are selected from SEQ ID NO: 114 and SEQ ID NO: 179; SEQ ID NO: 114 and SEQ ID NO: 180; SEQ ID NO: 114 and SEQ ID NO: 181; SEQ ID NO: 114 and SEQ ID NO: 182; SEQ ID NO: 114 and SEQ ID NO: 183; SEQ ID NO: 114 and SEQ ID NO: 184; SEQ ID NO: 114 and SEQ ID NO: 185; SEQ ID NO: 114 and SEQ ID NO: 186; SEQ ID NO: 114 and SEQ ID NO: 187; SEQ ID NO: 114 and SEQ ID NO: 188; SEQ ID NO: 114 and SEQ ID NO: 189; SEQ ID NO: 114 and SEQ ID NO: 190; SEQ ID NO: 114 and SEQ ID NO: 191; SEQ ID NO: 114 and SEQ ID NO: 192; SEQ ID NO: 114 and SEQ ID NO: 193; SEQ ID NO: 114 and SEQ ID NO: 194; SEQ ID NO: 114 and SEQ ID NO: 195; SEQ ID NO: 114 and SEQ ID NO: 196; SEQ ID NO: 114 and SEQ ID NO: 197; SEQ ID NO: 114 and SEQ ID NO: 198; SEQ ID NO: 114 and SEQ ID NO: 199; SEQ ID NO: 114 and SEQ ID NO: 200; SEQ ID NO: 114 and SEQ ID NO: 201; SEQ ID NO: 114 and SEQ ID NO: 202; and SEQ ID NO: 114 and SEQ ID NO: 203.

In some aspects, the CDR-H3-CDR-L3 pairs are selected from SEQ ID NO: 115 and SEQ ID NO: 179; SEQ ID NO: 115 and SEQ ID NO: 180; SEQ ID NO: 115 and SEQ ID NO: 181; SEQ ID NO: 115 and SEQ ID NO: 182; SEQ ID NO: 115 and SEQ ID NO: 183; SEQ ID NO: 115 and SEQ ID NO: 184; SEQ ID NO: 115 and SEQ ID NO: 185; SEQ ID NO: 115 and SEQ ID NO: 186; SEQ ID NO: 115 and SEQ ID NO: 187; SEQ ID NO: 115 and SEQ ID NO: 188; SEQ ID NO: 115 and SEQ ID NO: 189; SEQ ID NO: 115 and SEQ ID NO: 190; SEQ ID NO: 115 and SEQ ID NO: 191; SEQ ID NO: 115 and SEQ ID NO: 192; SEQ ID NO: 115 and SEQ ID NO: 193; SEQ ID NO: 115 and SEQ ID NO: 194; SEQ ID NO: 115 and SEQ ID NO: 195; SEQ ID NO: 115 and SEQ ID NO: 196; SEQ ID NO: 115 and SEQ ID NO: 197; SEQ ID NO: 115 and SEQ ID NO: 198; SEQ ID NO: 115 and SEQ ID NO: 199; SEQ ID NO: 115 and SEQ ID NO: 200; SEQ ID NO: 115 and SEQ ID NO: 201; SEQ ID NO: 115 and SEQ ID NO: 202; and SEQ ID NO: 115 and SEQ ID NO: 203.

In some aspects, the CDR-H3-CDR-L3 pairs are selected from SEQ ID NO: 116 and SEQ ID NO: 179; SEQ ID NO: 116 and SEQ ID NO: 180; SEQ ID NO: 116 and SEQ ID NO: 181; SEQ ID NO: 116 and SEQ ID NO: 182; SEQ ID NO: 116 and SEQ ID NO: 183; SEQ ID NO: 116 and SEQ ID NO: 184; SEQ ID NO: 116 and SEQ ID NO: 185; SEQ ID NO: 116 and SEQ ID NO: 186; SEQ ID NO: 116 and SEQ ID NO: 187; SEQ ID NO: 116 and SEQ ID NO: 188; SEQ ID NO: 116 and SEQ ID NO: 189; SEQ ID NO: 116 and SEQ ID NO: 190; SEQ ID NO: 116 and SEQ ID NO: 191; SEQ ID NO: 116 and SEQ ID NO: 192; SEQ ID NO: 116 and SEQ ID NO: 193; SEQ ID NO: 116 and SEQ ID NO: 194; SEQ ID NO: 116 and SEQ ID NO: 195; SEQ ID NO: 116 and SEQ ID NO: 196; SEQ ID NO: 116 and SEQ ID NO: 197; SEQ ID NO: 116 and SEQ ID NO: 198; SEQ ID NO: 116 and SEQ ID NO: 199; SEQ ID NO: 116 and SEQ ID NO: 200; SEQ ID NO: 116 and SEQ ID NO: 201; SEQ ID NO: 116 and SEQ ID NO: 202; and SEQ ID NO: 116 and SEQ ID NO: 203.

In some aspects, the CDR-H3-CDR-L3 pairs are selected from SEQ ID NO: 117 and SEQ ID NO: 179; SEQ ID NO: 117 and SEQ ID NO: 180; SEQ ID NO: 117 and SEQ ID NO: 181; SEQ ID NO: 117 and SEQ ID NO: 182; SEQ ID NO: 117 and SEQ ID NO: 183; SEQ ID NO: 117 and SEQ ID NO: 184; SEQ ID NO: 117 and SEQ ID NO: 185; SEQ ID NO: 117 and SEQ ID NO: 186; SEQ ID NO: 117 and SEQ ID NO: 187; SEQ ID NO: 117 and SEQ ID NO: 188; SEQ ID NO: 117 and SEQ ID NO: 189; SEQ ID NO: 117 and SEQ ID NO: 190; SEQ ID NO: 117 and SEQ ID NO: 191; SEQ ID NO: 117 and SEQ ID NO: 192; SEQ ID NO: 117 and SEQ ID NO: 193; SEQ ID NO: 117 and SEQ ID NO: 194; SEQ ID NO: 117 and SEQ ID NO: 195; SEQ ID NO: 117 and SEQ ID NO: 196; SEQ ID NO: 117 and SEQ ID NO: 197; SEQ ID NO: 117 and SEQ ID NO: 198; SEQ ID NO: 117 and SEQ ID NO: 199; SEQ ID NO: 117 and SEQ ID NO: 200; SEQ ID NO: 117 and SEQ ID NO: 201; SEQ ID NO: 117 and SEQ ID NO: 202; and SEQ ID NO: 117 and SEQ ID NO: 203.

In some aspects, the CDR-H3-CDR-L3 pairs are selected from SEQ ID NO: 118 and SEQ ID NO: 179; SEQ ID NO: 118 and SEQ ID NO: 180; SEQ ID NO: 118 and SEQ ID NO: 181; SEQ ID NO: 118 and SEQ ID NO: 182; SEQ ID NO: 118 and SEQ ID NO: 183; SEQ ID NO: 118 and SEQ ID NO: 184; SEQ ID NO: 118 and SEQ ID NO: 185; SEQ ID NO: 118 and SEQ ID NO: 186; SEQ ID NO: 118 and SEQ ID NO: 187; SEQ ID NO: 118 and SEQ ID NO: 188; SEQ ID NO: 118 and SEQ ID NO: 189; SEQ ID NO: 118 and SEQ ID NO: 190; SEQ ID NO: 118 and SEQ ID NO: 191; SEQ ID NO: 118 and SEQ ID NO: 192; SEQ ID NO: 118 and SEQ ID NO: 193; SEQ ID NO: 118 and SEQ ID NO: 194; SEQ ID NO: 118 and SEQ ID NO: 195; SEQ ID NO: 118 and SEQ ID NO: 196; SEQ ID NO: 118 and SEQ ID NO: 197; SEQ ID NO: 118 and SEQ ID NO: 198; SEQ ID NO: 118 and SEQ ID NO: 199; SEQ ID NO: 118 and SEQ ID NO: 200; SEQ ID NO: 118 and SEQ ID NO: 201; SEQ ID NO: 118 and SEQ ID NO: 202; and SEQ ID NO: 118 and SEQ ID NO: 203.

In some aspects, the CDR-H3-CDR-L3 pairs are selected from SEQ ID NO: 119 and SEQ ID NO: 179; SEQ ID NO: 119 and SEQ ID NO: 180; SEQ ID NO: 119 and SEQ ID NO: 181; SEQ ID NO: 119 and SEQ ID NO: 182; SEQ ID NO: 119 and SEQ ID NO: 183; SEQ ID NO: 119 and SEQ ID NO: 184; SEQ ID NO: 119 and SEQ ID NO: 185; SEQ ID NO: 119 and SEQ ID NO: 186; SEQ ID NO: 119 and SEQ ID NO: 187; SEQ ID NO: 119 and SEQ ID NO: 188; SEQ ID NO: 119 and SEQ ID NO: 189; SEQ ID NO: 119 and SEQ ID NO: 190; SEQ ID NO: 119 and SEQ ID NO: 191; SEQ ID NO: 119 and SEQ ID NO: 192; SEQ ID NO: 119 and SEQ ID NO: 193; SEQ ID NO: 119 and SEQ ID NO: 194; SEQ ID NO: 119 and SEQ ID NO: 195; SEQ ID NO: 119 and SEQ ID NO: 196; SEQ ID NO: 119 and SEQ ID NO: 197; SEQ ID NO: 119 and SEQ ID NO: 198; SEQ ID NO: 119 and SEQ ID NO: 199; SEQ ID NO: 119 and SEQ ID NO: 200; SEQ ID NO: 119 and SEQ ID NO: 201; SEQ ID NO: 119 and SEQ ID NO: 202; and SEQ ID NO: 119 and SEQ ID NO: 203.

In some aspects, the CDR-H3-CDR-L3 pairs are selected from SEQ ID NO: 120 and SEQ ID NO: 179; SEQ ID NO: 120 and SEQ ID NO: 180; SEQ ID NO: 120 and SEQ ID NO: 181; SEQ ID NO: 120 and SEQ ID NO: 182; SEQ ID NO: 120 and SEQ ID NO: 183; SEQ ID NO: 120 and SEQ ID NO: 184; SEQ ID NO: 120 and SEQ ID NO: 185; SEQ ID NO: 120 and SEQ ID NO: 186; SEQ ID NO: 120 and SEQ ID NO: 187; SEQ ID NO: 120 and SEQ ID NO: 188; SEQ ID NO: 120 and SEQ ID NO: 189; SEQ ID NO: 120 and SEQ ID NO: 190; SEQ ID NO: 120 and SEQ ID NO: 191; SEQ ID NO: 120 and SEQ ID NO: 192; SEQ ID NO: 120 and SEQ ID NO: 193; SEQ ID NO: 120 and SEQ ID NO: 194; SEQ ID NO: 120 and SEQ ID NO: 195; SEQ ID NO: 120 and SEQ ID NO: 196; SEQ ID NO: 120 and SEQ ID NO: 197; SEQ ID NO: 120 and SEQ ID NO: 198; SEQ ID NO: 120 and SEQ ID NO: 199; SEQ ID NO: 120 and SEQ ID NO: 200; SEQ ID NO: 120 and SEQ ID NO: 201; SEQ ID NO: 120 and SEQ ID NO: 202; and SEQ ID NO: 120 and SEQ ID NO: 203.

In some aspects, the CDR-H3-CDR-L3 pairs are selected from SEQ ID NO: 121 and SEQ ID NO: 179; SEQ ID NO: 121 and SEQ ID NO: 180; SEQ ID NO: 121 and SEQ ID NO: 181; SEQ ID NO: 121 and SEQ ID NO: 182; SEQ ID NO: 121 and SEQ ID NO: 183; SEQ ID NO: 121 and SEQ ID NO: 184; SEQ ID NO: 121 and SEQ ID NO: 185; SEQ ID NO: 121 and SEQ ID NO: 186; SEQ ID NO: 121 and SEQ ID NO: 187; SEQ ID NO: 121 and SEQ ID NO: 188; SEQ ID NO: 121 and SEQ ID NO: 189; SEQ ID NO: 121 and SEQ ID NO: 190; SEQ ID NO: 121 and SEQ ID NO: 191; SEQ ID NO: 121 and SEQ ID NO: 192; SEQ ID NO: 121 and SEQ ID NO: 193; SEQ ID NO: 121 and SEQ ID NO: 194; SEQ ID NO: 121 and SEQ ID NO: 195; SEQ ID NO: 121 and SEQ ID NO: 196; SEQ ID NO: 121 and SEQ ID NO: 197; SEQ ID NO: 121 and SEQ ID NO: 198; SEQ ID NO: 121 and SEQ ID NO: 199; SEQ ID NO: 121 and SEQ ID NO: 200; SEQ ID NO: 121 and SEQ ID NO: 201; SEQ ID NO: 121 and SEQ ID NO: 202; and SEQ ID NO: 121 and SEQ ID NO: 203.

In some aspects, the CDR-H3-CDR-L3 pairs are selected from SEQ ID NO: 122 and SEQ ID NO: 179; SEQ ID NO: 122 and SEQ ID NO: 180; SEQ ID NO: 122 and SEQ ID NO: 181; SEQ ID NO: 122 and SEQ ID NO: 182; SEQ ID NO: 122 and SEQ ID NO: 183; SEQ ID NO: 122 and SEQ ID NO: 184; SEQ ID NO: 122 and SEQ ID NO: 185; SEQ ID NO: 122 and SEQ ID NO: 186; SEQ ID NO: 122 and SEQ ID NO: 187; SEQ ID NO: 122 and SEQ ID NO: 188; SEQ ID NO: 122 and SEQ ID NO: 189; SEQ ID NO: 122 and SEQ ID NO: 190; SEQ ID NO: 122 and SEQ ID NO: 191; SEQ ID NO: 122 and SEQ ID NO: 192; SEQ ID NO: 122 and SEQ ID NO: 193; SEQ ID NO: 122 and SEQ ID NO: 194; SEQ ID NO: 122 and SEQ ID NO: 195; SEQ ID NO: 122 and SEQ ID NO: 196; SEQ ID NO: 122 and SEQ ID NO: 197; SEQ ID NO: 122 and SEQ ID NO: 198; SEQ ID NO: 122 and SEQ ID NO: 199; SEQ ID NO: 122 and SEQ ID NO: 200; SEQ ID NO: 122 and SEQ ID NO: 201; SEQ ID NO: 122 and SEQ ID NO: 202; and SEQ ID NO: 122 and SEQ ID NO: 203.

In some aspects, the CDR-H3-CDR-L3 pairs are selected from SEQ ID NO: 123 and SEQ ID NO: 179; SEQ ID NO: 123 and SEQ ID NO: 180; SEQ ID NO: 123 and SEQ ID NO: 181; SEQ ID NO: 123 and SEQ ID NO: 182; SEQ ID NO: 123 and SEQ ID NO: 183; SEQ ID NO: 123 and SEQ ID NO: 184; SEQ ID NO: 123 and SEQ ID NO: 185; SEQ ID NO: 123 and SEQ ID NO: 186; SEQ ID NO: 123 and SEQ ID NO: 187; SEQ ID NO: 123 and SEQ ID NO: 188; SEQ ID NO: 123 and SEQ ID NO: 189; SEQ ID NO: 123 and SEQ ID NO: 190; SEQ ID NO: 123 and SEQ ID NO: 191; SEQ ID NO: 123 and SEQ ID NO: 192; SEQ ID NO: 123 and SEQ ID NO: 193; SEQ ID NO: 123 and SEQ ID NO: 194; SEQ ID NO: 123 and SEQ ID NO: 195; SEQ ID NO: 123 and SEQ ID NO: 196; SEQ ID NO: 123 and SEQ ID NO: 197; SEQ ID NO: 123 and SEQ ID NO: 198; SEQ ID NO: 123 and SEQ ID NO: 199; SEQ ID NO: 123 and SEQ ID NO: 200; SEQ ID NO: 123 and SEQ ID NO: 201; SEQ ID NO: 123 and SEQ ID NO: 202; and SEQ ID NO: 123 and SEQ ID NO: 203.

In some aspects, the CDR-H3-CDR-L3 pairs are selected from SEQ ID NO: 124 and SEQ ID NO: 179; SEQ ID NO: 124 and SEQ ID NO: 180; SEQ ID NO: 124 and SEQ ID NO: 181; SEQ ID NO: 124 and SEQ ID NO: 182; SEQ ID NO: 124 and SEQ ID NO: 183; SEQ ID NO: 124 and SEQ ID NO: 184; SEQ ID NO: 124 and SEQ ID NO: 185; SEQ ID NO: 124 and SEQ ID NO: 186; SEQ ID NO: 124 and SEQ ID NO: 187; SEQ ID NO: 124 and SEQ ID NO: 188; SEQ ID NO: 124 and SEQ ID NO: 189; SEQ ID NO: 124 and SEQ ID NO: 190; SEQ ID NO: 124 and SEQ ID NO: 191; SEQ ID NO: 124 and SEQ ID NO: 192; SEQ ID NO: 124 and SEQ ID NO: 193; SEQ ID NO: 124 and SEQ ID NO: 194; SEQ ID NO: 124 and SEQ ID NO: 195; SEQ ID NO: 124 and SEQ ID NO: 196; SEQ ID NO: 124 and SEQ ID NO: 197; SEQ ID NO: 124 and SEQ ID NO: 198; SEQ ID NO: 124 and SEQ ID NO: 199; SEQ ID NO: 124 and SEQ ID NO: 200; SEQ ID NO: 124 and SEQ ID NO: 201; SEQ ID NO: 124 and SEQ ID NO: 202; and SEQ ID NO: 124 and SEQ ID NO: 203.

In some aspects, the CDR-H3-CDR-L3 pairs are selected from SEQ ID NO: 125 and SEQ ID NO: 179; SEQ ID NO: 125 and SEQ ID NO: 180; SEQ ID NO: 125 and SEQ ID NO: 181; SEQ ID NO: 125 and SEQ ID NO: 182; SEQ ID NO: 125 and SEQ ID NO: 183; SEQ ID NO: 125 and SEQ ID NO: 184; SEQ ID NO: 125 and SEQ ID NO: 185; SEQ ID NO: 125 and SEQ ID NO: 186; SEQ ID NO: 125 and SEQ ID NO: 187; SEQ ID NO: 125 and SEQ ID NO: 188; SEQ ID NO: 125 and SEQ ID NO: 189; SEQ ID NO: 125 and SEQ ID NO: 190; SEQ ID NO: 125 and SEQ ID NO: 191; SEQ ID NO: 125 and SEQ ID NO: 192; SEQ ID NO: 125 and SEQ ID NO: 193; SEQ ID NO: 125 and SEQ ID NO: 194; SEQ ID NO: 125 and SEQ ID NO: 195; SEQ ID NO: 125 and SEQ ID NO: 196; SEQ ID NO: 125 and SEQ ID NO: 197; SEQ ID NO: 125 and SEQ ID NO: 198; SEQ ID NO: 125 and SEQ ID NO: 199; SEQ ID NO: 125 and SEQ ID NO: 200; SEQ ID NO: 125 and SEQ ID NO: 201; SEQ ID NO: 125 and SEQ ID NO: 202; and SEQ ID NO: 125 and SEQ ID NO: 203.

In some aspects, the CDR-H3-CDR-L3 pairs are selected from SEQ ID NO: 126 and SEQ ID NO: 179; SEQ ID NO: 126 and SEQ ID NO: 180; SEQ ID NO: 126 and SEQ ID NO: 181; SEQ ID NO: 126 and SEQ ID NO: 182; SEQ ID NO: 126 and SEQ ID NO: 183; SEQ ID NO: 126 and SEQ ID NO: 184; SEQ ID NO: 126 and SEQ ID NO: 185; SEQ ID NO: 126 and SEQ ID NO: 186; SEQ ID NO: 126 and SEQ ID NO: 187; SEQ ID NO: 126 and SEQ ID NO: 188; SEQ ID NO: 126 and SEQ ID NO: 189; SEQ ID NO: 126 and SEQ ID NO: 190; SEQ ID NO: 126 and SEQ ID NO: 191; SEQ ID NO: 126 and SEQ ID NO: 192; SEQ ID NO: 126 and SEQ ID NO: 193; SEQ ID NO: 126 and SEQ ID NO: 194; SEQ ID NO: 126 and SEQ ID NO: 195; SEQ ID NO: 126 and SEQ ID NO: 196; SEQ ID NO: 126 and SEQ ID NO: 197; SEQ ID NO: 126 and SEQ ID NO: 198; SEQ ID NO: 126 and SEQ ID NO: 199; SEQ ID NO: 126 and SEQ ID NO: 200; SEQ ID NO: 126 and SEQ ID NO: 201; SEQ ID NO: 126 and SEQ ID NO: 202; and SEQ ID NO: 126 and SEQ ID NO: 203.

In some aspects, the CDR-H3-CDR-L3 pairs are selected from SEQ ID NO: 127 and SEQ ID NO: 179; SEQ ID NO: 127 and SEQ ID NO: 180; SEQ ID NO: 127 and SEQ ID NO: 181; SEQ ID NO: 127 and SEQ ID NO: 182; SEQ ID NO: 127 and SEQ ID NO: 183; SEQ ID NO: 127 and SEQ ID NO: 184; SEQ ID NO: 127 and SEQ ID NO: 185; SEQ ID NO: 127 and SEQ ID NO: 186; SEQ ID NO: 127 and SEQ ID NO: 187; SEQ ID NO: 127 and SEQ ID NO: 188; SEQ ID NO: 127 and SEQ ID NO: 189; SEQ ID NO: 127 and SEQ ID NO: 190; SEQ ID NO: 127 and SEQ ID NO: 191; SEQ ID NO: 127 and SEQ ID NO: 192; SEQ ID NO: 127 and SEQ ID NO: 193; SEQ ID NO: 127 and SEQ ID NO: 194; SEQ ID NO: 127 and SEQ ID NO: 195; SEQ ID NO: 127 and SEQ ID NO: 196; SEQ ID NO: 127 and SEQ ID NO: 197; SEQ ID NO: 127 and SEQ ID NO: 198; SEQ ID NO: 127 and SEQ ID NO: 199; SEQ ID NO: 127 and SEQ ID NO: 200; SEQ ID NO: 127 and SEQ ID NO: 201; SEQ ID NO: 127 and SEQ ID NO: 202; and SEQ ID NO: 127 and SEQ ID NO: 203.

In some aspects, the CDR-H3-CDR-L3 pairs are selected from SEQ ID NO: 128 and SEQ ID NO: 179; SEQ ID NO: 128 and SEQ ID NO: 180; SEQ ID NO: 128 and SEQ ID NO: 181; SEQ ID NO: 128 and SEQ ID NO: 182; SEQ ID NO: 128 and SEQ ID NO: 183; SEQ ID NO: 128 and SEQ ID NO: 184; SEQ ID NO: 128 and SEQ ID NO: 185; SEQ ID NO: 128 and SEQ ID NO: 186; SEQ ID NO: 128 and SEQ ID NO: 187; SEQ ID NO: 128 and SEQ ID NO: 188; SEQ ID NO: 128 and SEQ ID NO: 189; SEQ ID NO: 128 and SEQ ID NO: 190; SEQ ID NO: 128 and SEQ ID NO: 191; SEQ ID NO: 128 and SEQ ID NO: 192; SEQ ID NO: 128 and SEQ ID NO: 193; SEQ ID NO: 128 and SEQ ID NO: 194; SEQ ID NO: 128 and SEQ ID NO: 195; SEQ ID NO: 128 and SEQ ID NO: 196; SEQ ID NO: 128 and SEQ ID NO: 197; SEQ ID NO: 128 and SEQ ID NO: 198; SEQ ID NO: 128 and SEQ ID NO: 199; SEQ ID NO: 128 and SEQ ID NO: 200; SEQ ID NO: 128 and SEQ ID NO: 201; SEQ ID NO: 128 and SEQ ID NO: 202; and SEQ ID NO: 128 and SEQ ID NO: 203.

2.7.1.1. Variants of CDR-H3-CDR-L3 Pairs

In some embodiments, the CDR-H3-CDR-L3 pairs provided herein comprise a variant of an illustrative CDR-H3 and/or CDR-L1 sequence provided in this disclosure.

In some aspects, the CDR-H3 sequence comprises, consists of, or consists essentially of a variant of an illustrative CDR-H3 sequence provided in this disclosure. In some aspects, the CDR-H3 sequence comprises, consists of, or consists essentially of a sequence having at least 70%, 75%, 80%, 85%, 90%, or 95% identity with any of the illustrative CDR-H3 sequences provided in this disclosure. In some aspects, the CDR-H3 sequence comprises, consists of, or consists essentially of any of the illustrative CDR-H3 sequences provided in this disclosure, with 1, 2, or 3 amino acid substitutions. In some aspects, the amino acid substitutions are conservative amino acid substitutions.

In some aspects, the CDR-L3 sequence comprises, consists of, or consists essentially of a variant of an illustrative CDR-L3 sequence provided in this disclosure. In some aspects, the CDR-L3 sequence comprises, consists of, or consists essentially of a sequence having at least 70%, 75%, 80%, 85%, 90%, or 95% identity with any of the illustrative CDR-L3 sequences provided in this disclosure. In some aspects, the CDR-L3 sequence comprises, consists of, or consists essentially of any of the illustrative CDR-L3 sequences provided in this disclosure, with 1, 2, or 3 amino acid substitutions. In some aspects, the amino acid substitutions are conservative amino acid substitutions.

2.7.1.2. Excluded CDR-H3-CDR-L3 Pairs

In some embodiments, the CDR-H3-CDR-L3 pairs provided herein do not comprise certain CDR-H3-CDR-L3 pairs.

In some aspects, the CDR-H3 sequence is not selected from SEQ ID NOs: 306-310, and the CDR-L3 sequence is not selected from SEQ ID NOs: 321-325.

In some aspects, the CDR-H3-CDR-L3 pairs are not selected from SEQ ID NO: 306 and SEQ ID NO: 321; SEQ ID NO: 306 and SEQ ID NO: 322; SEQ ID NO: 306 and SEQ ID NO: 323; SEQ ID NO: 306 and SEQ ID NO: 324; and SEQ ID NO: 306 and SEQ ID NO: 325.

In some aspects, the CDR-H3-CDR-L3 pairs are not selected from SEQ ID NO: 307 and SEQ ID NO: 321; SEQ ID NO: 307 and SEQ ID NO: 322; SEQ ID NO: 307 and SEQ ID NO: 323; SEQ ID NO: 307 and SEQ ID NO: 324; and SEQ ID NO: 307 and SEQ ID NO: 325.

In some aspects, the CDR-H3-CDR-L3 pairs are not selected from SEQ ID NO: 308 and SEQ ID NO: 321; SEQ ID NO: 308 and SEQ ID NO: 322; SEQ ID NO: 308 and SEQ ID NO: 323; SEQ ID NO: 308 and SEQ ID NO: 324; and SEQ ID NO: 308 and SEQ ID NO: 325.

In some aspects, the CDR-H3-CDR-L3 pairs are not selected from SEQ ID NO: 309 and SEQ ID NO: 321; SEQ ID NO: 309 and SEQ ID NO: 322; SEQ ID NO: 309 and SEQ ID NO: 323; SEQ ID NO: 309 and SEQ ID NO: 324; and SEQ ID NO: 309 and SEQ ID NO: 325.

In some aspects, the CDR-H3-CDR-L3 pairs are not selected from SEQ ID NO: 310 and SEQ ID NO: 321; SEQ ID NO: 310 and SEQ ID NO: 322; SEQ ID NO: 310 and SEQ ID NO: 323; SEQ ID NO: 310 and SEQ ID NO: 324; and SEQ ID NO: 310 and SEQ ID NO: 325.

2.7.2. CDR-H1-CDR-L1 Pairs

In some embodiments, the antibody comprises a CDR-H1 sequence and a CDR-L1 sequence. In some aspects, the CDR-H1 sequence is part of a $V_H$ and the CDR-L1 sequence is part of a $V_L$.

In some aspects, the CDR-H1 sequence is a Chothia CDR-H1 sequence comprising, consisting of, or consisting essentially of SEQ ID NOs: 4-28, and the CDR-L1 sequence is a CDR-L1 sequence comprising, consisting of, or consisting essentially of SEQ ID NOs: 129-153.

In some aspects, the CDR-H1 sequence is a Kabat CDR-H1 sequence comprising, consisting of, or consisting essentially of SEQ ID NOs: 29-53, and the CDR-L1 sequence is a CDR-L1 sequence comprising, consisting of, or consisting essentially of SEQ ID NOs: 129-153.

2.7.2.1. Variants of CDR-H1-CDR-L1 Pairs

In some embodiments, the CDR-H1-CDR-L1 pairs provided herein comprise a variant of an illustrative CDR-H1 and/or CDR-L1 sequence provided in this disclosure.

In some aspects, the CDR-H1 sequence comprises, consists of, or consists essentially of a variant of an illustrative CDR-H1 sequence provided in this disclosure. In some aspects, the CDR-H1 sequence comprises, consists of, or consists essentially of a sequence having at least 70%, 75%, 80%, 85%, 90%, or 95% identity with any of the illustrative CDR-H1 sequences provided in this disclosure. In some aspects, the CDR-H1 sequence comprises, consists of, or consists essentially of any of the illustrative CDR-H1 sequences provided in this disclosure, with 1, 2, or 3 amino acid substitutions. In some aspects, the amino acid substitutions are conservative amino acid substitutions.

In some aspects, the CDR-L1 sequence comprises, consists of, or consists essentially of a variant of an illustrative CDR-L1 sequence provided in this disclosure. In some aspects, the CDR-L1 sequence comprises, consists of, or consists essentially of a sequence having at least 70%, 75%, 80%, 85%, 90%, or 95% identity with any of the illustrative CDR-L1 sequences provided in this disclosure. In some aspects, the CDR-L1 sequence comprises, consists of, or consists essentially of any of the illustrative CDR-L1 sequences provided in this disclosure, with 1, 2, or 3 amino acid substitutions. In some aspects, the amino acid substitutions are conservative amino acid substitutions.

2.7.2.2. Excluded CDR-H1-CDR-L1 Pairs

In some embodiments, the CDR-H1-CDR-L1 pairs provided herein do not comprise certain CDR-H1-CDR-L1 pairs.

In some aspects, the Chothia CDR-H1 sequence is not selected from SEQ ID NOs: 286-290, and the CDR-L1 sequence is not selected from SEQ ID NOs: 311-315. In some aspects, the Kabat CDR-H1 sequence is not selected from SEQ ID NOs: 290-295, and the CDR-L1 sequence is not selected from SEQ ID NOs: 311-315.

2.7.3. CDR-H2-CDR-L2 Pairs

In some embodiments, the antibody comprises a CDR-H2 sequence and a CDR-L2 sequence. In some aspects, the CDR-H2 sequence is part of a $V_H$ and the CDR-L2 sequence is part of a $V_L$.

In some aspects, the CDR-H2 sequence is a Chothia CDR-H2 sequence comprising, consisting of, or consisting essentially of SEQ ID NOs: 54-78, and the CDR-L2 sequence is a CDR-L2 sequence comprising, consisting of, or consisting essentially of SEQ ID NOs: 154-178.

In some aspects, the CDR-H1 sequence is a Kabat CDR-H2 sequence comprising, consisting of, or consisting essentially of SEQ ID NOs: 79-103, and the CDR-L2 sequence is a CDR-L2 sequence comprising, consisting of, or consisting essentially of SEQ ID NOs: 154-178.

2.7.3.1. Variants of CDR-H2-CDR-L2 Pairs

In some embodiments, the CDR-H2-CDR-L2 pairs provided herein comprise a variant of an illustrative CDR-H2 and/or CDR-L2 sequence provided in this disclosure.

In some aspects, the CDR-H2 sequence comprises, consists of, or consists essentially of a variant of an illustrative CDR-H2 sequence provided in this disclosure. In some aspects, the CDR-H2 sequence comprises, consists of, or consists essentially of a sequence having at least 70%, 75%, 80%, 85%, 90%, or 95% identity with any of the illustrative CDR-H2 sequences provided in this disclosure. In some aspects, the CDR-H2 sequence comprises, consists of, or consists essentially of any of the illustrative CDR-H2 sequences provided in this disclosure, with 1, 2, or 3 amino acid substitutions. In some aspects, the amino acid substitutions are conservative amino acid substitutions.

In some aspects, the CDR-L2 sequence comprises, consists of, or consists essentially of a variant of an illustrative CDR-L2 sequence provided in this disclosure. In some aspects, the CDR-L2 sequence comprises, consists of, or consists essentially of a sequence having at least 70%, 75%, 80%, 85%, 90%, or 95% identity with any of the illustrative CDR-L2 sequences provided in this disclosure. In some aspects, the CDR-L2 sequence comprises, consists of, or consists essentially of any of the illustrative CDR-L2 sequences provided in this disclosure, with 1, 2, or 3 amino acid substitutions. In some aspects, the amino acid substitutions are conservative amino acid substitutions.

2.7.3.2. Excluded CDR-H2-CDR-L2 Pairs

In some embodiments, the CDR-H2-CDR-L2 pairs provided herein do not comprise certain CDR-H2-CDR-L2 pairs.

In some aspects, the Chothia CDR-H2 sequence is not selected from SEQ ID NOs: 296-300, and the CDR-L2 sequence is not selected from SEQ ID NOs: 316-320. In some aspects, the Kabat CDR-H2 sequence is not selected from SEQ ID NOs: 301-305, and the CDR-L2 sequence is not selected from SEQ ID NOs: 316-320.

2.7.4. $V_H$-$V_L$ Pairs

In some embodiments, the antibody comprises a $V_H$ sequence and a $V_L$ sequence.

In some aspects, the $V_H$ sequence is a $V_H$ sequence comprising, consisting of, or consisting essentially of SEQ ID NOs: 229-253, and the $V_L$ sequence is a $V_L$ sequence comprising, consisting of, or consisting essentially of SEQ ID NOs: 254-278.

In some aspects, the $V_H$-$V_L$ pairs are selected from SEQ ID NO: 229 and SEQ ID NO: 254; SEQ ID NO: 229 and SEQ ID NO: 255; SEQ ID NO: 229 and SEQ ID NO: 256; SEQ ID NO: 229 and SEQ ID NO: 257; SEQ ID NO: 229 and SEQ ID NO: 258; SEQ ID NO: 229 and SEQ ID NO: 259; SEQ ID NO: 229 and SEQ ID NO: 260; SEQ ID NO: 229 and SEQ ID NO: 261; SEQ ID NO: 229 and SEQ ID NO: 262; SEQ ID NO: 229 and SEQ ID NO: 263; SEQ ID NO: 229 and SEQ ID NO: 264; SEQ ID NO: 229 and SEQ ID NO: 265; SEQ ID NO: 229 and SEQ ID NO: 266; SEQ ID NO: 229 and SEQ ID NO: 267; SEQ ID NO: 229 and SEQ ID NO: 268; SEQ ID NO: 229 and SEQ ID NO: 269; SEQ ID NO: 229 and SEQ ID NO: 270; SEQ ID NO: 229 and SEQ ID NO: 271; SEQ ID NO: 229 and SEQ ID NO: 272; SEQ ID NO: 229 and SEQ ID NO: 273; SEQ ID NO: 229 and SEQ ID NO: 274; SEQ ID NO: 229 and SEQ ID NO: 275; SEQ ID NO: 229 and SEQ ID NO: 276; SEQ ID NO: 229 and SEQ ID NO: 277; and SEQ ID NO: 229 and SEQ ID NO: 278.

In some aspects, the $V_H$-$V_L$ pairs are selected from SEQ ID NO: 230 and SEQ ID NO: 254; SEQ ID NO: 230 and SEQ ID NO: 255; SEQ ID NO: 230 and SEQ ID NO: 256; SEQ ID NO: 230 and SEQ ID NO: 257; SEQ ID NO: 230 and SEQ ID NO: 258; SEQ ID NO: 230 and SEQ ID NO: 259; SEQ ID NO: 230 and SEQ ID NO: 260; SEQ ID NO: 230 and SEQ ID NO: 261; SEQ ID NO: 230 and SEQ ID NO: 262; SEQ ID NO: 230 and SEQ ID NO: 263; SEQ ID NO: 230 and SEQ ID NO: 264; SEQ ID NO: 230 and SEQ ID NO: 265; SEQ ID NO: 230 and SEQ ID NO: 266; SEQ ID NO: 230 and SEQ ID NO: 267; SEQ ID NO: 230 and SEQ ID NO: 268; SEQ ID NO: 230 and SEQ ID NO: 269; SEQ ID NO: 230 and SEQ ID NO: 270; SEQ ID NO: 230 and SEQ ID NO: 271; SEQ ID NO: 230 and SEQ ID NO: 272; SEQ ID NO: 230 and SEQ ID NO: 273; SEQ ID NO: 230 and SEQ ID NO: 274; SEQ ID NO: 230 and SEQ ID NO: 275; SEQ ID NO: 230 and SEQ ID NO: 276; SEQ ID NO: 230 and SEQ ID NO: 277; and SEQ ID NO: 230 and SEQ ID NO: 278.

In some aspects, the $V_H$-$V_L$ pairs are selected from SEQ ID NO: 231 and SEQ ID NO: 254; SEQ ID NO: 231 and SEQ ID NO: 255; SEQ ID NO: 231 and SEQ ID NO: 256; SEQ ID NO: 231 and SEQ ID NO: 257; SEQ ID NO: 231 and SEQ ID NO: 258; SEQ ID NO: 231 and SEQ ID NO: 259; SEQ ID NO: 231 and SEQ ID NO: 260; SEQ ID NO: 231 and SEQ ID NO: 261; SEQ ID NO: 231 and SEQ ID NO: 262; SEQ ID NO: 231 and SEQ ID NO: 263; SEQ ID NO: 231 and SEQ ID NO: 264; SEQ ID NO: 231 and SEQ ID NO: 265; SEQ ID NO: 231 and SEQ ID NO: 266; SEQ ID NO: 231 and SEQ ID NO: 267; SEQ ID NO: 231 and SEQ ID NO: 268; SEQ ID NO: 231 and SEQ ID NO: 269; SEQ ID NO: 231 and SEQ ID NO: 270; SEQ ID NO: 231 and SEQ ID NO: 271; SEQ ID NO: 231 and SEQ ID NO: 272; SEQ ID NO: 231 and SEQ ID NO: 273; SEQ ID NO: 231 and SEQ ID NO: 274; SEQ ID NO: 231 and SEQ ID NO: 275; SEQ ID NO: 231 and SEQ ID NO: 276; SEQ ID NO: 231 and SEQ ID NO: 277; and SEQ ID NO: 231 and SEQ ID NO: 278.

In some aspects, the $V_H$-$V_L$ pairs are selected from SEQ ID NO: 232 and SEQ ID NO: 254; SEQ ID NO: 232 and SEQ ID NO: 255; SEQ ID NO: 232 and SEQ ID NO: 256; SEQ ID NO: 232 and SEQ ID NO: 257; SEQ ID NO: 232 and SEQ ID NO: 258; SEQ ID NO: 232 and SEQ ID NO: 259; SEQ ID NO: 232 and SEQ ID NO: 260; SEQ ID NO: 232 and SEQ ID NO: 261; SEQ ID NO: 232 and SEQ ID NO: 262; SEQ ID NO: 232 and SEQ ID NO: 263; SEQ ID NO: 232 and SEQ ID NO: 264; SEQ ID NO: 232 and SEQ ID NO: 265; SEQ ID NO: 232 and SEQ ID NO: 266; SEQ ID NO: 232 and SEQ ID NO: 267; SEQ ID NO: 232 and SEQ ID NO: 268; SEQ ID NO: 232 and SEQ ID NO: 269; SEQ ID NO: 232 and SEQ ID NO: 270; SEQ ID NO: 232 and SEQ ID NO: 271; SEQ ID NO: 232 and SEQ ID NO: 272; SEQ ID NO: 232 and SEQ ID NO: 273; SEQ ID NO: 232 and SEQ ID NO: 274; SEQ ID NO: 232 and SEQ ID NO: 275; SEQ ID NO: 232 and SEQ ID NO: 276; SEQ ID NO: 232 and SEQ ID NO: 277; and SEQ ID NO: 232 and SEQ ID NO: 278.

In some aspects, the $V_H$-$V_L$ pairs are selected from SEQ ID NO: 233 and SEQ ID NO: 254; SEQ ID NO: 233 and SEQ ID NO: 255; SEQ ID NO: 233 and SEQ ID NO: 256; SEQ ID NO: 233 and SEQ ID NO: 257; SEQ ID NO: 233 and SEQ ID NO: 258; SEQ ID NO: 233 and SEQ ID NO: 259; SEQ ID NO: 233 and SEQ ID NO: 260; SEQ ID NO: 233 and SEQ ID NO: 261; SEQ ID NO: 233 and SEQ ID NO: 262; SEQ ID NO: 233 and SEQ ID NO: 263; SEQ ID NO: 233 and SEQ ID NO: 264; SEQ ID NO: 233 and SEQ ID NO: 265; SEQ ID NO: 233 and SEQ ID NO: 266; SEQ ID NO: 233 and SEQ ID NO: 267; SEQ ID NO: 233 and SEQ ID NO: 268; SEQ ID NO: 233 and SEQ ID NO: 269;

SEQ ID NO: 233 and SEQ ID NO: 270; SEQ ID NO: 233 and SEQ ID NO: 271; SEQ ID NO: 233 and SEQ ID NO: 272; SEQ ID NO: 233 and SEQ ID NO: 273; SEQ ID NO: 233 and SEQ ID NO: 274; SEQ ID NO: 233 and SEQ ID NO: 275; SEQ ID NO: 233 and SEQ ID NO: 276; SEQ ID NO: 233 and SEQ ID NO: 277; and SEQ ID NO: 233 and SEQ ID NO: 278.

In some aspects, the $V_H$-$V_L$ pairs are selected from SEQ ID NO: 234 and SEQ ID NO: 254; SEQ ID NO: 234 and SEQ ID NO: 255; SEQ ID NO: 234 and SEQ ID NO: 256; SEQ ID NO: 234 and SEQ ID NO: 257; SEQ ID NO: 234 and SEQ ID NO: 258; SEQ ID NO: 234 and SEQ ID NO: 259; SEQ ID NO: 234 and SEQ ID NO: 260; SEQ ID NO: 234 and SEQ ID NO: 261; SEQ ID NO: 234 and SEQ ID NO: 262; SEQ ID NO: 234 and SEQ ID NO: 263; SEQ ID NO: 234 and SEQ ID NO: 264; SEQ ID NO: 234 and SEQ ID NO: 265; SEQ ID NO: 234 and SEQ ID NO: 266; SEQ ID NO: 234 and SEQ ID NO: 267; SEQ ID NO: 234 and SEQ ID NO: 268; SEQ ID NO: 234 and SEQ ID NO: 269; SEQ ID NO: 234 and SEQ ID NO: 270; SEQ ID NO: 234 and SEQ ID NO: 271; SEQ ID NO: 234 and SEQ ID NO: 272; SEQ ID NO: 234 and SEQ ID NO: 273; SEQ ID NO: 234 and SEQ ID NO: 274; SEQ ID NO: 234 and SEQ ID NO: 275; SEQ ID NO: 234 and SEQ ID NO: 276; SEQ ID NO: 234 and SEQ ID NO: 277; and SEQ ID NO: 234 and SEQ ID NO: 278.

In some aspects, the $V_H$-$V_L$ pairs are selected from SEQ ID NO: 235 and SEQ ID NO: 254; SEQ ID NO: 235 and SEQ ID NO: 255; SEQ ID NO: 235 and SEQ ID NO: 256; SEQ ID NO: 235 and SEQ ID NO: 257; SEQ ID NO: 235 and SEQ ID NO: 258; SEQ ID NO: 235 and SEQ ID NO: 259; SEQ ID NO: 235 and SEQ ID NO: 260; SEQ ID NO: 235 and SEQ ID NO: 261; SEQ ID NO: 235 and SEQ ID NO: 262; SEQ ID NO: 235 and SEQ ID NO: 263; SEQ ID NO: 235 and SEQ ID NO: 264; SEQ ID NO: 235 and SEQ ID NO: 265; SEQ ID NO: 235 and SEQ ID NO: 266; SEQ ID NO: 235 and SEQ ID NO: 267; SEQ ID NO: 235 and SEQ ID NO: 268; SEQ ID NO: 235 and SEQ ID NO: 269; SEQ ID NO: 235 and SEQ ID NO: 270; SEQ ID NO: 235 and SEQ ID NO: 271; SEQ ID NO: 235 and SEQ ID NO: 272; SEQ ID NO: 235 and SEQ ID NO: 273; SEQ ID NO: 235 and SEQ ID NO: 274; SEQ ID NO: 235 and SEQ ID NO: 275; SEQ ID NO: 235 and SEQ ID NO: 276; SEQ ID NO: 235 and SEQ ID NO: 277; and SEQ ID NO: 235 and SEQ ID NO: 278.

In some aspects, the $V_H$-$V_L$ pairs are selected from SEQ ID NO: 236 and SEQ ID NO: 254; SEQ ID NO: 236 and SEQ ID NO: 255; SEQ ID NO: 236 and SEQ ID NO: 256; SEQ ID NO: 236 and SEQ ID NO: 257; SEQ ID NO: 236 and SEQ ID NO: 258; SEQ ID NO: 236 and SEQ ID NO: 259; SEQ ID NO: 236 and SEQ ID NO: 260; SEQ ID NO: 236 and SEQ ID NO: 261; SEQ ID NO: 236 and SEQ ID NO: 262; SEQ ID NO: 236 and SEQ ID NO: 263; SEQ ID NO: 236 and SEQ ID NO: 264; SEQ ID NO: 236 and SEQ ID NO: 265; SEQ ID NO: 236 and SEQ ID NO: 266; SEQ ID NO: 236 and SEQ ID NO: 267; SEQ ID NO: 236 and SEQ ID NO: 268; SEQ ID NO: 236 and SEQ ID NO: 269; SEQ ID NO: 236 and SEQ ID NO: 270; SEQ ID NO: 236 and SEQ ID NO: 271; SEQ ID NO: 236 and SEQ ID NO: 272; SEQ ID NO: 236 and SEQ ID NO: 273; SEQ ID NO: 236 and SEQ ID NO: 274; SEQ ID NO: 236 and SEQ ID NO: 275; SEQ ID NO: 236 and SEQ ID NO: 276; SEQ ID NO: 236 and SEQ ID NO: 277; and SEQ ID NO: 236 and SEQ ID NO: 278.

In some aspects, the $V_H$-$V_L$ pairs are selected from SEQ ID NO: 237 and SEQ ID NO: 254; SEQ ID NO: 237 and SEQ ID NO: 255; SEQ ID NO: 237 and SEQ ID NO: 256; SEQ ID NO: 237 and SEQ ID NO: 257; SEQ ID NO: 237 and SEQ ID NO: 258; SEQ ID NO: 237 and SEQ ID NO: 259; SEQ ID NO: 237 and SEQ ID NO: 260; SEQ ID NO: 237 and SEQ ID NO: 261; SEQ ID NO: 237 and SEQ ID NO: 262; SEQ ID NO: 237 and SEQ ID NO: 263; SEQ ID NO: 237 and SEQ ID NO: 264; SEQ ID NO: 237 and SEQ ID NO: 265; SEQ ID NO: 237 and SEQ ID NO: 266; SEQ ID NO: 237 and SEQ ID NO: 267; SEQ ID NO: 237 and SEQ ID NO: 268; SEQ ID NO: 237 and SEQ ID NO: 269; SEQ ID NO: 237 and SEQ ID NO: 270; SEQ ID NO: 237 and SEQ ID NO: 271; SEQ ID NO: 237 and SEQ ID NO: 272; SEQ ID NO: 237 and SEQ ID NO: 273; SEQ ID NO: 237 and SEQ ID NO: 274; SEQ ID NO: 237 and SEQ ID NO: 275; SEQ ID NO: 237 and SEQ ID NO: 276; SEQ ID NO: 237 and SEQ ID NO: 277; and SEQ ID NO: 237 and SEQ ID NO: 278.

In some aspects, the $V_H$-$V_L$ pairs are selected from SEQ ID NO: 238 and SEQ ID NO: 254; SEQ ID NO: 238 and SEQ ID NO: 255; SEQ ID NO: 238 and SEQ ID NO: 256; SEQ ID NO: 238 and SEQ ID NO: 257; SEQ ID NO: 238 and SEQ ID NO: 258; SEQ ID NO: 238 and SEQ ID NO: 259; SEQ ID NO: 238 and SEQ ID NO: 260; SEQ ID NO: 238 and SEQ ID NO: 261; SEQ ID NO: 238 and SEQ ID NO: 262; SEQ ID NO: 238 and SEQ ID NO: 263; SEQ ID NO: 238 and SEQ ID NO: 264; SEQ ID NO: 238 and SEQ ID NO: 265; SEQ ID NO: 238 and SEQ ID NO: 266; SEQ ID NO: 238 and SEQ ID NO: 267; SEQ ID NO: 238 and SEQ ID NO: 268; SEQ ID NO: 238 and SEQ ID NO: 269; SEQ ID NO: 238 and SEQ ID NO: 270; SEQ ID NO: 238 and SEQ ID NO: 271; SEQ ID NO: 238 and SEQ ID NO: 272; SEQ ID NO: 238 and SEQ ID NO: 273; SEQ ID NO: 238 and SEQ ID NO: 274; SEQ ID NO: 238 and SEQ ID NO: 275; SEQ ID NO: 238 and SEQ ID NO: 276; SEQ ID NO: 238 and SEQ ID NO: 277; and SEQ ID NO: 238 and SEQ ID NO: 278.

In some aspects, the $V_H$-$V_L$ pairs are selected from SEQ ID NO: 239 and SEQ ID NO: 254; SEQ ID NO: 239 and SEQ ID NO: 255; SEQ ID NO: 239 and SEQ ID NO: 256; SEQ ID NO: 239 and SEQ ID NO: 257; SEQ ID NO: 239 and SEQ ID NO: 258; SEQ ID NO: 239 and SEQ ID NO: 259; SEQ ID NO: 239 and SEQ ID NO: 260; SEQ ID NO: 239 and SEQ ID NO: 261; SEQ ID NO: 239 and SEQ ID NO: 262; SEQ ID NO: 239 and SEQ ID NO: 263; SEQ ID NO: 239 and SEQ ID NO: 264; SEQ ID NO: 239 and SEQ ID NO: 265; SEQ ID NO: 239 and SEQ ID NO: 266; SEQ ID NO: 239 and SEQ ID NO: 267; SEQ ID NO: 239 and SEQ ID NO: 268; SEQ ID NO: 239 and SEQ ID NO: 269; SEQ ID NO: 239 and SEQ ID NO: 270; SEQ ID NO: 239 and SEQ ID NO: 271; SEQ ID NO: 239 and SEQ ID NO: 272; SEQ ID NO: 239 and SEQ ID NO: 273; SEQ ID NO: 239 and SEQ ID NO: 274; SEQ ID NO: 239 and SEQ ID NO: 275; SEQ ID NO: 239 and SEQ ID NO: 276; SEQ ID NO: 239 and SEQ ID NO: 277; and SEQ ID NO: 239 and SEQ ID NO: 278.

In some aspects, the $V_H$-$V_L$ pairs are selected from SEQ ID NO: 240 and SEQ ID NO: 254; SEQ ID NO: 240 and SEQ ID NO: 255; SEQ ID NO: 240 and SEQ ID NO: 256; SEQ ID NO: 240 and SEQ ID NO: 257; SEQ ID NO: 240 and SEQ ID NO: 258; SEQ ID NO: 240 and SEQ ID NO: 259; SEQ ID NO: 240 and SEQ ID NO: 260; SEQ ID NO: 240 and SEQ ID NO: 261; SEQ ID NO: 240 and SEQ ID NO: 262; SEQ ID NO: 240 and SEQ ID NO: 263; SEQ ID NO: 240 and SEQ ID NO: 264; SEQ ID NO: 240 and SEQ ID NO: 265; SEQ ID NO: 240 and SEQ ID NO: 266; SEQ ID NO: 240 and SEQ ID NO: 267; SEQ ID NO: 240 and SEQ ID NO: 268; SEQ ID NO: 240 and SEQ ID NO: 269; SEQ ID NO: 240 and SEQ ID NO: 270; SEQ ID NO: 240 and SEQ ID NO: 271; SEQ ID NO: 240 and SEQ ID NO: 272; SEQ ID NO: 240 and SEQ ID NO: 273; SEQ ID NO: 240 and SEQ ID NO: 274; SEQ ID NO: 240 and SEQ ID NO: 275; SEQ ID NO: 240 and SEQ ID NO: 276; SEQ ID NO: 240 and SEQ ID NO: 277; and SEQ ID NO: 240 and SEQ ID NO: 278.

In some aspects, the $V_H$-$V_L$ pairs are selected from SEQ ID NO: 241 and SEQ ID NO: 254; SEQ ID NO: 241 and SEQ ID NO: 255; SEQ ID NO: 241 and SEQ ID NO: 256; SEQ ID NO: 241 and SEQ ID NO: 257; SEQ ID NO: 241 and SEQ ID NO: 258; SEQ ID NO: 241 and SEQ ID NO: 259; SEQ ID NO: 241 and SEQ ID NO: 260; SEQ ID NO: 241 and SEQ ID NO: 261; SEQ ID NO: 241 and SEQ ID NO: 262; SEQ ID NO: 241 and SEQ ID NO: 263; SEQ ID NO: 241 and SEQ ID NO: 264; SEQ ID NO: 241 and SEQ ID NO: 265; SEQ ID NO: 241 and SEQ ID NO: 266; SEQ ID NO: 241 and SEQ ID NO: 267; SEQ ID NO: 241 and SEQ ID NO: 268; SEQ ID NO: 241 and SEQ ID NO: 269; SEQ ID NO: 241 and SEQ ID NO: 270; SEQ ID NO: 241 and SEQ ID NO: 271; SEQ ID NO: 241 and SEQ ID NO: 272; SEQ ID NO: 241 and SEQ ID NO: 273; SEQ ID NO: 241 and SEQ ID NO: 274; SEQ ID NO: 241 and SEQ ID NO: 275; SEQ ID NO: 241 and SEQ ID NO: 276; SEQ ID NO: 241 and SEQ ID NO: 277; and SEQ ID NO: 241 and SEQ ID NO: 278.

In some aspects, the $V_H$-$V_L$ pairs are selected from SEQ ID NO: 242 and SEQ ID NO: 254; SEQ ID NO: 242 and SEQ ID NO: 255; SEQ ID NO: 242 and SEQ ID NO: 256; SEQ ID NO: 242 and SEQ ID NO: 257; SEQ ID NO: 242 and SEQ ID NO: 258; SEQ ID NO: 242 and SEQ ID NO: 259; SEQ ID NO: 242 and SEQ ID NO: 260; SEQ ID NO: 242 and SEQ ID NO: 261; SEQ ID NO: 242 and SEQ ID NO: 262; SEQ ID NO: 242 and SEQ ID NO: 263; SEQ ID NO: 242 and SEQ ID NO: 264; SEQ ID NO: 242 and SEQ ID NO: 265; SEQ ID NO: 242 and SEQ ID NO: 266; SEQ ID NO: 242 and SEQ ID NO: 267; SEQ ID NO: 242 and SEQ ID NO: 268; SEQ ID NO: 242 and SEQ ID NO: 269; SEQ ID NO: 242 and SEQ ID NO: 270; SEQ ID NO: 242 and SEQ ID NO: 271; SEQ ID NO: 242 and SEQ ID NO: 272; SEQ ID NO: 242 and SEQ ID NO: 273; SEQ ID NO: 242 and SEQ ID NO: 274; SEQ ID NO: 242 and SEQ ID NO: 275; SEQ ID NO: 242 and SEQ ID NO: 276; SEQ ID NO: 242 and SEQ ID NO: 277; and SEQ ID NO: 242 and SEQ ID NO: 278.

In some aspects, the $V_H$-$V_L$ pairs are selected from SEQ ID NO: 243 and SEQ ID NO: 254; SEQ ID NO: 243 and SEQ ID NO: 255; SEQ ID NO: 243 and SEQ ID NO: 256; SEQ ID NO: 243 and SEQ ID NO: 257; SEQ ID NO: 243 and SEQ ID NO: 258; SEQ ID NO: 243 and SEQ ID NO: 259; SEQ ID NO: 243 and SEQ ID NO: 260; SEQ ID NO: 243 and SEQ ID NO: 261; SEQ ID NO: 243 and SEQ ID NO: 262; SEQ ID NO: 243 and SEQ ID NO: 263; SEQ ID NO: 243 and SEQ ID NO: 264; SEQ ID NO: 243 and SEQ ID NO: 265; SEQ ID NO: 243 and SEQ ID NO: 266; SEQ ID NO: 243 and SEQ ID NO: 267; SEQ ID NO: 243 and SEQ ID NO: 268; SEQ ID NO: 243 and SEQ ID NO: 269; SEQ ID NO: 243 and SEQ ID NO: 270; SEQ ID NO: 243 and SEQ ID NO: 271; SEQ ID NO: 243 and SEQ ID NO: 272; SEQ ID NO: 243 and SEQ ID NO: 273; SEQ ID NO: 243 and SEQ ID NO: 274; SEQ ID NO: 243 and SEQ ID NO: 275; SEQ ID NO: 243 and SEQ ID NO: 276; SEQ ID NO: 243 and SEQ ID NO: 277; and SEQ ID NO: 243 and SEQ ID NO: 278.

In some aspects, the $V_H$-$V_L$ pairs are selected from SEQ ID NO: 244 and SEQ ID NO: 254; SEQ ID NO: 244 and SEQ ID NO: 255; SEQ ID NO: 244 and SEQ ID NO: 256; SEQ ID NO: 244 and SEQ ID NO: 257; SEQ ID NO: 244 and SEQ ID NO: 258; SEQ ID NO: 244 and SEQ ID NO: 259; SEQ ID NO: 244 and SEQ ID NO: 260; SEQ ID NO: 244 and SEQ ID NO: 261; SEQ ID NO: 244 and SEQ ID NO: 262; SEQ ID NO: 244 and SEQ ID NO: 263; SEQ ID NO: 244 and SEQ ID NO: 264; SEQ ID NO: 244 and SEQ ID NO: 265; SEQ ID NO: 244 and SEQ ID NO: 266; SEQ ID NO: 244 and SEQ ID NO: 267; SEQ ID NO: 244 and SEQ ID NO: 268; SEQ ID NO: 244 and SEQ ID NO: 269; SEQ ID NO: 244 and SEQ ID NO: 270; SEQ ID NO: 244 and SEQ ID NO: 271; SEQ ID NO: 244 and SEQ ID NO: 272; SEQ ID NO: 244 and SEQ ID NO: 273; SEQ ID NO: 244 and SEQ ID NO: 274; SEQ ID NO: 244 and SEQ ID NO: 275; SEQ ID NO: 244 and SEQ ID NO: 276; SEQ ID NO: 244 and SEQ ID NO: 277; and SEQ ID NO: 244 and SEQ ID NO: 278.

In some aspects, the $V_H$-$V_L$ pairs are selected from SEQ ID NO: 245 and SEQ ID NO: 254; SEQ ID NO: 245 and SEQ ID NO: 255; SEQ ID NO: 245 and SEQ ID NO: 256; SEQ ID NO: 245 and SEQ ID NO: 257; SEQ ID NO: 245 and SEQ ID NO: 258; SEQ ID NO: 245 and SEQ ID NO: 259; SEQ ID NO: 245 and SEQ ID NO: 260; SEQ ID NO: 245 and SEQ ID NO: 261; SEQ ID NO: 245 and SEQ ID NO: 262; SEQ ID NO: 245 and SEQ ID NO: 263; SEQ ID NO: 245 and SEQ ID NO: 264; SEQ ID NO: 245 and SEQ ID NO: 265; SEQ ID NO: 245 and SEQ ID NO: 266; SEQ ID NO: 245 and SEQ ID NO: 267; SEQ ID NO: 245 and SEQ ID NO: 268; SEQ ID NO: 245 and SEQ ID NO: 269; SEQ ID NO: 245 and SEQ ID NO: 270; SEQ ID NO: 245 and SEQ ID NO: 271; SEQ ID NO: 245 and SEQ ID NO: 272; SEQ ID NO: 245 and SEQ ID NO: 273; SEQ ID NO: 245 and SEQ ID NO: 274; SEQ ID NO: 245 and SEQ ID NO: 275; SEQ ID NO: 245 and SEQ ID NO: 276; SEQ ID NO: 245 and SEQ ID NO: 277; and SEQ ID NO: 245 and SEQ ID NO: 278.

In some aspects, the $V_H$-$V_L$ pairs are selected from SEQ ID NO: 246 and SEQ ID NO: 254; SEQ ID NO: 246 and SEQ ID NO: 255; SEQ ID NO: 246 and SEQ ID NO: 256; SEQ ID NO: 246 and SEQ ID NO: 257; SEQ ID NO: 246 and SEQ ID NO: 258; SEQ ID NO: 246 and SEQ ID NO: 259; SEQ ID NO: 246 and SEQ ID NO: 260; SEQ ID NO: 246 and SEQ ID NO: 261; SEQ ID NO: 246 and SEQ ID NO: 262; SEQ ID NO: 246 and SEQ ID NO: 263; SEQ ID NO: 246 and SEQ ID NO: 264; SEQ ID NO: 246 and SEQ ID NO: 265; SEQ ID NO: 246 and SEQ ID NO: 266; SEQ ID NO: 246 and SEQ ID NO: 267; SEQ ID NO: 246 and SEQ ID NO: 268; SEQ ID NO: 246 and SEQ ID NO: 269; SEQ ID NO: 246 and SEQ ID NO: 270; SEQ ID NO: 246 and SEQ ID NO: 271; SEQ ID NO: 246 and SEQ ID NO: 272; SEQ ID NO: 246 and SEQ ID NO: 273; SEQ ID NO: 246 and SEQ ID NO: 274; SEQ ID NO: 246 and SEQ ID NO: 275; SEQ ID NO: 246 and SEQ ID NO: 276; SEQ ID NO: 246 and SEQ ID NO: 277; and SEQ ID NO: 246 and SEQ ID NO: 278.

In some aspects, the $V_H$-$V_L$ pairs are selected from SEQ ID NO: 247 and SEQ ID NO: 254; SEQ ID NO: 247 and SEQ ID NO: 255; SEQ ID NO: 247 and SEQ ID NO: 256; SEQ ID NO: 247 and SEQ ID NO: 257; SEQ ID NO: 247 and SEQ ID NO: 258; SEQ ID NO: 247 and SEQ ID NO: 259; SEQ ID NO: 247 and SEQ ID NO: 260; SEQ ID NO: 247 and SEQ ID NO: 261; SEQ ID NO: 247 and SEQ ID NO: 262; SEQ ID NO: 247 and SEQ ID NO: 263; SEQ ID NO: 247 and SEQ ID NO: 264; SEQ ID NO: 247 and SEQ ID NO: 265; SEQ ID NO: 247 and SEQ ID NO: 266; SEQ ID NO: 247 and SEQ ID NO: 267; SEQ ID NO: 247 and SEQ ID NO: 268; SEQ ID NO: 247 and SEQ ID NO: 269; SEQ ID NO: 247 and SEQ ID NO: 270; SEQ ID NO: 247 and SEQ ID NO: 271; SEQ ID NO: 247 and SEQ ID NO:

272; SEQ ID NO: 247 and SEQ ID NO: 273; SEQ ID NO: 247 and SEQ ID NO: 274; SEQ ID NO: 247 and SEQ ID NO: 275; SEQ ID NO: 247 and SEQ ID NO: 276; SEQ ID NO: 247 and SEQ ID NO: 277; and SEQ ID NO: 247 and SEQ ID NO: 278.

In some aspects, the $V_H$-$V_L$ pairs are selected from SEQ ID NO: 248 and SEQ ID NO: 254; SEQ ID NO: 248 and SEQ ID NO: 255; SEQ ID NO: 248 and SEQ ID NO: 256; SEQ ID NO: 248 and SEQ ID NO: 257; SEQ ID NO: 248 and SEQ ID NO: 258; SEQ ID NO: 248 and SEQ ID NO: 259; SEQ ID NO: 248 and SEQ ID NO: 260; SEQ ID NO: 248 and SEQ ID NO: 261; SEQ ID NO: 248 and SEQ ID NO: 262; SEQ ID NO: 248 and SEQ ID NO: 263; SEQ ID NO: 248 and SEQ ID NO: 264; SEQ ID NO: 248 and SEQ ID NO: 265; SEQ ID NO: 248 and SEQ ID NO: 266; SEQ ID NO: 248 and SEQ ID NO: 267; SEQ ID NO: 248 and SEQ ID NO: 268; SEQ ID NO: 248 and SEQ ID NO: 269; SEQ ID NO: 248 and SEQ ID NO: 270; SEQ ID NO: 248 and SEQ ID NO: 271; SEQ ID NO: 248 and SEQ ID NO: 272; SEQ ID NO: 248 and SEQ ID NO: 273; SEQ ID NO: 248 and SEQ ID NO: 274; SEQ ID NO: 248 and SEQ ID NO: 275; SEQ ID NO: 248 and SEQ ID NO: 276; SEQ ID NO: 248 and SEQ ID NO: 277; and SEQ ID NO: 248 and SEQ ID NO: 278.

In some aspects, the $V_H$-$V_L$ pairs are selected from SEQ ID NO: 249 and SEQ ID NO: 254; SEQ ID NO: 249 and SEQ ID NO: 255; SEQ ID NO: 249 and SEQ ID NO: 256; SEQ ID NO: 249 and SEQ ID NO: 257; SEQ ID NO: 249 and SEQ ID NO: 258; SEQ ID NO: 249 and SEQ ID NO: 259; SEQ ID NO: 249 and SEQ ID NO: 260; SEQ ID NO: 249 and SEQ ID NO: 261; SEQ ID NO: 249 and SEQ ID NO: 262; SEQ ID NO: 249 and SEQ ID NO: 263; SEQ ID NO: 249 and SEQ ID NO: 264; SEQ ID NO: 249 and SEQ ID NO: 265; SEQ ID NO: 249 and SEQ ID NO: 266; SEQ ID NO: 249 and SEQ ID NO: 267; SEQ ID NO: 249 and SEQ ID NO: 268; SEQ ID NO: 249 and SEQ ID NO: 269; SEQ ID NO: 249 and SEQ ID NO: 270; SEQ ID NO: 249 and SEQ ID NO: 271; SEQ ID NO: 249 and SEQ ID NO: 272; SEQ ID NO: 249 and SEQ ID NO: 273; SEQ ID NO: 249 and SEQ ID NO: 274; SEQ ID NO: 249 and SEQ ID NO: 275; SEQ ID NO: 249 and SEQ ID NO: 276; SEQ ID NO: 249 and SEQ ID NO: 277; and SEQ ID NO: 249 and SEQ ID NO: 278.

In some aspects, the $V_H$-$V_L$ pairs are selected from SEQ ID NO: 250 and SEQ ID NO: 254; SEQ ID NO: 250 and SEQ ID NO: 255; SEQ ID NO: 250 and SEQ ID NO: 256; SEQ ID NO: 250 and SEQ ID NO: 257; SEQ ID NO: 250 and SEQ ID NO: 258; SEQ ID NO: 250 and SEQ ID NO: 259; SEQ ID NO: 250 and SEQ ID NO: 260; SEQ ID NO: 250 and SEQ ID NO: 261; SEQ ID NO: 250 and SEQ ID NO: 262; SEQ ID NO: 250 and SEQ ID NO: 263; SEQ ID NO: 250 and SEQ ID NO: 264; SEQ ID NO: 250 and SEQ ID NO: 265; SEQ ID NO: 250 and SEQ ID NO: 266; SEQ ID NO: 250 and SEQ ID NO: 267; SEQ ID NO: 250 and SEQ ID NO: 268; SEQ ID NO: 250 and SEQ ID NO: 269; SEQ ID NO: 250 and SEQ ID NO: 270; SEQ ID NO: 250 and SEQ ID NO: 271; SEQ ID NO: 250 and SEQ ID NO: 272; SEQ ID NO: 250 and SEQ ID NO: 273; SEQ ID NO: 250 and SEQ ID NO: 274; SEQ ID NO: 250 and SEQ ID NO: 275; SEQ ID NO: 250 and SEQ ID NO: 276; SEQ ID NO: 250 and SEQ ID NO: 277; and SEQ ID NO: 250 and SEQ ID NO: 278.

In some aspects, the $V_H$-$V_L$ pairs are selected from SEQ ID NO: 251 and SEQ ID NO: 254; SEQ ID NO: 251 and SEQ ID NO: 255; SEQ ID NO: 251 and SEQ ID NO: 256; SEQ ID NO: 251 and SEQ ID NO: 257; SEQ ID NO: 251 and SEQ ID NO: 258; SEQ ID NO: 251 and SEQ ID NO: 259; SEQ ID NO: 251 and SEQ ID NO: 260; SEQ ID NO: 251 and SEQ ID NO: 261; SEQ ID NO: 251 and SEQ ID NO: 262; SEQ ID NO: 251 and SEQ ID NO: 263; SEQ ID NO: 251 and SEQ ID NO: 264; SEQ ID NO: 251 and SEQ ID NO: 265; SEQ ID NO: 251 and SEQ ID NO: 266; SEQ ID NO: 251 and SEQ ID NO: 267; SEQ ID NO: 251 and SEQ ID NO: 268; SEQ ID NO: 251 and SEQ ID NO: 269; SEQ ID NO: 251 and SEQ ID NO: 270; SEQ ID NO: 251 and SEQ ID NO: 271; SEQ ID NO: 251 and SEQ ID NO: 272; SEQ ID NO: 251 and SEQ ID NO: 273; SEQ ID NO: 251 and SEQ ID NO: 274; SEQ ID NO: 251 and SEQ ID NO: 275; SEQ ID NO: 251 and SEQ ID NO: 276; SEQ ID NO: 251 and SEQ ID NO: 277; and SEQ ID NO: 251 and SEQ ID NO: 278.

In some aspects, the $V_H$-$V_L$ pairs are selected from SEQ ID NO: 252 and SEQ ID NO: 254; SEQ ID NO: 252 and SEQ ID NO: 255; SEQ ID NO: 252 and SEQ ID NO: 256; SEQ ID NO: 252 and SEQ ID NO: 257; SEQ ID NO: 252 and SEQ ID NO: 258; SEQ ID NO: 252 and SEQ ID NO: 259; SEQ ID NO: 252 and SEQ ID NO: 260; SEQ ID NO: 252 and SEQ ID NO: 261; SEQ ID NO: 252 and SEQ ID NO: 262; SEQ ID NO: 252 and SEQ ID NO: 263; SEQ ID NO: 252 and SEQ ID NO: 264; SEQ ID NO: 252 and SEQ ID NO: 265; SEQ ID NO: 252 and SEQ ID NO: 266; SEQ ID NO: 252 and SEQ ID NO: 267; SEQ ID NO: 252 and SEQ ID NO: 268; SEQ ID NO: 252 and SEQ ID NO: 269; SEQ ID NO: 252 and SEQ ID NO: 270; SEQ ID NO: 252 and SEQ ID NO: 271; SEQ ID NO: 252 and SEQ ID NO: 272; SEQ ID NO: 252 and SEQ ID NO: 273; SEQ ID NO: 252 and SEQ ID NO: 274; SEQ ID NO: 252 and SEQ ID NO: 275; SEQ ID NO: 252 and SEQ ID NO: 276; SEQ ID NO: 252 and SEQ ID NO: 277; and SEQ ID NO: 252 and SEQ ID NO: 278.

In some aspects, the $V_H$-$V_L$ pairs are selected from SEQ ID NO: 253 and SEQ ID NO: 254; SEQ ID NO: 253 and SEQ ID NO: 255; SEQ ID NO: 253 and SEQ ID NO: 256; SEQ ID NO: 253 and SEQ ID NO: 257; SEQ ID NO: 253 and SEQ ID NO: 258; SEQ ID NO: 253 and SEQ ID NO: 259; SEQ ID NO: 253 and SEQ ID NO: 260; SEQ ID NO: 253 and SEQ ID NO: 261; SEQ ID NO: 253 and SEQ ID NO: 262; SEQ ID NO: 253 and SEQ ID NO: 263; SEQ ID NO: 253 and SEQ ID NO: 264; SEQ ID NO: 253 and SEQ ID NO: 265; SEQ ID NO: 253 and SEQ ID NO: 266; SEQ ID NO: 253 and SEQ ID NO: 267; SEQ ID NO: 253 and SEQ ID NO: 268; SEQ ID NO: 253 and SEQ ID NO: 269; SEQ ID NO: 253 and SEQ ID NO: 270; SEQ ID NO: 253 and SEQ ID NO: 271; SEQ ID NO: 253 and SEQ ID NO: 272; SEQ ID NO: 253 and SEQ ID NO: 273; SEQ ID NO: 253 and SEQ ID NO: 274; SEQ ID NO: 253 and SEQ ID NO: 275; SEQ ID NO: 253 and SEQ ID NO: 276; SEQ ID NO: 253 and SEQ ID NO: 277; and SEQ ID NO: 253 and SEQ ID NO: 278.

2.7.4.1. Variants of $V_H$-$V_L$ Pairs

In some embodiments, the $V_H$-$V_L$ pairs provided herein comprise a variant of an illustrative $V_H$ and/or $V_L$ sequence provided in this disclosure.

In some aspects, the $V_H$ sequence comprises, consists of, or consists essentially of a variant of an illustrative $V_H$ sequence provided in this disclosure. In some aspects, the $V_H$ sequence comprises, consists of, or consists essentially of a sequence having at least 85%, 90%, 95%, 96%, 97%, 98%, 99%, or 99.1% identity with any of the illustrative $V_H$ sequences provided in this disclosure.

In some embodiments, the $V_H$ sequence comprises, consists of, or consists essentially of any of the illustrative $V_H$ sequences provided in this disclosure having 20 or fewer, 19 or fewer, 18 or fewer, 17 or fewer, 16 or fewer, 15 or fewer, 14 or fewer, 13 or fewer, 12 or fewer, 11 or fewer, 10 or fewer, 9 or fewer, 8 or fewer, 7 or fewer, 6 or fewer, 5 or fewer, 4 or fewer, 3 or fewer, 2 or fewer, or 1 or fewer amino acid substitutions. In some aspects, the amino acid substitutions are conservative amino acid substitutions.

In some aspects, the $V_L$ sequence comprises, consists of, or consists essentially of a variant of an illustrative $V_L$ sequence provided in this disclosure. In some aspects, the $V_L$ sequence comprises, consists of, or consists essentially of a sequence having at least 85%, 90%, 95%, 96%, 97%, 98%, 99%, or 99.5% identity with any of the illustrative $V_L$ sequences provided in this disclosure.

In some embodiments, the $V_L$ sequence comprises, consists of, or consists essentially of any of the illustrative $V_L$ sequences provided in this disclosure having 20 or fewer, 19 or fewer, 18 or fewer, 17 or fewer, 16 or fewer, 15 or fewer, 14 or fewer, 13 or fewer, 12 or fewer, 11 or fewer, 10 or fewer, 9 or fewer, 8 or fewer, 7 or fewer, 6 or fewer, 5 or fewer, 4 or fewer, 3 or fewer, 2 or fewer, or 1 or fewer amino acid substitutions. In some aspects, the amino acid substitutions are conservative amino acid substitutions.

2.7.4.2. Excluded $V_H$-$V_L$ Pairs

In some embodiments, the $V_H$-$V_L$ pairs provided herein do not comprise certain $V_H$-$V_L$ pairs.

In some aspects, the $V_H$ sequence is not selected from SEQ ID NOs: 326-330, and the $V_L$ sequence is not selected from SEQ ID NOs: 331-335.

In some aspects, the $V_H$-$V_L$ pairs are not selected from SEQ ID NO: 326 and SEQ ID NO: 331; SEQ ID NO: 326 and SEQ ID NO: 332; SEQ ID NO: 326 and SEQ ID NO: 333; SEQ ID NO: 326 and SEQ ID NO: 334; and SEQ ID NO: 326 and SEQ ID NO: 335.

In some aspects, the $V_H$-$V_L$ pairs are not selected from SEQ ID NO: 327 and SEQ ID NO: 331; SEQ ID NO: 327 and SEQ ID NO: 332; SEQ ID NO: 327 and SEQ ID NO: 333; SEQ ID NO: 327 and SEQ ID NO: 334; and SEQ ID NO: 327 and SEQ ID NO: 335.

In some aspects, the $V_H$-$V_L$ pairs are not selected from SEQ ID NO: 328 and SEQ ID NO: 331; SEQ ID NO: 328 and SEQ ID NO: 332; SEQ ID NO: 328 and SEQ ID NO: 333; SEQ ID NO: 328 and SEQ ID NO: 334; and SEQ ID NO: 328 and SEQ ID NO: 335.

In some aspects, the $V_H$-$V_L$ pairs are not selected from SEQ ID NO: 329 and SEQ ID NO: 331; SEQ ID NO: 329 and SEQ ID NO: 332; SEQ ID NO: 329 and SEQ ID NO: 333; SEQ ID NO: 329 and SEQ ID NO: 334; and SEQ ID NO: 329 and SEQ ID NO: 335.

In some aspects, the $V_H$-$V_L$ pairs are not selected from SEQ ID NO: 330 and SEQ ID NO: 331; SEQ ID NO: 330 and SEQ ID NO: 332; SEQ ID NO: 330 and SEQ ID NO: 333; SEQ ID NO: 330 and SEQ ID NO: 334; and SEQ ID NO: 330 and SEQ ID NO: 335.

2.8. Antibodies Comprising All Six CDRs

In some embodiments, the antibody comprises a CDR-H1 sequence, a CDR-H2 sequence, a CDR-H3 sequence, a CDR-L1 sequence, and a CDR-L3 sequence. In some aspects, the CDR sequences are part of a $V_H$ (for CDR-H) or $V_L$ (for CDR-L).

In some aspects, the CDR-H1 sequence is a Chothia CDR-H1 sequence comprising, consisting of, or consisting essentially of SEQ ID NOs: 4-28; the CDR-H2 sequence is a Chothia CDR-H2 sequence comprising, consisting of, or consisting essentially of SEQ ID NOs: 59-78; the CDR-H3 sequence is a CDR-H3 sequence comprising, consisting of, or consisting essentially of SEQ ID NOs: 104-128; the CDR-L1 sequence is a CDR-L1 sequence comprising, consisting of, or consisting essentially of SEQ ID NOs: 129-153; the CDR-L2 sequence is a CDR-L2 sequence comprising, consisting of, or consisting essentially of SEQ ID NOs: 154-178; and the CDR-L3 sequence is a CDR-L3 sequence comprising, consisting of, or consisting essentially of SEQ ID NOs: 179-203.

In some aspects, the CDR-H1 sequence is a Kabat CDR-H1 sequence comprising, consisting of, or consisting essentially of SEQ ID NOs: 29-53; the CDR-H2 sequence is a Kabat CDR-H2 sequence comprising, consisting of, or consisting essentially of SEQ ID NOs: 79-103; the CDR-H3 sequence is a CDR-H3 sequence comprising, consisting of, or consisting essentially of SEQ ID NOs: 104-128; the CDR-L1 sequence is a CDR-L1 sequence comprising, consisting of, or consisting essentially of SEQ ID NOs: 129-153; the CDR-L2 sequence is a CDR-L2 sequence comprising, consisting of, or consisting essentially of SEQ ID NOs: 154-178; and the CDR-L3 sequence is a CDR-L3 sequence comprising, consisting of, or consisting essentially of SEQ ID NOs: 179-203.

2.8.1. Variants of Antibodies Comprising All Six CDRs

In some embodiments, the CDR-H1, CDR-H2, CDR-H3, CDR-L1, CDR-L2, and CDR-L3 provided herein comprise a variant of an illustrative CDR-H1, CDR-H2, CDR-H3, CDR-L1, CDR-L2, and/or CDR-L3 sequence provided in this disclosure.

In some aspects, the CDR-H1 sequence comprises, consists of, or consists essentially of a variant of an illustrative Chothia or Kabat CDR-H1 sequence provided in this disclosure. In some aspects, the CDR-H1 sequence comprises, consists of, or consists essentially of a sequence having at least 70%, 75%, 80%, 85%, 90%, or 95% identity with any of the illustrative Chothia or Kabat CDR-H1 sequences provided in this disclosure. In some aspects, the CDR-H1 sequence comprises, consists of, or consists essentially of any of the illustrative Chothia or Kabat CDR-H1 sequences provided in this disclosure, with 1, 2, or 3 amino acid substitutions. In some aspects, the amino acid substitutions are conservative amino acid substitutions.

In some aspects, the CDR-H2 sequence comprises, consists of, or consists essentially of a variant of an illustrative Chothia or Kabat CDR-H2 sequence provided in this disclosure. In some aspects, the CDR-H2 sequence comprises, consists of, or consists essentially of a sequence having at least 70%, 75%, 80%, 85%, 90%, or 95% identity with any of the illustrative Chothia or Kabat CDR-H2 sequences provided in this disclosure. In some aspects, the CDR-H2 sequence comprises, consists of, or consists essentially of any of the illustrative Chothia or Kabat CDR-H2 sequences provided in this disclosure, with 1, 2, or 3 amino acid substitutions. In some aspects, the amino acid substitutions are conservative amino acid substitutions.

In some aspects, the CDR-H3 sequence comprises, consists of, or consists essentially of a variant of an illustrative CDR-H3 sequence provided in this disclosure. In some aspects, the CDR-H3 sequence comprises, consists of, or consists essentially of a sequence having at least 70%, 75%, 80%, 85%, 90%, or 95% identity with any of the illustrative CDR-H3 sequences provided in this disclosure. In some aspects, the CDR-H3 sequence comprises, consists of, or consists essentially of any of the illustrative CDR-H3 sequences provided in this disclosure, with 1, 2, or 3 amino acid substitutions. In some aspects, the amino acid substitutions are conservative amino acid substitutions.

In some aspects, the CDR-L1 sequence comprises, consists of, or consists essentially of a variant of an illustrative CDR-L1 sequence provided in this disclosure. In some aspects, the CDR-L1 sequence comprises, consists of, or consists essentially of a sequence having at least 70%, 75%, 80%, 85%, 90%, or 95% identity with any of the illustrative CDR-L1 sequences provided in this disclosure. In some aspects, the CDR-L1 sequence comprises, consists of, or consists essentially of any of the illustrative CDR-L1 sequences provided in this disclosure, with 1, 2, or 3 amino acid substitutions. In some aspects, the amino acid substitutions are conservative amino acid substitutions.

In some aspects, the CDR-L2 sequence comprises, consists of, or consists essentially of a variant of an illustrative CDR-L2 sequence provided in this disclosure. In some aspects, the CDR-L2 sequence comprises, consists of, or consists essentially of a sequence having at least 70%, 75%, 80%, 85%, 90%, or 95% identity with any of the illustrative CDR-L2 sequences provided in this disclosure. In some aspects, the CDR-L2 sequence comprises, consists of, or consists essentially of any of the illustrative CDR-L2 sequences provided in this disclosure, with 1, 2, or 3 amino acid substitutions. In some aspects, the amino acid substitutions are conservative amino acid substitutions.

In some aspects, the CDR-L3 sequence comprises, consists of, or consists essentially of a variant of an illustrative CDR-L3 sequence provided in this disclosure. In some aspects, the CDR-L3 sequence comprises, consists of, or consists essentially of a sequence having at least 70%, 75%, 80%, 85%, 90%, or 95% identity with any of the illustrative CDR-L3 sequences provided in this disclosure. In some aspects, the CDR-L3 sequence comprises, consists of, or consists essentially of any of the illustrative CDR-L3 sequences provided in this disclosure, with 1, 2, or 3 amino acid substitutions. In some aspects, the amino acid substitutions are conservative amino acid substitutions.

2.8.2. Excluded Six CDR Combinations

In some embodiments, the CDR-H1, CDR-H2, CDR-H3, CDR-L1, CDR-L2, and CDR-L3 provided herein do not comprise certain CDR-H1, CDR-H2, CDR-H3, CDR-L1, CDR-L2, and/or CDR-L3.

In some aspects, the Chothia CDR-H1 sequence is not selected from SEQ ID NOs: 286-290; the Kabat CDR-H1 sequence is not selected from SEQ ID NOs: 291-295; the Chothia CDR-H2 sequence is not selected from SEQ ID NOs: 296-300; the Kabat CDR-H2 sequence is not selected from SEQ ID NOs: 301-305; the CDR-H3 sequence is not selected from 306-310; the CDR-L1 sequence is not selected from SEQ ID NOs: 311-315; the CDR-L2 sequence is not selected from SEQ ID NOs: 316-320; and/or the CDR-L3 sequence is not selected from SEQ ID NOs: 321-325.

2.9. Consensus Sequences

In some embodiments, provided herein are anti-EpCAM antibodies comprising one or more sequences defined by consensus sequences. Each consensus sequence is based, at least in part, on one or more alignments of two or more useful anti-EpCAM CDR sequences provided in this disclosure. Based on such alignments, a person of skill in the art would recognize that different amino acid residues may useful in certain positions of the CDRs. Accordingly, each consensus sequence encompasses two or more useful anti-EpCAM CDR sequences.

In some embodiments, the antibodies comprise one to six of the consensus CDR sequences provided herein. In some embodiments, the antibodies comprise two to six of the consensus CDR sequences provided herein. In some embodiments, the antibodies comprise three to six of the consensus CDR sequences provided herein. In some embodiments, the antibodies comprise four to six of the consensus CDR sequences provided herein. In some embodiments, the antibodies comprise five to six of the consensus CDR sequences provided herein. In some embodiments, the antibodies comprise six of the consensus CDR sequences provided herein. In some embodiments, the antibodies comprise a $V_L$ comprising the CDR-L consensus sequence(s). In some embodiments, the antibodies comprise a $V_H$ comprising the CDR-H consensus sequence(s). In some embodiments, the antibodies comprise a $V_H$ comprising the CDR-H consensus sequence(s) and a $V_L$ comprising the CDR-L consensus sequence(s).

2.9.1. CDR-H3 Consensus Sequences

In some embodiments, the antibody comprises a CDR-H3 sequence defined by the consensus sequence $\alpha_1$-W-$\alpha_3$-$\alpha_4$-Q-$\alpha_6$-$\alpha_7$-Y-$\alpha_9$-$\alpha_{10}$-D-Y, where $\alpha_1$ is G, A, or D; $\alpha_3$ is H or N; $\alpha_4$ is P, D, or R; $\alpha_6$ is T, S, or D; $\alpha_7$ is L, M, or Y; $\alpha_9$ is D, G, H, or N; and $\alpha_{10}$ is L, Q, R, or V.

In some embodiments, the antibody comprises a CDR-H3 sequence defined by the consensus sequence L-R-N-W-$\beta_5$-$\beta_6$-P-M-D-Y, where $\beta_5$ is E or D; and $\beta_6$ is G or M.

2.9.2. Chothia CDR-H1 Consensus Sequences

In some embodiments, the antibody comprises a Chothia CDR-H1 sequence defined by the consensus sequence G-F-T-F-$\gamma_5$-$\gamma_6$-$\gamma_7$, where $\gamma_5$ is S, R, G, or C; $\gamma_6$ is G, V, A, or S; and $\gamma_7$ is S, T, A, C, E, or F.

In some embodiments, the antibody comprises a Chothia CDR-H1 sequence defined by the consensus sequence $\delta_1$-Y-A-F-$\delta_5$-N-$\delta_7$, where $\delta_1$ is G or D; $\delta_5$ is A or T; and $\delta_7$ is R or S.

2.9.3. Chothia CDR-H2 Consensus Sequences

In some embodiments, the antibody comprises a Chothia CDR-H2 sequence defined by the consensus sequence $\varepsilon_1$-G-$\varepsilon_3$-$\varepsilon_4$-G-$\varepsilon_6$, where $\varepsilon_1$ is D, A, or G; $\varepsilon_3$ is G, H, or S; $\varepsilon_4$ is E, D, V, G, or Q; and $\varepsilon_6$ is S, Y, or N.

2.9.4. Kabat CDR-H1 Consensus Sequences

In some embodiments, the antibody comprises a Kabat CDR-H1 sequence defined by the consensus sequence $\zeta_1$-$\zeta_2$-S-M-S, where $\zeta_1$ is G, V, A, or S; and $\zeta_2$ is S, T, A, C, E, or F.

In some embodiments, the antibody comprises a Kabat CDR-H1 sequence defined by the consensus sequence N-$\eta_2$-W-L-G, where $\eta_2$ is R or S.

2.9.5. Kabat CDR-H2 Consensus Sequences

In some embodiments, the antibody comprises a Kabat CDR-H2 sequence defined by the consensus sequence A-I-$\theta_3$-G-$\theta_5$-$\theta_6$-G-$\theta_8$-T-$\theta_{10}$-Y-A-D-S—V—$\theta_{16}$-$\theta_{17}$, where $\theta_3$ is D, A, or G; $\theta_5$ is G, H, or S; $\theta_6$ is E, D, V, G, or Q; $\theta_8$ is S, Y, or N; $\theta_{10}$ is G, A, N, or S; $\theta_{16}$ is K or R; and $\theta_{17}$ is G or D.

2.9.6. CDR-L3 Consensus Sequences

In some embodiments, the antibody comprises a CDR-L3 sequence defined by the consensus sequence Q-Q-$\iota_3$-$\iota_4$-$\iota_5$-$\iota_6$-P-$\iota_8$-T, where $\iota_3$ is L, D, H, N, R, T, V, or Y; $\iota_4$ is V, A, L, Q, S, E, F, M, or W; $\iota_5$ is T, A, P, S, E, F, N, or Y; $\iota_6$ is S, A, I, N, G, K, P, R, or V; and $\iota_8$ is P or A.

In some embodiments, the antibody comprises a CDR-L3 sequence defined by the consensus sequence Q-N-D-$\kappa_4$-$\kappa_5$-Y-P-L-T, where $\kappa_4$ is L, S, or Y; and $\kappa_5$ is S or R.

In some aspects, if $\kappa_4$ is Y, then $\kappa_5$ is not S.

2.9.7. CDR-L2 Consensus Sequences

In some embodiments, the antibody comprises a CDR-L2 sequence defined by the consensus sequence $\lambda_1$-A-S-T-R-E-S, where $\lambda_1$ is W or R.

In some aspects, $\lambda_1$ is not W.

2.9.8. CDR-L1 Consensus Sequences

In some embodiments, the antibody comprises a CDR-L1 sequence defined by the consensus sequence $\mu_1$-A-S-Q-$\mu_5$-$\mu_6$-$\mu_7$-$\mu_8$-$\mu_9$-$\mu_{10}$-$\mu_{11}$-A, where $\mu_1$ is R or S; $\mu_5$ is S, V, G, T, K, N, P, or R; $\mu_6$ is V, L, C, D, G, or I; $\mu_7$ is S, P, A, H, K, or T; $\mu_8$ is S, T, N, or P; $\mu_9$ is S, G, N, R, or T; $\mu_{10}$ is Y, S, V, D, K, or T; and $\mu_{11}$ is L, M, or I.

3. Germline

In some embodiments, the antibody that specifically binds EpCAM is an antibody comprising a variable region that is encoded by a particular germline gene, or a variant thereof. The illustrative antibodies provided herein comprise variable regions that are encoded by the heavy chain variable region germline genes VH3-23 and VH5-51, or variants thereof; and the light chain variable region germline genes Vκ3-20 and Vκ4-1, or variants thereof.

One of skill in the art would recognize that the CDR sequences provided herein may also be useful when combined with variable regions encoded by other variable region germline genes, or variants thereof. In particular, the CDR sequences provided herein may be useful when combined with variable regions encoded by variable region germline genes, or variants thereof, that are structurally similar to the variable region germline genes recited above. For example, in some embodiments, a CDR-H sequence provided herein may be combined with a variable region encoded by a variable region germline gene selected from the $V_H3$ or $V_H5$ families, or a variant thereof. In some embodiments, a CDR-L sequence provided herein may be combined with a variable region encoded by a variable region germline gene selected from the Vκ3 or Vκ4 families, or a variant thereof.

4. Affinity

In some embodiments, the affinity of the antibody for EpCAM as indicated by $K_D$, is less than about $10^{-5}$ M, less than about $10^{-6}$ M, less than about $10^{-7}$ M, less than about $10^{-8}$ M, less than about $10^{-9}$ M, less than about $10^{-10}$ M, less than about $10^{-11}$ M, or less than about $10^{-12}$ M. In some embodiments, the affinity of the antibody is between about $10^{-7}$ M and $10^{-11}$ M. In some embodiments, the affinity of the antibody is between about $10^{-7}$ M and $10^{-10}$ M. In some embodiments, the affinity of the antibody is between about $10^{-7}$ M and $10^{-9}$ M. In some embodiments, the affinity of the antibody is between about $10^{-7}$ M and $10^{-8}$ M. In some embodiments, the affinity of the antibody is between about $10^{-8}$ M and $10^{-11}$ M. In some embodiments, the affinity of the antibody is between about $10^{-8}$ M and $10^{-10}$ M. In some embodiments, the affinity of the antibody is between about $10^{-9}$ M and $10^{-11}$ M. In some embodiments, the affinity of the antibody is between about $10^{-10}$ M and $10^{-11}$ M.

In some embodiments, the affinity of the antibody for human EpCAM, as determined by surface plasmon resonance at 25° C., and as indicated by $K_D$, is between about $7.21\times10^{-9}$ M and about $1.93\times10^{-10}$ M. In some embodiments, the affinity of the antibody for human EpCAM is about $7.21\times10^{-9}$ M, about $6.91\times10^{-9}$ M, about $6.70\times10^{-9}$ M, about $6.17\times10^{-9}$ M, about $5.46\times10^{-9}$ M, about $5.24\times10^{-9}$ M, about $4.17\times10^{-9}$ M, about $3.99\times10^{-9}$ M, about $3.93\times10^{-9}$ M, about $3.56\times10^{-9}$ M, about $3.50\times10^{-9}$ M, about $3.44\times10^{-9}$ M, about $3.43\times10^{-9}$ M, about $2.75\times10^{-9}$ M, about $2.54\times10^{-9}$ M, about $1.78\times10^{-9}$ M, about $1.49\times10^{-9}$ M, about $1.45\times10^{-9}$ M, about $1.41\times10^{-9}$ M, about $1.19\times10^{-9}$ M, about $9.83\times10^{-10}$ M, about $9.04\times10^{-10}$ M, or about $1.93\times10^{-10}$ M.

In some embodiments, the affinity of the antibody for human EpCAM expressed on the surface of a cell, as indicated by $K_D$, is between about 3.68 and about 1.08 nM. In some embodiments the affinity of the antibody for human EpCAM expressed on the surface of a cell is about 3.68 nM, about 3.24 nM, about 3 nM, about 2.6 nM, about 2.59 nM, about 2.49 nM, about 2.47 nM, about 2 nM, about 1.96 nM, about 1.91 nM, about 1.89 nM, about 1.85 nM, about 1.79 nM, about 1.71 nM, about 1.69 nM, about 1.6 nM, about 1.54 nM, about 1.5 nM, about 1.45 nM, about 1.2 nM, about 1.17 nM, about 1.14 nM, or about 1.08 nM. In some embodiments, the cell is a CHO cell.

In some embodiments, the affinity of the antibody for human EpCAM expressed on the surface of a cell, as indicated by $K_D$, is between about 6.9 and about 3.6 nM. In some embodiments, the affinity of the antibody for human EpCAM expressed on the surface of a cell is about 6.9 nM, about 6.7 nM, or about 3.6 nM. In some embodiments, the cell is an HCT 116 cell (ATCC No. CCL-247).

In some embodiments, the affinity of the antibody for human EpCAM expressed on the surface of a cell, as indicated by $K_D$, is between about 7.6 and about 2.7 nM. In some embodiments, the affinity of the antibody for human EpCAM expressed on the surface of a cell is about 7.6 nM, about 5.2 nM, or about 2.7 nM. In some embodiments, the cell is a JIMT-1 cell (DSMZ No. ACC 589).

In some embodiments, the affinity of the antibody for cynomolgus EpCAM, as determined by surface plasmon resonance at 25° C., and as indicated by $K_D$, is between about $1.62\times10^{-7}$ M and about $1.17\times10^{-9}$ M. In some embodiments, the affinity of the antibody for cynomolgus EpCAM is about $1.62\times10^{-7}$ M, about $1.20\times10^{-7}$ M, about $4.52\times10^{-8}$ M, about $3.99\times10^{-8}$ M, about $3.52\times10^{-8}$ M, about $2.97\times10^{-8}$ M, about $2.91\times10^{-8}$ M, about $2.29\times10^{-8}$ M, about $1.82\times10^{-8}$ M, about $1.52\times10^{-8}$ M, about $8.59\times10^{-9}$ M, about $8.10\times10^{-9}$ M, about $7.52\times10^{-9}$ M, about $7.22\times10^{-9}$ M, about $4.41\times10^{-9}$ M, or about $1.17\times10^{-9}$ M.

In some embodiments, the antibody is characterized by a ratio of affinity for human EpCAM to affinity for cynomolgus EpCAM, each as determined by surface plasmon resonance at 25° C., and as indicated by $K_D$. In some embodiments, the ratio is from about 0.029 to about 6.162. In some embodiments, the ratio is about 0.029, about 0.034, about 0.043, about 0.051, about 0.076, about 0.098, about 0.105, about 0.155, about 0.184, about 0.352, about 0.366, about 0.441, about 0.610, about 0.762, about 0.794, or about 6.162.

In some embodiments, the affinity of the antibody for cynomolgus EpCAM expressed on the surface of a cell, as indicated by $K_D$, is between about 2.99 and about 0.66 nM. In some embodiments, the affinity of the antibody for cynomolgus EpCAM expressed on the surface of a cell is about 2.99 nM, about 2.5 nM, about 1.83 nM, about 1.79 nM, about 1.62 nM, about 1.59 nM, about 1.38 nM, about 1.35 nM, about 1.21 nM, about 1.2 nM, about 1.07 nM, about 0.99 nM, about 0.9 nM, about 0.87 nM, about 0.7 nM, or about 0.66 nM. In some embodiments, the cell is a CHO cell.

In some embodiments the antibody has a $k_a$ of at least about $10^4$ M$^{-1}\times$sec$^{-1}$. In some embodiments the antibody has a $k_a$ of at least about $10^5$ M$^{-1}\times$sec$^{-1}$. In some embodiments the antibody has a $k_a$ of at least about $10^6$ M$^{-1}\times$sec$^{-1}$. In some embodiments the antibody has a $k_a$ of between about $10^4$ M$^{-1}\times$sec$^{-1}$ and about $10^5$ M$^{-1}\times$sec$^{-1}$. In some embodiments the antibody has a $k_a$ of between about $10^5$ M$^{-1}\times$sec$^{-1}$ and about $10^6$ M$^{-1}\times$sec$^{-1}$.

In some embodiments the antibody has a $k_a$ when associating with human EpCAM, as determined by surface plasmon resonance at 25° C., of between about $6.52\times10^4$ M$^{-1}\times$sec$^{-1}$ and about $3.51\times10^5$ M$^{-1}\times$sec$^{-1}$. In some embodiments the antibody has a $k_a$ when associating with human EpCAM of about $6.52\times10^4$ M$^{-1}\times$sec$^{-1}$, about $9.03\times10^4$ M$^{-1}\times$sec$^{-1}$, about $1.03\times10^5$ M$^{-1}\times$sec$^{-1}$, about $1.40\times10^5$ $M^{-1} \times sec^{-1}$, about $1.43 \times 10^5$ $M^{-1} \times sec^{-1}$, about $1.49 \times 10^5$ $M^{-1} \times sec^{-1}$, about $1.66 \times 10^5$ $M^{-1} \times sec^{-1}$, about $1.70 \times 10^5$ $M^{-1} \times sec^{-1}$, about $1.76 \times 10^5$ $M^{-1} \times sec^{-1}$, about $1.82 \times 10^5$ $M^{-1} \times sec^{-1}$, about $1.92 \times 10^5$ $M^{-1} \times sec^{-1}$, about $2.00 \times 10^5$ $M^{-1} \times sec^{-1}$, about $2.05 \times 10^5$ $M^{-1} \times sec^{-1}$, about $2.10 \times 10^5$ $M^{-1} \times sec^{-1}$, about $2.20 \times 10^5$ $M^{-1} \times sec^{-1}$, about $2.35 \times 10^5$ $M^{-1} \times sec^{-1}$, about $2.54 \times 10^5$ $M^{-1} \times sec^{-1}$, about $2.56 \times 10^5$ $M^{-1} \times sec^{-1}$, about $2.57 \times 10^5$ $M^{-1} \times sec^{-1}$, about $2.84 \times 10^5$ $M^{-1} \times sec^{-1}$, about $2.88 \times 10^5$ $M^{-1} \times sec^{-1}$, about $3.10 \times 10^5$ $M^{-1} \times sec^{-1}$, or about $3.51 \times 10^5$ $M^{-1} \times sec^{-1}$.

In some embodiments the antibody has a $k_d$ of about $10^{-5}$ $sec^{-1}$ or less. In some embodiments the antibody has a $k_d$ of about $10^{-4}$ $sec^{-1}$ or less. In some embodiments the antibody has a $k_d$ of about $10^{-3}$ $sec^{-1}$ or less. In some embodiments the antibody has a $k_d$ of between about $10^{-2}$ $sec^{-1}$ and about $10^{-5}$ $sec^{-1}$. In some embodiments the antibody has a $k_d$ of between about $10^{-2}$ $sec^{-1}$ and about $10^{-4}$ $sec^{-1}$. In some embodiments the antibody has a $k_d$ of between about $10^{-3}$ $sec^{-1}$ and about $10^{-5}$ $sec^{-1}$.

In some embodiments the antibody has a $k_d$ when dissociating from human EpCAM, as determined by surface plasmon resonance at 25° C., of between about $1.75 \times 10^{-3}$ $sec^{-1}$ and about $1.74 \times 10^{-5}$ $sec^{-1}$. In some embodiments the antibody has a $k_d$ when dissociating from human EpCAM of about $1.75 \times 10^{-3}$ $sec^{-1}$, about $1.69 \times 10^{-3}$ $sec^{-1}$, about $1.58 \times 10^{-3}$ $sec^{-1}$, about $1.23 \times 10^{-3}$ $sec^{-1}$, about $1.00 \times 10^{-3}$ $sec^{-1}$, about $9.39 \times 10^{-4}$ $sec^{-1}$, about $9.08 \times 10^{-4}$ $sec^{-1}$, about $7.90 \times 10^{-4}$ $sec^{-1}$, about $7.87 \times 10^{-4}$ $sec^{-1}$, about $7.84 \times 10^{-4}$ $sec^{-1}$, about $6.04 \times 10^{-4}$ $sec^{-1}$, about $5.98 \times 10^{-4}$ $sec^{-1}$, about $5.10 \times 10^{-4}$ $sec^{-1}$, about $4.12 \times 10^{-4}$ $sec^{-1}$, about $3.75 \times 10^{-4}$ $sec^{-1}$, about $3.06 \times 10^{-4}$ $sec^{-1}$, about $2.97 \times 10^{-4}$ $sec^{-1}$, about $2.57 \times 10^{-4}$ $sec^{-1}$, about $2.57 \times 10^{-4}$ $sec^{-1}$, about $2.56 \times 10^{-4}$ $sec^{-1}$, about $2.54 \times 10^{-4}$ $sec^{-1}$, about $1.97 \times 10^{-4}$ $sec^{-1}$, or about $1.74 \times 10^{-5}$ $sec^{-1}$.

In some aspects, the $K_D$, $k_a$, and $k_d$ are determined at 25° C. In some embodiments, the $K_D$, $k_a$, and $k_d$ are determined by surface plasmon resonance. In some embodiments, the $K_D$, $k_a$, and $k_d$ are determined according to the methods described in the Examples provided herein.

5. Epitope Bins

In some embodiments, the antibody binds the same epitope as the scFv antibody provided in SEQ ID NO: 336. In some embodiments, the antibody binds to a different epitope from the scFv antibody provided in SEQ ID NO: 336. In some embodiments, the antibody binds to part of the epitope bound by the scFv antibody provided in SEQ ID NO: 336.

In some embodiments, the antibody binds to the same epitope as the scFv-Fc antibody provided in SEQ ID NO: 210, which binds to an epitope encoded by exons 4-7 of the EpCAM gene.

6. Glycosylation Variants

In certain embodiments, an antibody may be altered to increase, decrease or eliminate the extent to which it is glycosylated. Glycosylation of polypeptides is typically either "N-linked" or "O-linked."

"N-linked" glycosylation refers to the attachment of a carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site.

"O-linked" glycosylation refers to the attachment of one of the sugars N-acetylgalactosamine, galactose, or xylose to a hydroxyamino acid, most commonly serine or threonine, although 5-hydroxyproline or 5-hydroxylysine may also be used.

Addition or deletion of N-linked glycosylation sites to the antibody may be accomplished by altering the amino acid sequence such that one or more of the above-described tripeptide sequences is created or removed. Addition or deletion of O-linked glycosylation sites may be accomplished by addition, deletion, or substitution of one or more serine or threonine residues in or to (as the case may be) the sequence of an antibody.

7. Fc Variants

In certain embodiments, amino acid modifications may be introduced into the Fc region of an antibody provided herein to generate an Fc region variant. In certain embodiments, the Fc region variant possesses some, but not all, effector functions. Such antibodies may be useful, for example, in applications in which the half-life of the antibody in vivo is important, yet certain effector functions are unnecessary or deleterious. Examples of effector functions include complement-dependent cytotoxicity (CDC) and antibody-directed complement-mediated cytotoxicity (ADCC). Numerous substitutions or substitutions or deletions with altered effector function are known in the art.

An alteration in in CDC and/or ADCC activity can be confirmed using in vitro and/or in vivo assays. For example, Fc receptor (FcR) binding assays can be conducted to measure FcγR binding. The primary cells for mediating ADCC, NK cells, express FcγRIII only, whereas monocytes express FcγRI, FcγRII and FcγRIII. FcR expression on hematopoietic cells is summarized in Ravetch and Kinet, *Ann. Rev. Immunol.*, 1991, 9:457-492, incorporated by reference in its entirety.

Non-limiting examples of in vitro assays to assess ADCC activity of a molecule of interest are provided in U.S. Pat. Nos. 5,500,362 and 5,821,337; Hellstrom et al., *Proc. Natl. Acad. Sci. USA.*, 1986, 83:7059-7063; Hellstrom et al., *Proc. Natl. Acad. Sci. U.S.A.*, 1985, 82:1499-1502; and Bruggemann et al., *J. Exp. Med.*, 1987, 166:1351-1361; each of which is incorporated by reference in its entirety. Useful effector cells for such assays include peripheral blood mononuclear cells (PBMC) and Natural Killer (NK) cells. Alternatively, or additionally, ADCC activity of the molecule of interest may be assessed in vivo, using an animal model such as that disclosed in Clynes et al. *Proc. Natl. Acad. Sci. U.S.A.*, 1998, 95:652-656, incorporated by reference in its entirety.

C1q binding assays may also be carried out to confirm that the antibody is unable to bind C1q and hence lacks CDC activity. Examples of C1q binding assays include those described in WO 2006/029879 and WO 2005/100402, each of which is incorporated by reference in its entirety.

Complement activation assays include those described, for example, in Gazzano-Santoro et al., *J. Immunol. Methods*, 1996, 202:163-171; Cragg et al., *Blood*, 2003, 101: 1045-1052; and Cragg and Glennie, *Blood*, 2004, 103:2738-2743; each of which is incorporated by reference in its entirety.

FcRn binding and in vivo clearance (half-life determination) can also be measured, for example, using the methods described in Petkova et al., *Intl. Immunol.*, 2006, 18:1759-1769, incorporated by reference in its entirety.

8. Preparation of Antibodies

8.1. Antigen Preparation

The EpCAM antigen to be used for isolation of the antibodies may be intact EpCAM or a fragment of EpCAM. The intact EpCAM, or fragment of EpCAM, may be in the form of an isolated protein or protein expressed by a cell. Other forms of EpCAM useful for generating antibodies will be apparent to those skilled in the art.

8.2. Monoclonal Antibodies

Monoclonal antibodies may be obtained, for example, using the hybridoma method first described by Kohler et al., *Nature*, 1975, 256:495-497 (incorporated by reference in its entirety), and/or by recombinant DNA methods (see e.g., U.S. Pat. No. 4,816,567, incorporated by reference in its entirety). Monoclonal antibodies may also be obtained, for example, using phage or yeast-based libraries. See e.g., U.S. Pat. Nos. 8,258,082 and 8,691,730, each of which is incorporated by reference in its entirety.

In the hybridoma method, a mouse or other appropriate host animal is immunized to elicit lymphocytes that produce or are capable of producing antibodies that will specifically bind to the protein used for immunization. Alternatively, lymphocytes may be immunized in vitro. Lymphocytes are then fused with myeloma cells using a suitable fusing agent, such as polyethylene glycol, to form a hybridoma cell. See Goding J. W., *Monoclonal Antibodies: Principles and Practice* 3$^{rd}$ ed. (1986) Academic Press, San Diego, Calif., incorporated by reference in its entirety.

The hybridoma cells are seeded and grown in a suitable culture medium that contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

Useful myeloma cells are those that fuse efficiently, support stable high-level production of antibody by the selected antibody-producing cells, and are sensitive media conditions, such as the presence or absence of HAT medium. Among these, preferred myeloma cell lines are murine myeloma lines, such as those derived from MOP-21 and MC-11 mouse tumors (available from the Salk Institute Cell Distribution Center, San Diego, Calif.), and SP-2 or X63-Ag8-653 cells (available from the American Type Culture Collection, Rockville, Md.). Human myeloma and mouse-human heteromyeloma cell lines also have been described for the production of human monoclonal antibodies. See e.g., Kozbor, *J. Immunol.*, 1984, 133:3001, incorporated by reference in its entirety.

After the identification of hybridoma cells that produce antibodies of the desired specificity, affinity, and/or biological activity, selected clones may be subcloned by limiting dilution procedures and grown by standard methods. See Goding, supra. Suitable culture media for this purpose include, for example, D-MEM or RPMI-1640 medium. In addition, the hybridoma cells may be grown in vivo as ascites tumors in an animal.

DNA encoding the monoclonal antibodies may be readily isolated and sequenced using conventional procedures (e.g., by using oligonucleotide probes that are capable of binding specifically to genes encoding the heavy and light chains of the monoclonal antibodies). Thus, the hybridoma cells can serve as a useful source of DNA encoding antibodies with the desired properties. Once isolated, the DNA may be placed into expression vectors, which are then transfected into host cells such as bacteria (e.g., *E. coli*), yeast (e.g., *Saccharomyces* or *Pichia* sp.), COS cells, Chinese hamster ovary (CHO) cells, or myeloma cells that do not otherwise produce antibody, to produce the monoclonal antibodies.

8.3. Humanized Antibodies

Humanized antibodies may be generated by replacing most, or all, of the structural portions of a non-human monoclonal antibody with corresponding human antibody sequences. Consequently, a hybrid molecule is generated in which only the antigen-specific variable, or CDR, is composed of non-human sequence. Methods to obtain humanized antibodies include those described in, for example, Winter and Milstein, *Nature*, 1991, 349:293-299; Rader et al., *Proc. Nat. Acad. Sci. USA.*, 1998, 95:8910-8915; Steinberger et al., *J. Biol. Chem.*, 2000, 275:36073-36078; Queen et al., *Proc. Natl. Acad. Sci. U.S.A.*, 1989, 86:10029-10033; and U.S. Pat. Nos. 5,585,089, 5,693,761, 5,693,762, and 6,180,370; each of which is incorporated by reference in its entirety.

8.4. Human Antibodies

Human antibodies can be generated by a variety of techniques known in the art, for example by using transgenic animals (e.g., humanized mice). See, e.g., Jakobovits et al., *Proc. Natl. Acad. Sci. U.S.A.*, 1993, 90:2551; Jakobovits et al., *Nature*, 1993, 362:255-258; Bruggermann et al., *Year in Immuno.*, 1993, 7:33; and U.S. Pat. Nos. 5,591,669, 5,589,369 and 5,545,807; each of which is incorporated by reference in its entirety. Human antibodies can also be derived from phage-display libraries (see e.g., Hoogenboom et al., *J. Mol. Biol.*, 1991, 227:381-388; Marks et al., *J. Mol. Biol.*, 1991, 222:581-597; and U.S. Pat. Nos. 5,565,332 and 5,573,905; each of which is incorporated by reference in its entirety). Human antibodies may also be generated by in vitro activated B cells (see e.g., U.S. Pat. Nos. 5,567,610 and 5,229,275, each of which is incorporated by reference in its entirety). Human antibodies may also be derived from yeast-based libraries (see e.g., U.S. Pat. No. 8,691,730, incorporated by reference in its entirety).

9. Vectors, Host Cells, and Recombinant Methods

The invention also provides isolated nucleic acids encoding anti-EpCAM antibodies, vectors and host cells comprising the nucleic acids, and recombinant techniques for the production of the antibodies.

For recombinant production of the antibody, the nucleic acid(s) encoding it may be isolated and inserted into a replicable vector for further cloning (i.e., amplification of the DNA) or expression. In some aspects, the nucleic acid may be produced by homologous recombination, for example as described in U.S. Pat. No. 5,204,244, incorporated by reference in its entirety.

Many different vectors are known in the art. The vector components generally include, but are not limited to, one or more of the following: a signal sequence, an origin of replication, one or more marker genes, an enhancer element, a promoter, and a transcription termination sequence, for example as described in U.S. Pat. No. 5,534,615, incorporated by reference in its entirety.

Illustrative examples of suitable host cells are provided below. these host cells are not meant to be limiting.

Suitable host cells include any prokaryotic (e.g., bacterial), lower eukaryotic (e.g., yeast), or higher eukaryotic (e.g., mammalian) cells. Suitable prokaryotes include eubacteria, such as Gram-negative or Gram-positive organisms, for example, Enterobacteriaceae such as *Escherichia* (*E. coli*), *Enterobacter, Erwinia, Klebsiella, Proteus, Salmonella* (*S. typhimurium*), *Serratia* (*S. marcescans*), *Shigella*, Bacilli (*B. subtilis* and *B. licheniformis*), *Pseudomonas* (*P. aeruginosa*), and *Streptomyces*. One useful *E. coli* cloning host is *E. coli* 294, although other strains such as *E. coli* B, *E. coli* X1776, and *E. coli* W3110 are suitable.

In addition to prokaryotes, eukaryotic microbes such as filamentous fungi or yeast are also suitable cloning or expression hosts for anti-EpCAM antibody-encoding vectors. *Saccharomyces cerevisiae*, or common baker's yeast, is a commonly used lower eukaryotic host microorganism. However, a number of other genera, species, and strains are available and useful, such as *Schizosaccharomyces pombe*, *Kluyveromyces* (*K. lactis, K. fragilis, K. bulgaricus K. wickeramii, K. waltii, K. drosophilarum, K. thermotolerans*, and *K. marxianus*), *Yarrowia, Pichia pastoris, Candida* (*C. albicans*), *Trichoderma reesia, Neurospora crassa, Schwanniomyces* (*S. occidentalis*), and filamentous fungi such as, for example *Penicillium, Tolypocladium*, and *Aspergillus* (*A. nidulans* and *A. niger*).

Useful mammalian host cells include COS-7 cells, HEK293 cells; baby hamster kidney (BHK) cells; Chinese hamster ovary (CHO); mouse sertoli cells; African green monkey kidney cells (VERO-76), and the like.

The host cells used to produce the anti-EpCAM antibody of this invention may be cultured in a variety of media. Commercially available media such as, for example, Ham's F10, Minimal Essential Medium (MEM), RPMI-1640, and Dulbecco's Modified Eagle's Medium (DMEM) are suitable for culturing the host cells. In addition, any of the media described in Ham et al., *Meth. Enz.*, 1979, 58:44; Barnes et al., *Anal. Biochem.*, 1980, 102:255; and U.S. Pat. Nos. 4,767,704, 4,657,866, 4,927,762, 4,560,655, and 5,122,469, or WO 90/03430 and WO 87/00195 may be used. Each of the foregoing references is incorporated by reference in its entirety.

Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics, trace elements (defined as inorganic compounds usually present at final concentrations in the micromolar range), and glucose or an equivalent energy source. Any other necessary supplements may also be included at appropriate concentrations that would be known to those skilled in the art.

The culture conditions, such as temperature, pH, and the like, are those previously used with the host cell selected for expression, and will be apparent to the ordinarily skilled artisan.

When using recombinant techniques, the antibody can be produced intracellularly, in the periplasmic space, or directly secreted into the medium. If the antibody is produced intracellularly, as a first step, the particulate debris, either host cells or lysed fragments, is removed, for example, by centrifugation or ultrafiltration. For example, Carter et al. (*Bio/Technology*, 1992, 10:163-167) describes a procedure for isolating antibodies which are secreted to the periplasmic space of *E. coli*. Briefly, cell paste is thawed in the presence of sodium acetate (pH 3.5), EDTA, and phenylmethylsulfonylfluoride (PMSF) over about 30 min. Cell debris can be removed by centrifugation.

In some embodiments, the antibody is produced in a cell-free system. In some aspects, the cell-free system is an in vitro transcription and translation system as described in Yin et al., *mAbs*, 2012, 4:217-225, incorporated by reference in its entirety. In some aspects, the cell-free system utilizes a cell-free extract from a eukaryotic cell or from a prokaryotic cell. In some aspects, the prokaryotic cell is *E. coli*. Cell-free expression of the antibody may be useful, for example, where the antibody accumulates in a cell as an insoluble aggregate, or where yields from periplasmic expression are low.

Where the antibody is secreted into the medium, supernatants from such expression systems are generally first concentrated using a commercially available protein concentration filter, for example, an Amicon® or Millipore® Pellcon® ultrafiltration unit. A protease inhibitor such as PMSF may be included in any of the foregoing steps to inhibit proteolysis and antibiotics may be included to prevent the growth of adventitious contaminants.

The antibody composition prepared from the cells can be purified using, for example, hydroxylapatite chromatography, gel electrophoresis, dialysis, and affinity chromatography, with affinity chromatography being a particularly useful purification technique. The suitability of protein A as an affinity ligand depends on the species and isotype of any immunoglobulin Fc domain that is present in the antibody. Protein A can be used to purify antibodies that are based on human γ1, γ2, or γ4 heavy chains (Lindmark et al., *J. Immunol. Meth.*, 1983, 62:1-13, incorporated by reference in its entirety). Protein G is useful for all mouse isotypes and for human γ3 (Guss et al., *EMBO J.*, 1986, 5:1567-1575, incorporated by reference in its entirety).

The matrix to which the affinity ligand is attached is most often agarose, but other matrices are available. Mechanically stable matrices such as controlled pore glass or poly(styrenedivinyl)benzene allow for faster flow rates and shorter processing times than can be achieved with agarose. Where the antibody comprises a $C_{H3}$ domain, the BakerBond ABX® resin is useful for purification.

Other techniques for protein purification, such as fractionation on an ion-exchange column, ethanol precipitation, Reverse Phase HPLC, chromatography on silica, chromatography on heparin Sepharose®, chromatofocusing, SDS-PAGE, and ammonium sulfate precipitation are also available, and can be applied by one of skill in the art.

Following any preliminary purification step(s), the mixture comprising the antibody of interest and contaminants may be subjected to low pH hydrophobic interaction chromatography using an elution buffer at a pH between about 2.5 to about 4.5, generally performed at low salt concentrations (e.g., from about 0 to about 0.25 M salt).

10. Pharmaceutical Compositions and Methods of Administration

Any of the antibodies provided herein can be provided in any appropriate pharmaceutical composition and be administered by any suitable route of administration. Suitable routes of administration include, but are not limited to, the inhalation, intraarterial, intradermal, intramuscular, intraperitoneal, intravenous, nasal, parenteral, pulmonary, and subcutaneous routes.

The pharmaceutical composition may comprise one or more pharmaceutical excipients. Any suitable pharmaceutical excipient may be used, and one of ordinary skill in the art is capable of selecting suitable pharmaceutical excipients. Accordingly, the pharmaceutical excipients provided below are intended to be illustrative, and not limiting. Additional pharmaceutical excipients include, for example, those described in the *Handbook of Pharmaceutical Excipients*, Rowe et al. (Eds.) 6th Ed. (2009), incorporated by reference in its entirety.

In some embodiments, the pharmaceutical composition comprises an anti-foaming agent. Any suitable anti-foaming agent may be used. In some aspects, the anti-foaming agent is selected from an alcohol, an ether, an oil, a wax, a silicone, a surfactant, and combinations thereof. In some aspects, the anti-foaming agent is selected from a mineral oil, a vegetable oil, ethylene bis stearamide, a paraffin wax, an ester wax, a fatty alcohol wax, a long chain fatty alcohol, a fatty acid soap, a fatty acid ester, a silicon glycol, a fluorosilicone, a polyethylene glycol-polypropylene glycol copolymer, polydimethylsiloxane-silicon dioxide, ether, octyl alcohol, capryl alcohol, sorbitan trioleate, ethyl alcohol, 2-ethylhexanol, dimethicone, oleyl alcohol, simethicone, and combinations thereof.

In some embodiments, the pharmaceutical composition comprises a cosolvent. Illustrative examples of cosolvents include ethanol, poly(ethylene) glycol, butylene glycol, dimethylacetamide, glycerin, and propylene glycol.

In some embodiments, the pharmaceutical composition comprises a buffer. Illustrative examples of buffers include acetate, borate, carbonate, lactate, malate, phosphate, citrate, hydroxide, diethanolamine, monoethanolamine, glycine, methionine, guar gum, and monosodium glutamate.

In some embodiments, the pharmaceutical composition comprises a carrier or filler. Illustrative examples of carriers or fillers include lactose, maltodextrin, mannitol, sorbitol, chitosan, stearic acid, xanthan gum, and guar gum.

In some embodiments, the pharmaceutical composition comprises a surfactant. Illustrative examples of surfactants include d-alpha tocopherol, benzalkonium chloride, benzethonium chloride, cetrimide, cetylpyridinium chloride, docusate sodium, glyceryl behenate, glyceryl monooleate, lauric acid, macrogol 15 hydroxystearate, myristyl alcohol, phospholipids, polyoxyethylene alkyl ethers, polyoxyethylene sorbitan fatty acid esters, polyoxyethylene stearates, polyoxylglycerides, sodium lauryl sulfate, sorbitan esters, and vitamin E polyethylene(glycol) succinate.

In some embodiments, the pharmaceutical composition comprises an anti-caking agent. Illustrative examples of anti-caking agents include calcium phosphate (tribasic), hydroxymethyl cellulose, hydroxypropyl cellulose, and magnesium oxide.

Other excipients that may be used with the pharmaceutical compositions include, for example, albumin, antioxidants, antibacterial agents, antifungal agents, bioabsorbable polymers, chelating agents, controlled release agents, diluents, dispersing agents, dissolution enhancers, emulsifying agents, gelling agents, ointment bases, penetration enhancers, preservatives, solubilizing agents, solvents, stabilizing agents, and sugars. Specific examples of each of these agents are described, for example, in the *Handbook of Pharmaceutical Excipients*, Rowe et al. (Eds.) 6th Ed. (2009), The Pharmaceutical Press, incorporated by reference in its entirety.

In some embodiments, the pharmaceutical composition comprises a solvent. In some aspects, the solvent is saline solution, such as a sterile isotonic saline solution or dextrose solution. In some aspects, the solvent is water for injection.

In some embodiments, the pharmaceutical compositions are in a particulate form, such as a microparticle or a nanoparticle. Microparticles and nanoparticles may be formed from any suitable material, such as a polymer or a lipid. In some aspects, the microparticles or nanoparticles are micelles, liposomes, or polymersomes.

Further provided herein are anhydrous pharmaceutical compositions and dosage forms comprising an antibody, since water can facilitate the degradation of some antibodies.

Anhydrous pharmaceutical compositions and dosage forms provided herein can be prepared using anhydrous or low moisture containing ingredients and low moisture or low humidity conditions. Pharmaceutical compositions and dosage forms that comprise lactose and at least one active ingredient that comprises a primary or secondary amine can be anhydrous if substantial contact with moisture and/or humidity during manufacturing, packaging, and/or storage is expected.

An anhydrous pharmaceutical composition should be prepared and stored such that its anhydrous nature is maintained. Accordingly, anhydrous compositions can be packaged using materials known to prevent exposure to water such that they can be included in suitable formulary kits. Examples of suitable packaging include, but are not limited to, hermetically sealed foils, plastics, unit dose containers (e.g., vials), blister packs, and strip packs.

10.1. Parenteral Dosage Forms

In certain embodiments, provided are parenteral dosage forms. Parenteral dosage forms can be administered to subjects by various routes including, but not limited to, subcutaneous, intravenous (including bolus injection), intramuscular, and intraarterial. Because their administration typically bypasses subjects' natural defenses against contaminants, parenteral dosage forms are typically, sterile or capable of being sterilized prior to administration to a subject. Examples of parenteral dosage forms include, but are not limited to, solutions ready for injection, dry products ready to be dissolved or suspended in a pharmaceutically acceptable vehicle for injection, suspensions ready for injection, and emulsions.

Suitable vehicles that can be used to provide parenteral dosage forms are well known to those skilled in the art. Examples include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate.

Excipients that increase the solubility of one or more of the antibodies disclosed herein can also be incorporated into the parenteral dosage forms.

10.2. Dosage and Unit Dosage Forms

In human therapeutics, the doctor will determine the posology which he considers most appropriate according to a preventive or curative treatment and according to the age, weight, condition and other factors specific to the subject to be treated.

In certain embodiments, a composition provided herein is a pharmaceutical composition or a single unit dosage form. Pharmaceutical compositions and single unit dosage forms provided herein comprise a prophylactically or therapeutically effective amount of one or more prophylactic or therapeutic antibodies.

The amount of the antibody or composition which will be effective in the prevention or treatment of a disorder or one or more symptoms thereof will vary with the nature and severity of the disease or condition, and the route by which the antibody is administered. The frequency and dosage will also vary according to factors specific for each subject depending on the specific therapy (e.g., therapeutic or prophylactic agents) administered, the severity of the disorder, disease, or condition, the route of administration, as well as age, body, weight, response, and the past medical history of the subject. Effective doses may be extrapolated from dose-response curves derived from in vitro or animal model test systems.

In certain embodiments, exemplary doses of a composition include milligram or microgram amounts of the antibody per kilogram of subject or sample weight (e.g., about 10 micrograms per kilogram to about 50 milligrams per kilogram, about 100 micrograms per kilogram to about 25 milligrams per kilogram, or about 100 microgram per kilogram to about 10 milligrams per kilogram). In certain embodiment, the dosage of the antibody provided herein, based on weight of the antibody, administered to prevent, treat, manage, or ameliorate a disorder, or one or more symptoms thereof in a subject is 0.1 mg/kg, 1 mg/kg, 2 mg/kg, 3 mg/kg, 4 mg/kg, 5 mg/kg, 6 mg/kg, 10 mg/kg, or 15 mg/kg or more of a subject's body weight. In another embodiment, the dosage of the composition or a composition provided herein administered to prevent, treat, manage, or ameliorate a disorder, or one or more symptoms thereof in a subject is 0.1 mg to 200 mg, 0.1 mg to 100 mg, 0.1 mg to 50 mg, 0.1 mg to 25 mg, 0.1 mg to 20 mg, 0.1 mg to 15 mg, 0.1 mg to 10 mg, 0.1 mg to 7.5 mg, 0.1 mg to 5 mg, 0.1 to 2.5 mg, 0.25 mg to 20 mg, 0.25 to 15 mg, 0.25 to 12 mg, 0.25 to 10 mg, 0.25 mg to 7.5 mg, 0.25 mg to 5 mg, 0.25 mg to 2.5 mg, 0.5 mg to 20 mg, 0.5 to 15 mg, 0.5 to 12 mg, 0.5 to 10 mg, 0.5 mg to 7.5 mg, 0.5 mg to 5 mg, 0.5 mg to 2.5 mg, 1 mg to 20 mg, 1 mg to 15 mg, 1 mg to 12 mg, 1 mg to 10 mg, 1 mg to 7.5 mg, 1 mg to 5 mg, or 1 mg to 2.5 mg.

The dose can be administered according to a suitable schedule, for example, once, two times, three times, or for times weekly. It may be necessary to use dosages of the antibody outside the ranges disclosed herein in some cases, as will be apparent to those of ordinary skill in the art. Furthermore, it is noted that the clinician or treating physician will know how and when to interrupt, adjust, or terminate therapy in conjunction with subject response.

Different therapeutically effective amounts may be applicable for different diseases and conditions, as will be readily known by those of ordinary skill in the art. Similarly, amounts sufficient to prevent, manage, treat or ameliorate such disorders, but insufficient to cause, or sufficient to reduce, adverse effects associated with the antibodies provided herein are also encompassed by the herein described dosage amounts and dose frequency schedules. Further, when a subject is administered multiple dosages of a composition provided herein, not all of the dosages need be the same. For example, the dosage administered to the subject may be increased to improve the prophylactic or therapeutic effect of the composition or it may be decreased to reduce one or more side effects that a particular subject is experiencing.

In certain embodiments, treatment or prevention can be initiated with one or more loading doses of an antibody or composition provided herein followed by one or more maintenance doses.

In certain embodiments, a dose of an antibody or composition provided herein can be administered to achieve a steady-state concentration of the antibody in blood or serum of the subject. The steady-state concentration can be determined by measurement according to techniques available to those of skill or can be based on the physical characteristics of the subject such as height, weight and age.

In certain embodiments, administration of the same composition may be repeated and the administrations may be separated by at least 1 day, 2 days, 3 days, 5 days, 10 days, 15 days, 30 days, 45 days, 2 months, 75 days, 3 months, or 6 months. In other embodiments, administration of the same prophylactic or therapeutic agent may be repeated and the administration may be separated by at least 1 day, 2 days, 3 days, 5 days, 10 days, 15 days, 30 days, 45 days, 2 months, 75 days, 3 months, or 6 months.

11. Therapeutic Applications

For therapeutic applications, the antibodies of the invention are administered to a mammal, generally a human, in a pharmaceutically acceptable dosage form such as those known in the art and those discussed above. For example, the antibodies of the invention may be administered to a human intravenously as a bolus or by continuous infusion over a period of time, by intramuscular, intraperitoneal, intra-cerebrospinal, subcutaneous, intra-articular, intrasynovial, intrathecal, or intratumoral routes. The antibodies also are suitably administered by peritumoral, intralesional, or perilesional routes, to exert local as well as systemic therapeutic effects. The intraperitoneal route may be particularly useful, for example, in the treatment of ovarian tumors.

The antibodies provided herein may be useful for the treatment of any disease or condition involving EpCAM. In some embodiments, the disease or condition is a disease or condition that can be diagnosed by overexpression of EpCAM. In some embodiments, the disease or condition is a disease or condition that can benefit from treatment with an anti-EpCAM antibody. In some embodiments, the disease or condition is a cancer.

Any suitable cancer may be treated with the antibodies provided herein. Illustrative suitable cancers include, for example, acute lymphoblastic leukemia (ALL), acute myeloid leukemia (AML), adrenocortical carcinoma, anal cancer, appendix cancer, astrocytoma, basal cell carcinoma, brain tumor, bile duct cancer, bladder cancer, bone cancer, breast cancer, bronchial tumor, carcinoma of unknown primary origin, cardiac tumor, cervical cancer, chordoma, colon cancer, colorectal cancer, craniopharyngioma, ductal carcinoma, embryonal tumor, endometrial cancer, ependymoma, esophageal cancer, esthesioneuroblastoma, fibrous histiocytoma, Ewing sarcoma, eye cancer, germ cell tumor, gallbladder cancer, gastric cancer, gastrointestinal carcinoid tumor, gastrointestinal stromal tumor, gestational trophoblastic disease, glioma, head and neck cancer, hepatocellular cancer, histiocytosis, Hodgkin lymphoma, hypopharyngeal cancer, intraocular melanoma, islet cell tumor, Kaposi sarcoma, kidney cancer, Langerhans cell histiocytosis, laryngeal cancer, lip and oral cavity cancer, liver cancer, lobular carcinoma in situ, lung cancer, macroglobulinemia, malignant fibrous histiocytoma, melanoma, Merkel cell carcinoma, mesothelioma, metastatic squamous neck cancer with occult primary, midline tract carcinoma involving NUT gene, mouth cancer, multiple endocrine neoplasia syndrome, multiple myeloma, mycosis fungoides, myelodysplastic syndrome, myelodysplastic/myeloproliferative neoplasm, nasal cavity and par nasal sinus cancer, nasopharyngeal cancer, neuroblastoma, non-small cell lung cancer, oropharyngeal cancer, osteosarcoma, ovarian cancer, pancreatic cancer, papillomatosis, paraganglioma, parathyroid cancer, penile cancer, pharyngeal cancer, pheochromocytomas, pituitary tumor, pleuropulmonary blastoma, primary central nervous system lymphoma, prostate cancer, rectal cancer, renal cell cancer, renal pelvis and ureter cancer, retinoblastoma, rhabdoid tumor, salivary gland cancer, Sezary syndrome, skin cancer, small cell lung cancer, small intestine cancer, soft tissue sarcoma, spinal cord tumor, stomach cancer, T-cell lymphoma, teratoid tumor, testicular cancer, throat cancer, thymoma and thymic carcinoma, thyroid cancer, urethral cancer, uterine cancer, vaginal cancer, vulvar cancer, and Wilms tumor.

In particular embodiments, the cancer is a cancer of epithelial origin. In some aspects, the cancer is a carcinoma. In some aspects, the cancer is selected from an adenocarcinoma, a squamous cell carcinoma, an adenosquamos carcinoma, an anaplastic carcinoma, a large cell carcinoma, small cell carcinoma, and carcinoma of unknown primary origin.

12. Diagnostic Applications

In some embodiments, the antibodies provided herein are used in diagnostic applications. For example, an ant-EpCAM antibody may be useful in assays for EpCAM protein. In some aspects the antibody can be used to detect the expression of EpCAM in various cells and tissues. These assays may be useful, for example, in making a diagnosis and/or prognosis for a disease, such as a cancer.

In some diagnostic and prognostic applications, the antibody may be labeled with a detectable moiety. Suitable detectable moieties include, but are not limited to radioisotopes, fluorescent labels, and enzyme-substrate labels. In another embodiment, the anti-EpCAM antibody need not be labeled, and the presence of the antibody can be detected using a labeled antibody which specifically binds to the anti-EpCAM antibody.

13. Affinity Purification Reagents

The antibodies of the invention may be used as affinity purification agents. In this process, the antibodies may be immobilized on a solid phase such a resin or filter paper, using methods well known in the art. The immobilized antibody is contacted with a sample containing the EpCAM protein (or fragment thereof) to be purified, and thereafter the support is washed with a suitable solvent that will remove substantially all the material in the sample except the EpCAM protein, which is bound to the immobilized antibody. Finally, the support is washed with another suitable solvent, such as glycine buffer, pH 5.0, that will release the EpCAM protein from the antibody.

14. Kits

In some embodiments, an anti-EpCAM antibody provided herein is provided in the form of a kit, i.e., a packaged combination of reagents in predetermined amounts with instructions for performing a procedure. In some embodiments, the procedure is a diagnostic assay. In other embodiments, the procedure is a therapeutic procedure.

In some embodiments, the kit further comprises a solvent for the reconstitution of the anti-EpCAM antibody. In some embodiments, the anti-EpCAM antibody is provided in the form of a pharmaceutical composition.

EXAMPLES

Example 1: Generation and Primary Screening of Anti-EpCAM Antibodies

Antibody scFv libraries were constructed using a standard overlap extension PCR protocol with mutagenic primers targeting complementary determining regions (CDRs). See Heckman and Pease, *Nat. Protoc.*, 2007, 2:924-932, incorporated by reference in its entirety. Selections for novel antibodies were performed using standard ribosome display protocols. See Dreier and Plückthun, *Methods Mol. Biol.*, 2003, 687:283-306, Clifton, N.J., incorporated by reference in its entirety. scFv-based selection was performed according to published protocols. See Hanes and Plückthun, *Proc. Natl. Acad. Sci. U.S.A.*, 1997, 94:4937-4942, incorporated by reference in its entirety. After multiple rounds of selection, the DNA from RT-PCR output was cloned into an optimized vector for cell-free expression using standard molecular biology techniques. See Yin et al., *mAbs*, 2012, 4:217-225, incorporated by reference in its entirety. All constructs were HIS- and FLAG-tagged to streamline purification and testing during screening.

Libraries of antibody variants generated by selection workflow were transformed into *E. coli* and grown on agar plates with antibiotic (kanamycin). Individual colonies were grown in liquid broth (TB+kanamycin), and used as a template for DNA amplification via rolling circle amplification (RCA). The variants were then expressed in cell-free protein synthesis reactions as described in Zawada et al., *Biotechnol. Bioeng.*, 2011, 108:1570-1578, incorporated by reference in its entirety.

Briefly, cell-free extracts were treated with 50 µM iodoacetamide for 30 min at room temperature (20° C.) and added to a premix containing cell-free components (see Groff et al., *mAbs*, 2014, 6:671-678, incorporated by reference in its entirety) and 10% (v/v) RCA DNA template (approximately 10 µg/mL DNA) for variants of interest. Sixty microliters of cell-free reactions were incubated at 30° C. for 12 hr on a shaker at 650 rpm in 96-well plates. Four hundred to one-thousand-five-hundred colonies were screened, depending on the predicted diversity of different selection campaigns.

Following synthesis, each reaction was diluted 1:50 into PBST (PBS at pH 7.4 with 0.2% Tween-20+0.2% BSA) and expressed variants were tested for functional activity via ELISA-based binding to recombinant human EpCAM extracellular domain (ECD) (Gln 24-Lys 265; Acro Biosystems; Cat. No. EPM-H5223). Standard ELISA-based methods were employed. Specifically, 384-well plates were coated with 2 µg/mL recombinant EpCAM diluted in bicarbonate buffer, and then blocked with BSA. Antibody variants of interest were allowed to bind to the EpCAM-coated plates, and detected with secondary antibodies (e.g., HRP-conjugated anti-human Fc or anti-FLAG) and then detected with chemiluminescent substrate (Pierce ELISA SuperSignal Substrate). Chemiluminescence was quantified on a Molecular Devices SpectraMax® M5 plate reader. Top hits were selected based on ELISA signal or signal/noise ratio and their nucleotides were sequenced. Based on functional activity and sequence analysis, a subset of variants was selected for further scale-up and characterization.

Example 2: Secondary Screening of Antibodies

The top leads from the initial round of screening were cultured and plasmid minipreps were performed using a QIAprep® 96 Turbo miniprep kit (Qiagen) according to the manufacturer's instructions. 10 µg/mL miniprepped DNA was added to 4 mL cell-free reactions and incubated overnight for 12 hr at 30° C., at 650 rpm.

Expressed variants from clarified cell-free reactions were purified via immobilized metal ion affinity chromatography (IMAC) purification using a semi-automated high throughput batch purification method. Briefly, purifications were performed in a 96-well plate format where 50 μL/well of IMAC resin (Ni Sepharose High Performance, GE Healthcare) was equilibrated in IMAC binding buffer (50 mM Tris pH 8.0, 300 mM NaCl, 10 mM imidazole), incubated with 1 mL cell-free reaction for 15 minutes followed by two washes in IMAC binding buffer. His-tagged antibody variants were then eluted using 200 μL IMAC elution buffer (50 mM Tris pH 8.0, 300 mM NaCl, 500 mM imidazole) and buffer exchanged into PBS using a 96-well Zeba plate (7 kD MWCO, Thermo Fisher). Purified antibodies were quantified via high throughput capillary electrophoresis using the LabChip GXII (Perkin Elmer) against a Herceptin standard curve, according to the manufacturer's instructions.

Example 3: Affinity and Kinetic Binding Analyses

Monoclonal Anti-FLAG M2 IgG (Sigma-Aldrich # F9291) was immobilized onto a CMS chip (GE Life Sciences) using amine coupling chemistry (from Amine Coupling Kit, GE Life Sciences). The immobilization steps were carried out at a flow rate of 25 μL/min in 1×HBS-EP+ buffer (GE Life Sciences; 10× Stock diluted before use). The sensor surfaces were activated for 7 min with a mixture of NHS (0.05 M) and EDC (0.2 M). The Anti-Flag M2 IgG was injected over all 4 flow cells at a concentration of 25 μg/mL in 10 mM sodium acetate, pH 4.5, for 7 min. Ethanolamine (1 M, pH 8.5) was injected for 7 min to block any remaining activated groups. An average of 12,000 response units (RU) of capture antibody was immobilized on each flow cell.

Off-rate and Kinetic binding experiments were performed at 25° C. using 1×HBS-EP+ buffer. Test and control antibodies were injected over the Anti-FLAG surface at concentrations of 5-10 μg/mL for 12 seconds at a flow rate of 10 μL/min on flow cells 2, 3 and 4, followed by a buffer wash for 30 seconds at the same flow rate. Kinetic characterization of antibody samples was carried out with a single concentration of antigen (for off-rate ranking) or a 1:2 dilution series of antigen (for kinetic characterization) and 1 injection of 0 nM antigen. After capturing ligand (antibody) on the anti-FLAG surface, the analyte (human EpCAM-His) was bound at 50, 25, 12.5, 6.25 and 0 nM for 180 seconds, followed by a 600 second dissociation phase at a flow rate of 50 μl/min. Between each ligand capture and analyte binding cycle, regeneration was carried out using 2 injections of 10 mM glycine pH 2.0 for 30 seconds at 30 μL/min, followed by a 30 second buffer wash step.

The data were fit with the Biacore T200 Evaluation software, using a 1:1 Langmuir binding model. $K_D$ (affinity, nM) was determined as a ratio of the kinetic rate constants calculated from the fits of the association and dissociation phases.

Example 4: EpCAM Epitope Binning ELISA

An anti-EpCAM antibody, 5-10 scFv-Fc (SEQ ID NO: 362), was adsorbed on Nunc 384-well white Maxisorp plates at 2 μg/mL in in sodium bicarbonate buffer (pH 8.9) and incubated at 30° C. for 1 hour or overnight at 4° C. The plate was washed 3 times with PBS pH 7.4 with 0.05% Tween and blocked with 2% bovine serum albumin (BSA) in PBS pH 7.4+0.1% Tween for 1 hour at 30° C. The block was removed by aspiration.

A dilution series of antibody was mixed with 1 nM biotinylated EpCAM-Fc (R&D Systems) in 0.2% BSA in PBS pH 7.4+0.1% Tween (diluent buffer) and incubated at 30° C. for 1 hour. The plate was washed, and streptavidin-HRP (horseradish peroxidase; Thermo Pierce) was diluted 1:10,000 in diluent buffer, added to each well, and incubated at 30° C. for 1 hour. The plate was washed and detected by SuperSignal West Pico Chemiluminescent Substrate (Thermo Pierce). Luminescence was detected on a SpectraMax plate reader (Molecular Devices).

Example 5: Fluorescence-Assisted Cell Sorting (FACS)-Based Cell Sorting

CHO-k cells were transfected to stably express EpCAM on the cell surface. CHO parental and stably transfected CHO-EpCAM (human, cynomolgus and mouse EpCAM-expressing cells) cells were washed with DPBS, detached with Accutase™ (BD Biosciences; San Jose, Calif.), and resuspended in ice-cold FACS buffer (DPBS buffer supplemented with 0.5% bovine serum albumin).

A total of 200,000 cells per 96-well were incubated on ice for 60 mins with 100 nM of test antibodies diluted in FACS buffer. Cells were washed twice with FACS buffer and incubated on ice for 30 mins with R-phycoerythrin AffiniPure F(ab')$_2$ fragment, goat anti-Human IgG, Fcγ fragment specific secondary detection antibody (Jackson ImmunoResearch Laboratories, West Grove, Pa.) diluted at 1:200 with FACS buffer. Cells were washed twice with FACS buffer, fixed in 4% paraformaldehyde in PBS (Santa Cruz Biotechnology; Dallas, Tex.) for 20 mins on ice in the dark, washed twice with FACS buffer and analyzed using the BD LSR II Flow Cytometer (BD Biosciences; San Jose, Calif.). Data were analyzed using FlowJo (FlowJo, LLC; Ashland, Oreg.) to determine mean fluorescence intensities. Binding constants were calculated using the statistical software, GraphPad Prism (GraphPad Software; La Jolla, Calif.) using the nonlinear regression equation, one site-specific binding with Hill slope. Secondary antibody alone was used as a control, in addition to measuring non-specific EpCAM antibody binding to CHO parental cells. For some variants, binding to human tumor cells, HCT 116 and JIMT1 cells were also evaluated.

Example 6: Epitope Binding and Domain Mapping

The EpCAM domain bound by the anti-human EpCAM Abs was mapped by cell binding analysis on stably transfected CHO cells expressing human/mouse chimeric EpCAM constructs. Since anti-human EpCAM Abs do not have cross-reactive binding to mouse EpCAM, chimeric human/mouse EpCAM constructs were generated to map the binding region on human EpCAM. To make the expression constructs, human and mouse EpCAM amino acid sequences corresponding to exon 2, exon 3 and exons 4-9 were switched with the alternative mouse and human amino acid sequences, respectively. The following constructs were generated and expressed in CHO cells: 1) MHH, 2) HMH, 3) HHM, 4) HMM, 5) MHM and 6) MMH, where the three letters denote human (H) or mouse (M) amino acid sequences in exon 2, exon 3 and exons 4-9, respectively. EpCAM Abs were tested for binding to the different chimeric cell lines at a concentration of 10 μg/mL by FACS binding analysis.

The results show that the SRP1464-A08 and SRP1464-B04 antibodies provided herein bind an epitope on EpCAM that is encoded by exons 4-7 of the EpCAM gene. On the other hand, 1332-A05 binds to an epitope encoded by exon 2.

Based on sequence similarity, it is expected that other SRP1464-antibodies, as well as the (parent) SRP1304-antibodies and (child) SRP1557-antibodies also bind an epitope on EpCAM that is encoded by exons 4-7. Similarly, it is expected that other SRP1332-antibodies also bind an epitope encoded by exon 2.

Despite the fact that they bind epitopes encoded by different exons both the SRP1332-A05 antibody (exon 2) and the 1464-A08 and 1464-B04 antibodies (exons 4-7) competed with a known exon 2 binder (SEQ ID NO: 336) in an experiment where each antibody was tested for its ability to block binding of the known exon 2 binder. This suggests that the epitope encoded by exon 2 (bound by SRP1332- and SEQ ID NO: 336) and exons 4-7 (bound by SRP1464-) are proximal to each other in the folded EpCAM structure, as expressed on the cell surface.

Example 7: Refined Epitope Binding and Competition Assay

The EpCAM domain bound by the anti-human EpCAM Abs within exons 4-7 was mapped by additional cell binding analysis on stably transfected CHO cells expressing human/mouse chimeric EpCAM constructs for exons 4 and 5 only. To make the expression constructs, human EpCAM amino acid sequences within parts of exon 4 and/or exons were replaced with mouse EpCAM amino acid sequences. The following constructs were generated and expressed in CHO cells: 1) MH, 2) HM, and 3) MM, where the two letters denote human (H) or mouse (M) amino acid sequences within exons 4 and exon 5, respectively. EpCAM Abs were tested for binding to the different chimeric cell lines at a concentration of 10 µg/mL by FACS binding analysis.

The results show that the SRP1464-B04 and SRP1557-G01 antibodies provided herein bind an epitope on EpCAM that is encoded by exon 5 of the EpCAM gene. Positive control Adecatumumab (known to bind exon 5) also bound to exon 5 in the same assay. This is further confirmed by competition binding experiment using CHO cells expressing human EpCAM, which showed that both SRP1464-B04 and SRP1557-G01 compete with Adecatumumab for binding to EpCAM.

Based on sequence similarity, it is expected that other SRP1464-antibodies, as well as the (parent) SRP1304-antibodies and other (child) SRP1557-antibodies also bind an epitope on EpCAM that is encoded by exon 5.

It should be noted that though the SRP1464-B04 and SRP1557-G01 antibodies bind to the same exon as, and compete for binding with, Adecatumumab, both SRP1464-B04 and SRP1557-G01 have significant binding affinity for cynomolgous EpCAM protein (see Tables 5 and 6, below), while Adecatumumab does not have significant binding affinity for cynomolgous EpCAM. See Münz et al., *Cancer Cell Int*, 2010, 10:44. Cynomolgous cross-reactivity is advantageous because it evaluation of the toxicity of antibodies in a primate model, allowing such evaluation without exposing human subjects to molecules of unknown toxicity. Thus, the SRP1464-B04 and SRP1557-G01 antibodies demonstrate a significant and unexpected biological property not found in known antibodies binding exon 5 of human EpCAM.

Example 8: Characteristics of Illustrative Anti-EpCAM Antibodies

FIG. 1 provides an alignment of the "1304," "1464," and "1557" $V_H$ sequences provided herein. FIG. 2 provides an alignment of the "1332" $V_H$ sequences provided herein. FIG. 3 provides an alignment of the "1304," "1464," and "1557" $V_L$ sequences provided herein. FIG. 4 provides an alignment of the "1332" $V_L$ sequences provided herein.

Tables 5-7 show results obtained using the illustrative antibodies described herein.

Table 5 shows results obtained from certain antibodies provided herein. Antibody SRP-1304-G11 was isolated from a naive library constructing using trinucleotides to introduce variability into CDRs. SRP-1464-A02, SRP-1464-A08, and SRP-1464-B04 were isolated from a first affinity maturation library that was based on SRP-1304-G11, and constructed using a soft randomization approach.

Briefly, during soft randomization, polynucleotides encoding the antibodies were synthesized by incorporating low levels (~30%) of non-parent nucleotides at each position within a CDR. For example, for a parent polynucleotide with A at a position to be soft randomized, a series of oligonucleotides were synthesized where about 70% have A at the position, 10% have C at the position, 10% have G at the position, and 10% have T at the position. As a result, when each position in a codon is soft randomized, approximately 34.3% of codons will remain unchanged, but any of the other 19 amino acids may also occur at the soft randomized position.

TABLE 5

| scFv-Fc Antibody | Human EpCAM (Biacore) | | | Human EpCAM (ELISA) | Cyno EpCAM (ELISA) | Human EpCAM (CHO) | Human EpCAM (HCT-116) | Human EpCAM (JIMT1) | Epitope BinExon 5 |
|---|---|---|---|---|---|---|---|---|---|
| | $k_a$ (1/Ms) | $k_a$ (1/s) | $K_D$ (M) | $EC_{50}$ (nM) | $EC_{50}$ (nM) | $K_D$ (nM) | $K_D$ (nM) | $K_D$ (nM) | |
| SRP1304-G11 (SEQ ID NO: 204) | 1.03E+05 | 4.12E−04 | 3.99E−09 | not determined | not determined | 3 | not determined | not determined | not determined |
| SRP1464-A02 (SEQ ID NO: 208) | 2.00E+05 | 1.97E−04 | 9.83E−10 | 0.009 | not detected | 2.6 | 6.7 | 5.2 | not determined |
| SRP1464-A08 (SEQ ID NO: 209) | 9.03E+04 | 1.74E−05 | 1.93E−10 | 0.39 | not detected | 1.2 | 3.6 | 2.7 | yes |
| SRP1464-B04 (SEQ ID NO: 210) | 6.52E+04 | 2.56E−04 | 3.93E−09 | 0.39 | 16.18 | 2 | 6.9 | 7.6 | yes |

Table 6 shows results obtained from antibodies isolated from a second affinity matured library, constructed using soft randomization, based on the SRP1464-B04 antibody.

The "$EC_{50}$" value is the concentration of the antibody at which half-maximum signal is achieved in an ELISA assay where EpCAM protein is adsorbed onto a plate and then bound by the respective antibody provided herein. The anti-EpCAM antibody is detected with horseradish peroxidase (HRP)-conjugated anti-human Fc antibody.

TABLE 6

Results obtained from antibodies isolated from a first affinity matured library, based on the SRP1464-B04 antibody provided in Table 5.

| scFv-Fc Antibody | Human EpCAM (Biacore) | | | Cyno EpCAM (Biacore) | Human EpCAM (CHO) | Cyno EpCAM (CHO) | Epitope bin Exon 5 |
| --- | --- | --- | --- | --- | --- | --- | --- |
| | $k_a$ (1/Ms) | $k_d$ (1/s) | $K_D$ (M) | $K_D$ (M) | $K_D$ (nM) | $K_D$ (nM) | |
| SRP1557-A04 (SEQ ID NO: 211) | 2.10E+05 | 3.75E−04 | 1.78E−09 | 1.82E−08 | 1.85 | 2.5 | Not tested |
| SRP1557-A05 (SEQ ID NO: 212) | 2.20E+05 | 7.84E−04 | 3.56E−09 | 2.29E−08 | 2.49 | 1.83 | Not tested |
| SRP1557-B03 (SEQ ID NO: 213) | 1.49E+05 | 5.10E−04 | 3.43E−09 | 1.20E−07 | 1.45 | 1.59 | Not tested |
| SRP1557-B10 (SEQ ID NO: 214) | 1.43E+05 | 5.98E−04 | 4.17E−09 | 3.99E−08 | 1.71 | 1.35 | Not tested |
| SRP1557-C06 (SEQ ID NO: 215) | 1.66E+05 | 9.08E−04 | 5.46E−09 | 2.97E−08 | 1.08 | 0.7 | Not tested |
| SRP1557-E07 (SEQ ID NO: 216) | 2.56E+05 | 1.58E−03 | 6.17E−09 | 8.10E−09 | 1.54 | 0.9 | Not tested |
| SRP1557-E08 (SEQ ID NO: 217) | 2.88E+05 | 7.90E−04 | 2.75E−09 | 7.52E−09 | 1.17 | 1.2 | Not tested |
| SRP1557-E11 (SEQ ID NO: 218) | 1.76E+05 | 6.04E−04 | 3.44E−09 | 4.52E−08 | 1.69 | 1.07 | Not tested |
| SRP1557-F01 (SEQ ID NO: 219) | 2.35E+05 | 1.69E−03 | 7.21E−09 | 1.17E−09 | 1.96 | 1.21 | Not tested |
| SRP1557-F02 (SEQ ID NO: 220) | 1.70E+05 | 2.54E−04 | 1.49E−09 | 2.91E−08 | 1.91 | 0.9 | Not tested |
| SRP1557-F03 (SEQ ID NO: 221) | 1.92E+05 | 1.00E−03 | 5.24E−09 | 8.59E−09 | 1.5 | 0.66 | Not tested |
| SRP1557-F05 (SEQ ID NO: 222) | ND | ND | ND | ND | 3.24 | 2.99 | Not tested |
| SRP1557-G01 (SEQ ID NO: 223) | 3.51E+05 | 1.23E−03 | 3.50E−09 | 4.41E−09 | 1.79 | 1.79 | yes |
| SRP1557-G03 (SEQ ID NO: 224) | 2.54E+05 | 1.75E−03 | 6.91E−09 | 1.62E−07 | 1.91 | 1.38 | Not tested |
| SRP1557-G04 (SEQ ID NO: 225) | ND | ND | ND | ND | 3.68 | 1.83 | Not tested |
| SRP1557-G06 (SEQ ID NO: 226) | 1.40E+05 | 9.39E−04 | 6.70E−09 | 1.52E−08 | 2.47 | 1.62 | Not tested |
| SRP1557-H04 (SEQ ID NO: 227) | 3.10E+05 | 7.87E−04 | 2.54E−09 | 7.22E−09 | 1.89 | 0.87 | Not tested |
| SRP1557-H10 (SEQ ID NO: 228) | 2.57E+05 | 3.06E−04 | 1.19E−09 | 3.52E−08 | 2.59 | 0.99 | Not tested |

Table 7 shows results obtained from antibodies isolated from a third affinity matured library constructed by performing soft randomization on a different antibody.

TABLE 7

Results obtained from antibodies isolated from a third affinity matured library.

| scFv-Fc Antibody | Human EpCAM (Biacore) | | | Human EpCAM (CHO) | Human EpCAM (ELISA) | Cyno EpCAM (ELISA) | Epitope |
|---|---|---|---|---|---|---|---|
| | $k_a$ (1/Ms) | $k_d$ (1/s) | $K_D$ (M) | $K_D$ (nM) | $EC_{50}$ (nM) | $EC_{50}$ (nM) | bin Exon 5 |
| SRP1332-C01 (SEQ ID NO: 206) | 2.84E+05 | 2.57E−04 | 9.04E−10 | 1.6 | 0.33 | not detected | Yes |
| SRP1332-A05 (SEQ ID NO: 205) | 2.05E+05 | 2.97E−04 | 1.45E−09 | 2 | 0.47 | not detected | Yes |
| SRP1332-F11 (SEQ ID NO: 207) | 1.82E+05 | 2.57E−04 | 1.41E−09 | 1.14 | 0.47 | not detected | Yes |

Example 9: Sequences

Table 8 provides sequences referred to herein. In Table 8, the numbering scheme is indicated as Chothia or Kabat for the sequences where the scheme is significant, e.g., for CDR-H1 and CDR-H2 regions. Otherwise, the scheme is not indicated, and those of skill will recognize that either numbering scheme, or another, can apply.

TABLE 8

Sequences.

| SEQ ID NO: | Molecule | Region | Scheme | Sequence | Length |
|---|---|---|---|---|---|
| 1 | hEpCAM | | | MAPPQVLAFGLLLAAATATFAAAQEECVCENYKLAVNCFVNNNRQCQCTSVGAQNTVICSKLAAKCLVMKAEMNGSKLGRRAKPEGALQNNDGLYDPDCDESGLFKAKQCNGTSTCWCVNTAGVRRTDKDTEITCSERVRTYWIIIELKHKAREKPYDSKSLRTALQKEITTRYQLDPKFITSILYENNVITIDLVQNSSQKTQNDVDIADVAYYFEKDVKGESLFHSKKMDLTVNGEQLDLDPGQTLIYYVDEKAPEFSMQGLKAGVIAVIVVVIAVVAGIVVLVISRKKRMAKYEKAEIKEMGEMHRELNA | 314 |
| 2 | cEpCAM | | | MAQSGQQCLQEEQETSLQQHYSFFVFLNFLECVCENYKLAVNCFLNDNGQCQCTSIGAQNTVLCSKLAAKCLVMKAEMNGSKLGRRAKPEGALQNNDGLYDPDCDESGLFKAKQONGTSTCWCVNTAGVRRTDKDTEITCSERVRTYWIIIELKHKAREKPYDVQSLRTALEEEAIKTRYQLDPKFITNILYEDNVITIDLVQNSSQKTQNDVDIADVAYYFEKDVKGESLFHSKKMDLRVNGEQLDLDPGQTLIYYVDEKAPEFSMQGLKAGVIAVIVVVIAIVAGIVVLVISRKKRMAKYEKAEIKEMGEIHRELNA | 319 |
| 3 | mEpCAM | | | MAGPQALAFGLLLAVVTATLAAAQRDCVCDNYKLATSCSLNEYGECQCTSYGTQNTVICSKLASKCLAMKAEMTHSKSGRRIKPEGAIQNNDGLYDPDCDEQGLFKAKQONGTATCWCVNTAGVRRTDKDTEITCSERVRTYWIIIELKHKERESPYDHQSLQTALQEAFTSRYKLNQKFIKNIMYENNVITIDLMQNSSQKTQDDVDIADVAYYFEKDVKGESLFHSSKSMDLRVNGEPLDLDPGQTLIYYVDEKAPEFSMQGLTAGIIAVIVVVSLAVIAGIVVLVISTRKKSAKYEKAEIKEMGEIHRELNA | 315 |
| 4 | 1304-G11 | CDR-H1 | Chothia | GFTFSGS | 7 |
| 5 | 1332-A05 | CDR-H1 | Chothia | DYAFANR | 7 |
| 6 | 1332-C01 | CDR-H1 | Chothia | GYAFTNS | 7 |
| 7 | 1332-F11 | CDR-H1 | Chothia | GYAFANR | 7 |

TABLE 8-continued

Sequences.

| SEQ ID NO: | Molecule | Region | Scheme | Sequence | Length |
|---|---|---|---|---|---|
| 8 | 1464-A02 | CDR-H1 | Chothia | GFTFGVE | 7 |
| 9 | 1464-A08 | CDR-H1 | Chothia | GFTFSGS | 7 |
| 10 | 1464-B04 | CDR-H1 | Chothia | GFTFSGS | 7 |
| 11 | 1557-A04 | CDR-H1 | Chothia | GFTFSGS | 7 |
| 12 | 1557-A05 | CDR-H1 | Chothia | GFTFGGS | 7 |
| 13 | 1557-B03 | CDR-H1 | Chothia | GFTFRSS | 7 |
| 14 | 1557-B10 | CDR-H1 | Chothia | GFTFSGC | 7 |
| 15 | 1557-C06 | CDR-H1 | Chothia | GFTFRGA | 7 |
| 16 | 1557-E07 | CDR-H1 | Chothia | GFTFSGS | 7 |
| 17 | 1557-E08 | CDR-H1 | Chothia | GFTFRAS | 7 |
| 18 | 1557-E11 | CDR-H1 | Chothia | GFTFRGS | 7 |
| 19 | 1557-F01 | CDR-H1 | Chothia | GFTFSGS | 7 |
| 20 | 1557-F02 | CDR-H1 | Chothia | GFTFRGS | 7 |
| 21 | 1557-F03 | CDR-H1 | Chothia | GFTFSGS | 7 |
| 22 | 1557-F05 | CDR-H1 | Chothia | GFTFRGS | 7 |
| 23 | 1557-G01 | CDR-H1 | Chothia | GFTFSVT | 7 |
| 24 | 1557-G03 | CDR-H1 | Chothia | GFTFGGS | 7 |
| 25 | 1557-G04 | CDR-H1 | Chothia | GFTFCGS | 7 |
| 26 | 1557-G06 | CDR-H1 | Chothia | GFTFSGF | 7 |
| 27 | 1557-H04 | CDR-H1 | Chothia | GFTFSVT | 7 |
| 28 | 1557-H10 | CDR-H1 | Chothia | GFTFSGS | 7 |
| 29 | 1304-G11 | CDR-H1 | Kabat | GSSMS | 5 |
| 30 | 1332-A05 | CDR-H1 | Kabat | NRWLG | 5 |
| 31 | 1332-C01 | CDR-H1 | Kabat | NSWLG | 5 |
| 32 | 1332-F11 | CDR-H1 | Kabat | NRWLG | 5 |
| 33 | 1464-A02 | CDR-H1 | Kabat | VESMS | 5 |
| 34 | 1464-A08 | CDR-H1 | Kabat | GSSMS | 5 |
| 35 | 1464-B04 | CDR-H1 | Kabat | GSSMS | 5 |
| 36 | 1557-A04 | CDR-H1 | Kabat | GSSMS | 5 |
| 37 | 1557-A05 | CDR-H1 | Kabat | GSSMS | 5 |
| 38 | 1557-B03 | CDR-H1 | Kabat | SSSMS | 5 |
| 39 | 1557-B10 | CDR-H1 | Kabat | GCSMS | 5 |
| 40 | 1557-C06 | CDR-H1 | Kabat | GASMS | 5 |
| 41 | 1557-E07 | CDR-H1 | Kabat | GSSMS | 5 |
| 42 | 1557-E08 | CDR-H1 | Kabat | ASSMS | 5 |
| 43 | 1557-E11 | CDR-H1 | Kabat | GSSMS | 5 |
| 44 | 1557-F01 | CDR-H1 | Kabat | GSSMS | 5 |
| 45 | 1557-F02 | CDR-H1 | Kabat | GSSMS | 5 |

TABLE 8-continued

Sequences.

| SEQ ID NO: | Molecule | Region | Scheme | Sequence | Length |
|---|---|---|---|---|---|
| 46 | 1557-F03 | CDR-H1 | Kabat | GSSMS | 5 |
| 47 | 1557-F05 | CDR-H1 | Kabat | GSSMS | 5 |
| 48 | 1557-G01 | CDR-H1 | Kabat | VTSMS | 5 |
| 49 | 1557-G03 | CDR-H1 | Kabat | GSSMS | 5 |
| 50 | 1557-G04 | CDR-H1 | Kabat | GSSMS | 5 |
| 51 | 1557-G06 | CDR-H1 | Kabat | GFSMS | 5 |
| 52 | 1557-H04 | CDR-H1 | Kabat | VTSMS | 5 |
| 53 | 1557-H10 | CDR-H1 | Kabat | GSSMS | 5 |
| 54 | 1304-G11 | CDR-H2 | Chothia | DGGDGY | 6 |
| 55 | 1332-A05 | CDR-H2 | Chothia | FPGSGN | 6 |
| 56 | 1332-C01 | CDR-H2 | Chothia | FPGSGN | 6 |
| 57 | 1332-F11 | CDR-H2 | Chothia | FPGSGN | 6 |
| 58 | 1464-A02 | CDR-H2 | Chothia | DGGDGY | 6 |
| 59 | 1464-A08 | CDR-H2 | Chothia | AGGDGY | 6 |
| 60 | 1464-B04 | CDR-H2 | Chothia | DGGEGY | 6 |
| 61 | 1557-A04 | CDR-H2 | Chothia | DGGEGS | 6 |
| 62 | 1557-A05 | CDR-H2 | Chothia | GGGEGS | 6 |
| 63 | 1557-B03 | CDR-H2 | Chothia | GGHEGY | 6 |
| 64 | 1557-B10 | CDR-H2 | Chothia | AGGEGN | 6 |
| 65 | 1557-C06 | CDR-H2 | Chothia | DGSQGS | 6 |
| 66 | 1557-E07 | CDR-H2 | Chothia | DGGEGS | 6 |
| 67 | 1557-E08 | CDR-H2 | Chothia | DGGVGS | 6 |
| 68 | 1557-E11 | CDR-H2 | Chothia | DGGEGS | 6 |
| 69 | 1557-F01 | CDR-H2 | Chothia | DGGEGS | 6 |
| 70 | 1557-F02 | CDR-H2 | Chothia | DGGEGS | 6 |
| 71 | 1557-F03 | CDR-H2 | Chothia | AGGGGS | 6 |
| 72 | 1557-F05 | CDR-H2 | Chothia | DGGEGS | 6 |
| 73 | 1557-G01 | CDR-H2 | Chothia | AGGEGS | 6 |
| 74 | 1557-G03 | CDR-H2 | Chothia | GGGEGy | 6 |
| 75 | 1557-G04 | CDR-H2 | Chothia | DGGVGS | 6 |
| 76 | 1557-G06 | CDR-H2 | Chothia | DGGEGS | 6 |
| 77 | 1557-H04 | CDR-H2 | Chothia | AGGEGS | 6 |
| 78 | 1557-H10 | CDR-H2 | Chothia | DGGEGS | 6 |
| 79 | 1304-G11 | CDR-H2 | Kabat | AIDGGDGYTNYADSVRG | 17 |
| 80 | 1332-A05 | CDR-H2 | Kabat | DIFPGSGNIHYNEKFKG | 17 |
| 81 | 1332-C01 | CDR-H2 | Kabat | DIFPGSGNIHYNEKFKG | 17 |
| 82 | 1332-F11 | CDR-H2 | Kabat | DIFPGSGNIHYNEKFKG | 17 |
| 83 | 1464-A02 | CDR-H2 | Kabat | AIDGGDGYTGYADSVKD | 17 |

TABLE 8-continued

Sequences.

| SEQ ID NO: | Molecule | Region | Scheme | Sequence | Length |
|---|---|---|---|---|---|
| 84 | 1464-A08 | CDR-H2 | Kabat | AIAGGDGYTGYADSVKG | 17 |
| 85 | 1464-B04 | CDR-H2 | Kabat | AIDGGEGYTSYADSVKG | 17 |
| 86 | 1557-A04 | CDR-H2 | Kabat | AIDGGEGSTAYADSVKG | 17 |
| 87 | 1557-A05 | CDR-H2 | Kabat | AIGGGEGSTGYADSVKG | 17 |
| 88 | 1557-B03 | CDR-H2 | Kabat | AIGGHEGYTGYADSVKG | 17 |
| 89 | 1557-B10 | CDR-H2 | Kabat | AIAGGEGNTGYADSVKG | 17 |
| 90 | 1557-C06 | CDR-H2 | Kabat | AIDGSQGSTGYADSVKG | 17 |
| 91 | 1557-E07 | CDR-H2 | Kabat | AIDGGEGSTGYADSVKG | 17 |
| 92 | 1557-E08 | CDR-H2 | Kabat | AIDGGVGSTGYADSVKG | 17 |
| 93 | 1557-E11 | CDR-H2 | Kabat | AIDGGEGSTGYADSVKG | 17 |
| 94 | 1557-F01 | CDR-H2 | Kabat | AIDGGEGSTGYADSVKG | 17 |
| 95 | 1557-F02 | CDR-H2 | Kabat | AIDGGEGSTGYADSVKG | 17 |
| 96 | 1557-F03 | CDR-H2 | Kabat | AIAGGGGSTGYADSVKG | 17 |
| 97 | 1557-F05 | CDR-H2 | Kabat | AIDGGEGSTGYADSVKG | 17 |
| 98 | 1557-G01 | CDR-H2 | Kabat | AIAGGEGSTGYADSVKG | 17 |
| 99 | 1557-G03 | CDR-H2 | Kabat | AIGGGEGYTGYADSVKG | 17 |
| 100 | 1557-G04 | CDR-H2 | Kabat | AIDGGVGSTGYADSVKG | 17 |
| 101 | 1557-G06 | CDR-H2 | Kabat | AIDGGEGSTGYADSVKG | 17 |
| 102 | 1557-H04 | CDR-H2 | Kabat | AIAGGEGSTGYADSVKG | 17 |
| 103 | 1557-H10 | CDR-H2 | Kabat | AIDGGEGSTGYADSVKG | 17 |
| 104 | 1304-G11 | CDR-H3 | | GWHPQTYYGLDY | 12 |
| 105 | 1332-A05 | CDR-H3 | | LRNWEGPMDY | 10 |
| 106 | 1332-C01 | CDR-H3 | | LRNWDMPMDY | 10 |
| 107 | 1332-F11 | CDR-H3 | | LRNWEGPMDY | 10 |
| 108 | 1464-A02 | CDR-H3 | | AWHPQTYYGVDY | 12 |
| 109 | 1464-A08 | CDR-H3 | | GWHRQDYYGQDY | 12 |
| 110 | 1464-B04 | CDR-H3 | | GWHPQTLYDLDY | 12 |
| 111 | 1557-A04 | CDR-H3 | | GWHPQTMYDLDY | 12 |
| 112 | 1557-A05 | CDR-H3 | | GWHDQSLYDRDY | 12 |
| 113 | 1557-B03 | CDR-H3 | | GWNPQTLYHLDY | 12 |
| 114 | 1557-B10 | CDR-H3 | | GWHPQTLYDLDY | 12 |
| 115 | 1557-C06 | CDR-H3 | | GWHPQTMYDLDY | 12 |
| 116 | 1557-E07 | CDR-H3 | | GWHPQTLYDLDY | 12 |
| 117 | 1557-E08 | CDR-H3 | | GWHPQTLYDLDY | 12 |
| 118 | 1557-E11 | CDR-H3 | | GWHPQSLYDLDY | 12 |
| 119 | 1557-F01 | CDR-H3 | | GWHPQTLYDLDY | 12 |
| 120 | 1557-F02 | CDR-H3 | | GWHPQTMYNLDY | 12 |
| 121 | 1557-F03 | CDR-H3 | | GWHPQTLYDLDY | 12 |

TABLE 8-continued

Sequences.

| SEQ ID NO: | Molecule | Region | Scheme | Sequence | Length |
|---|---|---|---|---|---|
| 122 | 1557-F05 | CDR-H3 | | DWHPQTLYDLDY | 12 |
| 123 | 1557-G01 | CDR-H3 | | GWHPQTLYDLDY | 12 |
| 124 | 1557-G03 | CDR-H3 | | GWHPQTLYDLDY | 12 |
| 125 | 1557-G04 | CDR-H3 | | GWHPQTLYDLDY | 12 |
| 126 | 1557-G06 | CDR-H3 | | GWHPQTLYHLDY | 12 |
| 127 | 1557-H04 | CDR-H3 | | GWHPQTLYDLDY | 12 |
| 128 | 1557-H10 | CDR-H3 | | GWHPQSMYDLDY | 12 |
| 129 | 1304-G11 | CDR-L1 | | RASQSVSSSYLA | 12 |
| 130 | 1332-A05 | CDR-L1 | | KSSQSLLNSGNQKNYLT | 17 |
| 131 | 1332-C01 | CDR-L1 | | KSSQSLLNSGNQKNYLT | 17 |
| 132 | 1332-F11 | CDR-L1 | | KSSQSLLNSGNQKNYLT | 17 |
| 133 | 1464-A02 | CDR-L1 | | RASQSVSSSYLA | 12 |
| 134 | 1464-A08 | CDR-L1 | | RASQSVSSSYLA | 12 |
| 135 | 1464-B04 | CDR-L1 | | RASQSVSSSYLA | 12 |
| 136 | 1557-A04 | CDR-L1 | | RASQNVSTNYLA | 12 |
| 137 | 1557-A05 | CDR-L1 | | SASQTVSSSYIA | 12 |
| 138 | 1557-B03 | CDR-L1 | | RASQKCSSSSMA | 12 |
| 139 | 1557-B10 | CDR-L1 | | RASQGLASRYMA | 12 |
| 140 | 1557-C06 | CDR-L1 | | RASQRGTSSYLA | 12 |
| 141 | 1557-E07 | CDR-L1 | | RASQVLSSSSLA | 12 |
| 142 | 1557-E08 | CDR-L1 | | RASQGDSSSVLA | 12 |
| 143 | 1557-E11 | CDR-L1 | | RASQPVPNTTLA | 12 |
| 144 | 1557-F01 | CDR-L1 | | RASQSVSSSKLA | 12 |
| 145 | 1557-F02 | CDR-L1 | | RASQSVSSSYLA | 12 |
| 146 | 1557-F03 | CDR-L1 | | RASQSVKTSDLA | 12 |
| 147 | 1557-F05 | CDR-L1 | | RASQTVSPSVLA | 12 |
| 148 | 1557-G01 | CDR-L1 | | RASQVLSSSSLA | 12 |
| 149 | 1557-G03 | CDR-L1 | | RASQSVHSSYLA | 12 |
| 150 | 1557-G04 | CDR-L1 | | RASQSVSSSYLA | 12 |
| 151 | 1557-G06 | CDR-L1 | | RASQSIPSSYLA | 12 |
| 152 | 1557-H04 | CDR-L1 | | RASQSVSTGYLA | 12 |
| 153 | 1557-H10 | CDR-L1 | | RASQVLSSSSLA | 12 |
| 154 | 1304-G11 | CDR-L2 | | GASSRAT | 7 |
| 155 | 1332-A05 | CDR-L2 | | WASTRES | 7 |
| 156 | 1332-C01 | CDR-L2 | | WASTRES | 7 |
| 157 | 1332-F11 | CDR-L2 | | RASTRES | 7 |
| 158 | 1464-A02 | CDR-L2 | | GASSRAT | 7 |
| 159 | 1464-A08 | CDR-L2 | | GASSRAT | 7 |

TABLE 8-continued

Sequences.

| SEQ ID NO: | Molecule | Region | Scheme | Sequence | Length |
|---|---|---|---|---|---|
| 160 | 1464-B04 | CDR-L2 | | GASSRAT | 7 |
| 161 | 1557-A04 | CDR-L2 | | GASSRAT | 7 |
| 162 | 1557-A05 | CDR-L2 | | GASSRAT | 7 |
| 163 | 1557-B03 | CDR-L2 | | GASSRAT | 7 |
| 164 | 1557-B10 | CDR-L2 | | GASSRAT | 7 |
| 165 | 1557-C06 | CDR-L2 | | GASSRAT | 7 |
| 166 | 1557-E07 | CDR-L2 | | GASSRAT | 7 |
| 167 | 1557-E08 | CDR-L2 | | GASSRAT | 7 |
| 168 | 1557-E11 | CDR-L2 | | GASSRAT | 7 |
| 169 | 1557-F01 | CDR-L2 | | GASSRAT | 7 |
| 170 | 1557-F02 | CDR-L2 | | GASSRAT | 7 |
| 171 | 1557-F03 | CDR-L2 | | GASSRAT | 7 |
| 172 | 1557-F05 | CDR-L2 | | GASSRAT | 7 |
| 173 | 1557-G01 | CDR-L2 | | GASSRAT | 7 |
| 174 | 1557-G03 | CDR-L2 | | GASSRAT | 7 |
| 175 | 1557-G04 | CDR-L2 | | GASSRAT | 7 |
| 176 | 1557-G06 | CDR-L2 | | GASSRAT | 7 |
| 177 | 1557-H04 | CDR-L2 | | GASSRAT | 7 |
| 178 | 1557-H10 | CDR-L2 | | GASSRAT | 7 |
| 179 | 1304-G11 | CDR-L3 | | QQYWGPPT | 9 |
| 180 | 1332-A05 | CDR-L3 | | QNDLSYPLT | 9 |
| 181 | 1332-C01 | CDR-L3 | | QNDYRYPLT | 9 |
| 182 | 1332-F11 | CDR-L3 | | QNDSSYPLT | 9 |
| 183 | 1464-A02 | CDR-L3 | | QQTSEAPPT | 9 |
| 184 | 1464-A08 | CDR-L3 | | QQNQAAPAT | 9 |
| 185 | 1464-B04 | CDR-L3 | | QQLVTSPPT | 9 |
| 186 | 1557-A04 | CDR-L3 | | QQLVTNPPT | 9 |
| 187 | 1557-A05 | CDR-L3 | | QQLLTSPPT | 9 |
| 188 | 1557-B03 | CDR-L3 | | QQLQTSPPT | 9 |
| 189 | 1557-B10 | CDR-L3 | | QQVMTIPPT | 9 |
| 190 | 1557-C06 | CDR-L3 | | QQHVTSPPT | 9 |
| 191 | 1557-E07 | CDR-L3 | | QQRAAPPPT | 9 |
| 192 | 1557-E08 | CDR-L3 | | QQLVPSPPT | 9 |
| 193 | 1557-E11 | CDR-L3 | | QQLVPSPPT | 9 |
| 194 | 1557-F01 | CDR-L3 | | QQLETIPPT | 9 |
| 195 | 1557-F02 | CDR-L3 | | QQLFNSPPT | 9 |
| 196 | 1557-F03 | CDR-L3 | | QQLVSKPPT | 9 |
| 197 | 1557-F05 | CDR-L3 | | QQLVTNPPT | 9 |

TABLE 8-continued

Sequences.

| SEQ ID NO: | Molecule | Region | Scheme | Sequence | Length |
|---|---|---|---|---|---|
| 198 | 1557-G01 | CDR-L3 | | QQLVTSPPT | 9 |
| 199 | 1557-G03 | CDR-L3 | | QQLLSSPPT | 9 |
| 200 | 1557-G04 | CDR-L3 | | QQDSFVPPT | 9 |
| 201 | 1557-G06 | CDR-L3 | | QQLATSPPT | 9 |
| 202 | 1557-H04 | CDR-L3 | | QQLVTRPPT | 9 |
| 203 | 1557-H10 | CDR-L3 | | QQLVTAPPT | 9 |
| 204 | 1304-G11 | scFv-Fc | | MEVQLLESGGGLVRPGGSLRLSCAASGFTF SGSSMSWVRQAPGKGLEWVGAIDGGDGYTN YADSVRGRFTISRDNSKNTLYLQMNSLRAE DTAVYYCAKGWHPQTYYGLDYWGQGTLVTV SSGGGGSGGGGSGGGGSEIVLTQSPGTLSL SPGERATLSCRASQSVSSSYLAWYQQKPGQ APRLLIYGASSRATGIPDRFSGSSSGTDFT LTISRLEPEDFAVYYCQQYWYGPPTFGQGT KVEIKAAGSDQEPKSSDKTHTCPPCSAPEL LGGSSVFLFPPKPKDTLMISRTPEVTCVVV DVSHEDPEVKFNWYVDGVEVHNAKTKPREE QYNSTYRVVSVLTVLHQDWLNGKEYKCKVS NKALPAPIEKTISKAKGQPREPQVYTLPPS RDELTKNQVSLTCLVKGFYPSDIAVEWESN GQPENNYKTTPPVLDSDGSFFLYSKLTVDK SRWQQGNVFSCSVMHEALHNHYTQKSLSLS PGKGGSHHHHHH | 492 |
| 205 | 1332-A05 | scFv-Fc | | MELVMTQSPSSLTVTAGEKVTMSCKSSQSL LNSGNQKNYLTWYQQKPGQPPKLLIYWAST RESGVPDRFTGSGSGTDFTLTISSVQAEDL AVYYCQNDLSYPLTFGAGTKLEIKGGGGSG GGGSGGGGSEVQLLEQSGAELVRPGTSVKI SCKASDYAFANRWLGWVKQRPGHGLEWIGD IFPGSGNIHYNEKFKGKATLTADKSSSTAY MQLSSLTFEDSAVYFCARLRNWEGPMDYWG QGTTVTVSSAAGSDQEPKSSDKTHTCPPCS APELLGGSSVFLFPPKPKDTLMISRTPEVT CVVVDVSHEDPEVKFNWYVDGVEVHNAKTK PREEQYNSTYRVVSVLTVLHQDWLNGKEYK CKVSNKALPAPIEKTISKAKGQPREPQVYT LPPSRDELTKNQVSLTCLVKGFYPSDIAVE WESNGQPENNYKTTPPVLDSDGSFFLYSKL TVDKSRWQQGNVFSCSVMHEALHNHYTQKS LSLSPGKGSGDYKDDDDKGSGHHHHHH | 507 |
| 206 | 1332-C01 | scFv-Fc | | MELVMTQSPSSLTVTAGEKVTMSCKSSQSL LNSGNQKNYLTWYQQKPGQPPKLLIYWAST RESGVPDRFTGSGSGTDFTLTISSVQAEDL AVYYCQNDYRYPLTFGAGTKLEIKGGGGSG GGGSGGGGSEVQLLEQSGAELVRPGTSVKI SCKASGYAFTNSWLGWVKQRPGHGLEWIGD IFPGSGNIHYNEKFKGKATLTADKSSSTAY MQLSSLTFEDSAVYFCARLRNWDMPMDYWG QGTTVTVSSAAGSDQEPKSSDKTHTCPPCS APELLGGSSVFLFPPKPKDTLMISRTPEVT CVVVDVSHEDPEVKFNWYVDGVEVHNAKTK PREEQYNSTYRVVSVLTVLHQDWLNGKEYK CKVSNKALPAPIEKTISKAKGQPREPQVYT LPPSRDELTKNQVSLTCLVKGFYPSDIAVE WESNGQPENNYKTTPPVLDSDGSFFLYSKL TVDKSRWQQGNVFSCSVMHEALHNHYTQKS LSLSPGKGSGDYKDDDDKGSGHHHHHH | 507 |
| 207 | 1332-F11 | scFv-Fc | | MELVMTQSPSSLTVTAGEKVTMSCKSSQSL LNSGNQKNYLTWYQQKPGQPPKLLIYRAST RESGVPDRFTGSGSGTDFTLTISSVQAEDL AVYYCQNDSSYPLTFGAGTKLEIKGGGGSG GGGSGGGGSEVQLLEQSGAELVRPGTSVKI SCKASGYAFANRWLGWVKQRPGHGLEWIGD IFPGSGNIHYNEKFKGKATLTADKSSSTAY MQLSSLTFEDSAVYFCARLRNWEGPMDYWG QGTTVTVSSAAGSDQEPKSSDKTHTCPPCS APELLGGSSVFLFPPKPKDTLMISRTPEVT | 507 |

TABLE 8-continued

Sequences.

| SEQ ID NO: | Molecule | Region | Scheme | Sequence | Length |
|---|---|---|---|---|---|
| | | | | CVVVDVSHEDPEVKFNWYVDGVEVHNAKTK PREEQYNSTYRVVSVLTVLHQDWLNGKEYK CKVSNKALPAPIEKTISKAKGQPREPQVYT LPPSRDELTKNQVSLTCLVKGFYPSDIAVE WESNGQPENNYKTTPPVLDSDGSFFLYSKL TVDKSRWQQGNVFSCSVMHEALHNHYTQKS LSLSPGKGSGDYKDDDDKGSGHHHHHH | |
| 208 | 1464-A02 | scFv-Fc | | MEVQLLESGGGLVQPGGSLRLSCAASGFTF GVESMSWVRQAPGKGLEWVGAIDGGDYTG YADSVKDRFTISRDNSKNTLYLQMNSLRAE DTAVYYCAKAWHPQTYYGVDYWGQGTLVTV SSGGGGSGGGGSGGGGSEIVLTQSPGTLSL SPGERATLSCRASQSVSSSYLAWYQQKPGQ APRLLIYGASSRATGIPDRFSGSGSGTDFT LTISRLEPEDFAVYYCQQTSEAPPTFGQGT KVEIKAAGSDQEPKSSDKTHTCPPCSAPEL LGGSSVFLFPPKPKDTLMISRTPEVTCVVV DVSHEDPEVKFNWYVDGVEVHNAKTKPREE QYNSTYRVVSVLTVLHQDWLNGKEYKCKVS NKALPAPIEKTISKAKGQPREPQVYTLPPS RDELTKNQVSLTCLVKGFYPSDIAVEWESN GQPENNYKTTPPVLDSDGSFFLYSKLTVDK SRWQQGNVFSCSVMHEALHNHYTQKSLSLS PGKGSGDYKDDDDKGSGHHHHHH | 503 |
| 209 | 1464-A08 | svFv-Fc | | MEVQLLESGGGLVQPGGSLRLSCAASGFTF SGSSMSWVRQAPGKGLEWVGAIAGGDYTG YADSVKGRFTISRDNSKNTLYLQMNSLRAE DTAVYYCAKGWHRQDYYGQDYWGQGTLVTV SSGGGGSGGGGSGGGGSEIVLTQSPGTLSL SPGERATLGCRASQSVSSSYLAWYQQKPGQ APRLLIYGASSRATGIPDRFSGSGSGTDFT LTISRLEPEDFAVYYCQQNQAAPATFGQGT KVEIKAAGSDQEPKSSDKTHTCPPCSAPEL LGGSSVFLFPPKPKDTLMISRTPEVTCVVV DVSHEDPEVKFNWYVDGVEVHNAKTKPREE QYNSTYRVVSVLTVLHQDWLNGKEYKCKVS NKALPAPIEKTISKAKGQPREPQVYTLPPS RDELTKNQVSLTCLVKGFYPSDIAVEWESN GQPENNYKTTPPVLDSDGSFFLYSKLTVDK SRWQQGNVFSCSVMHEALHNHYTQKSLSLS PGKGSGDYKDDDDKGSGHHHHHH | 503 |
| 210 | 1464-B04 | scFv-Fc | | MEVQLLESGGGLVQPGGSLRLSCAASGFTF SGSSMSWVRQAPGKGLEWVGAIDGGEGYTS YADSVKGRFTISRDNSKNTLYLQMNSLRAE DTAVYYCAKGWHPQTLYDLDYWGQGTLVTV SSGGGGSGGGGSGGGGSEIVLTQSPGTLSL SPGERATLSCRASQSVSSSYLAWYQQKPGQ APRLLIYGASSRATGIPDRFSGSGSGTDFT LTISRLEPEDFAVYYCQQLVTSPPTFGQGT KVEIKAAGSDQEPKSSDKTHTCPPCSAPEL LGGSSVFLFPPKPKDTLMISRTPEVTCVVV DVSHEDPEVKFNWYVDGVEVHNAKTKPREE QYNSTYRVVSVLTVLHQDWLNGKEYKCKVS NKALPAPIEKTISKAKGQPREPQVYTLPPS RDELTKNQVSLTCLVKGFYPSDIAVEWESN GQPENNYKTTPPVLDSDGSFFLYSKLTVDK SRWQQGNVFSCSVMHEALHNHYTQKSLSLS PGKGSGDYKDDDDKGSGHHHHHH | 503 |
| 211 | 1557-A04 | scFv-Fc | | MEVQLLESGGGLVQPGGSLRLSCAASGFTF SGSSMSWVRQAPGKGLEWVGAIDGGEGSTA YADSVKGRFTISRDNSKNTLYLQMNSLRAE DTAVYYCAKGWHPQTMYDLDYWGQGTLVTV SSGGGGSGGGGSGGGGNEIVLTQSPGTLSL SPGERATLSCRASQNVSTNYLAWYQQKPGQ APRLLIYGASSRATGIPDRFSGSGSGTDFT LTISRLEPEDFAVYYCQQLVTNPPTFGQGT KVEIKAAGSDQEPKSSDKTHTCPPCSAPEL LGGSSVFLFPPKPKDTLMISRTPEVTCVVV DVSHEDPEVKFNWYVDGVEVHNAKTKPREE QYNSTYRVVSVLTVLHQDWLNGKEYKCKVS NKALPAPIEKTISKAKGQPREPQVYTLPPS RDELTKNQVSLTCLVKGFYPSDIAVEWESN | 503 |

TABLE 8-continued

Sequences.

| SEQ ID NO: | Molecule | Region | Scheme | Sequence | Length |
|---|---|---|---|---|---|
| | | | | GQPENNYKTTPPVLDSDGSFFLYSKLTVDK SRWQQGNVFSCSVMHEALHNHYTQKSLSLS PGKGSGDYKDDDDKGSGHHHHHH | |
| 212 | 1557-A05 | scFv-Fc | | MEVQLLESGGGLVQPGGSLRLSCAASGFTF GGSSMSWVRQAPGKGLEWVGAIGGGEGSTG YADSVKGRFTISRDNSKNTLYLQMNSLRAE DTAVYYCAKGWHDSLYDRDYWGQGTLVTV SSGGGGSGGGGSGGGGSEIVLTQSPGTLSL SPGERATLSCSASQTVSSSYIAWYQQKPGQ APRLLIYGASSRATGIPDRFGGSGSGTDFT LTISRLEPEDFAVYYCQQLLTSPPTFGQGT KVEIKAAGSDQEPKSSDKTHTCPPCSAPEL LGGSSVFLFPPKPKDTLMISRTPEVTCVVV DVSHEDPEVKFNWYVDGVEVHNAKTKPREE QYNSTYRVVSVLTVLHQDWLNGKEYKCKVS NKALPAPIEKTISKAKGQPREPQVYTLPPS RDELTKNQVSLTCLVKGFYPSDIAVEWESN GQPENNYKTTPPVLDSDGSFFLYSKLTVDK SRWQQGNVFSCSVMHEALHNHYTQKSLSLS PGKGSGDYKDDDDKGSGHHHHHH | 503 |
| 213 | 1557-B03 | scFv-Fc | | MEVQLLESGGGLVQPGGSLRLSCAASGFTF RSSSMSWVRQAPGKGLEWVGAIGGHEGYTG YADSVKGRFTISRDNSKNTLYLQMNSLRAE DTAVYYCAKGWNPQTLYHLDYWGQGTLVTV SSGGGGSGGGGSGGGGSEIVLTQSPGTLSL SPGERATLSCRASQKCSSSSMAWYQQKPGQ APRLLIYGASSRATGIPDRFSGSGSGTDFT LTISRLEPEDFAVYYCQQLQTSPPTFGQGT KVEIKAAGSDQEPKSSDKTHTCPPCSAPEL LGGSSVFLFPPKPKDTLMISRTPEVTCVVV DVSHEDPEVKFNWYVDGVEVHNAKTKPREE QYNSTYRVVSVLTVLHQDWLNGKEYKCKVS NKALPAPIEKTISKAKGQPREPQVYTLPPS RDELTKNQVSLTCLVKGFYPSDIAVEWESN GQPENNYKTTPPVLDSDGSFFLYSKLTVDK SRWQQGNVFSCSVMHEALHNHYTQKSLSLS PGKGSGDYKDDDDKGSGHHHHHH | 503 |
| 214 | 1557-B10 | scFv-Fc | | MEVQLLESGGGLVQPGGSLRLSCAASGFTF SGCSMSWVRQAPGKGLEWVGAIAGGEGNTG YADSVKGRFTISRDNSKNTLYLQMNSLRAE DTAVYYCAKGWHPQTLYDLDYWGQGTLVTV SSGGGGSGGGGSGGGGSEIVLTQSPGTLSL SPGERATLSCRASQGLASRYMAWYQQKPGQ APRLLIYGASSRATGIPDRFSGSGSGTDFT LTISRLEPEDFAVYYCQQVMTIPPTFGQGT KVEIKAAGSDQEPKSSDKTHTCPPCSAPEL LGGSSVFLFPPKPKDTLMISRTPEVTCVVV DVSHEDPEVKFNWYVDGVEVHNAKTKPREE QYNSTYRVVSVLTVLHQDWLNGKEYKCKVS NKALPAPIEKTISKAKGQPREPQVYTLPPS RDELTKNQVSLTCLVKGFYPSDIAVEWESN GQPENNYKTTPPVLDSDGSFFLYSKLTVDK SRWQQGNVFSCSVMHEALHNHYTQKSLSLS PGKGSGDYKDDDDKGSGHHHHHH | 503 |
| 215 | 1557-C06 | svFv-Fc | | MEVQLLESGGGLVQPGGSLRLSCAASGFTF RGASMSWVRQAPGKGLEWVGAIDGSQGSTG YADSVKGRFTISRDNSKNTLYLQMNSLRAE DTAVYYCAKGWHPQTMYDLDYWGQGTLVTV SSGGCGSGGGGSGGGGSEIVLTQSPGTLSL SPGERATLSCRASQRGTSSYLAWYQQKPGQ APRLLIYGASSRATGIPDRFSGSGSGTDFT LTISRLEPEDFAVYYCQQHVTSPPTFGQGT KVEIKAAGSDQEPKSSDKTHTCPPCSAPEL LGGSSVFLFPPKPKDTLMISRTPEVTCVVV DVSHEDPEVKFNWYVDGVEVHNAKTKPREE QYNSTYRVVSVLTVLHQDWLNGKEYKCKVS NKALPAPIEKTISKAKGQPREPQVYTLPPS RDELTKNQVSLTCLVKGFYPSDIAVEWESN GQPENNYKTTPPVLDSDGSFFLYSKLTVDK SRWQQGNVFSCSVMHEALHNHYTQKSLSLS PGKGSGDYKDDDDKGSGHHHHHH | 503 |

TABLE 8-continued

Sequences.

| SEQ ID NO: | Molecule | Region | Scheme | Sequence | Length |
|---|---|---|---|---|---|
| 216 | 1557-E07 | scFv-Fc | | MEVQLLESGGGLVQPGGSLRLSCAASGFTF<br>SGSSMSWVRQAPGKGLEWVGAIDGGEGSTG<br>YADSVKGRFTISRDNSKNTLYLQMNSLRAE<br>DTAVYYCAKGWHPQTLYDLDYWGQGTLVTV<br>SSGGGGSGGGGSGGGGSEIVLTQSPGTLSL<br>SPGERATMSCRASQVLSSSSLAWYQQKPGQ<br>APRLLIYGASSRATGIPDRFSGSGSGTDFA<br>LTISRLEPEDFAVYYCQQRAAPPPTFGQGT<br>KVEIKAAGSDQEPKSSDKTHTCPPCSAPEL<br>LGGSSVFLFPPKPKDTLMISRTPEVTCVVV<br>DVSHEDPEVKFNWYVDGVEVHNAKTKPREE<br>QYNSTYRVVSVLTVLHQDWLNGKEYKCKVS<br>NKALPAPIEKTISKAKGQPREPQVYTLPPS<br>RDELTKNQVSLTCLVKGFYPSDIAVEWESN<br>GQPENNYKTTPPVLDSDGSFFLYSKLTVDK<br>SRWQQGNVFSCSVMHEALHNHYTQKSLSLS<br>PGKGSGDYKDDDDKGSGHHHHHH | 503 |
| 217 | 1557-E08 | scFv-Fc | | MEVQLLESGGGLVQPGGSLRLSCAASGFTF<br>RASSMSWMRQAPGKGLEWVGAIDGGVGSTG<br>YADSVKGRFTISRDNSKNTLYLQMNSLRAE<br>DTAVYYCAKGWHPQTLYDLDYWGQGTLVTV<br>SSGGGGSGGGGSGGGGSEIVLTQSPGTLSL<br>SPGERATLSCRASQGDSSSVLAWYQQKPGQ<br>APRLLIYGASSRATGIPDRFSGSGSGTDFT<br>LTISRLEPEDFAVYYCQQLVPSPPTFGQGT<br>KVEIKAAGSDQEPKSSDKTHTCPPCSAPEL<br>LGGSSVFLFPPKPKDTLMISRTPEVTCVVV<br>DVSHEDPEVKFNWYVDGVEVHNAKTKPREE<br>QYNSTYRVVSVLTVLHQDWLNGKEYKCKVS<br>NKALPAPIEKTISKAKGQPREPQVYTLPPS<br>RDELTKNQVSLTCLVKGFYPSDIAVEWESN<br>GQPENNYKTTPPVLDSDGSFFLYSKLTVDK<br>SRWQQGNVFSCSVMHEALHNHYTQKSLSLS<br>PGKGSGDYKDDDDKGSGHHHHHH | 503 |
| 218 | 1557-E11 | scFv-Fc | | MEVQLLESGGGLVQPGGSLRLSCAASGFTF<br>RGSSMSWVRQAPGKGLEWVGAIDGGEGSTG<br>YADSVKGRFTINRDNSKNTLYLQMNSLRAE<br>DTAVYYCAKGWHPQSLYDLDYWGQGTLVTV<br>SSGGGGSGGGDSGGGGSEIVLTQSPGTLSL<br>SPGERATLSCRASQPVPNTTLAWYQQKPGQ<br>APRLLIYGASSRATGIPDRFSGSGSGTDFT<br>LTISRLEPEDFAAYYCQQLVPSPPTFGQGT<br>KVEIKAAGSDQEPKSSDKTHTCPPCSAPEL<br>LGGSSVFLFPPKPKDTLMISRTPEVTCVVV<br>DVSHEDPEVKFNWYVDGVEVHNAKTKPREE<br>QYNSTYRVVSVLTVLHQDWLNGKEYKCKVS<br>NKALPAPIEKTISKAKGQPREPQVYTLPPS<br>RDELTKNQVSLTCLVKGFYPSDIAVEWESN<br>GQPENNYKTTPPVLDSDGSFFLYSKLTVDK<br>SRWQQGNVFSCSVMHEALHNHYTQKSLSLS<br>PGKGSGDYKDDDDKGSGHHHHHH | 503 |
| 219 | 1557-F01 | scFv-Fc | | MEVQLLESGGGLVQPGGSLRLSCAASGFTF<br>SGSSMSWVRQAPGKGLEWVGAIDGGEGSTG<br>YADSVKGRFTISRDNSKNTLYLQMNSLRAE<br>DTAVYYCAKGWHPQTLYDLDYWGQGTLVTV<br>SSGGGGSGGGGSGGGGSEIVLTQSPGTLSL<br>SPGERATLSCRASQSVSSSKLAWYQQKPGQ<br>APRLLIYGASSRATGIPDRFSGYGSGTDFT<br>LTISRLEPEDFAVYYCQQLETIPPTFGQGT<br>KVEIKAAGSDQEPKSSDKTHTCPPCSAPEL<br>LGGSSVFLFPPKPKDTLMISRTPEVTCVVV<br>DVSHEDPEVKFNWYVDGVEVHNAKTKPREE<br>QYNSTYRVVSVLTVLHQDWLNGKEYKCKVS<br>NKALPAPIEKTISKAKGQPREPQVYTLPPS<br>RDELTKNQVSLTCLVKGFYPSDIAVEWESN<br>GQPENNYKTTPPVLDSDGSFFLYSKLTVDK<br>SRWQQGNVFSCSVMHEALHNHYTQKSLSLS<br>PGKGSGDYKDDDDKGSGHHHHHH | 503 |
| 220 | 1557-F02 | scFv-Fv | | MEVQLLESGGGLVQPGGSLRLSCAASGFTF<br>RGSSMSWVRQAPGKGLEWVGAIDGGEGSTG<br>YADSVKGRFTISRDNSKNTLYLQMNSLRAE<br>DTAVYYCAKGWHPQTMYNLDYWGQGTLVTV | 503 |

TABLE 8-continued

Sequences.

| SEQ ID NO: | Molecule | Region | Scheme | Sequence | Length |
|---|---|---|---|---|---|
| | | | | SSGGGGSGGGGSGGGGSEIVLTQSPGTLSL SPGERATLSCRASQSVSSSYLAWYQQKPGQ APRLLIYGASSRATGIPDRFSGSGSGTDFT LTISRLEPEDFAVYYCQQLFNSPPTFGQGT KVEIKAAGSDQEPKSSDKTHTCPPCSAPEL LGGSSVFLFPPKPKDTLMISRTPEVTCVVV DVSHEDPEVKFNWYVDGVEVHNAKTKPREE QYNSTYRVVSVLTVLHQDWLNGKEYKCKVS NKALPAPIEKTISKAKGQPREPQVYTLPPS RDELTKNQVSLTCLVKGFYPSDIAVEWESN GQPENNYKTTPPVLDSDGSFFLYSKLTVDK SRWQQGNVFSCSVMHEALHNHYTQKSLSLS PGKGSGDYKDDDDKGSGHHHHHH | |
| 221 | 1557-F03 | scFv-Fc | | MEVQLLESGGGLVQPGGSLRLSCAASGFTF SGSSMSWVRQAPGKGLEWVGAIAGGGGSTG YADSVKGRFTISRDNSKNTLYLQMNSLRAE DTAVYYCAKGWHPQTLYDLDYWGQGTLVTV SSGGGGSGGGGSGGGGSEIVLTQSPGTLSL SPGERATLSCRASQSVKTSDLAWYQQKPGQ APRLLIYGASSRATGIPDRFSGSGSGTDFT LTISRLEPEDFAVYYCQQLVSKPPTFGQGT KVEIKAAGSDQEPKSSDKTHTCPPCSAPEL LGGSSVFLFPPKPKDTLMISRTPEVTCVVV DVSHEDPEVKFNWYVDGVEVHNAKTKPREE QYNSTYRVVSVLTVLHQDWLNGKEYKCKVS NKALPAPIEKTISKAKGQPREPQVYTLPPS RDELTKNQVSLTCLVKGFYPSDIAVEWESN GQPENNYKTTPPVLDSDGSFFLYSKLTVDK SRWQQGNVFSCSVMHEALHNHYTQKSLSLS PGKGSGDYKDDDDKGSGHHHHHH | 503 |
| 222 | 1557-F05 | scFv-Fc | | MEVQLLESGGGLVQPGGSLRLSCAASGFTF RGSSMSWVRQAPGKGLEWVGAIDGGEGSTG YADSVKGRFTISRDNSKNTLYLQMNSLRAE DTAVYYCAKDWHPQTLYDLDYWGQGTLVTV SSGGGGSGGGGSGGGGSEIVLTQSPGTLSL SPGERATLSCRASQTVSPSVLAWYQQKPGQ APRLLIYGASSRATGIPGRFSGSGSGTDFT LTISRLEPEDFAVYYCQQLVTNPPTFGQGT KVEIKAAGSDQEPKSSDKTHTCPPCSAPEL LGGSSVFLFPPKPKDTLMISRTPEVTCVVV DVSHEDPEVKFNWYVDGVEVHNAKTKPREE QYNSTYRVVSVLTVLHQDWLNGKEYKCKVS NKALPAPIEKTISKAKGQPREPQVYTLPPS RDELTKNQVSLTCLVKGFYPSDIAVEWESN GQPENNYKTTPPVLDSDGSFFLYSKLTVDK SRWQQGNVFSCSVMHEALHNHYTQKSLSLS PGKGSGDYKDDDDKGSGHHHHHH | 503 |
| 223 | 1557-G01 | scFv-Fc | | MEVQLLESGGGLVQPGGSLRLSCAASGFTF SVTSMSWMRQAPGKGLEWVGAIAGGEGSTG YADSVKGRFTISRDNSKNTLYLQMNSLRAE DTAVYYCAKGWHPQTLYDLDYWGQGTLVTV SSGGGGSGGGGSGGGGSEIVLTQSPGTLSL SPGERATMSCRASQVLSSSSLAWYQQKPGQ APRLLIYGASSRATGIPDRFSGSGSGTDFT LTISRLEPEDFAVYYCQQLVTSPPTFGQGT KVEIKAAGSDQEPKSSDKTHTCPPCSAPEL LGGSSVFLFPPKPKDTLMISRTPEVTCVVV DVSHEDPEVKFNWYVDGVEVHNAKTKPREE QYNSTYRVVSVLTVLHQDWLNGKEYKCKVS NKALPAPIEKTISKAKGQPREPQVYTLPPS RDELTKNQVSLTCLVKGFYPSDIAVEWESN GQPENNYKTTPPVLDSDGSFFLYSKLTVDK SRWQQGNVFSCSVMHEALHNHYTQKSLSLS PGKGSGDYKDDDDKGSGHHHHHH | 503 |
| 224 | 1557-G03 | scFv-Fc | | MEVQLLESGGGLVQPGGSLRLSCAASGFTF GGSSMSWVRQAPGKGLEWVGAIGGGEGYTG YADSVKGRFTISRDNSKNTLYLQMNSLRAE DTAVYYCAKGWHPQTLYDLDYWGQGTLVTV SSGGGGSGGGGSGGGGSEIVLTQSPGTLSL SPGERATLSCRASQSVHSSYLAWYQQKPGQ APRLLIYGASSRATGIPDRFSGSGSGTDFT LTISRLEPEDFAVYYCQQLLSSPPTFGQGT | 503 |

TABLE 8-continued

Sequences.

| SEQ ID NO: | Molecule | Region | Scheme | Sequence | Length |
|---|---|---|---|---|---|
| | | | | KVEIKAAGSDQEPKSSDKTHTCPPCSAPEL<br>LGGSSVFLFPPKPKDTLMISRTPEVTCVVV<br>DVSHEDPEVKFNWYVDGVEVHNAKTKPREE<br>QYNSTYRVVSVLTVLHQDWLNGKEYKCKVS<br>NKALPAPIEKTISKAKGQPREPQVYTLPPS<br>RDELTKNQVSLTCLVKGFYPSDIAVEWESN<br>GQPENNYKTTPPVLDSDGSFFLYSKLTVDK<br>SRWQQGNVFSCSVMHEALHNHYTQKSLSLS<br>PGKGSGDYKDDDDKGSGHHHHHH | |
| 225 | 1557-G04 | scFv-Fc | | MEVQLLESGGGLVQPGGSLRLSCAASGFTF<br>CGSSMSWVRQAPGKGLEWVGAIDGGVGSTG<br>YADSVKGRFTISRDNSKNTLYLQMNSLRAE<br>DTAVYYCAKGWHPQTLYDLDYWGQGTLVTV<br>SSGGGDSGGGGSGGGGSEIVLTQSPGTLSL<br>SPGERATLSCRASQSVSSSYLAWYQQKPGQ<br>APRLLIYGASSRATGIPDRFSGSGSGTDFT<br>LTISRLEPEDFAVYYCQQDSFVPPTFGQGT<br>KVEIKAAGSDQEPKSSDKTHTCPPCSAPEL<br>LGGSSVFLFPPKPKDTLMISRTPEVTCVVV<br>DVSHEDPEVKFNWYVDGVEVHNAKTKPREE<br>QYNSTYRVVSVLTVLHQDWLNGKEYKCKVS<br>NKALPAPIEKTISKAKGQPREPQVYTLPPS<br>RDELTKNQVSLTCLVKGFYPSDIAVEWESN<br>GQPENNYKTTPPVLDSDGSFFLYSKLTVDK<br>SRWQQGNVFSCSVMHEALHNHYTQKSLSLS<br>PGKGSGDYKDDDDKGSGHHHHHH | 503 |
| 226 | 1557-G06 | scFv-Fc | | MEVQLLESGGGLVQPGGSLRLSCAASGFTF<br>SGFSMSWVRQAPGKGLEWVGAIDGGEGSTG<br>YADSVKGRFTISRDNSKNTLYLQMNSLRAE<br>DTAVYYCAKGWHPQTLYHLDYWGQGTLVTV<br>SSGGGGSGGGGSGGGGSEIVLTQSPGTLSL<br>SPGERATLSCRASQSIPSSYLAWYQQEPGQ<br>APRLLIYGASSRATGIPDRFSGSGSGTDFT<br>LTISRLEPEDFAVYYCQQLATSPPTFGQGT<br>KVEIKAAGSDQEPKSSDKTHTCPPCSAPEL<br>LGGSSVFLFPPKPKDTLMISRTPEVTCVVV<br>DVSHEDPEVKFNWYVDGVEVHNAKTKPREE<br>QYNSTYRVVSVLTVLHQDWLNGKEYKCKVS<br>NKALPAPIEKTISKAKGQPREPQVYTLPPS<br>RDELTKNQVSLTCLVKGFYPSDIAVEWESN<br>GQPENNYKTTPPVLDSDGSFFLYSKLTVDK<br>SRWQQGNVFSCSVMHEALHNHYTQKSLSLS<br>PGKGSGDYKDDDDKGSGHHHHHH | 503 |
| 227 | 1557-H04 | scFv-Fc | | MEVQLLESGGGLVQPGGSLRLSCAASGFTF<br>SVTSMSWMRQAPGKGLEWVGAIAGGEGSTG<br>YADSVKGRFTISRDNSKNTLYLQMNSLRAE<br>DTAVYYCAKGWHPQTLYDLDYWGQGTLVTV<br>SSGGGGSDGGGSGGGGSEIVLTQGPSTLSL<br>SPGERATLSCRASQSVSTGYLAWYQQKPGQ<br>APRLLIYGASSRATGIPDRFSGSGSGTDFT<br>LTISRLEPEDFAVYYCQQLVTRPPTFGQGT<br>KVEIKAAGSDQEPKSSDKTHTCPPCSAPEL<br>LGGSSVFLFPPKPKDTLMISRTPEVTCVVV<br>DVSHEDPEVKFNWYVDGVEVHNAKTKPREE<br>QYNSTYRVVSVLTVLHQDWLNGKEYKCKVS<br>NKALPAPIEKTISKAKGQPREPQVYTLPPS<br>RDELTKNQVSLTCLVKGFYPSDIAVEWESN<br>GQPENNYKTTPPVLDSDGSFFLYSKLTVDK<br>SRWQQGNVFSCSVMHEALHNHYTQKSLSLS<br>PGKGSGDYKDDDDKGSGHHHHHH | 503 |
| 228 | 1557-H10 | scFv-Fc | | MEVQLLESGGGLVQPGGSLRLSCAASGFTF<br>SGSSMSWVRQAPGKGLEWVGAIDGGEGSTG<br>YADSVKGRFTISRDNSKNTLYLQMNSLRAE<br>DTAVYYCAKGWHPQSMYDLDYWGQGTLVTV<br>SSGGGGSGGGGSGGGGSEIVLTQSPGTLSL<br>SPGERATMSCRASQVLSSSSLAWYQQKPGQ<br>APRLLIYGASSRATGIPDRFSGSGSGTDFT<br>LTISRLEPEDFAVYYCQQLVTAPPTFGQGT<br>KVEIKAAGSDQEPKSSDKTHTCPPCSAPEL<br>LGGSSVFLFPPKPKDTLMISRTPEVTCVVV<br>DVSHEDPEVKFNWYVDGVEVHNAKTKPREE<br>QYNSTYRVVSVLTVLHQDWLNGKEYKCKVS | 503 |

TABLE 8-continued

Sequences.

| SEQ ID NO: | Molecule | Region | Scheme | Sequence | Length |
|---|---|---|---|---|---|
| | | | | NKALPAPIEKTISKAKGQPREPQVYTLPPS RDELTKNQVSLTCLVKGFYPSDIAVEWESN GQPENNYKTTPPVLDSDGSFFLYSKLTVDK SRWQQGNVFSCSVMHEALHNHYTQKSLSLS PGKGSGDYKDDDDKGSGHHHHHH | |
| 229 | 1304-G11 | VH | | EVQLLESGGGLVRPGGSLRLSCAASGFTFS GSSMSWVRQAPGKGLEWVGAIDGGDGYTNY ADSVRGRFTISRDNSKNTLYLQMNSLRAED TAVYYCAKGWHPQTYYGLDYWGQGTLVTVS S | 121 |
| 230 | 1332-A05 | VH | | EVQLLEQSGAELVRPGTSVKISCKASDYAF ANRWLGWVKQRPGHGLEWIGDIFPGSGNIH YNEKFKGKATLTADKSSSTAYMQLSSLTFE DSAVYFCARLRNWEGPMDYWGQGTTVTVSS | 120 |
| 231 | 1332-C01 | VH | | EVQLLEQSGAELVRPGTSVKISCKASGYAF TNSWLGWVKQRPGHGLEWIGDIFPGSGNIH YNEKFKGKATLTADKSSSTAYMQLSSLTFE DSAVYFCARLRNWDMPMDYWGQGTTVTVSS | 120 |
| 232 | 1332-F11 | VH | | EVQLLEQSGAELVRPGTSVKISCKASGYAF ANRWLGWVKQRPGHGLEWIGDIFPGSGNIH YNEKFKGKATLTADKSSSTAYMQLSSLTFE DSAVYFCARLRNWEGPMDYWGQGTTVTVSS | 120 |
| 233 | 1464-A02 | VH | | EVQLLESGGGLVQPGGSLRLSCAASGFTFG VESMSWVRQAPGKGLEWVGAIDGGDGYTGY ADSVKDRFTISRDNSKNTLYLQMNSLRAED TAVYYCAKAWHPQTYYGVDYWGQGTLVTVS S | 121 |
| 234 | 1464-A08 | VH | | EVQLLESGGGLVQPGGSLRLSCAASGFTFS GSSMSWVRQAPGKGLEWVGAIAGGDGYTGY ADSVKGRFTISRDNSKNTLYLQMNSLRAED TAVYYCAKGWHRDYYGQDYWGQGTLVTVS S | 121 |
| 235 | 1464-B04 | VH | | EVQLLESGGGLVQPGGSLRLSCAASGFTFS GSSMSWVRQAPGKGLEWVGAIDGGEGYTSY ADSVKGRFTISRDNSKNTLYLQMNSLRAED TAVYYCAKGWHPQTLYDLDYWGQGTLVTVS S | 121 |
| 236 | 1557-A04 | VH | | EVQLLESGGGLVQPGGSLRLSCAASGFTFS GSSMSWVRQAPGKGLEWVGAIDGGEGSTAY ADSVKGRFTISRDNSKNTLYLQMNSLRAED TAVYYCAKGWHPQTMYDLDYWGQGTLVTVS S | 121 |
| 237 | 1557-A05 | VH | | EVQLLESGGGLVQPGGSLRLSCAASGFTFG GSSMSWVRQAPGKGLEWVGAIGGGEGSTGY ADSVKGRFTISRDNSKNTLYLQMNSLRAED TAVYYCAKGWHDQSLYDRDYWGQGTLVTVS S | 121 |
| 238 | 1557-B03 | VH | | EVQLLESGGGLVQPGGSLRLSCAASGFTFR SSSMSWVRQAPGKGLEWVGAIGGHEGYTGY ADSVKGRFTISRDNSKNTLYLQMNSLRAED TAVYYCAKGWNPQTLYHLDYWGQGTLVTVS S | 121 |
| 239 | 1557-B10 | VH | | EVQLLESGGGLVQPGGSLRLSCAASGFTFS GCSMSWVRQAPGKGLEWVGAIAGGEGNTGY ADSVKGRFTISRDNSKNTLYLQMNSLRAED TAVYYCAKGWHPQTLYDLDYWGQGTLVTVS S | 121 |
| 240 | 1557-C06 | VH | | EVQLLESGGGLVQPGGSLRLSCAASGFTFR GASMSWVRQAPGKGLEWVGAIDGSQGSTGY ADSVKGRFTISRDNSKNTLYLQMNSLRAED TAVYYCAKGWHPQTMYDLDYWGQGTLVTVS S | 121 |

TABLE 8-continued

Sequences.

| SEQ ID NO: | Molecule | Region | Scheme | Sequence | Length |
|---|---|---|---|---|---|
| 241 | 1557-E07 | VH | | EVQLLESGGGLVQPGGSLRLSCAASGFTFS GSSMSWVRQAPGKGLEWVGAIDGGEGSTGY ADSVKGRFTISRDNSKNTLYLQMNSLRAED TAVYYCAKGWHPQTLYDLDYWGQGTLVTVS S | 121 |
| 242 | 1557-E08 | VH | | EVQLLESGGGLVQPGGSLRLSCAASGFTFR ASSMSWMRQAPGKGLEWVGAIDGGVGSTGY ADSVKGRFTISRDNSKNTLYLQMNSLRAED TAVYYCAKGWHPQTLYDLDYWGQGTLVTVS S | 121 |
| 243 | 1557-E11 | VH | | EVQLLESGGGLVQPGGSLRLSCAASGFTFR GSSMSWVRQAPGKGLEWVGAIDGGEGSTGY ADSVKGRFTINRDNSKNTLYLQMNSLRAED TAVYYCAKGWHPQSLYDLDYWGQGTLVTVS S | 121 |
| 244 | 1557-F01 | VH | | EVQLLESGGGLVQPGGSLRLSCAASGFTFS GSSMSWVRQAPGKGLEWVGAIDGGEGSTGY ADSVKGRFTISRDNSKNTLYLQMNSLRAED TAVYYCAKGWHPQTLYDLDYWGQGTLVTVS S | 121 |
| 245 | 1557-F02 | VH | | EVQLLESGGGLVQPGGSLRLSCAASGFTFR GSSMSWVRQAPGKGLEWVGAIDGGEGSTGY ADSVKGRFTISRDNSKNTLYLQMNSLRAED TAVYYCAKGWHPQTMYNLDYWGQGTLVTVS S | 121 |
| 246 | 1557-F03 | VH | | EVQLLESGGGLVQPGGSLRLSCAASGFTFS GSSMSWVRQAPGKGLEWVGAIAGGGGSTGY ADSVKGRFTISRDNSKNTLYLQMNSLRAED TAVYYCAKGWHPQTLYDLDYWGQGTLVTVS S | 121 |
| 247 | 1557-F05 | VH | | EVQLLESGGGLVQPGGSLRLSCAASGFTFR GSSMSWVRQAPGKGLEWVGAIDGGEGSTGY ADSVKGRFTISRDNSKNTLYLQMNSLRAED TAVYYCAKDWHPQTLYDLDYWGQGTLVTVS S | 121 |
| 248 | 1557-G01 | VH | | EVQLLESGGGLVQPGGSLRLSCAASGFTFS VTSMSWMRQAPGKGLEWVGAIAGGEGSTGY ADSVKGRFTISRDNSKNTLYLQMNSLRAED TAVYYCAKGWHPQTLYDLDYWGQGTLVTVS S | 121 |
| 249 | 1557-G03 | VH | | EVQLLESGGGLVQPGGSLRLSCAASGFTFG GSSMSWVRQAPGKGLEWVGAIGGGEGYTGY ADSVKGRFTISRDNSKNTLYLQMNSLRAED TAVYYCAKGWHPQTLYDLDYWGQGTLVTVS S | 121 |
| 250 | 1557-G04 | VH | | EVQLLESGGGLVQPGGSLRLSCAASGFTFC GSSMSWVRQAPGKGLEWVGAIDGGVGSTGY ADSVKGRFTISRDNSKNTLYLQMNSLRAED TAVYYCAKGWHPQTLYDLDYWGQGTLVTVS S | 121 |
| 251 | 1557-G06 | VH | | EVQLLESGGGLVQPGGSLRLSCAASGFTFS GFSMSWVRQAPGKGLEWVGAIDGGEGSTGY ADSVKGRFTISRDNSKNTLYLQMNSLRAED TAVYYCAKGWHPQTLYHLDYWGQGTLVTVS S | 121 |
| 252 | 1557-H04 | VH | | EVQLLESGGGLVQPGGSLRLSCAASGFTFS VTSMSWMRQAPGKGLEWVGAIAGGEGSTGY ADSVKGRFTISRDNSKNTLYLQMNSLRAED TAVYYCAKGWHPQTLYDLDYWGQGTLVTVS S | 121 |
| 253 | 1557-H10 | VH | | EVQLLESGGGLVQPGGSLRLSCAASGFTFS GSSMSWVRQAPGKGLEWVGAIDGGEGSTGY ADSVKGRFTISRDNSKNTLYLQMNSLRAED | 121 |

TABLE 8-continued

Sequences.

| SEQ ID NO: | Molecule | Region | Scheme | Sequence | Length |
|---|---|---|---|---|---|
| | | | | TAVYYCAKGWHPQSMYDLDYWGQGTLVTVSS | |
| 254 | 1304-G11 | VL | | EIVLTQSPGTLSLSPGERATLSCRASQSVSSSYLAWYQQKPGQAPRLLIYGASSRATGIPDRFSGSSSGTDFTLTISRLEPEDFAVYYCQQYWGPPTFGQGTKVEIK | 108 |
| 255 | 1332-A05 | VL | | ELVMTQSPSSLTVTAGEKVTMSCKSSQSLLNSGNQKNYLTWYQQKPGQPPKLLIYWASTRESGVPDRFTGSGSGTDFTLTISSVQAEDLAVYYCQNDLSYPLTFGAGTKLEIK | 113 |
| 256 | 1332-C01 | VL | | ELVMTQSPSSLTVTAGEKVTMSCKSSQSLLNSGNQKNYLTWYQQKPGQPPKLLIYWASTRESGVPDRFTGSGSGTDFTLTISSVQAEDLAVYYCQNDYRYPLTFGAGTKLEIK | 113 |
| 257 | 1332-F11 | VL | | ELVMTQSPSSLTVTAGEKVTMSCKSSQSLLNSGNQKNYLTWYQQKPGQPPKLLIYRASTRESGVPDRFTGSGSGTDFTLTISSVQAEDLAVYYCQNDSSYPLTFGAGTKLEIK | 113 |
| 258 | 1464-A02 | VL | | EIVLTQSPGTLSLSPGERATLSCRASQSVSSSYLAWYQQKPGQAPRLLIYGASSRATGIPDRFSGSGSGTDFTLTISRLEPEDFAVYYCQQTSEAPPTFGQGTKVEIK | 108 |
| 259 | 1464-A08 | VL | | EIVLTQSPGTLSLSPGERATLGCRASQSVSSSYLAWYQQKPGQAPRLLIYGASSRATGIPDRFSGSGSGTDFTLTISRLEPEDFAVYYCQQNQAAPATFGQGTKVEIK | 108 |
| 260 | 1464-B04 | VL | | EIVLTQSPGTLSLSPGERATLSCRASQSVSSSYLAWYQQKPGQAPRLLIYGASSRATGIPDRFSGSGSGTDFTLTISRLEPEDFAVYYCQQLVTSPPTFGQGTKVEIK | 108 |
| 261 | 1557-A04 | VL | | EIVLTQSPGTLSLSPGERATLSCRASQNVSTNYLAWYQQKPGQAPRLLIYGASSRATGIPDRFSGSGSGTDFTLTISRLEPEDFAVYYCQQLVTNPPTFGQGTKVEIK | 108 |
| 262 | 1557-A05 | VL | | EIVLTQSPGTLSLSPGERATLSCSASQTVSSSYIAWYQQKPGQAPRLLIYGASSRATGIPDRFGGSGSGTDFTLTISRLEPEDFAVYYCQQLLTSPPTFGQGTKVEIK | 108 |
| 263 | 1557-B03 | VL | | EIVLTQSPGTLSLSPGERATLSCRASQKCSSSSMAWYQQKPGQAPRLLIYGASSRATGIPDRFSGSGSGTDFTLTISRLEPEDFAVYYCQQLQTSPPTFGQGTKVEIK | 108 |
| 264 | 1557-B10 | VL | | EIVLTQSPGTLSLSPGERATLSCRASQGLASRYMAWYQQKPGQAPRLLIYGASSRATGIPDRFSGSGSGTDFTLTISRLEPEDFAVYYCQQVMTIPPTFGQGTKVEIK | 108 |
| 265 | 1557-C06 | VL | | EIVLTQSPGTLSLSPGERATLSCRASQRGTSSYLAWYQQKPGQAPRLLIYGASSRATGIPDRFSGSGSGTDFTLTISRLEPEDFAVYYCQQHVTSPPTFGQGTKVEIK | 108 |
| 266 | 1557-E07 | VL | | EIVLTQSPGTLSLSPGERATMSCRASQVLSSSSLAWYQQKPGQAPRLLIYGASSRATGIPDRFSGSGSGTDFALTISRLEPEDFAVYYCQQRAAPPPTFGQGTKVEIK | 108 |
| 267 | 1557-E08 | VL | | EIVLTQSPGTLSLSPGERATLSCRASQGDSSSVLAWYQQKPGQAPRLLIYGASSRATGIPDRFSGSGSGTDFTLTISRLEPEDFAVYYCQQLVPSPPTFGQGTKVEIK | 108 |
| 268 | 1557-E11 | VL | | EIVLTQSPGTLSLSPGERATLSCRASQPVPNTTLAWYQQKPGQAPRLLIYGASSRATGIP | 108 |

TABLE 8-continued

Sequences.

| SEQ ID NO: | Molecule | Region | Scheme | Sequence | Length |
|---|---|---|---|---|---|
| | | | | DRFSGSGSGTDFTLTISRLEPEDFAAYYCQ QLVPSPPTFGQGTKVEIK | |
| 269 | 1557-F01 | VL | | EIVLTQSPGTLSLSPGERATLSCRASQSVS SSKLAWYQQKPGQAPRLLIYGASSRATGIP DRFSGYGSGTDFTLTISRLEPEDFAVYYCQ QLETIPPTFGQGTKVEIK | 108 |
| 270 | 1557-F02 | VL | | EIVLTQSPGTLSLSPGERATLSCRASQSVS SSYLAWYQQKPGQAPRLLIYGASSRATGIP DRFSGSGSGTDFTLTISRLEPEDFAVYYCQ QLFNSPPTFGQGTKVEIK | 108 |
| 271 | 1557-F03 | VL | | EIVLTQSPGTLSLSPGERATLSCRASQSVK TSDLAWYQQKPGQAPRLLIYGASSRATGIP DRFSGSGSGTDFTLTISRLEPEDFAVYYCQ QLVSKPPTFGQGTKVEIK | 108 |
| 272 | 1557-F05 | VL | | EIVLTQSPGTLSLSPGERATLSCRASQTVS PSVLAWYQQKPGQAPRLLIYGASSRATGIP GRFSGSGSGTDFTLTISRLEPEDFAVYYCQ QLVTNPPTFGQGTKVEIK | 108 |
| 273 | 1557-G01 | VL | | EIVLTQSPGTLSLSPGERATMSCRASQVLS SSSLAWYQQKPGQAPRLLIYGASSRATGIP DRFSGSGSGTDFTLTISRLEPEDFAVYYCQ QLVTSPPTFGQGTKVEIK | 108 |
| 274 | 1557-G03 | VL | | EIVLTQSPGTLSLSPGERATLSCRASQSVH SSYLAWYQQKPGQAPRLLIYGASSRATGIP DRFSGSGSGTDFTLTISRLEPEDFAVYYCQ QLLSSPPTFGQGTKVEIK | 108 |
| 275 | 1557-G04 | VL | | EIVLTQSPGTLSLSPGERATLSCRASQSVS SSYLAWYQQKPGQAPRLLIYGASSRATGIP DRFSGSGSGTDFTLTISRLEPEDFAVYYCQ QDSFVPPTFGQGTKVEIK | 108 |
| 276 | 1557-G06 | VL | | EIVLTQSPGTLSLSPGERATLSCRASQSIP SSYLAWYQQEPGQAPRLLIYGASSRATGIP DRFSGSGSGTDFTLTISRLEPEDFAVYYCQ QLATSPPTFGQGTKVEIK | 108 |
| 277 | 1557-H04 | VL | | EIVLTQGPSTLSLSPGERATLSCRASQSVS TGYLAWYQQKPGQAPRLLIYGASSRATGIP DRFSGSGSGTDFTLTISRLEPEDFAVYYCQ QLVTRPPTFGQGTKVEIK | 108 |
| 278 | 1557-H10 | VL | | EIVLTQSPGTLSLSPGERATMSCRASQVLS SSSLAWYQQKPGQAPRLLIYGASSRATGIP DRFSGSGSGTDFTLTISRLEPEDFAVYYCQ QLVTAPPTFGQGTKVEIK | 108 |
| 279 | IgG1 Constant Region | | | ASTKGPSVFPLAPSSKSTSGGTAALGCLVK DYFPEPVTVSWNSGALTSGVHTFPAVLQSS GLYSLSSVVTVPSSSLGTQTYICNVNHKPS NTKVDKKVEPKSCDKTHTCPPCPAPELLGG PSVFLFPPKPKDTLMISRTPEVTCVVVDVS HEDPEVKFNWYVDGVEVHNAKTKPREEQYN STYRVVSVLTVLHQDWLNGKEYKCKVSNKA LPAPIEKTISKAKGQPREPQVYTLPPSREE MTKNQVSLTCLVKGFYPSDIAVEWESNGQP ENNYKTTPPVLDSDGSFFLYSKLTVDKSRW QQGNVFSCSVMHEALHNHYTQKSLSLSPGK | 330 |
| 280 | IgG1 Fc from scFv-Fc | | | AAGSDQEPKSSDKTHTCPPCSAPELLGGSS VFLFPPKPKDTLMISRTPEVTCVVVDVSHE DPEVKFNWYVDGVEVHNAKTKPREEQYNST YRVVSVLTVLHQDWLNGKEYKCKVSNKALP APIEKTISKAKGQPREPQVYTLPPSRDELT KNQVSLTCLVKGFYPSDIAVEWESNGQPEN NYKTTPPVLDSDGSFFLYSKLTVDKSRWQQ GNVFSCSVMHEALHNHYTQKSLSLSPGKGS<br><br>GDYKDDDDKGSG | 252<br><br>252 |

TABLE 8-continued

Sequences.

| SEQ ID NO: | Molecule | Region | Scheme | Sequence | Length |
|---|---|---|---|---|---|
| 281 | Lambda Constant Region | | | GQPKAAPSVTLFPPSSEELQANKATLVCLI SDFYPGAVTVAWKADSSPVKAGVETTTPSK QSNNKYAASSYLSLTPEQWKSHRSYSCQVT HEGSTVEKTVAPTECS | 106 |
| 282 | Kappa Constant Region | | | RTVAAPSVFIFPPSDEQLKSGTASVVCLLN NFYPREAKVQWKVDNALQSGNSQESVTEQD SKDSTYSLSSTLTLSKADYEKHKVYACEVT HQGLSSPVTKSFNRGEC | 107 |
| 283 | Linker | | | GGGGSGGGGSGGGGS | 15 |
| 284 | Linker | | | AAGSDQ | 6 |
| 285 | His Tag with Linker | | | GSGDYKDDDDKGSGHHHHHH | 20 |
| 286 | mAb_3-1 | CDR-H1 | Chothia | GYAFTNY | 7 |
| 287 | mAb_3-5 | CDR-H1 | Chothia | GYTFTSY | 7 |
| 288 | mAb_4-1 | CDR-H1 | Chothia | GYAFTNY | 7 |
| 289 | mAb_4-7 | CDR-H1 | Chothia | GYTFTNY | 7 |
| 290 | mAb_5-10 | CDR-H1 | Chothia | GYAFTNY | 7 |
| 291 | mAb_3-1 | CDR-H1 | Kabat | NYWLG | 5 |
| 292 | mAb_3-5 | CDR-H1 | Kabat | SYGLS | 5 |
| 293 | mAb_4-1 | CDR-H1 | Kabat | NYWLG | 5 |
| 294 | mAb_4-7 | CDR-H1 | Kabat | NYGLS | 5 |
| 295 | mAb_5-10 | CDR-H1 | Kabat | NYWLG | 5 |
| 296 | mAb_3-1 | CDR-H2 | Chothia | FPGSGN | 6 |
| 297 | mAb_3-5 | CDR-H2 | Chothia | YPRIGN | 6 |
| 298 | mAb_4-1 | CDR-H2 | Chothia | FPGSGN | 6 |
| 299 | mAb_4-7 | CDR-H2 | Chothia | YPRIGN | 6 |
| 300 | mAb_5-10 | CDR-H2 | Chothia | FPGSGN | 6 |
| 301 | mAb_3-1 | CDR-H2 | Kabat | DLFPGSGNTHYNERFRG | 17 |
| 302 | mAb_3-5 | CDR-H2 | Kabat | EVYPRIGNAYYNEKFKG | 17 |
| 303 | mAb_4-1 | CDR-H2 | Kabat | DIFPGSGNAHYNEKFKG | 17 |
| 304 | mAb_4-7 | CDR-H2 | Kabat | EVYPRIGNAYYNEKFKG | 17 |
| 305 | mAb_5-10 | CDR-H2 | Kabat | DIFPGSGNIHYNEKFKG | 17 |
| 306 | mAb_3-1 | CDR-H3 | | LRNWDEAMDY | 10 |
| 307 | mAb_3-5 | CDR-H3 | | RGSYGSNYDWYFDV | 14 |
| 308 | mAb_4-1 | CDR-H3 | | LRNWDEAMDY | 10 |
| 309 | mAb_4-7 | CDR-H3 | | RGSYDTNYDWYFDV | 14 |
| 310 | mAb_5-10 | CDR-H3 | | LRNWDEPMDY | 10 |
| 311 | mAb_3-1 | CDR-L1 | | RASKSISKYLA | 11 |
| 312 | mAb_3-5 | CDR-L1 | | RSSQSLVHSNGNTYLH | 16 |
| 313 | mAb_4-1 | CDR-L1 | | KSSQSLLNSGNQKNYLA | 17 |
| 314 | mAb_4-7 | CDR-L1 | | RSSQSLVHSNGNTYLH | 16 |
| 315 | mAb_5-10 | CDR-L1 | | KSSQSLLNSGNQKNYLT | 17 |

TABLE 8-continued

Sequences.

| SEQ ID NO: | Molecule | Region | Scheme | Sequence | Length |
|---|---|---|---|---|---|
| 316 | mAb_3-1 | CDR-L2 | | SGSTLQS | 7 |
| 317 | mAb_3-5 | CDR-L2 | | KVSNRFS | 7 |
| 318 | mAb_4-1 | CDR-L2 | | GASTRES | 7 |
| 319 | mAb_4-7 | CDR-L2 | | KVSNRFS | 7 |
| 320 | mAb_5-10 | CDR-L2 | | WASTRES | 7 |
| 321 | mAb_3-1 | CDR-L3 | | QQHNEYPYT | 9 |
| 322 | mAb_3-5 | CDR-L3 | | SQSTHVPYT | 9 |
| 323 | mAb_4-1 | CDR-L3 | | QNDYSYPYT | 9 |
| 324 | mAb_4-7 | CDR-L3 | | SQSTHVPYT | 9 |
| 325 | mAb_5-10 | CDR-L3 | | QNDYSYPLT | 9 |
| 326 | mAb_3-1 | VH | | EVQLLEQSGAELVKPGASVKISCKASGYAFTNYWLGWVKQRPGHGLEWIGDLFPGSGNTHYNERFRGKATLTADKSSSTAFMQLSSLTSEDSAVYFCARLRNWDEAMDYWGQGTTVTVSS | |
| 327 | mAb_3-5 | VH | | EVQLLEQSGAELVRPGTSVKLSCKASGYTFTSYGLSWVKQRTGQGLEWIGEVYPRIGNAYYNEKFKGKATLTADKSSSTASMELRSLTSEDSAVYFCARRGSYGSNYDWYFDVWGQGTTVTVSS | |
| 328 | mAb_4-1 | VH | | EVQLLEQSGAELVRPGTSVKISCKASGYAFTNYWLGWVKQRPGHGLEWVGDIFPGSGNAHYNEKFKGKATLTADKSSYTAYMQLSSLTSEDSAVYFCARLRNWDEAMDYWGQGTTVTVSS | |
| 329 | mAb_4-7 | VH | | EVQLLEQSGAELARPGASVKLSCKASGYTFTNYGLSWVKQRPGQVLEWIGEVYPRIGNAYYNEKFKGKATLTADKSSSTASMELRSLTSEDSAVYFCARRGSYDTNYDWYFDVWGQGTTVTVSS | |
| 330 | mAb_5-10 | VH | | EVQLLEQSGAELVRPGTSVKISCKASGYAFTNYWLGWVKQRPGHGLEWIGDIFPGSGNIHYNEKFKGKATLTADKSSSTAYMQLSSLTFEDSAVYFCARLRNWDEPMDYWGQGTTVTVSS | |
| 331 | mAb_3-1 | VL | | ELVMTQSPSYLAASPGETITINCRASKSISKYLAWYQEKPGKTNKLLIYSGSTLQSGIPSRFSGSGSGTDFTLTISSLEPEDFAMYYCQQHNEYPYTFGGGTKLEIK | |
| 332 | mAb_3-5 | VL | | ELVMTQTPLSLPVSLGDQASISCRSSQSLVHSNGNTYLHWYLQKPGQSPKLLIYKVSNRFSGVPDRFSGSGSGTDFTLKISRVEAEDLGVYFCSQSTHVPYTFGGGTKLEIK | |
| 333 | mAb_4-1 | VL | | ELVMTQSPSSLSVSAGEKVTMSCKSSQSLLNSGNQKNYLAWYQQKPGQPPKLLIYGASTRESGVPDRFTGSGSGTDFTLTISSVQAEDLAVYYCQNDYSYPYTFGGGTKLEIK | |
| 334 | mAb_4-7 | VL | | ELVMTQTPLSLPVSLGDQASISCRSSQSLVHSNGNTYLHWYLQKPGQSPKLLIYKVSNRFSGVPDRFSGSGSGTDFTLKISRVEAEDLGVYFCSQSTHVPYTFGGGTKLEIK | |
| 335 | mAb_5-10 | VL | | ELVMTQSPSSLTVTAGEKVTMSCKSSQSLLNSGNQKNYLTWYQQKPGQPPKLLIYWASTRESGVPDRFTGSGSGTDFTLTISSVQAEDLAVYYCQNDYSYPLTFGAGTKLEIK | |
| 336 | mAb_5-10 | scFv | | ELVMTQSPSSLTVTAGEKVTMSCKSSQSLLNSGNQKNYLTWYQQKPGQPPKLLIYWASTRESGVPDRFTGSGSGTDFTLTISSVQAEDL | |

TABLE 8-continued

Sequences.

| SEQ ID NO: | Molecule | Region | Scheme | Sequence | Length |
|---|---|---|---|---|---|
| | | | | AVYYCQNDYSYPLTFGAGTKLEIKGGGGSG GGGSGGGGSEVQLLEQSGAELVRPGTSVKI SCKASGYAFTNYWLGWVKQRPGHGLEWIGD IFPGSGNIHYNEKFKGKATLTADKSSSTAY MQLSSLTFEDSAVYFCARLRNWDEPMDYWG QGTTVTVSS | |
| 337 | 1304-G11 | scFv | | MEVQLLESGGGLVRPGGSLRLSCAASGFTF SGSSMSWVRQAPGKGLEWVGAIDGGDGYTN YADSVRGRFTISRDNSKNTLYLQMNSLRAE DTAVYYCAKGWHPQTYYGLDYWGQGTLVTV SSGGGGSGGGGSGGGGSEIVLTQSPGTLSL SPGERATLSCRASQSVSSSYLAWYQQKPGQ APRLLIYGASSRATGIPDRFSGSSSGTDFT LTISRLEPEDFAVYYCQQYWYGPPTFGQGT KVEIK | 245 |
| 338 | 1332-A05 | scFv | | MELVMTQSPSSLTVTAGEKVTMSCKSSQSL LNSGNQKNYLTWYQQKPGQPPKLLIYWAST RESGVPDRFTGSGSGTDFTLTISSVQAEDL AVYYCQNDLSYPLTFGAGTKLEIKGGGGSG GGGSGGGGSEVQLLEQSGAELVRPGTSVKI SCKASDYAFANRWLGWVKQRPGHGLEWIGD IFPGSGNIHYNEKFKGKATLTADKSSSTAY MQLSSLTFEDSAVYFCARLRNWEGPMDYWG QGTTVTVSS | 249 |
| 339 | 1332-C01 | scFv | | MELVMTQSPSSLTVTAGEKVTMSCKSSQSL LNSGNQKNYLTWYQQKPGQPPKLLIYWAST RESGVPDRFTGSGSGTDFTLTISSVQAEDL AVYYCQNDYRYPLTFGAGTKLEIKGGGGSG GGGSGGGGSEVQLLEQSGAELVRPGTSVKI SCKASGYAFTNSWLGWVKQRPGHGLEWIGD IFPGSGNIHYNEKFKGKATLTADKSSSTAY MQLSSLTFEDSAVYFCARLRNWDMPMDYWG QGTTVTVSS | 249 |
| 340 | 1332-F11 | scFv | | MELVMTQSPSSLTVTAGEKVTMSCKSSQSL LNSGNQKNYLTWYQQKPGQPPKLLIYRAST RESGVPDRFTGSGSGTDFTLTISSVQAEDL AVYYCQNDSSYPLTFGAGTKLEIKGGGGSG GGGSGGGGSEVQLLEQSGAELVRPGTSVKI SCKASGYAFANRWLGWVKQRPGHGLEWIGD IFPGSGNIHYNEKFKGKATLTADKSSSTAY MQLSSLTFEDSAVYFCARLRNWEGPMDYWG QGTTVTVSS | 249 |
| 341 | 1464-A02 | scFv | | MEVQLLESGGGLVQPGGSLRLSCAASGFTF GVESMSWVRQAPGKGLEWVGAIDGGDGYTG YADSVKDRFTISRDNSKNTLYLQMNSLRAE DTAVYYCAKAWHPQTYYGVDYWGQGTLVTV SSGGGGSGGGGSGGGGSEIVLTQSPGTLSL SPGERATLSCRASQSVSSSYLAWYQQKPGQ APRLLIYGASSRATGIPDRFSGSGSGTDFT LTISRLEPEDFAVYYCQQTSEAPPTFGQGT KVEIK | 245 |
| 342 | 1464-A08 | scFv | | MEVQLLESGGGLVQPGGSLRLSCAASGFTF SGSSMSWVRQAPGKGLEWVGAIAGGDGYTG YADSVKGRFTISRDNSKNTLYLQMNSLRAE DTAVYYCAKGWHRQDYYGQDYWGQGTLVTV SSGGGGSGGGGSGGGGSEIVLTQSPGTLSL SPGERATLGCRASQSVSSSYLAWYQQKPGQ APRLLIYGASSRATGIPDRFSGSGSGTDFT LTISRLEPEDFAVYYCQQNQAAPATFGQGT KVEIK | 245 |
| 343 | 1464-1304 | scFv | | MEVQLLESGGGLVQPGGSLRLSCAASGFTF SGSSMSWVRQAPGKGLEWVGAIDGGEGYTS YADSVKGRFTISRDNSKNTLYLQMNSLRAE DTAVYYCAKGWHPQTLYDLDYWGQGTLVTV SSGGGGSGGGGSGGGGSEIVLTQSPGTLSL SPGERATLSCRASQSVSSSYLAWYQQKPGQ APRLLIYGASSRATGIPDRFSGSGSGTDFT LTISRLEPEDFAVYYCQQLVTSPPTFGQGT KVEIK | 245 |

TABLE 8-continued

Sequences.

| SEQ ID NO: | Molecule | Region | Scheme | Sequence | Length |
|---|---|---|---|---|---|
| 344 | 1557-A04 | scFv | | MEVQLLESGGGLVQPGGSLRLSCAASGFTF SGSSMSWVRQAPGKGLEWVGAIDGGEGSTA YADSVKGRFTISRDNSKNTLYLQMNSLRAE DTAVYYCAKGWHPQTMYDLDYWGQGTLVTV SSGGGGSGGGGSGGGGNEIVLTQSPGTLSL SPGERATLSCRASQNVSTNYLAWYQQKPGQ APRLLIYGASSRATGIPDRFSGSGSGTDFT LTISRLEPEDFAVYYCQQLVTNPPTFGQGT KVEIK | 245 |
| 345 | 1557-A05 | scFv | | MEVQLLESGGGLVQPGGSLRLSCAASGFTF GGSSMSWVRQAPGKGLEWVGAIGGGEGSTG YADSVKGRFTISRDNSKNTLYLQMNSLRAE DTAVYYCAKGWHDQSLYDRDYWGQGTLVTV SSGGGGSGGGGSGGGGSEIVLTQSPGTLSL SPGERATLSCSASQTVSSSYIAWYQQKPGQ APRLLIYGASSRATGIPDRFGGSGSGTDFT LTISRLEPEDFAVYYCQQLLTSPPTFGQGT KVEIK | 245 |
| 346 | 1557-B03 | scFv | | MEVQLLESGGGLVQPGGSLRLSCAASGFTF RSSSMSWVRQAPGKGLEWVGAIGGHEGYTG YADSVKGRFTISRDNSKNTLYLQMNSLRAE DTAVYYCAKGWNPQTLYHLDYWGQGTLVTV SSGGGGSGGGGSGGGGSEIVLTQSPGTLSL SPGERATLSCRASQKCSSSSMAWYQQKPGQ APRLLIYGASSRATGIPDRFSGSGSGTDFT LTISRLEPEDFAVYYCQQLQTSPPTFGQGT KVEIK | 245 |
| 347 | 1557-B10 | scFv | | MEVQLLESGGGLVQPGGSLRLSCAASGFTF SGCSMSWVRQAPGKGLEWVGAIAGGEGNTG YADSVKGRFTISRDNSKNTLYLQMNSLRAE DTAVYYCAKGWHPQTLYDLDYWGQGTLVTV SSGGGGSGGGGSGGGGSEIVLTQSPGTLSL SPGERATLSCRASQGLASRYMAWYQQKPGQ APRLLIYGASSRATGIPDRFSGSGSGTDFT LTISRLEPEDFAVYYCQQVMTIPPTFGQGT KVEIK | 245 |
| 348 | 1557-C06 | scFv | | MEVQLLESGGGLVQPGGSLRLSCAASGFTF RGASMSWVRQAPGKGLEWVGAIDGSQGSTG YADSVKGRFTISRDNSKNTLYLQMNSLRAE DTAVYYCAKGWHPQTMYDLDYWGQGTLVTV SSGGCGSGGGGSGGGGSEIVLTQSPGTLSL SPGERATLSCRASQRGTSSYLAWYQQKPGQ APRLLIYGASSRATGIPDRFSGSGSGTDFT LTISRLEPEDFAVYYCQQHVTSPPTFGQGT KVEIK | 245 |
| 349 | 1557-E07 | scFv | | MEVQLLESGGGLVQPGGSLRLSCAASGFTF SGSSMSWVRQAPGKGLEWVGAIDGGEGSTG YADSVKGRFTISRDNSKNTLYLQMNSLRAE DTAVYYCAKGWHPQTLYDLDYWGQGTLVTV SSGGGGSGGGGSGGGGSEIVLTQSPGTLSL SPGERATMSCRASQVLSSSSLAWYQQKPGQ APRLLIYGASSRATGIPDRFSGSGSGTDFA LTISRLEPEDFAVYYCQQRAAPPPTFGQGT KVEIK | 245 |
| 350 | 1557-E08 | scFv | | MEVQLLESGGGLVQPGGSLRLSCAASGFTF RASSMSWMRQAPGKGLEWVGAIDGGVGSTG YADSVKGRFTISRDNSKNTLYLQMNSLRAE DTAVYYCAKGWHPQTLYDLDYWGQGTLVTV SSGGGGSGGGGSGGGGSEIVLTQSPGTLSL SPGERATLSCRASQGDSSSVLAWYQQKPGQ APRLLIYGASSRATGIPDRFSGSGSGTDFT LTISRLEPEDFAVYYCQQLVPSPPTFGQGT KVEIK | 245 |
| 351 | 1557-E11 | scFv | | MEVQLLESGGGLVQPGGSLRLSCAASGFTF RGSSMSWVRQAPGKGLEWVGAIDGGEGSTG YADSVKGRFTINRDNSKNTLYLQMNSLRAE DTAVYYCAKGWHPQSLYDLDYWGQGTLVTV SSGGGGSGGGDSGGGGSEIVLTQSPGTLSL | 245 |

TABLE 8-continued

Sequences.

| SEQ ID NO: | Molecule | Region | Scheme | Sequence | Length |
|---|---|---|---|---|---|
| | | | | SPGERATLSCRASQPVPNTTLAWYQQKPGQ APRLLIYGASSRATGIPDRFSGSGSGTDFT LTISRLEPEDFAAYYCQQLVPSPPTFGQGT KVEIK | |
| 352 | 1557-F01 | scFv | | MEVQLLESGGGLVQPGGSLRLSCAASGFTF SGSSMSWVRQAPGKGLEWVGAIDGGEGSTG YADSVKGRFTISRDNSKNTLYLQMNSLRAE DTAVYYCAKGWHPQTLYDLDYWGQGTLVTV SSGGGGSGGGGSGGGGSEIVLTQSPGTLSL SPGERATLSCRASQSVSSSKLAWYQQKPGQ APRLLIYGASSRATGIPDRFSGYGSGTDFT LTISRLEPEDFAVYYCQQLETIPPTFGQGT KVEIK | 245 |
| 353 | 1557-F02 | scFv | | MEVQLLESGGGLVQPGGSLRLSCAASGFTF RGSSMSWVRQAPGKGLEWVGAIDGGEGSTG YADSVKGRFTISRDNSKNTLYLQMNSLRAE DTAVYYCAKGWHPQTMYNLDYWGQGTLVTV SSGGGGSGGGGSGGGGSEIVLTQSPGTLSL SPGERATLSCRASQSVSSSYLAWYQQKPGQ APRLLIYGASSRATGIPDRFSGSGSGTDFT LTISRLEPEDFAVYYCQQLFNSPPTFGQGT KVEIK | 245 |
| 354 | 1557-F03 | scFv | | MEVQLLESGGGLVQPGGSLRLSCAASGFTF SGSSMSWVRQAPGKGLEWVGAIAGGGGSTG YADSVKGRFTISRDNSKNTLYLQMNSLRAE DTAVYYCAKGWHPQTLYDLDYWGQGTLVTV SSGGGGSGGGGSGGGGSEIVLTQSPGTLSL SPGERATLSCRASQSVKTSDLAWYQQKPGQ APRLLIYGASSRATGIPDRFSGSGSGTDFT LTISRLEPEDFAVYYCQQLVSKPPTFGQGT KVEIK | 245 |
| 355 | 1557-F05 | scFv | | MEVQLLESGGGLVQPGGSLRLSCAASGFTF RGSSMSWVRQAPGKGLEWVGAIDGGEGSTG YADSVKGRFTISRDNSKNTLYLQMNSLRAE DTAVYYCAKDWHPQTLYDLDYWGQGTLVTV SSGGGGSGGGGSGGGGSEIVLTQSPGTLSL SPGERATLSCRASQTVSPSVLAWYQQKPGQ APRLLIYGASSRATGIPDRFSGSGSGTDFT LTISRLEPEDFAVYYCQQLVTNPPTFGQGT KVEIK | 245 |
| 356 | 1557-G01 | scFv | | MEVQLLESGGGLVQPGGSLRLSCAASGFTF SVTSMSWMRQAPGKGLEWVGAIAGGEGSTG YADSVKGRFTISRDNSKNTLYLQMNSLRAE DTAVYYCAKGWHPQTLYDLDYWGQGTLVTV SSGGGGSGGGGSGGGGSEIVLTQSPGTLSL SPGERATMSCRASQVLSSSSLAWYQQKPGQ APRLLIYGASSRATGIPDRFSGSGSGTDFT LTISRLEPEDFAVYYCQQLVTSPPTFGQGT KVEIK | 245 |
| 357 | 1557-G03 | scFv | | MEVQLLESGGGLVQPGGSLRLSCAASGFTF GGSSMSWVRQAPGKGLEWVGAIGGGEGYTG YADSVKGRFTISRDNSKNTLYLQMNSLRAE DTAVYYCAKGWHPQTLYDLDYWGQGTLVTV SSGGGGSGGGGSGGGGSEIVLTQSPGTLSL SPGERATLSCRASQSVHSSYLAWYQQKPGQ APRLLIYGASSRATGIPDRFSGSGSGTDFT LTISRLEPEDFAVYYCQQLLSSPPTFGQGT KVEIK | 245 |
| 358 | 1557-G04 | scFv | | MEVQLLESGGGLVQPGGSLRLSCAASGFTF CGSSMSWVRQAPGKGLEWVGAIDGGVGSTG YADSVKGRFTISRDNSKNTLYLQMNSLRAE DTAVYYCAKGWHPQTLYDLDYWGQGTLVTV SSGGGDSGGGGSGGGGSEIVLTQSPGTLSL SPGERATLSCRASQSVSSSYLAWYQQKPGQ APRLLIYGASSRATGIPDRFSGSGSGTDFT LTISRLEPEDFAVYYCQQDSFVPPTFGQGT KVEIK | 245 |

TABLE 8-continued

Sequences.

| SEQ ID NO: | Molecule | Region | Scheme | Sequence | Length |
|---|---|---|---|---|---|
| 359 | 1557-G06 | scFv | | MEVQLLESGGGLVQPGGSLRLSCAASGFTF SGFSMSWVRQAPGKGLEWVGAIDGGEGSTG YADSVKGRFTISRDNSKNTLYLQMNSLRAE DTAVYYCAKGWHPQTLYHLDYWGQGTLVTV SSGGGGSGGGGSGGGGSEIVLTQSPGTLSL SPGERATLSCRASQSIPSSYLAWYQQPEGQ APRLLIYGASSRATGIPDRFSGSGSGTDFT LTISRLEPEDFAVYYCQQLATSPPTFGQGT KVEIK | 245 |
| 360 | 1557-H04 | scFv | | MEVQLLESGGGLVQPGGSLRLSCAASGFTF SVTSMSWMRQAPGKGELWVGAIAGGEGSTG YADSVKGRFTISRDNSKNTLYLQMNSLRAE DTAVYYCAKGWHPQTLYDLDYWGQGTLVTV SSGGGGSDGGGSGGGGSEIVLTQGPSTLSL SPGERATLSCRASQSVSTGYLAWYQQKPGQ APRLLIYGASSRATGIPDRFSGSGSGTDFT LTISRLEPEDFAVYYCQQLVTRPPTFGQGT KVEIK | 245 |
| 361 | 1557-H10 | scFv | | MEVQLLESGGGLVQPGGSLRLSCAASGFTF SGSSMSWVRQAPGKGLEWVGAIDGGEGSTG YADSVKGRFTISRDNSKNTLYLQMNSLRAE DTAVYYCAKGWHPQSMYDLDYWGQGTLVTV SSGGGGSGGGGSGGGGSEIVLTQSPGTLSL SPGERATMSCRASQVLSSSSLAWYQQKPGQ APRLLIYGASSRATGIPDRFSGSGSGTDFT LTISRLEPEDFAVYYCQQLVTAPPTFGQGT KVEIK | 245 |
| 362 | mAB_5-10 | scFv-Fc | | MELVMTQSPSSLTVTAGEKVTMSCKSSQSL LNSGNQKNYLTWYQQKPGQPPKLLIYWAST RESGVPDRFTGSGSGTDFTLTISSVQAEDL AVYYCQNDYSYPLTFGAGTKLEIKGGGGSG GGGSGGGGSEVQLLEQSGAELVRPGTSVKI SCKASGYAFTNYWLGWYVKQRPGHGLEIGD IFPGSGNIHYNEKFKGKATLTADKSSSTAY MQLSSLTFEDSAVYFCARLRNWDEPMDYWG QGTTVTVSSAAGSDQEPKSSDKTHTCPPCS APELLGGSSVFLFPPKPKDTLMISRTPEVT CVVVDVSHEDPEVKFNWYVDGVEVHNAKTK PREEQYNSTYRVVSVLTVLHQDWLNGKEYK CKVSNKALPAPIEKTISKAKGQPREPQVYT LPPSRDELTKNQVSLTCLVKGFYPSDIAVE WESNGQPENNYKTTPPVLDSDGSFFLYSKL TVDKSRWQQGNVFSCSVMHEALHNHYTQKS LSLSPGKGGSHHHHHH | |

EQUIVALENTS

The disclosure set forth above may encompass multiple distinct inventions with independent utility. Although each of these inventions has been disclosed in its preferred form(s), the specific embodiments thereof as disclosed and illustrated herein are not to be considered in a limiting sense, because numerous variations are possible. The subject matter of the inventions includes all novel and nonobvious combinations and subcombinations of the various elements, features, functions, and/or properties disclosed herein. The following claims particularly point out certain combinations and subcombinations regarded as novel and nonobvious. Inventions embodied in other combinations and subcombinations of features, functions, elements, and/or properties may be claimed in this application, in applications claiming priority from this application, or in related applications. Such claims, whether directed to a different invention or to the same invention, and whether broader, narrower, equal, or different in scope in comparison to the original claims, also are regarded as included within the subject matter of the inventions of the present disclosure.

What is claimed is:

1. An isolated antibody or an antigen-binding fragment thereof, that specifically binds to human EpCAM, wherein the antibody comprises:
   a. a $V_H$ comprising: a CDR-H1 comprising SEQ ID NO: 23; a CDR-H2 comprising SEQ ID NO: 73; and a CDR-H3 comprising SEQ ID NO: 123, and a $V_L$ region comprising a CDR L1 comprising SEQ ID NO: 148; a CDR L2 comprising SEQ ID NO: 173, and a CDR L3 comprising SEQ ID NO: 198, according to the Chothia numbering scheme;
   b. a $V_H$ comprising: a CDR-H1 comprising SEQ ID NO: 48; a CDR-H2 comprising SEQ ID NO: 98; and a CDR-H3 comprising SEQ ID NO: 123, and a $V_L$ region comprising a CDR L1 comprising SEQ ID NO: 148; a CDR L2 comprising SEQ ID NO: 173, and a CDR L3 comprising SEQ ID NO: 198, according to the Kabat numbering scheme;
   c. a $V_H$ comprising: a CDR-H1 comprising SEQ ID NO: 27; a CDR-H2 comprising SEQ ID NO: 77; and a CDR-H3 comprising SEQ ID NO: 127, and a $V_L$ region comprising a CDR L1 comprising SEQ ID NO: 152; a CDR L2 comprising SEQ ID NO: 177, and a CDR L3 comprising SEQ ID NO: 202, according to the Kabat numbering scheme;
   d. a $V_H$ comprising: a CDR-H1 comprising SEQ ID NO: 52; a CDR-H2 comprising SEQ ID NO: 102; and a CDR-H3 comprising SEQ ID NO: 127, and a $V_L$ region comprising a CDR L1 comprising SEQ ID NO: 152; a CDR L2 comprising SEQ ID NO: 177, and a CDR L3 comprising SEQ ID NO: 202, according to the Kabat numbering scheme;
   e. a $V_H$ comprising: a CDR-H1 comprising SEQ ID NO: 28; a CDR-H2 comprising SEQ ID NO: 78; and a CDR-H3 comprising SEQ ID NO: 128, and a $V_L$ region comprising a CDR L1 comprising SEQ ID NO: 153; a CDR L2 comprising SEQ ID NO: 178, and a CDR L3 comprising SEQ ID NO: 203, according to the Chothia numbering scheme; or f. a $V_H$ comprising: a CDR-H1 comprising SEQ ID NO: 53; a CDR-H2 comprising SEQ ID NO: 103; and a CDR-H3 comprising SEQ ID NO: 128, and a $V_L$ region comprising a CDR L1 comprising SEQ ID NO: 153; a CDR L2 comprising SEQ ID NO: 178, and a CDR L3 comprising SEQ ID NO: 203, according to the Kabat numbering scheme.

2. The antibody of claim 1 (part a), wherein the antibody comprises:
a $V_H$ region SEQ ID NO: 248, and a $V_L$ region SEQ ID NO: 273.

3. The antibody of claim 1 (part b), wherein the antibody comprises:
a $V_H$ region SEQ ID NO: 248, and a $V_L$ region SEQ ID NO: 273.

4. The antibody of claim 1 (part c), wherein the antibody comprises:
a $V_H$ region SEQ ID NO: 252, and a $V_L$ region SEQ ID NO: 277.

5. The antibody of claim 1 (part d), wherein the antibody comprises:
a $V_H$ region SEQ ID NO: 252, and a $V_L$ region SEQ ID NO: 277.

6. The antibody of claim 1 (part e), wherein the antibody comprises:
a $V_H$ region SEQ ID NO: 253, and a $V_L$ region SEQ ID NO: 278.

7. The antibody of claim 1 (part f), wherein the antibody comprises:
a $V_H$ region SEQ ID NO: 253, and a $V_L$ region SEQ ID NO: 278.

8. The antibody of claim 1, wherein the antibody comprises at least one constant region domain.

9. The antibody of claim 8, wherein the constant region comprises a sequence selected from SEQ ID NOs: 279, 281, or 282.

10. The antibody of claim 1, wherein the antibody is a monoclonal antibody.

11. The antibody of claim 1, wherein the antibody is an IgA, an IgD, an IgE, an IgG, or an IgM.

12. The antibody of claim 1, wherein the antibody is humanized.

13. The antibody of claim 1, wherein the antibody is aglycosylated.

14. The antibody of claim 1, wherein the antibody is an antigen-binding fragment.

15. The antibody of claim 14, wherein the antigen-binding fragment is selected from an Fv fragment, a Fab fragment, a F(ab')₂ fragment, a Fab' fragment, an scFv (sFv) fragment, and an scFv-Fc fragment.

16. The antibody of claim 1, wherein the antigen-binding fragment is an scFv fragment.

17. The antibody of claim 16, wherein the scFv fragment comprises a sequence selected from SEQ ID NOs: 356, 360, and 361, with or without the N-terminal M residue.

18. The antibody of claim 1, wherein the antigen-binding fragment is an scFv-Fc fragment.

19. The antibody of claim 18, wherein the scFv-Fc fragment comprises a sequence selected from SEQ ID NOs: 223, 227, and 228, with or without the N-terminal M residue.

20. The antibody of claim 1, wherein the antibody has a $k_a$ of about $6.52 \times 10^4$ M⁻¹×sec⁻¹ to about $3.51 \times 10^5$ M⁻¹×sec⁻¹ when associating with human EpCAM at a temperature of 25° C.

21. The antibody of claim 1, wherein the antibody has a $k_d$ of about $1.75 \times 10^{-3}$ sec⁻¹ to about $1.74 \times 10^{-5}$ sec⁻¹ when dissociating from human EpCAM at a temperature of 25° C.

22. The antibody of claim 1, wherein the antibody has a $K_D$ of about $7.21 \times 10^{-9}$ M to about $1.93 \times 10^{-10}$ M when bound to human EpCAM at a temperature of 25° C.

23. The antibody of claim 1, wherein the antibody specifically binds cynomolgus EpCAM.

24. The antibody of claim 1, wherein the antibody has a $K_D$ of about $1.62 \times 10^{-7}$ M to about $1.17 \times 10^{-9}$ M when bound to cynomolgus EpCAM at a temperature of 25° C.

25. The antibody of claim 24, wherein the ratio of $K_D$ for human EpCAM to $K_D$ for cynomolgus EpCAM is about 0.029 to about 6.162.

26. A kit comprising the antibody of claim 1, and instructions for use of the antibody.

27. A pharmaceutical composition comprising the antibody of claim 1 and a pharmaceutically acceptable carrier.

28. An isolated antibody or an antigen-binding fragment thereof, that specifically binds to human EpCAM, wherein the antibody comprises:
a. three heavy chain CDRs and three light chain CDRs of an antibody comprising the $V_H$ region SEQ ID NO: 248, and the $V_L$ region SEQ ID NO: 273;
b. three heavy chain CDRs and three light chain CDRs of an antibody comprising the $V_H$ region SEQ ID NO: 252, and the $V_L$ region SEQ ID NO: 277; or c. three heavy chain CDRs and three light chain CDRs of an antibody comprising the $V_H$ region SEQ ID NO: 253, and the $V_L$ region SEQ ID NO: 278.

29. The antibody or antigen-binding fragment of claim 28, wherein the CDRs comprise
a. a $V_H$ comprising: a CDR-H1 comprising SEQ ID NO: 23; a CDR-H2 comprising SEQ ID NO: 73; and a CDR-H3 comprising SEQ ID NO: 123, and a $V_L$ region comprising a CDR L1 comprising SEQ ID NO: 148; a CDR L2 comprising SEQ ID NO: 173, and a CDR L3 comprising SEQ ID NO: 198, according to the Chothia numbering scheme;
b. a $V_H$ comprising: a CDR-H1 comprising SEQ ID NO: 48; a CDR-H2 comprising SEQ ID NO: 98; and a CDR-H3 comprising SEQ ID NO: 123, and a $V_L$ region comprising a CDR L1 comprising SEQ ID NO: 148; a CDR L2 comprising SEQ ID NO: 173, and a CDR L3 comprising SEQ ID NO: 198, according to the Kabat numbering scheme;
c. a $V_H$ comprising: a CDR-H1 comprising SEQ ID NO: 27; a CDR-H2 comprising SEQ ID NO: 77; and a CDR-H3 comprising SEQ ID NO: 127, and a $V_L$ region comprising a CDR L1 comprising SEQ ID NO: 152; a CDR L2 comprising SEQ ID NO: 177, and a CDR L3 comprising SEQ ID NO: 202, according to the Kabat numbering scheme;
d. a $V_H$ comprising: a CDR-H1 comprising SEQ ID NO: 52; a CDR-H2 comprising SEQ ID NO: 102; and a CDR-H3 comprising SEQ ID NO: 127, and a $V_L$ region comprising a CDR L1 comprising SEQ ID NO: 152; a CDR L2 comprising SEQ ID NO: 177, and a CDR L3 comprising SEQ ID NO: 202, according to the Kabat numbering scheme;
e. a $V_H$ comprising: a CDR-H1 comprising SEQ ID NO: 28; a CDR-H2 comprising SEQ ID NO: 78; and a CDR-H3 comprising SEQ ID NO: 128, and a $V_L$ region comprising a CDR L1 comprising SEQ ID NO: 153; a CDR L2 comprising SEQ ID NO: 178, and a CDR L3 comprising SEQ ID NO: 203, according to the Chothia numbering scheme; or
f. a $V_H$ comprising: a CDR-H1 comprising SEQ ID NO: 53; a CDR-H2 comprising SEQ ID NO: 103; and a CDR-H3 comprising SEQ ID NO: 128, and a $V_L$ region comprising a CDR L1 comprising SEQ ID NO: 153; a CDR L2 comprising SEQ ID NO: 178, and a CDR L3 comprising SEQ ID NO: 203, according to the Kabat numbering scheme.

* * * * *